(12) United States Patent
Spiegelman et al.

(10) Patent No.: US 11,291,706 B2
(45) Date of Patent: Apr. 5, 2022

(54) METHODS FOR IDENTIFICATION, ASSESSMENT, PREVENTION, AND TREATMENT OF METABOLIC DISORDERS USING SLIT2

(71) Applicant: Dana-Farber Cancer Institute, Inc., Boston, MA (US)

(72) Inventors: Bruce M. Spiegelman, Waban, MA (US); Katrin J. Svensson, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/741,326

(22) PCT Filed: Jul. 15, 2016

(86) PCT No.: PCT/US2016/042543
§ 371 (c)(1),
(2) Date: Jan. 2, 2018

(87) PCT Pub. No.: WO2017/011763
PCT Pub. Date: Jan. 19, 2017

(65) Prior Publication Data
US 2018/0193416 A1    Jul. 12, 2018

Related U.S. Application Data

(60) Provisional application No. 62/193,359, filed on Jul. 16, 2015.

(51) Int. Cl.
| | | |
|---|---|---|
| *A61K 38/17* | (2006.01) | |
| *G01N 33/50* | (2006.01) | |
| *C07K 14/47* | (2006.01) | |
| *C07K 14/705* | (2006.01) | |
| *A61K 9/00* | (2006.01) | |

(52) U.S. Cl.
CPC ........ *A61K 38/1709* (2013.01); *A61K 9/0019* (2013.01); *C07K 14/4702* (2013.01); *C07K 14/705* (2013.01); *G01N 33/5023* (2013.01); *G01N 2333/4703* (2013.01); *G01N 2500/04* (2013.01); *G01N 2500/10* (2013.01)

(58) Field of Classification Search
CPC .................. A61K 38/1709; C07K 14/4702
See application file for complete search history.

(56) References Cited

U.S. PATENT DOCUMENTS
2013/0074199 A1    3/2013   Spiegelman et al.
2018/0193416 A1    7/2018   Spiegelman et al.

FOREIGN PATENT DOCUMENTS
| | | | |
|---|---|---|---|
| WO | WO-2006/007400 A2 | 1/2006 | |
| WO | WO-2007/128884 A1 | 11/2007 | |
| WO | WO-2008/06330 A2 | 1/2008 | |
| WO | WO-2014194402 A1 * | 12/2014 | ............. A61K 45/06 |

OTHER PUBLICATIONS

Zhang et al., "Slit2/Robo4 Signaling Modulates HIV-1 gp120-Induced Lymphatic Hyperpermeability", PLOS Pathogens, 2012 pp. 1-13 (Year: 2012).*
Fredriksson et al., "Analysis of inhibition by H89 of UCP1 gene expression and thermogenesis indicates protein kinase A mediation of b3-adrenergic signalling rather than b3-andrenoceptor antagonism by H89", Biochimica et Biophysics Acta, 2001, pp. 206-217 (Year: 2001).*
Fredholm et al., "The Effect of Alkylxanthines and Other Phosphodiesterase Inhibitors on Adenosine-Receptor Mediated Decrease in Lipolysis and Cyclic AMP Accumulation in Rat Fat Cells", Acta pharmacol. et toxicol., 1984, 64-71 (Year: 1984).*
GenBank: AAD25539.1, SLIT2 [Homo sapiens], 1999 (Year: 1999).*
Buechler et al. "Adipose tissue fibrosis", World Journal of Diabetes, May 15, 2015, pp. 548-553 (Year: 2015).*
Ghiglotti et al. "Adipose Tissue Immune Response: Novel Triggers and Consequences for Chronic Inflammatory Conditions", Inflammation, 2014, pp. 1337-1353 (Year: 2014).*
The Human Protein Atlas, "ROBOT1", www.proteinatlas.org/ENSG00000169855-ROBO1, 2015 (Year: 2015).*
International Search Report and Written Opinion for International Application No. PCT/US16/42543 dated Sep. 28, 2016.
Cohen et al., "Brown and beige fat: molecular parts of a thermogenic machine," Diabetes, 64(7):2346-2351 (2015).
Extended European Search Report for EP Application No. 16825258.3 dated Jan. 21, 2019.
Harms et al., "Brown and beige fat: development, function and therapeutic potential," Nature Medicine, 19(10):1252-1263 (2013).
Lim et al., "Slit2 Exerts Anti-Inflammatory Actions in Human Placenta and is Decreased with Maternal Obesity," American Journal of Reproductive Immunology, 73(1):66-78 (2014).
Svensson et al. "A Secreted Slit2 Fragment Regulates Adipose Tissue Thermogenesis and Metabolic Function," Cell Metabolism, 23(3):454-466 (2016).
Zhao et al., "Isoflurane post-conditioning protects primary cultures of cortical neurons against oxygen and glucose deprivation injury via upregulation of Slit2/Robo1," Brain Research, 1537:283-289 (2013).
Zhou et al., "The role of SLIT-ROBO signaling in proliferative diabetic retinopathy and retinal pigment epithelial cells," Molecular Vision, 17:1526-1536 (2011).

* cited by examiner

*Primary Examiner* — Lianko G Garyu
(74) *Attorney, Agent, or Firm* — Foley Hoag LLP

(57) ABSTRACT

The present invention relates to methods for identifying, assessing, preventing, and treating metabolic disorders and modulating metabolic processes using Slit2.

4 Claims, 35 Drawing Sheets
Specification includes a Sequence Listing.

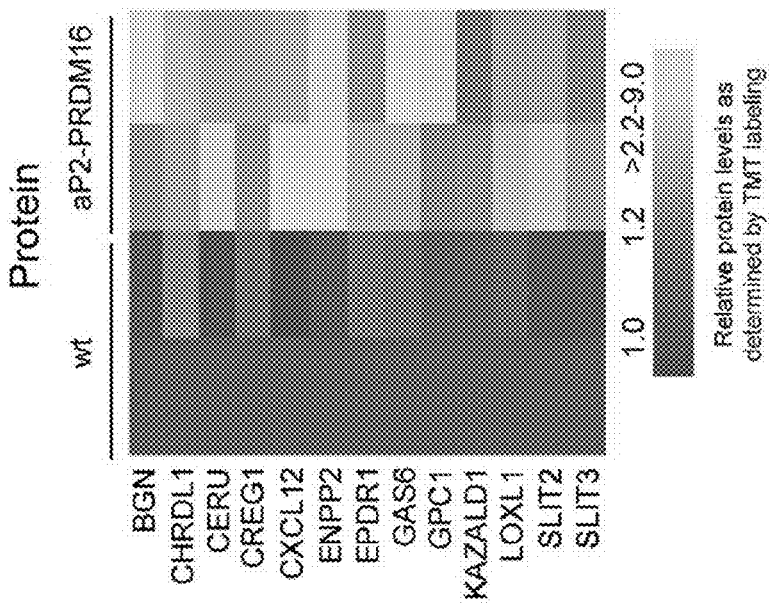
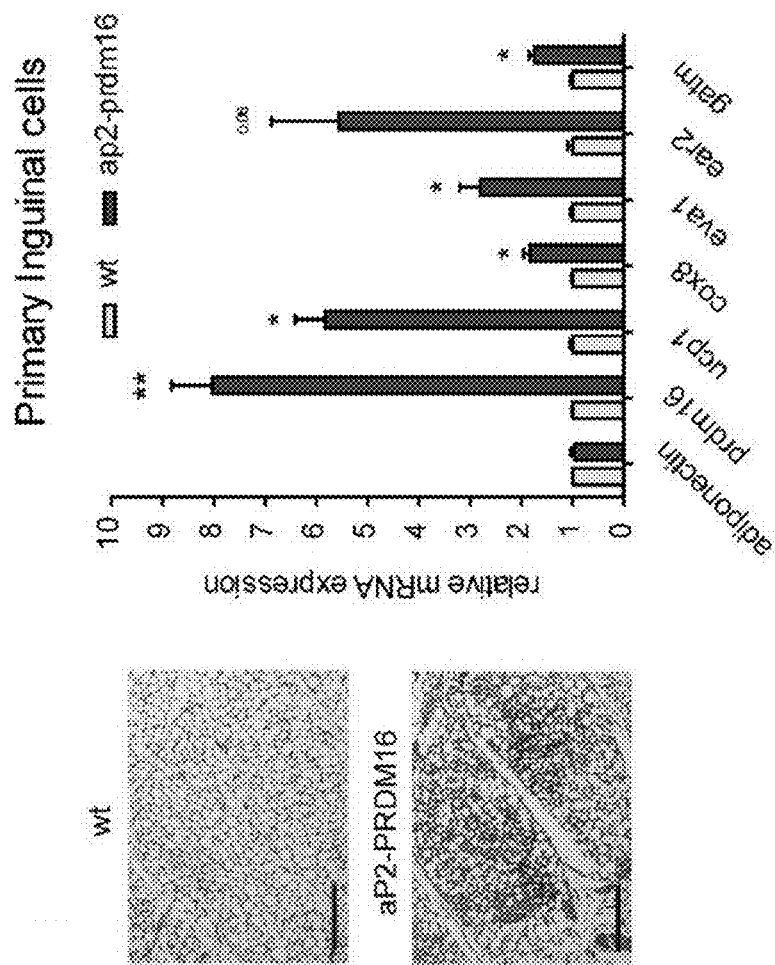
FIG. 1A  FIG. 1B  FIG. 1C

FIG. 2A

Q9R1B9 | SLIT2_MOUSE Slit homolog 2 protein

(illegible sequence block) (SEQ ID NO: 125)

Matched peptides shown in bold

Q9WVB4 | SLIT3_MOUSE Slit homolog 3 protein

(illegible sequence block) (SEQ ID NO: 126)

Matched peptides shown in bold

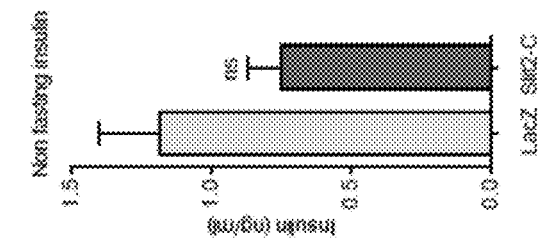
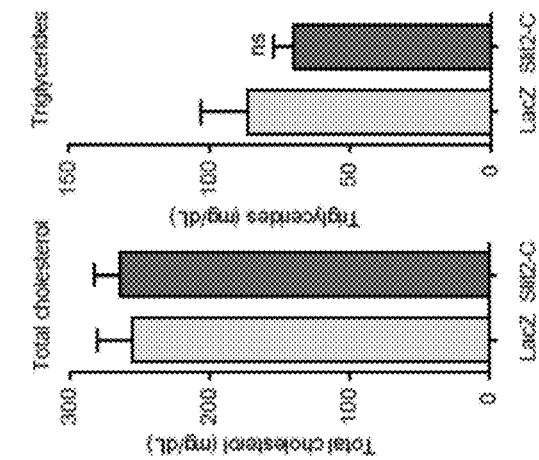
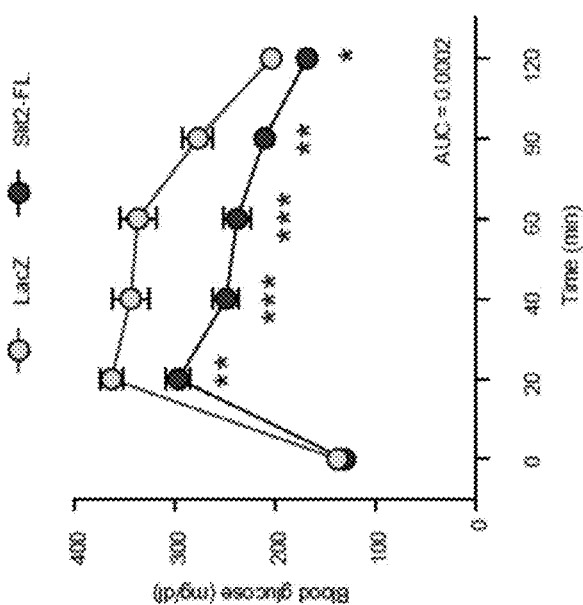
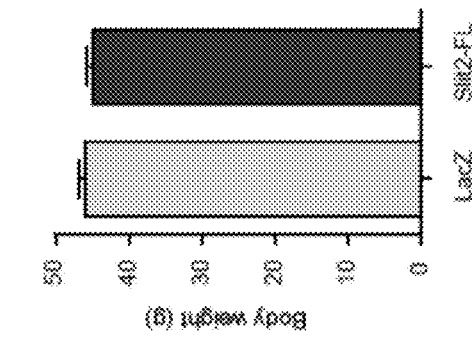
FIG. 9E FIG. 9F FIG. 9G FIG. 9H FIG. 9I

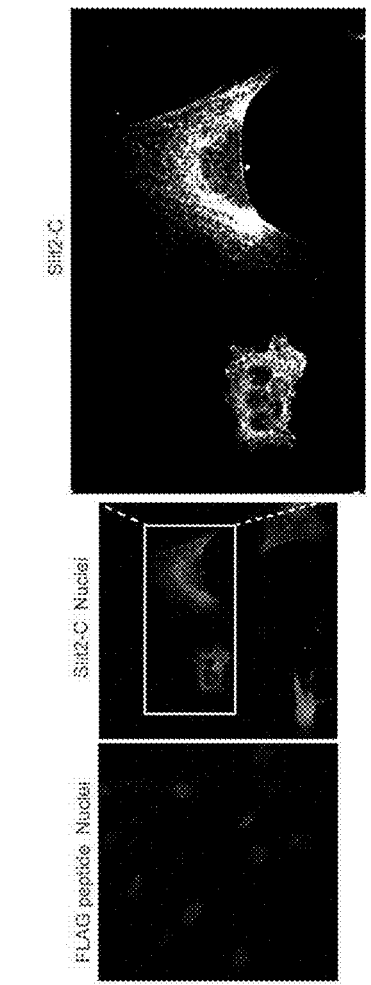
FIG. 10J  FIG. 10K  FIG. 10L
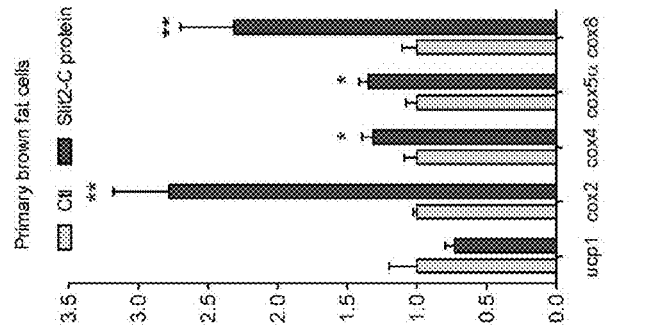
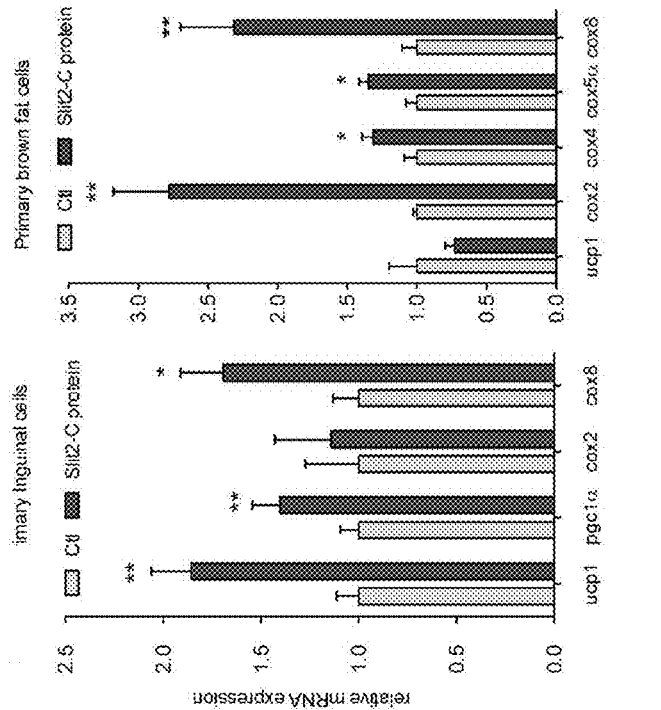
FIG. 10N
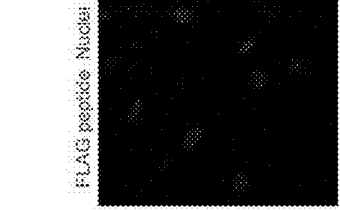
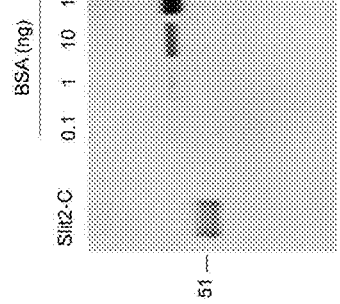
FIG. 10M

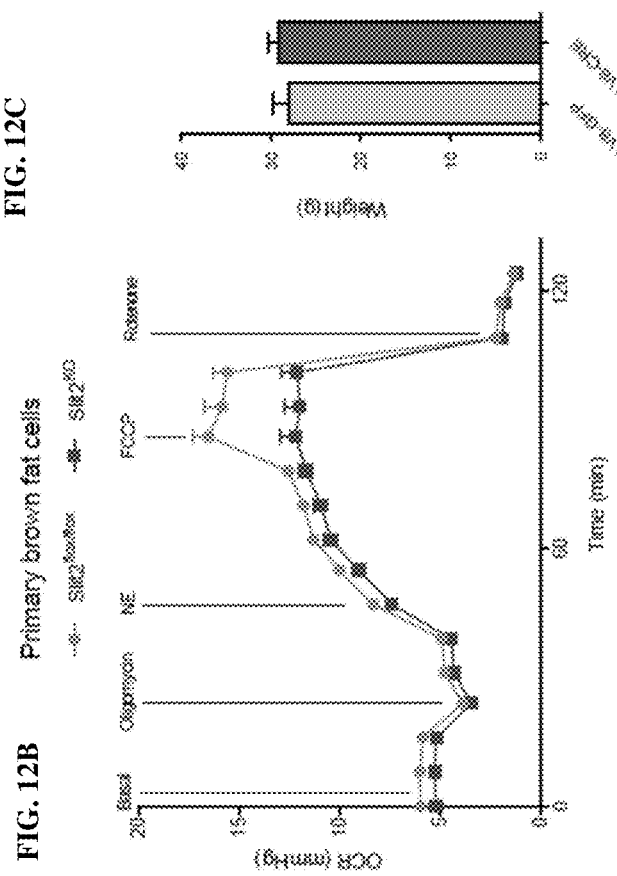
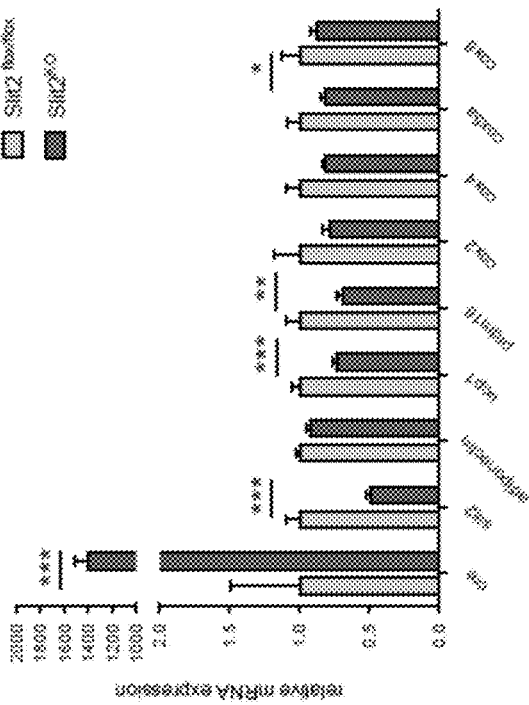
FIG. 12A  FIG. 12B  FIG. 12C

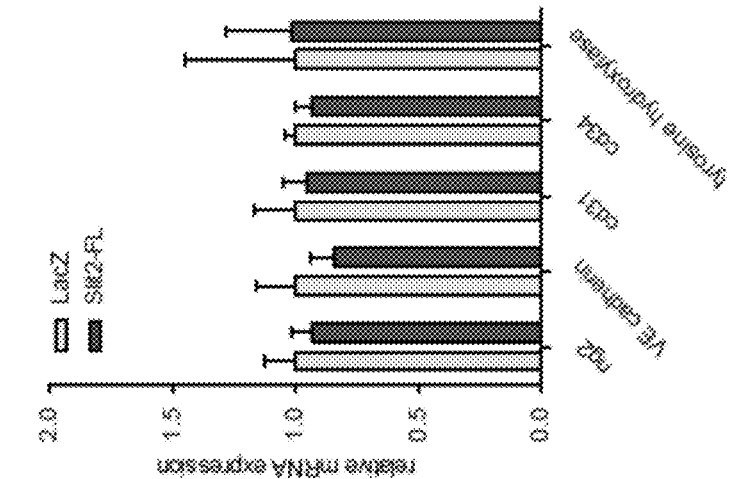
FIG. 12D  FIG. 12E  FIG. 12F
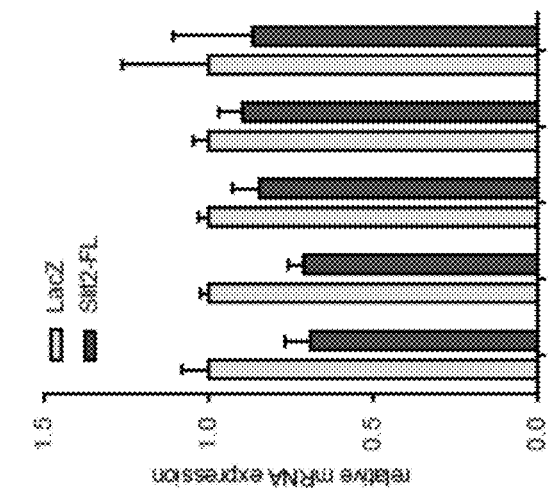
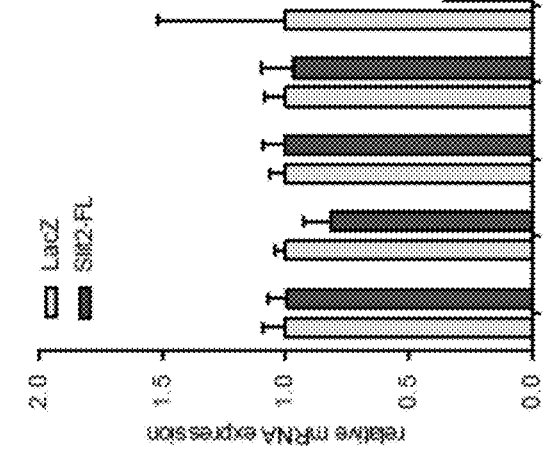

SEQUENCE LISTING

<160> NUMBER OF SEQ ID NOS: 127

<210> SEQ ID NO 1
<211> LENGTH: 4590
<212> TYPE: DNA
<213> ORGANISM: Homo sapiens

<400> SEQUENCE: 1

```
atgcgcggcg ttggctggca gatgctgtcc ctgtcgctgg ggttagtgct ggcgatcctg      60
aacaaggtgg caccgcaggc gtgcccggcg cagtgctctt gctcgggcag cacagtggac     120
tgtcacgggc tggcgctgcg cagcgtgccc aggaatatcc cccgcaacac cgagagactg     180
gatttaaatg gaataacat cacaagaatt acgaagacag attttgctgg tcttagacat      240
```

```
ctaagagttc ttcagcttat ggagaataag attagcacca ttgaaagagg agcattccag      300
gatcttaaag aactagagag actgcgttta aacagaaatc accttcagct gtttcctgag      360
ttgctgtttc ttgggactgc gaagctatac aggcttgatc tcagtgaaaa ccaaattcag      420
gcaatcccaa ggaaagcttt ccgtggggca gttgacataa aaaatttgca actggattac      480
aaccagatca gctgtattga agatggggca ttcagggctc tccgggacct ggaagtgctc      540
actctcaaca ataacaacat tactagactt tctgtggcaa gtttcaacca tatgcctaaa      600
cttaggactt ttcgactgca ttcaaacaac ctgtattgtg actgccacct ggcctggctc      660
tccgactggc ttcgccaaag gcctcgggtt ggtctgtaca ctcagtgtat gggcccctcc      720
cacctgagag gccataatgt agccgaggtt caaaaacgag aatttgtctg cagtggtcac      780
cagtcattta tggctccttc ttgtagtgtt ttgcactgcc ctgccgcctg tacctgtagc      840
aacaatatcg tagactgtcg tgggaaaggt ctcactgaga tccccacaaa tcttccagag      900
accatcacag aaatacgttt ggaacagaac acaatcaaag tcatccctcc tggagctttc      960
tcaccatata aaaagcttag acgaattgac ctgagcaata atcagatctc tgaacttgca     1020
ccagatgctt tccaaggact acgctctctg aattcacttg tcctctatgg aaataaaatc     1080
acagaactcc ccaaaagttt atttgaagga ctgttttcct tacagctcct attattgaat     1140
gccaacaaga taaactgcct tcgggtagat gcttttcagg atctccacaa cttgaacctt     1200
ctctccctat atgacaacaa gcttcagacc atcgccaagg ggacctttc acctcttcgg      1260 gccattcaaa ctatgcattt ggcccagaac ccctttattt gtgactgcca tctcaagtgg     1320
ctagcggatt atctccatac caacccgatt gagaccagtg gtgcccgttg caccagcccc     1380
cgccgcctgg caaacaaaag aattggacag atcaaaagca agaaattccg ttgttcagct     1440
aaagaacagt atttcattcc aggtacagaa gattatcgat caaaattaag tggagactgc     1500
tttgcggatc tggcttgccc tgaaaagtgt cgctgtgaag gaaccacagt agattgctct     1560
aatcaaaagc tcaacaaaat cccggagcac attccccagt acactgcaga gttgcgtctc     1620
aataataatg aatttaccgt gttggaagcc acaggaatct ttaagaaact tcctcaatta     1680
cgtaaaataa actttagcaa caataagatc acagatattg aggagggagc atttgaagga     1740
gcatctggtg taaatgaaat acttcttacg agtaatcgtt tggaaaatgt gcagcataag     1800
atgttcaagg gattggaaag cctcaaaact ttgatgttga gaagcaatcg aataacctgt     1860
gtggggaatg acagtttcat aggactcagt tctgtgcgtt tgctttcttt gtatgataat     1920
caaattacta cagttgcacc aggggcattt gatactctcc attctttatc tactctaaac     1980
ctcttggcca atccttttaa ctgtaactgc tacctggctt ggttgggaga gtggctgaga     2040
aagaagagaa ttgtcacggg aaatcctaga tgtcaaaaac catacttcct gaaagaaata     2100
cccatccagg atgtggccat tcaggacttc acttgtgatg acggaaatga tgacaatagt     2160
tgctccccac tttctcgctg tcctactgaa tgtacttgct tggatacagt cgtccgatgt     2220
agcaacaagg gtttgaaggt cttgccgaaa ggtattccaa gagatgtcac agagttgtat     2280
ctggatggaa accaatttac actggttccc aaggaactct ccaactacaa acatttaaca     2340
cttatagact taagtaacaa cagaataagc acgctttcta atcagagctt cagcaacatg     2400
acccagctcc tcaccttaat tcttagttac aaccgtctga gatgtattcc tcctcgcacc     2460
tttgatggat taaagtctct tcgattactt tctctacatg gaaatgacat ttctgttgtg     2520
cctgaaggtg ctttcaatga tctttctgca ttatcacatc tagcaattgg agccaaccct     2580
```

| | | |
|---|---|---|
| ctttactgtg attgtaacat gcagtggtta tccgactggg tgaagtcgga atataaggag | 2640 | |
| cctggaattg ctcgttgtgc tggtcctgga gaaatggcag ataaactttt actcacaact | 2700 | |
| ccctccaaaa aatttacctg tcaaggtcct gtggatgtca atattctagc taagtgtaac | 2760 | |
| ccctgcctat caaatccgtg taaaaatgat ggcacatgta atagtgatcc agttgacttt | 2820 | |
| taccgatgca cctgtccata tggtttcaag gggcaggact gtgatgtccc aattcatgcc | 2880 | |
| tgcatcagta acccatgtaa acatggagga acttgccact taaggaagg agaagaagat | 2940 | |
| ggattctggt gtatttgtgc tgatggattt gaaggagaaa attgtgaagt caacgttgat | 3000 | |
| gattgtgaag ataatgactg tgaaaataat tctacatgtg tcgatggcat taataactac | 3060 | |
| acatgccttt gcccacctga gtatacaggt gagttgtgtg aggagaagct ggacttctgt | 3120 | |
| gcccaggacc tgaaccccctg ccagcacgat tcaaagtgca tcctaactcc aaagggattc | 3180 | |
| aaatgtgact gcacaccagg gtacgtaggt gaacactgcg acatcgattt tgacgactgc | 3240 | |
| caagacaaca gtgtaaaaaa cggagcccac tgcacagatg cagtgaacgg ctatacgtgc | 3300 | |
| atatgccccg aaggttacag tggcttgttc tgtgagtttt ctccacccat ggtcctccct | 3360 | |
| cgtaccagcc cctgtgataa ttttgattgt cagaatggag ctcagtgtat cgtcagaata | 3420 | |
| aatgagccaa tatgtcagtg tttgcctggc tatcaggag aaaagtgtga aaaattggtt | 3480 | |
| agtgtgaatt ttataaacaa agagtcttat cttcagattc cttcagccaa ggttcggcct | 3540 | |
| cagacgaaca taacacttca gattgccaca gatgaagaca gcggaatcct cctgtataag | 3600 | |
| ggtgacaaag accatatcgc ggtagaactc tatcggggggc gtgttcgtgc cagctatgac | 3660 | |
| accggctctc atccagcttc tgccatttac agtgtggaga caatcaatga tggaaacttc | 3720 | |
| cacattgtgg aactacttgc cttggatcag agtctctctt tgtccgtgga tggtgggaac | 3780 | |
| cccaaaatca tcactaactt gtcaaagcag tccactctga tttttgactc tccactctat | 3840 | |
| gtaggaggca tgccagggaa gagtaacgtg gcatctctgc gccaggcccc tgggcagaac | 3900 | |
| ggaaccagct tccacggctg catccggaac ctttacatca acagtgagct gcaggacttc | 3960 | |
| cagaaggtgc cgatgcaaac aggcatttttg cctggctgtg agccatgcca caagaaggtg | 4020 | |
| tgtgcccatg gcacatgcca gcccagcagc caggcaggct tcacctgcga gtgccaggaa | 4080 | |
| ggatggatgg ggcccctctg tgaccaacgg accaatgacc cttgccttgg aaataaatgc | 4140 | |
| gtacatggca cctgcttgcc catcaatgcg ttctcctaca gctgtaagtg cttggagggc | 4200 | |
| catggaggtg tcctctgtga tgaagaggag gatctgttta acccatgcca ggcgatcaag | 4260 | |
| tgcaagcatg gaagtgcag gctttcaggt ctggggcagc cctactgtga atgcagcagt | 4320 | |
| ggatacacgg gggacagctg tgatcgagaa atctcttgtc gaggggaaag gataagagat | 4380 | |
| tattaccaaa agcagcaggg ctatgctgct tgccaaacaa ccaagaaggt gtcccgatta | 4440 | |
| gagtgcagag gtgggtgtgc aggagggcag tgctgtggac cgctgaggag caagcggcgg | 4500 | |
| aaatactctt tcgaatgcac tgacggctcc tcctttgtgg acgaggttga gaaagtggtg | 4560 | |
| aagtgcggct gtacgaggtg tgtgtcctaa | 4590 | |

<210> SEQ ID NO 2
<211> LENGTH: 1529
<212> TYPE: PRT
<213> ORGANISM: Homo sapiens

<400> SEQUENCE: 2

```
Met Arg Gly Val Gly Trp Gln Met Leu Ser Leu Ser Leu Gly Leu Val
1               5                   10                  15
```

Leu Ala Ile Leu Asn Lys Val Ala Pro Gln Ala Cys Pro Ala Gln Cys
                20                  25                  30

Ser Cys Ser Gly Ser Thr Val Asp Cys His Gly Leu Ala Leu Arg Ser
            35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
                100                 105                 110

Asn His Leu Gln Leu Phe Pro Glu Leu Leu Phe Leu Gly Thr Ala Lys
            115                 120                 125

Leu Tyr Arg Leu Asp Leu Ser Glu Asn Gln Ile Gln Ala Ile Pro Arg
            130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
            195                 200                 205

Asn Asn Leu Tyr Cys Asp Cys His Leu Ala Trp Leu Ser Asp Trp Leu
210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
            245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
            275                 280                 285

Lys Gly Leu Thr Glu Ile Pro Thr Asn Leu Pro Glu Thr Ile Thr Glu
            290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
            355                 360                 365

Glu Gly Leu Phe Ser Leu Gln Leu Leu Leu Leu Asn Ala Asn Lys Ile
            370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
            420                 425                 430

-continued

```
Ile Cys Asp Cys His Leu Lys Trp Leu Ala Asp Tyr Leu His Thr Asn
            435                 440                 445

Pro Ile Glu Thr Ser Gly Ala Arg Cys Thr Ser Pro Arg Arg Leu Ala
    450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
        515                 520                 525

Glu His Ile Pro Gln Tyr Thr Ala Glu Leu Arg Leu Asn Asn Asn Glu
    530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
        595                 600                 605

Lys Thr Leu Met Leu Arg Ser Asn Arg Ile Thr Cys Val Gly Asn Asp
    610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
                645                 650                 655

Ser Thr Leu Asn Leu Leu Ala Asn Pro Phe Asn Cys Asn Cys Tyr Leu
            660                 665                 670

Ala Trp Leu Gly Glu Trp Leu Arg Lys Lys Arg Ile Val Thr Gly Asn
        675                 680                 685

Pro Arg Cys Gln Lys Pro Tyr Phe Leu Lys Glu Ile Pro Ile Gln Asp
    690                 695                 700

Val Ala Ile Gln Asp Phe Thr Cys Asp Asp Gly Asn Asp Asp Asn Ser
705                 710                 715                 720

Cys Ser Pro Leu Ser Arg Cys Pro Thr Glu Cys Thr Cys Leu Asp Thr
                725                 730                 735

Val Val Arg Cys Ser Asn Lys Gly Leu Lys Val Leu Pro Lys Gly Ile
            740                 745                 750

Pro Arg Asp Val Thr Glu Leu Tyr Leu Asp Gly Asn Gln Phe Thr Leu
        755                 760                 765

Val Pro Lys Glu Leu Ser Asn Tyr Lys His Leu Thr Leu Ile Asp Leu
    770                 775                 780

Ser Asn Asn Arg Ile Ser Thr Leu Ser Asn Gln Ser Phe Ser Asn Met
785                 790                 795                 800

Thr Gln Leu Leu Thr Leu Ile Leu Ser Tyr Asn Arg Leu Arg Cys Ile
                805                 810                 815

Pro Pro Arg Thr Phe Asp Gly Leu Lys Ser Leu Arg Leu Leu Ser Leu
            820                 825                 830

His Gly Asn Asp Ile Ser Val Val Pro Glu Gly Ala Phe Asn Asp Leu
        835                 840                 845
```

```
Ser Ala Leu Ser His Leu Ala Ile Gly Ala Asn Pro Leu Tyr Cys Asp
850                 855                 860
Cys Asn Met Gln Trp Leu Ser Asp Trp Val Lys Ser Glu Tyr Lys Glu
865                 870                 875                 880
Pro Gly Ile Ala Arg Cys Ala Gly Pro Gly Glu Met Ala Asp Lys Leu
            885                 890                 895
Leu Leu Thr Thr Pro Ser Lys Lys Phe Thr Cys Gln Gly Pro Val Asp
            900                 905                 910
Val Asn Ile Leu Ala Lys Cys Asn Pro Cys Leu Ser Asn Pro Cys Lys
            915                 920                 925
Asn Asp Gly Thr Cys Asn Ser Asp Pro Val Asp Phe Tyr Arg Cys Thr
930                 935                 940
Cys Pro Tyr Gly Phe Lys Gly Gln Asp Cys Asp Val Pro Ile His Ala
945                 950                 955                 960
Cys Ile Ser Asn Pro Cys Lys His Gly Gly Thr Cys His Leu Lys Glu
                965                 970                 975
Gly Glu Glu Asp Gly Phe Trp Cys Ile Cys Ala Asp Gly Phe Glu Gly
                980                 985                 990
Glu Asn Cys Glu Val Asn Val Asp  Asp Cys Glu Asp Asn  Asp Cys Glu
                995                 1000                1005
Asn Asn  Ser Thr Cys Val Asp  Gly Ile Asn Asn Tyr  Thr Cys Leu
    1010                1015                1020
Cys Pro  Pro Glu Tyr Thr Gly  Glu Leu Cys Glu Glu  Lys Leu Asp
    1025                1030                1035
Phe Cys  Ala Gln Asp Leu Asn  Pro Cys Gln His Asp  Ser Lys Cys
    1040                1045                1050
Ile Leu  Thr Pro Lys Gly Phe  Lys Cys Asp Cys Thr  Pro Gly Tyr
    1055                1060                1065
Val Gly  Glu His Cys Asp Ile  Asp Phe Asp Asp Cys  Gln Asp Asn
    1070                1075                1080
Lys Cys  Lys Asn Gly Ala His  Cys Thr Asp Ala Val  Asn Gly Tyr
    1085                1090                1095
Thr Cys  Ile Cys Pro Glu Gly  Tyr Ser Gly Leu Phe  Cys Glu Phe
    1100                1105                1110
Ser Pro  Pro Met Val Leu Pro  Arg Thr Ser Pro Cys  Asp Asn Phe
    1115                1120                1125
Asp Cys  Gln Asn Gly Ala Gln  Cys Ile Val Arg Ile  Asn Glu Pro
    1130                1135                1140
Ile Cys  Gln Cys Leu Pro Gly  Tyr Gln Gly Glu Lys  Cys Glu Lys
    1145                1150                1155
Leu Val  Ser Val Asn Phe Ile  Asn Lys Glu Ser Tyr  Leu Gln Ile
    1160                1165                1170
Pro Ser  Ala Lys Val Arg Pro  Gln Thr Asn Ile Thr  Leu Gln Ile
    1175                1180                1185
Ala Thr  Asp Glu Asp Ser Gly  Ile Leu Leu Tyr Lys  Gly Asp Lys
    1190                1195                1200
Asp His  Ile Ala Val Glu Leu  Tyr Arg Gly Arg Val  Arg Ala Ser
    1205                1210                1215
Tyr Asp  Thr Gly Ser His Pro  Ala Ser Ala Ile Tyr  Ser Val Glu
    1220                1225                1230
Thr Ile  Asn Asp Gly Asn Phe  His Ile Val Glu Leu  Leu Ala Leu
    1235                1240                1245
```

```
Asp Gln Ser Leu Ser Leu Ser Val Asp Gly Gly Asn Pro Lys Ile
    1250                1255                1260

Ile Thr Asn Leu Ser Lys Gln Ser Thr Leu Asn Phe Asp Ser Pro
    1265                1270                1275

Leu Tyr Val Gly Gly Met Pro Gly Lys Ser Asn Val Ala Ser Leu
    1280                1285                1290

Arg Gln Ala Pro Gly Gln Asn Gly Thr Ser Phe His Gly Cys Ile
    1295                1300                1305

Arg Asn Leu Tyr Ile Asn Ser Glu Leu Gln Asp Phe Gln Lys Val
    1310                1315                1320

Pro Met Gln Thr Gly Ile Leu Pro Gly Cys Glu Pro Cys His Lys
    1325                1330                1335

Lys Val Cys Ala His Gly Thr Cys Gln Pro Ser Ser Gln Ala Gly
    1340                1345                1350

Phe Thr Cys Glu Cys Gln Glu Gly Trp Met Gly Pro Leu Cys Asp
    1355                1360                1365

Gln Arg Thr Asn Asp Pro Cys Leu Gly Asn Lys Cys Val His Gly
    1370                1375                1380

Thr Cys Leu Pro Ile Asn Ala Phe Ser Tyr Ser Cys Lys Cys Leu
    1385                1390                1395

Glu Gly His Gly Gly Val Leu Cys Asp Glu Glu Asp Leu Phe
    1400                1405                1410

Asn Pro Cys Gln Ala Ile Lys Cys Lys His Gly Lys Cys Arg Leu
    1415                1420                1425

Ser Gly Leu Gly Gln Pro Tyr Cys Glu Cys Ser Ser Gly Tyr Thr
    1430                1435                1440

Gly Asp Ser Cys Asp Arg Glu Ile Ser Cys Arg Gly Glu Arg Ile
    1445                1450                1455

Arg Asp Tyr Tyr Gln Lys Gln Gly Tyr Ala Ala Cys Gln Thr
    1460                1465                1470

Thr Lys Lys Val Ser Arg Leu Glu Cys Arg Gly Gly Cys Ala Gly
    1475                1480                1485

Gly Gln Cys Cys Gly Pro Leu Arg Ser Lys Arg Arg Lys Tyr Ser
    1490                1495                1500

Phe Glu Cys Thr Asp Gly Ser Ser Phe Val Asp Glu Val Glu Lys
    1505                1510                1515

Val Val Lys Cys Gly Cys Thr Arg Cys Val Ser
    1520                1525

<210> SEQ ID NO 3
<211> LENGTH: 4578
<212> TYPE: DNA
<213> ORGANISM: Homo sapiens

<400> SEQUENCE: 3
atgcgcggcg ttggctggca gatgctgtcc ctgtcgctgg ggttagtgct ggcgatcctg      60
aacaaggtgg caccgcaggc gtgcccggcg cagtgctctt gctcgggcag cacagtggac     120
tgtcacgggc tggcgctgcg cagcgtgccc aggaatatcc cccgcaacac cgagagactg     180
gatttaaatg gaaataacat cacaagaatt acgaagacag attttgctgg tcttagacat     240
ctaagagttc ttcagcttat ggagaataag attagcacca ttgaaagagg agcattccag     300
gatcttaaag aactagagag actgcgttta aacagaaatc accttcagct gtttcctgag     360
ttgctgtttc ttgggactgc gaagctatac aggcttgatc tcagtgaaaa ccaaattcag     420
```

```
gcaatcccaa ggaaagcttt ccgtggggca gttgacataa aaaatttgca actggattac    480
aaccagatca gctgtattga agatgggca ttcagggctc tccgggacct ggaagtgctc    540
actctcaaca ataacaacat tactagactt tctgtggcaa gtttcaacca tatgcctaaa    600
cttaggactt ttcgactgca ttcaaacaac ctgtattgtg actgccacct ggcctggctc    660
tccgactggc ttcgccaaag gcctcgggtt ggtctgtaca ctcagtgtat gggcccctcc    720
cacctgagag gccataatgt agccgaggtt caaaaacgag aatttgtctg cagtgatgag    780
gaagaaggtc accagtcatt tatggctcct tcttgtagtg ttttgcactg ccctgccgcc    840
tgtacctgta gcaacaatat cgtagactgt cgtgggaaag gtctcactga gatccccaca    900
aatcttccag agaccatcac agaaatacgt ttggaacaga acacaatcaa agtcatccct    960
cctggagctt tctcaccata taaaaagctt agacgaattg acctgagcaa taatcagatc   1020
tctgaacttg caccagatgc tttccaagga ctacgctctc tgaattcact tgtcctctat   1080
ggaaataaaa tcacagaact ccccaaaagt ttatttgaag gactgttttc cttacagctc   1140
ctattattga atgccaacaa gataaactgc cttcgggtag atgcttttca ggatctccac   1200
aacttgaacc ttctctccct atatgacaac aagcttcaga ccatcgccaa ggggaccttt   1260
tcacctcttc gggccattca aactatgcat ttggcccaga accccttat tgtgactgc   1320
catctcaagt ggctagcgga ttatctccat accaacccga ttgagaccag tggtgcccgt   1380
tgcaccagcc ccgccgcct ggcaaacaaa agaattggac agatcaaaag caagaaattc   1440
cgttgttcag gtacagaaga ttatcgatca aaattaagtg gagactgctt tgcggatctg   1500
gcttgccctg aaaagtgtcg ctgtgaagga accacagtag attgctctaa tcaaaagctc   1560
aacaaaatcc cggagcacat tccccagtac actgcagagt tgcgtctcaa taataatgaa   1620
tttaccgtgt tggaagccac aggaatcttt aagaaacttc ctcaattacg taaaataaac   1680
tttagcaaca ataagatcac agatattgag gagggagcat ttgaaggagc atctggtgta   1740
aatgaaatac ttcttacgag taatcgtttg gaaaatgtgc agcataagat gttcaaggga   1800
ttggaaagcc tcaaaacttt gatgttgaga agcaatcgaa taacctgtgt ggggaatgac   1860
agtttcatag gactcagttc tgtgcgtttg cttttctttgt atgataatca aattactaca   1920
gttgcaccag gggcatttga tactctccat tctttatcta ctctaaacct cttggccaat   1980
cctttttaact gtaactgcta cctggcttgg ttgggagagt ggctgagaaa gaagagaatt   2040
gtcacgggaa atcctagatg tcaaaaacca tacttcctga agaaatacc catccaggat   2100
gtggccattc aggacttcac ttgtgatgac ggaaatgatg acaatagttg ctccccactt   2160
tctcgctgtc ctactgaatg tacttgcttg gatacagtcg tccgatgtag caacaagggt   2220
ttgaaggtct tgccgaaagg tattccaaga gatgtcacag agttgtatct ggatggaaac   2280
caatttacac tggttcccaa ggaactctcc aactacaaac atttaacact tatagactta   2340
agtaacaaca gaataagcac gctttctaat cagagcttca gcaacatgac ccagctcctc   2400
accttaattc ttagttacaa ccgtctgaga tgtattcctc ctcgcacctt tgatggatta   2460
aagtctcttc gattactttc tctacatgga aatgacattt ctgttgtgcc tgaaggtgct   2520
ttcaatgatc tttctgcatt atcacatcta gcaattggag ccaaccctct ttactgtgat   2580
tgtaacatgc agtggttatc cgactgggtg aagtcggaat ataaggagcc tggaattgct   2640
cgttgtgctg gtcctggaga aatggcagat aaacttttac tcacaactcc ctccaaaaaa   2700
tttacctgtc aaggtcctgt ggatgtcaat attctagcta agtgtaaccc ctgcctatca   2760
```

-continued

| | |
|---|---|
| aatccgtgta aaaatgatgg cacatgtaat agtgatccag ttgactttta ccgatgcacc | 2820 |
| tgtccatatg gtttcaaggg gcaggactgt gatgtcccaa ttcatgcctg catcagtaac | 2880 |
| ccatgtaaac atggaggaac ttgccactta aggaaggag aagaagatgg attctggtgt | 2940 |
| atttgtgctg atggatttga aggagaaaat tgtgaagtca acgttgatga ttgtgaagat | 3000 |
| aatgactgtg aaaataattc tacatgtgtc gatggcatta ataactacac atgcctttgc | 3060 |
| ccacctgagt atacaggtga gttgtgtgag gagaagctgg acttctgtgc ccaggacctg | 3120 |
| aaccctgcc agcacgattc aaagtgcatc ctaactccaa agggattcaa atgtgactgc | 3180 |
| acaccagggt acgtaggtga acactgcgac atcgattttg acgactgcca agacaacaag | 3240 |
| tgtaaaaacg gagcccactg cacagatgca gtgaacggct atacgtgcat atgccccgaa | 3300 |
| ggttacagtg gcttgttctg tgagttttct ccacccatgg tcctccctcg taccagcccc | 3360 |
| tgtgataatt ttgattgtca gaatggagct cagtgtatcg tcagaataaa tgagccaata | 3420 |
| tgtcagtgtt tgcctggcta tcaggggagaa aagtgtgaaa aattggttag tgtgaatttt | 3480 |
| ataaacaaag agtcttatct tcagattcct tcagccaagg ttcggcctca gacgaacata | 3540 |
| acacttcaga ttgccacaga tgaagacagc ggaatcctcc tgtataaggg tgacaaagac | 3600 |
| catatcgcgg tagaactcta tcgggggcgt gttcgtgcca gctatgacac cggctctcat | 3660 |
| ccagcttctg ccatttacag tgtggagaca atcaatgatg gaaacttcca cattgtggaa | 3720 |
| ctacttgcct tggatcagag tctctctttg tccgtggatg gtgggaaccc caaaatcatc | 3780 |
| actaacttgt caaagcagtc cactctgaat tttgactctc cactctatgt aggaggcatg | 3840 |
| ccagggaaga gtaacgtggc atctctgcgc caggcccctg ggcagaacgg aaccagcttc | 3900 |
| cacggctgca tccggaacct ttacatcaac agtgagctgc aggacttcca gaaggtgccg | 3960 |
| atgcaaacag gcattttgcc tggctgtgag ccatgccaca agaaggtgtg tgcccatggc | 4020 |
| acatgccagc ccagcagcca ggcaggcttc acctgcgagt gccaggaagg atggatgggg | 4080 |
| cccctctgtg accaacggac caatgaccct tgccttggaa ataaatgcgt acatggcacc | 4140 |
| tgcttgccca tcaatgcgtt ctcctacagc tgtaagtgct gggagggcca tggaggtgtc | 4200 |
| ctctgtgatg aagaggagga tctgtttaac ccatgccagg cgatcaagtg caagcatggg | 4260 |
| aagtgcaggc tttcaggtct ggggcagccc tactgtgaat gcagcagtgg atacacgggg | 4320 |
| gacagctgtg atcgagaaat ctcttgtcga ggggaaagga taagagatta ttaccaaaag | 4380 |
| cagcagggct atgctgcttg ccaaacaacc aagaaggtgt cccgattaga gtgcagaggt | 4440 |
| gggtgtgcag gagggcagtg ctgtggaccg ctgaggagca agcggcggaa atactctttc | 4500 |
| gaatgcactg acggctcctc ctttgtggac gaggttgaga aagtggtgaa gtgcggctgt | 4560 |
| acgaggtgtg tgtcctaa | 4578 |

<210> SEQ ID NO 4
<211> LENGTH: 1525
<212> TYPE: PRT
<213> ORGANISM: Homo sapiens

<400> SEQUENCE: 4

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

-continued

```
Val Pro Arg Asn Ile Pro Arg Asn Thr Glu Arg Leu Asp Leu Asn Gly
 50                  55                  60

Asn Asn Ile Thr Arg Ile Thr Lys Thr Asp Phe Ala Gly Leu Arg His
 65                  70                  75                  80

Leu Arg Val Leu Gln Leu Met Glu Asn Lys Ile Ser Thr Ile Glu Arg
                 85                  90                  95

Gly Ala Phe Gln Asp Leu Lys Glu Leu Glu Arg Leu Arg Leu Asn Arg
                100                 105                 110

Asn His Leu Gln Leu Phe Pro Glu Leu Leu Phe Leu Gly Thr Ala Lys
             115                 120                 125

Leu Tyr Arg Leu Asp Leu Ser Glu Asn Gln Ile Gln Ala Ile Pro Arg
130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
                180                 185                 190

Ala Ser Phe Asn His Met Pro Lys Leu Arg Thr Phe Arg Leu His Ser
            195                 200                 205

Asn Asn Leu Tyr Cys Asp Cys His Leu Ala Trp Leu Ser Asp Trp Leu
210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Gly His Gln Ser Phe Met Ala Pro Ser Cys
                260                 265                 270

Ser Val Leu His Cys Pro Ala Ala Cys Thr Cys Ser Asn Asn Ile Val
            275                 280                 285

Asp Cys Arg Gly Lys Gly Leu Thr Glu Ile Pro Thr Asn Leu Pro Glu
290                 295                 300

Thr Ile Thr Glu Ile Arg Leu Glu Gln Asn Thr Ile Lys Val Ile Pro
305                 310                 315                 320

Pro Gly Ala Phe Ser Pro Tyr Lys Lys Leu Arg Arg Ile Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
355                 360                 365

Lys Ser Leu Phe Glu Gly Leu Phe Ser Leu Gln Leu Leu Leu Leu Asn
370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Ile Ala
                405                 410                 415

Lys Gly Thr Phe Ser Pro Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
450                 455                 460
```

```
Arg Arg Leu Ala Asn Lys Arg Ile Gly Gln Ile Lys Ser Lys Lys Phe
465                 470                 475                 480

Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Lys Leu Asn Lys Ile Pro Glu His Ile Pro
        515                 520                 525

Gln Tyr Thr Ala Glu Leu Arg Leu Asn Asn Asn Glu Phe Thr Val Leu
    530                 535                 540

Glu Ala Thr Gly Ile Phe Lys Lys Leu Pro Gln Leu Arg Lys Ile Asn
545                 550                 555                 560

Phe Ser Asn Asn Lys Ile Thr Asp Ile Glu Glu Gly Ala Phe Glu Gly
                565                 570                 575

Ala Ser Gly Val Asn Glu Ile Leu Leu Thr Ser Asn Arg Leu Glu Asn
            580                 585                 590

Val Gln His Lys Met Phe Lys Gly Leu Glu Ser Leu Lys Thr Leu Met
        595                 600                 605

Leu Arg Ser Asn Arg Ile Thr Cys Val Gly Asn Asp Ser Phe Ile Gly
610                 615                 620

Leu Ser Ser Val Arg Leu Leu Ser Leu Tyr Asp Asn Gln Ile Thr Thr
625                 630                 635                 640

Val Ala Pro Gly Ala Phe Asp Thr Leu His Ser Leu Ser Thr Leu Asn
                645                 650                 655

Leu Leu Ala Asn Pro Phe Asn Cys Asn Cys Tyr Leu Ala Trp Leu Gly
            660                 665                 670

Glu Trp Leu Arg Lys Lys Arg Ile Val Thr Gly Asn Pro Arg Cys Gln
        675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Thr Glu Cys Thr Cys Leu Asp Thr Val Val Arg Cys
                725                 730                 735

Ser Asn Lys Gly Leu Lys Val Leu Pro Lys Gly Ile Pro Arg Asp Val
            740                 745                 750

Thr Glu Leu Tyr Leu Asp Gly Asn Gln Phe Thr Leu Val Pro Lys Glu
        755                 760                 765

Leu Ser Asn Tyr Lys His Leu Thr Leu Ile Asp Leu Ser Asn Asn Arg
770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
            820                 825                 830

Ile Ser Val Val Pro Glu Gly Ala Phe Asn Asp Leu Ser Ala Leu Ser
        835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880
```

-continued

Arg Cys Ala Gly Pro Gly Glu Met Ala Asp Lys Leu Leu Leu Thr Thr
                885                 890                 895
Pro Ser Lys Lys Phe Thr Cys Gln Gly Pro Val Asp Val Asn Ile Leu
        900                 905                 910
Ala Lys Cys Asn Pro Cys Leu Ser Asn Pro Cys Lys Asn Asp Gly Thr
        915                 920                 925
Cys Asn Ser Asp Pro Val Asp Phe Tyr Arg Cys Thr Cys Pro Tyr Gly
    930                 935                 940
Phe Lys Gly Gln Asp Cys Asp Val Pro Ile His Ala Cys Ile Ser Asn
945                 950                 955                 960
Pro Cys Lys His Gly Gly Thr Cys His Leu Lys Glu Gly Glu Asp
        965                 970                 975
Gly Phe Trp Cys Ile Cys Ala Asp Gly Phe Glu Gly Glu Asn Cys Glu
            980                 985                 990
Val Asn Val Asp Asp Cys Glu Asp Asn Asp Cys Glu Asn Asn Ser Thr
            995                 1000                1005
Cys Val Asp Gly Ile Asn Asn Tyr Thr Cys Leu Cys Pro Pro Glu
    1010                1015                1020
Tyr Thr Gly Glu Leu Cys Glu Glu Lys Leu Asp Phe Cys Ala Gln
    1025                1030                1035
Asp Leu Asn Pro Cys Gln His Asp Ser Lys Cys Ile Leu Thr Pro
    1040                1045                1050
Lys Gly Phe Lys Cys Asp Cys Thr Pro Gly Tyr Val Gly Glu His
    1055                1060                1065
Cys Asp Ile Asp Phe Asp Cys Gln Asp Asn Lys Cys Lys Asn
    1070                1075                1080
Gly Ala His Cys Thr Asp Ala Val Asn Gly Tyr Thr Cys Ile Cys
    1085                1090                1095
Pro Glu Gly Tyr Ser Gly Leu Phe Cys Glu Phe Ser Pro Pro Met
    1100                1105                1110
Val Leu Pro Arg Thr Ser Pro Cys Asp Asn Phe Asp Cys Gln Asn
    1115                1120                1125
Gly Ala Gln Cys Ile Val Arg Ile Asn Glu Pro Ile Cys Gln Cys
    1130                1135                1140
Leu Pro Gly Tyr Gln Gly Glu Lys Cys Glu Lys Leu Val Ser Val
    1145                1150                1155
Asn Phe Ile Asn Lys Glu Ser Tyr Leu Gln Ile Pro Ser Ala Lys
    1160                1165                1170
Val Arg Pro Gln Thr Asn Ile Thr Leu Gln Ile Ala Thr Asp Glu
    1175                1180                1185
Asp Ser Gly Ile Leu Leu Tyr Lys Gly Asp Lys Asp His Ile Ala
    1190                1195                1200
Val Glu Leu Tyr Arg Gly Arg Val Arg Ala Ser Tyr Asp Thr Gly
    1205                1210                1215
Ser His Pro Ala Ser Ala Ile Tyr Ser Val Glu Thr Ile Asn Asp
    1220                1225                1230
Gly Asn Phe His Ile Val Glu Leu Leu Ala Leu Asp Gln Ser Leu
    1235                1240                1245
Ser Leu Ser Val Asp Gly Gly Asn Pro Lys Ile Ile Thr Asn Leu
    1250                1255                1260
Ser Lys Gln Ser Thr Leu Asn Phe Asp Ser Pro Leu Tyr Val Gly
    1265                1270                1275

```
Gly Met Pro Gly Lys Ser Asn Val Ala Ser Leu Arg Gln Ala Pro
    1280            1285                1290
Gly Gln Asn Gly Thr Ser Phe His Gly Cys Ile Arg Asn Leu Tyr
    1295            1300                1305
Ile Asn Ser Glu Leu Gln Asp Phe Gln Lys Val Pro Met Gln Thr
    1310            1315                1320
Gly Ile Leu Pro Gly Cys Glu Pro Cys His Lys Lys Val Cys Ala
    1325            1330                1335
His Gly Thr Cys Gln Pro Ser Ser Gln Ala Gly Phe Thr Cys Glu
    1340            1345                1350
Cys Gln Glu Gly Trp Met Gly Pro Leu Cys Asp Gln Arg Thr Asn
    1355            1360                1365
Asp Pro Cys Leu Gly Asn Lys Cys Val His Gly Thr Cys Leu Pro
    1370            1375                1380
Ile Asn Ala Phe Ser Tyr Ser Cys Lys Cys Leu Glu Gly His Gly
    1385            1390                1395
Gly Val Leu Cys Asp Glu Glu Asp Leu Phe Asn Pro Cys Gln
    1400            1405                1410
Ala Ile Lys Cys Lys His Gly Lys Cys Arg Leu Ser Gly Leu Gly
    1415            1420                1425
Gln Pro Tyr Cys Glu Cys Ser Ser Gly Tyr Thr Gly Asp Ser Cys
    1430            1435                1440
Asp Arg Glu Ile Ser Cys Arg Gly Glu Arg Ile Arg Asp Tyr Tyr
    1445            1450                1455
Gln Lys Gln Gln Gly Tyr Ala Ala Cys Gln Thr Thr Lys Lys Val
    1460            1465                1470
Ser Arg Leu Glu Cys Arg Gly Gly Cys Ala Gly Gly Gln Cys Cys
    1475            1480                1485
Gly Pro Leu Arg Ser Lys Arg Arg Lys Tyr Ser Phe Glu Cys Thr
    1490            1495                1500
Asp Gly Ser Ser Phe Val Asp Glu Val Glu Lys Val Val Lys Cys
    1505            1510                1515
Gly Cys Thr Arg Cys Val Ser
    1520            1525

<210> SEQ ID NO 5
<211> LENGTH: 4566
<212> TYPE: DNA
<213> ORGANISM: Homo sapiens

<400> SEQUENCE: 5
atgcgcggcg ttggctggca gatgctgtcc ctgtcgctgg ggttagtgct ggcgatcctg      60
aacaaggtgg caccgcaggc gtgcccggcg cagtgctctt gctcgggcag cacagtggac     120
tgtcacgggc tggcgctgcg cagcgtgccc aggaatatcc cccgcaacac cgagagactg     180
gatttaaatg gaataacat cacaagaatt acgaagacag attttgctgg tcttagacat     240
ctaagagttc ttcagcttat ggagaataag attagcacca ttgaaagagg agcattccag     300
gatcttaaag aactagagag actgcgttta aacagaaatc accttcagct gtttcctgag     360
ttgctgtttc ttgggactgc gaagctatac aggcttgatc tcagtgaaaa ccaaattcag     420
gcaatcccaa ggaaagcttt ccgtggggca gttgacataa aaatttgca actggattac     480 aaccagatca gctgtattga agatgggggca ttcaggggctc tccgggacct ggaagtgctc     540
actctcaaca ataacaacat tactagactt tctgtggcaa gtttcaacca tatgcctaaa     600
```

```
cttaggactt ttcgactgca ttcaaacaac ctgtattgtg actgccacct ggcctggctc      660
tccgactggc ttcgccaaag gcctcgggtt ggtctgtaca ctcagtgtat gggcccctcc      720
cacctgagag gccataatgt agccgaggtt caaaaacgag aatttgtctg cagtggtcac      780
cagtcattta tggctccttc ttgtagtgtt ttgcactgcc ctgccgcctg tacctgtagc      840
aacaatatcg tagactgtcg tgggaaaggt ctcactgaga tccccacaaa tcttccagag      900
accatcacag aaatacgttt ggaacagaac acaatcaaag tcatccctcc tggagctttc      960
tcaccatata aaaagcttag acgaattgac ctgagcaata atcagatctc tgaacttgca     1020
ccagatgctt tccaaggact acgctctctg aattcacttg tcctctatgg aaataaaatc     1080
acagaactcc ccaaaagttt atttgaagga ctgttttcct tacagctcct attattgaat     1140
gccaacaaga taaactgcct tcgggtagat gcttttcagg atctccacaa cttgaacctt     1200
ctctccctat atgacaacaa gcttcagacc atcgccaagg ggaccttttc acctcttcgg     1260
gccattcaaa ctatgcattt ggcccagaac cctttatttt gtgactgcca tctcaagtgg     1320
ctagcggatt atctccatac caacccgatt gagaccagtg gtgcccgttg caccagcccc     1380
cgccgcctgg caaacaaaag aattggacag atcaaaagca agaaattccg ttgttcaggt     1440
acagaagatt atcgatcaaa attaagtgga gactgctttg cggatctggc ttgccctgaa     1500
aagtgtcgct gtgaaggaac cacagtagat tgctctaatc aaaagctcaa caaaatcccg     1560
gagcacattc cccagtacac tgcagagttg cgtctcaata ataatgaatt taccgtgttg     1620
gaagccacag gaatctttaa gaaacttcct caattacgta aaataaactt tagcaacaat     1680
aagatcacag atattgagga gggagcattt gaaggagcat ctggtgtaaa tgaaatactt     1740
cttacgagta atcgtttgga aaatgtgcag cataagatgt tcaagggatt ggaaagcctc     1800
aaaactttga tgttgagaag caatcgaata acctgtgtgg ggaatgacag tttcatagga     1860
ctcagttctg tgcgtttgct ttctttgtat gataatcaaa ttactacagt tgcaccaggg     1920
gcatttgata ctctccattc tttatctact ctaaacctct ggccaatcc ttttaactgt      1980 aactgctacc tggcttggtt gggagagtgg ctgagaaaga agagaattgt cacgggaaat     2040
cctagatgtc aaaaaccata cttcctgaaa gaaataccca tccaggatgt ggccattcag     2100
gacttcactt gtgatgacgg aaatgatgac aatagttgct ccccactttc tcgctgtcct     2160
actgaatgta cttgcttgga tacagtcgtc cgatgtagca acaagggttt gaaggtcttg     2220
ccgaaaggta ttccaagaga tgtcacagag ttgtatctgg atggaaacca atttacactg     2280
gttcccaagg aactctccaa ctacaaacat ttaacactta tagacttaag taacaacaga     2340
ataagcacgc tttctaatca gagcttcagc aacatgaccc agctcctcac cttaattctt     2400
agttacaacc gtctgagatg tattcctcct cgcacctttg atggattaaa gtctcttcga     2460
ttactttctc tacatggaaa tgacatttct gttgtgcctg aaggtgcttt caatgatctt     2520
tctgcattat cacatctagc aattggagcc aaccctcttt actgtgattg taacatgcag     2580
tggttatccg actgggtgaa gtcggaatat aaggagcctg gaattgctcg ttgtgctggt     2640
cctggagaaa tggcagataa acttttactc acaactccct ccaaaaaatt tacctgtcaa     2700
ggtcctgtgg atgtcaatat tctagctaag tgtaacccct gcctatcaaa tccgtgtaaa     2760
aatgatggca catgtaatag tgatccagtt gactttttacc gatgcacctg tccatatggt     2820
ttcaaggggc aggactgtga tgtcccaatt catgcctgca tcagtaaccc atgtaaacat     2880
ggaggaactt gccactaaa ggaaggagaa gaagatggat tctggtgtat ttgtgctgat     2940
```

-continued

```
ggatttgaag gagaaaattg tgaagtcaac gttgatgatt gtgaagataa tgactgtgaa      3000
aataattcta catgtgtcga tggcattaat aactacacat gcctttgccc acctgagtat      3060
acaggtgagt tgtgtgagga gaagctggac ttctgtgccc aggacctgaa cccctgccag      3120
cacgattcaa agtgcatcct aactccaaag ggattcaaat gtgactgcac accagggtac      3180
gtaggtgaac actgcgacat cgattttgac gactgccaag acaacaagtg taaaaacgga      3240
gcccactgca cagatgcagt gaacggctat acgtgcatat gccccgaagg ttacagtggc      3300
ttgttctgtg agttttctcc acccatggtc ctccctcgta ccagcccctg tgataatttt      3360
gattgtcaga atggagctca gtgtatcgtc agaataaatg agccaatatg tcagtgtttg      3420
cctggctatc agggagaaaa gtgtgaaaaa ttggttagtg tgaattttat aaacaaagag      3480
tcttatcttc agattccttc agccaaggtt cggcctcaga cgaacataac acttcagatt      3540
gccacagatg aagacagcgg aatcctcctg tataagggtg acaaagacca tatcgcggta      3600
gaactctatc gggggcgtgt tcgtgccagc tatgacaccg gctctcatcc agcttctgcc      3660
atttacagtg tggagacaat caatgatgga aacttccaca ttgtggaact acttgccttg      3720
gatcagagtc tctctttgtc cgtggatggt gggaacccca aaatcatcac taacttgtca      3780
aagcagtcca ctctgaattt tgactctcca ctctatgtag gaggcatgcc agggaagagt      3840
aacgtggcat ctctgcgcca ggcccctggg cagaacggaa ccagcttcca cggctgcatc      3900
cggaaccttt acatcaacag tgagctgcag gacttccaga aggtgccgat gcaaacaggc      3960
attttgcctg gctgtgagcc atgccacaag aaggtgtgtg cccatggcac atgccagccc      4020
agcagccagg caggcttcac ctgcgagtgc caggaaggat ggatggggcc cctctgtgac      4080
caacggacca atgacccttg ccttggaaat aaatgcgtac atggcacctg cttgcccatc      4140
aatgcgttct cctacagctg taagtgcttg gagggcatg gaggtgtcct ctgtgatgaa      4200
gaggaggatc tgtttaaccc atgccaggcg atcaagtgca gcatgggaa gtgcaggctt      4260 tcaggtctgg ggcagcccta ctgtgaatgc agcagtggaa cacgggggga cagctgtgat      4320
cgagaaatct cttgtcgagg ggaaaggata agagattatt accaaaagca gcagggctat      4380
gctgcttgcc aaacaaccaa gaaggtgtcc cgattagagt gcagaggtgg gtgtgcagga      4440
gggcagtgct gtggaccgct gaggagcaag cggcggaaat actctttcga atgcactgac      4500
ggctcctcct tgtggacga ggttgagaaa gtggtgaagt gcggctgtac gaggtgtgtg      4560
tcctaa                                                                 4566
```

<210> SEQ ID NO 6
<211> LENGTH: 1521
<212> TYPE: PRT
<213> ORGANISM: Homo sapiens

<400> SEQUENCE: 6

```
Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80
```

-continued

```
Leu Arg Val Leu Gln Leu Met Glu Asn Lys Ile Ser Thr Ile Glu Arg
             85                  90                  95
Gly Ala Phe Gln Asp Leu Lys Glu Leu Glu Arg Leu Arg Leu Asn Arg
            100                 105                 110
Asn His Leu Gln Leu Phe Pro Glu Leu Leu Phe Leu Gly Thr Ala Lys
            115                 120                 125
Leu Tyr Arg Leu Asp Leu Ser Glu Asn Gln Ile Gln Ala Ile Pro Arg
            130                 135                 140
Lys Ala Phe Arg Gly Ala Val Asp Ile Lys Asn Leu Gln Leu Asp Tyr
145                 150                 155                 160
Asn Gln Ile Ser Cys Ile Glu Asp Gly Ala Phe Arg Ala Leu Arg Asp
                165                 170                 175
Leu Glu Val Leu Thr Leu Asn Asn Asn Ile Thr Arg Leu Ser Val
                180                 185                 190
Ala Ser Phe Asn His Met Pro Lys Leu Arg Thr Phe Arg Leu His Ser
                195                 200                 205
Asn Asn Leu Tyr Cys Asp Cys His Leu Ala Trp Leu Ser Asp Trp Leu
            210                 215                 220
Arg Gln Arg Pro Arg Val Gly Leu Tyr Thr Gln Cys Met Gly Pro Ser
225                 230                 235                 240
His Leu Arg Gly His Asn Val Ala Glu Val Gln Lys Arg Glu Phe Val
                245                 250                 255
Cys Ser Gly His Gln Ser Phe Met Ala Pro Ser Cys Ser Val Leu His
                260                 265                 270
Cys Pro Ala Ala Cys Thr Cys Ser Asn Asn Ile Val Asp Cys Arg Gly
            275                 280                 285
Lys Gly Leu Thr Glu Ile Pro Thr Asn Leu Pro Glu Thr Ile Thr Glu
            290                 295                 300
Ile Arg Leu Glu Gln Asn Thr Ile Lys Val Ile Pro Pro Gly Ala Phe
305                 310                 315                 320
Ser Pro Tyr Lys Lys Leu Arg Arg Ile Asp Leu Ser Asn Asn Gln Ile
                325                 330                 335
Ser Glu Leu Ala Pro Asp Ala Phe Gln Gly Leu Arg Ser Leu Asn Ser
                340                 345                 350
Leu Val Leu Tyr Gly Asn Lys Ile Thr Glu Leu Pro Lys Ser Leu Phe
            355                 360                 365
Glu Gly Leu Phe Ser Leu Gln Leu Leu Leu Leu Asn Ala Asn Lys Ile
            370                 375                 380
Asn Cys Leu Arg Val Asp Ala Phe Gln Asp Leu His Asn Leu Asn Leu
385                 390                 395                 400
Leu Ser Leu Tyr Asp Asn Lys Leu Gln Thr Ile Ala Lys Gly Thr Phe
                405                 410                 415
Ser Pro Leu Arg Ala Ile Gln Thr Met His Leu Ala Gln Asn Pro Phe
                420                 425                 430
Ile Cys Asp Cys His Leu Lys Trp Leu Ala Asp Tyr Leu His Thr Asn
            435                 440                 445
Pro Ile Glu Thr Ser Gly Ala Arg Cys Thr Ser Pro Arg Arg Leu Ala
            450                 455                 460
Asn Lys Arg Ile Gly Gln Ile Lys Ser Lys Phe Arg Cys Ser Gly
465                 470                 475                 480
Thr Glu Asp Tyr Arg Ser Lys Leu Ser Gly Asp Cys Phe Ala Asp Leu
                485                 490                 495
```

```
Ala Cys Pro Glu Lys Cys Arg Cys Glu Gly Thr Thr Val Asp Cys Ser
            500                 505                 510

Asn Gln Lys Leu Asn Lys Ile Pro Glu His Ile Pro Gln Tyr Thr Ala
            515                 520                 525

Glu Leu Arg Leu Asn Asn Asn Glu Phe Thr Val Leu Glu Ala Thr Gly
            530                 535                 540

Ile Phe Lys Lys Leu Pro Gln Leu Arg Lys Ile Asn Phe Ser Asn Asn
545                 550                 555                 560

Lys Ile Thr Asp Ile Glu Gly Ala Phe Glu Gly Ala Ser Gly Val
                565                 570                 575

Asn Glu Ile Leu Leu Thr Ser Asn Arg Leu Glu Asn Val Gln His Lys
            580                 585                 590

Met Phe Lys Gly Leu Glu Ser Leu Lys Thr Leu Met Leu Arg Ser Asn
            595                 600                 605

Arg Ile Thr Cys Val Gly Asn Asp Ser Phe Ile Gly Leu Ser Ser Val
            610                 615                 620

Arg Leu Leu Ser Leu Tyr Asp Asn Gln Ile Thr Thr Val Ala Pro Gly
625                 630                 635                 640

Ala Phe Asp Thr Leu His Ser Leu Ser Thr Leu Asn Leu Leu Ala Asn
            645                 650                 655

Pro Phe Asn Cys Asn Cys Tyr Leu Ala Trp Leu Gly Glu Trp Leu Arg
            660                 665                 670

Lys Lys Arg Ile Val Thr Gly Asn Pro Arg Cys Gln Lys Pro Tyr Phe
            675                 680                 685

Leu Lys Glu Ile Pro Ile Gln Asp Val Ala Ile Gln Asp Phe Thr Cys
            690                 695                 700

Asp Asp Gly Asn Asp Asp Asn Ser Cys Ser Pro Leu Ser Arg Cys Pro
705                 710                 715                 720

Thr Glu Cys Thr Cys Leu Asp Thr Val Arg Cys Ser Asn Lys Gly
                725                 730                 735

Leu Lys Val Leu Pro Lys Gly Ile Pro Arg Asp Val Thr Glu Leu Tyr
            740                 745                 750

Leu Asp Gly Asn Gln Phe Thr Leu Val Pro Lys Glu Leu Ser Asn Tyr
            755                 760                 765

Lys His Leu Thr Leu Ile Asp Leu Ser Asn Asn Arg Ile Ser Thr Leu
            770                 775                 780

Ser Asn Gln Ser Phe Ser Asn Met Thr Gln Leu Leu Thr Leu Ile Leu
785                 790                 795                 800

Ser Tyr Asn Arg Leu Arg Cys Ile Pro Pro Arg Thr Phe Asp Gly Leu
                805                 810                 815

Lys Ser Leu Arg Leu Leu Ser Leu His Gly Asn Asp Ile Ser Val Val
            820                 825                 830

Pro Glu Gly Ala Phe Asn Asp Leu Ser Ala Leu Ser His Leu Ala Ile
            835                 840                 845

Gly Ala Asn Pro Leu Tyr Cys Asp Cys Asn Met Gln Trp Leu Ser Asp
            850                 855                 860

Trp Val Lys Ser Glu Tyr Lys Glu Pro Gly Ile Ala Arg Cys Ala Gly
865                 870                 875                 880

Pro Gly Glu Met Ala Asp Lys Leu Leu Leu Thr Thr Pro Ser Lys Lys
                885                 890                 895

Phe Thr Cys Gln Gly Pro Val Asp Val Asn Ile Leu Ala Lys Cys Asn
            900                 905                 910
```

```
Pro Cys Leu Ser Asn Pro Cys Lys Asn Asp Gly Thr Cys Asn Ser Asp
            915                 920                 925

Pro Val Asp Phe Tyr Arg Cys Thr Cys Pro Tyr Gly Phe Lys Gly Gln
    930                 935                 940

Asp Cys Asp Val Pro Ile His Ala Cys Ile Ser Asn Pro Cys Lys His
945                 950                 955                 960

Gly Gly Thr Cys His Leu Lys Glu Gly Glu Glu Asp Gly Phe Trp Cys
                965                 970                 975

Ile Cys Ala Asp Gly Phe Glu Gly Glu Asn Cys Glu Val Asn Val Asp
            980                 985                 990

Asp Cys Glu Asp Asn Asp Cys Glu  Asn Asn Ser Thr Cys  Val Asp Gly
            995                1000               1005

Ile Asn  Asn Tyr Thr Cys Leu  Cys Pro Pro Glu Tyr  Thr Gly Glu
    1010              1015              1020

Leu Cys Glu Glu Lys Leu Asp  Phe Cys Ala Gln Asp  Leu Asn Pro
        1025             1030               1035

Cys Gln His Asp Ser Lys Cys  Ile Leu Thr Pro Lys  Gly Phe Lys
        1040             1045               1050

Cys Asp Cys Thr Pro Gly Tyr  Val Gly Glu His Cys  Asp Ile Asp
        1055             1060               1065

Phe Asp  Asp Cys Gln Asp Asn  Lys Cys Lys Asn Gly  Ala His Cys
        1070             1075              1080

Thr Asp  Ala Val Asn Gly Tyr  Thr Cys Ile Cys Pro  Glu Gly Tyr
        1085             1090              1095

Ser Gly Leu Phe Cys Glu Phe  Ser Pro Pro Met Val  Leu Pro Arg
        1100             1105              1110

Thr Ser  Pro Cys Asp Asn Phe  Asp Cys Gln Asn Gly  Ala Gln Cys
        1115             1120              1125

Ile Val  Arg Ile Asn Glu Pro  Ile Cys Gln Cys Leu  Pro Gly Tyr
        1130             1135              1140

Gln Gly  Glu Lys Cys Glu Lys  Leu Val Ser Val Asn  Phe Ile Asn
        1145             1150              1155

Lys Glu  Ser Tyr Leu Gln Ile  Pro Ser Ala Lys Val  Arg Pro Gln
        1160             1165              1170

Thr Asn  Ile Thr Leu Gln Ile  Ala Thr Asp Glu Asp  Ser Gly Ile
        1175             1180              1185

Leu Leu  Tyr Lys Gly Asp Lys  Asp His Ile Ala Val  Glu Leu Tyr
        1190             1195              1200

Arg Gly  Arg Val Arg Ala Ser  Tyr Asp Thr Gly Ser  His Pro Ala
        1205             1210              1215

Ser Ala  Ile Tyr Ser Val Glu  Thr Ile Asn Asp Gly  Asn Phe His
        1220             1225              1230

Ile Val  Glu Leu Leu Ala Leu  Asp Gln Ser Leu Ser  Leu Ser Val
        1235             1240              1245

Asp Gly  Gly Asn Pro Lys Ile  Ile Thr Asn Leu Ser  Lys Gln Ser
        1250             1255              1260

Thr Leu  Asn Phe Asp Ser Pro  Leu Tyr Val Gly Gly  Met Pro Gly
        1265             1270              1275

Lys Ser  Asn Val Ala Ser Leu  Arg Gln Ala Pro Gly  Gln Asn Gly
        1280             1285              1290

Thr Ser  Phe His Gly Cys Ile  Arg Asn Leu Tyr Ile  Asn Ser Glu
        1295             1300              1305
```

```
Leu Gln Asp Phe Gln Lys Val Pro Met Gln Thr Gly Ile Leu Pro
    1310            1315                1320
Gly Cys Glu Pro Cys His Lys Lys Val Cys Ala His Gly Thr Cys
    1325            1330                1335
Gln Pro Ser Ser Gln Ala Gly Phe Thr Cys Glu Cys Gln Glu Gly
    1340            1345                1350
Trp Met Gly Pro Leu Cys Asp Gln Arg Thr Asn Asp Pro Cys Leu
    1355            1360                1365
Gly Asn Lys Cys Val His Gly Thr Cys Leu Pro Ile Asn Ala Phe
    1370            1375                1380
Ser Tyr Ser Cys Lys Cys Leu Glu Gly His Gly Gly Val Leu Cys
    1385            1390                1395
Asp Glu Glu Glu Asp Leu Phe Asn Pro Cys Gln Ala Ile Lys Cys
    1400            1405                1410
Lys His Gly Lys Cys Arg Leu Ser Gly Leu Gly Gln Pro Tyr Cys
    1415            1420                1425
Glu Cys Ser Ser Gly Tyr Thr Gly Asp Ser Cys Asp Arg Glu Ile
    1430            1435                1440
Ser Cys Arg Gly Glu Arg Ile Arg Asp Tyr Tyr Gln Lys Gln Gln
    1445            1450                1455
Gly Tyr Ala Ala Cys Gln Thr Thr Lys Lys Val Ser Arg Leu Glu
    1460            1465                1470
Cys Arg Gly Gly Cys Ala Gly Gly Gln Cys Cys Gly Pro Leu Arg
    1475            1480                1485
Ser Lys Arg Arg Lys Tyr Ser Phe Glu Cys Thr Asp Gly Ser Ser
    1490            1495                1500
Phe Val Asp Glu Val Glu Lys Val Val Lys Cys Gly Cys Thr Arg
    1505            1510                1515
Cys Val Ser
    1520

<210> SEQ ID NO 7
<211> LENGTH: 4629
<212> TYPE: DNA
<213> ORGANISM: Mus musculus

<400> SEQUENCE: 7
atgagtggca ttggctggca gacactgtcc ctatcgctgg ggttagtgtt gtcgatcttg     60
aacaaggtgg cgccgcaggc gtgcccggcc cagtgctcct gttcaggcag cacggtggac    120
tgtcatgggc tggcactgcg cagtgtgccc aggaatatcc cccgcaacac cgagagactg    180
gatttgaatg gaataacat cacgaggatc acgaagatag attttgctgg tctcaggcac    240
ctcagagttc ttcagctcat ggagaacaga atcagcacca tcgagagggg agcattccag    300
gatcttaagg agctggaaag actgcgttta acagaaata accttcagtt gtttcctgag    360
ctgctgtttc tcgggactgc gaagctctac cggcttgatc tcagtgaaaa tcaaattcaa    420
gcaattccaa ggaaggcttt ccgtggggca gttgacatta aaaacctgca actggattac    480
aaccagatca gctgcattga agatggggcg ttcagagctc tacgagatct ggaagtgctc    540
actctgaaca ataacaatat tactagactt tcagtggcaa gtttcaacca tatgcctaaa    600
cttaggacat ttcgactcca ctcgaacaac ttgtactgcg actgccacct agcctggctc    660
tcagactggc ttcgccaaag gccacgggtg ggcttgtaca ctcagtgtat gggcccatcc    720
cacctgaggg gccacaatgt agcagaggtt caaaaacgag agtttgtctg cagtgatgag    780
```

-continued

```
gaagaaggtc accagtcatt catggctccc tcctgcagtg tgctgcactg ccccgctgct    840
tgtacctgta gcaacaacat tgtagactgc cgagggaaag gtctcactga gatccccaca    900
aatctgcctg agaccatcac agaaatacgt ttggaacaga actccatcag ggtcatccct    960
ccaggagcct tctcaccata caaaaagctt agacgactag acctgagcaa caaccagatc   1020
tctgaacttg caccagatgc cttccaagga ctgcgctctc tgaattcact tgtcctgtat   1080
ggaaataaaa tcacagaact cccaaaaagt ttattcgaag gactattttc cttgcagcta   1140
ctattattga atgccaacaa gataaactgc cttcgggtag atgcttttca ggacctgcac   1200
aacttgaacc ttctctcctt atatgacaat aagcttcaga cggttgccaa gggcaccttc   1260
tcagccctca gagccatcca aactatgcat ttgcccagaa tccttttcat tgtgactgc    1320
catctcaagt ggctagcgga ttatctccac accaacccaa ttgagaccag cggtgcccgt   1380
tgcaccagcc cccgccgcct ggcaaacaaa agaattggac agatcaaaag caagaaattc   1440
cgttgttcag ctaaagaaca gtatttcatt ccaggtacag aagattatcg atcaaaatta   1500
agtggagact gctttgcaga cttggcttgt cctgagaagt gtcgctgtga agggaccaca   1560
gtagactgct ccaatcaaag actcaacaaa atccctgacc atattcccca gtacacagca   1620
gagctgcgtc tcaataataa tgaattcaca gtgttagaag ccacgggaat atttaagaaa   1680
cttcctcagt tacgtaaaat caactttagc aacaataaga tcacggatat cgaggagggt   1740
gcatttgaag gcgcgtctgg tgtgaatgaa attcttctca ccagtaaccg tttggaaaat   1800
gttcagcata agatgttcaa aggactggag agcctcaaaa cattgatgct gagaagtaat   1860
cgaataagct gtgttgggaa cgacagtttc ataggactcg gctctgtgcg tctgctctct   1920
ttatatgaca atcaaattac cacagtggca ccaggagcat ttgattctct ccattcatta   1980
tccactctaa acctcttggc caatcctttc aactgtaact gtcacctggc atggctggga   2040
gaatggctca gaaggaaaag aattgtaaca ggaaatcctc gatgccaaaa accctacttc   2100
ctgaaggaaa tcccaatcca ggatgtagcc attcaggact tcacctgtga tgatggaaat   2160
gatgacaata gttgctctcc actctcccgt tgtccttctg aatgtacctg cttggataca   2220
gtggtacgat gtagcaacaa gggcttgaag gttttgccta aggtattcc aaaagatgtc    2280
acagagctgt atctggatgg gaaccagttt acgctggtcc cgaaggaact ctctaactac   2340
aaacatttaa cacttataga cttaagtaac aaccgaataa gcacccttc caatcaaagc    2400
ttcagcaaca tgacccagct tctcacctta atcctcagtt acaaccgtct gagatgtatc   2460
cctccacgaa cctttgatgg attgaagtct cttcggttac tgtctttaca tggaaatgac   2520
atttctgttg tgcctgaagg tgccttcaat gacttgtcag ccttgtcaca cttagcgatt   2580
ggagccaacc ctctttactg tgattgtaac atgcagtggg tatccgactg ggtgaagtcg   2640
gaatataagg aacctggaat tgcacgctgt gccggccctg agaaatggc agataaatta    2700
ttactcacta ctccctccaa aaaatttaca tgtcaaggtc ccgtggatat cactattcaa   2760
gccaagtgta atccctgctt atcaaatcca tgtaaaaatg atggcacctg taacaatgac   2820
cccgttgatt tttatcgatg tacctgccca tatggattca agggtcagga ctgtgatgtc   2880
cccattcatg cttgtatcag taatccatgt aaacatggag aacttgtca cttaaaggaa    2940
ggagagaatg ctggattctg gtgcacttgt gctgatgggt ttgaaggaga aaactgtgaa   3000
gtcaatattg atgattgtga agataatgat tgtgaaaata ttctacatg cgttgatgga    3060
attaacaact acacatgtct ttgcccaccg gaatacacag ctgctaatct gaatgaggtg   3120
```

```
gaaaaaggtg aactgtgtga ggaaaagctg gacttctgtg cacaagactt gaatccctgc    3180
cagcatgact ccaagtgcat cctgactcca aagggattca agtgtgactg cactccagga    3240
tacattggtg agcactgtga cattgacttt gatgactgcc aagataacaa gtgtaaaaac    3300
ggtgctcact gcacagatgc cgtgaacgga tacacgtgcg tctgtcctga aggctacagt    3360
ggcttgttct gtgagttttc tccacccatg gtcctccctc gcaccagccc ctgtgataat    3420
tttgattgcc agaatggagc ccagtgtatc atcaggataa atgaaccaat atgccagtgt    3480
ttgcctggct acctgggaga aagtgtgag aaattggtca gtgtgaattt tgtaaacaaa    3540
gagtcctatc ttcagattcc ttcagccaag gttcggcctc agacaaacat cacacttcag    3600
attgccacag atgaagacag cggcatcctc ttgtataaag gtgacaaaga ccacattgcc    3660
gtggaactct atagagggcg agttcgagcc agctatgaca ccggctctca tccggcttct    3720
gccatttaca gtgtggagac aatcaatgat ggaaacttcc acattgtgga gctactgacc    3780
ctggattcca gtctttccct ctctgtggat ggaggaagcc ctaaagtcat caccaatttg    3840
tcaaaacaat ctactctgaa tttcgactct ccactctatg taggaggcat gcctgggaaa    3900
aataacgtgg catccctgcg ccaggcccct gggcaaaatg gcaccagctt ccatggctgt    3960
atccggaacc tttacattaa cagtgagctg caggacttcc ggaaaatgcc tatgcaaacc    4020
ggaattctgc ctggctgtga accatgccac aagaaagtat gtgcccatgg catgtgccag    4080
cccagcagcc aatcaggctt cacctgtgaa tgtgaggaag ggtggatggg cccctctgt    4140
gaccagagaa ccaatgatcc ctgcctcgga aacaaatgtg tgcatgggac ctgcctgccc    4200
atcaatgcct tctcctatag ttgcaagtgc ctggagggcc atggcggtgt cctctgtgat    4260
gaagaagaag atctctttaa cccctgccag atgatcaagt gcaagcatgg gaagtgcagg    4320
ctttctggag tgggccagcc ctattgtgaa tgcaacagtg gattcaccgg ggacagctgt    4380
gatagagaaa tttcttgtcg aggggaacgg ataagggact attaccagaa gcagcaggt    4440
tacgctgcct gtcaaacaac taagaaagta tctcgcttgg aatgcagagg cgggtgcgct    4500
ggaggccagt gctgtggacc tctgagaagc aagaggcgga atactctttt cgaatgcaca    4560
gatggctcct catttgtgga cgaggttgag aaagtggtga agtgcggctg cgcgagatgt    4620
gcctcctaa                                                          4629
```

<210> SEQ ID NO 8
<211> LENGTH: 1542
<212> TYPE: PRT
<213> ORGANISM: Mus musculus

<400> SEQUENCE: 8

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95
```

```
Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
            115                 120                 125

Leu Tyr Arg Leu Asp Leu Ser Glu Asn Gln Ile Gln Ala Ile Pro Arg
        130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
        210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
290                 295                 300

Thr Ile Thr Glu Ile Arg Leu Glu Gln Asn Ser Ile Arg Val Ile Pro
305                 310                 315                 320

Pro Gly Ala Phe Ser Pro Tyr Lys Lys Leu Arg Arg Leu Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Val Ala
                405                 410                 415

Lys Gly Thr Phe Ser Ala Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
        450                 455                 460

Arg Arg Leu Ala Asn Lys Arg Ile Gly Gln Ile Lys Ser Lys Lys Phe
465                 470                 475                 480

Arg Cys Ser Ala Lys Glu Gln Tyr Phe Ile Pro Gly Thr Glu Asp Tyr
                485                 490                 495

Arg Ser Lys Leu Ser Gly Asp Cys Phe Ala Asp Leu Ala Cys Pro Glu
            500                 505                 510
```

```
Lys Cys Arg Cys Glu Gly Thr Thr Val Asp Cys Ser Asn Gln Arg Leu
            515                 520                 525

Asn Lys Ile Pro Asp His Ile Pro Gln Tyr Thr Ala Glu Leu Arg Leu
        530                 535                 540

Asn Asn Asn Glu Phe Thr Val Leu Glu Ala Thr Gly Ile Phe Lys Lys
545                 550                 555                 560

Leu Pro Gln Leu Arg Lys Ile Asn Phe Ser Asn Asn Lys Ile Thr Asp
                565                 570                 575

Ile Glu Glu Gly Ala Phe Glu Gly Ser Gly Val Asn Glu Ile Leu
            580                 585                 590

Leu Thr Ser Asn Arg Leu Glu Asn Val Gln His Lys Met Phe Lys Gly
        595                 600                 605

Leu Glu Ser Leu Lys Thr Leu Met Leu Arg Ser Asn Arg Ile Ser Cys
        610                 615                 620

Val Gly Asn Asp Ser Phe Ile Gly Leu Gly Ser Val Arg Leu Leu Ser
625                 630                 635                 640

Leu Tyr Asp Asn Gln Ile Thr Thr Val Ala Pro Gly Ala Phe Asp Ser
                645                 650                 655

Leu His Ser Leu Ser Thr Leu Asn Leu Leu Ala Asn Pro Phe Asn Cys
            660                 665                 670

Asn Cys His Leu Ala Trp Leu Gly Glu Trp Leu Arg Arg Lys Arg Ile
        675                 680                 685

Val Thr Gly Asn Pro Arg Cys Gln Lys Pro Tyr Phe Leu Lys Glu Ile
        690                 695                 700

Pro Ile Gln Asp Val Ala Ile Gln Asp Phe Thr Cys Asp Asp Gly Asn
705                 710                 715                 720

Asp Asp Asn Ser Cys Ser Pro Leu Ser Arg Cys Pro Ser Glu Cys Thr
                725                 730                 735

Cys Leu Asp Thr Val Val Arg Cys Ser Asn Lys Gly Leu Lys Val Leu
            740                 745                 750

Pro Lys Gly Ile Pro Lys Asp Val Thr Glu Leu Tyr Leu Asp Gly Asn
        755                 760                 765

Gln Phe Thr Leu Val Pro Lys Glu Leu Ser Asn Tyr Lys His Leu Thr
        770                 775                 780

Leu Ile Asp Leu Ser Asn Asn Arg Ile Ser Thr Leu Ser Asn Gln Ser
785                 790                 795                 800

Phe Ser Asn Met Thr Gln Leu Leu Thr Leu Ile Leu Ser Tyr Asn Arg
                805                 810                 815

Leu Arg Cys Ile Pro Pro Arg Thr Phe Asp Gly Leu Lys Ser Leu Arg
            820                 825                 830

Leu Leu Ser Leu His Gly Asn Asp Ile Ser Val Val Pro Glu Gly Ala
        835                 840                 845

Phe Asn Asp Leu Ser Ala Leu Ser His Leu Ala Ile Gly Ala Asn Pro
850                 855                 860

Leu Tyr Cys Asp Cys Asn Met Gln Trp Leu Ser Asp Trp Val Lys Ser
865                 870                 875                 880

Glu Tyr Lys Glu Pro Gly Ile Ala Arg Cys Ala Gly Pro Gly Glu Met
                885                 890                 895

Ala Asp Lys Leu Leu Leu Thr Thr Pro Ser Lys Lys Phe Thr Cys Gln
            900                 905                 910

Gly Pro Val Asp Ile Thr Ile Gln Ala Lys Cys Asn Pro Cys Leu Ser
        915                 920                 925
```

-continued

```
Asn Pro Cys Lys Asn Asp Gly Thr Cys Asn Asn Asp Pro Val Asp Phe
    930                 935                 940
Tyr Arg Cys Thr Cys Pro Tyr Gly Phe Lys Gly Gln Asp Cys Asp Val
945                 950                 955                 960
Pro Ile His Ala Cys Ile Ser Asn Pro Cys Lys His Gly Gly Thr Cys
                965                 970                 975
His Leu Lys Glu Gly Glu Asn Ala Gly Phe Trp Cys Thr Cys Ala Asp
            980                 985                 990
Gly Phe Glu Gly Glu Asn Cys Glu Val Asn Ile Asp Asp Cys Glu Asp
        995                 1000                1005
Asn Asp Cys Glu Asn Asn Ser Thr Cys Val Asp Gly Ile Asn Asn
    1010                1015                1020
Tyr Thr Cys Leu Cys Pro Pro Glu Tyr Thr Ala Ala Asn Leu Asn
    1025                1030                1035
Glu Val Glu Lys Gly Glu Leu Cys Glu Glu Lys Leu Asp Phe Cys
    1040                1045                1050
Ala Gln Asp Leu Asn Pro Cys Gln His Asp Ser Lys Cys Ile Leu
    1055                1060                1065
Thr Pro Lys Gly Phe Lys Cys Asp Cys Thr Pro Gly Tyr Ile Gly
    1070                1075                1080
Glu His Cys Asp Ile Asp Phe Asp Asp Cys Gln Asp Asn Lys Cys
    1085                1090                1095
Lys Asn Gly Ala His Cys Thr Asp Ala Val Asn Gly Tyr Thr Cys
    1100                1105                1110
Val Cys Pro Glu Gly Tyr Ser Gly Leu Phe Cys Glu Phe Ser Pro
    1115                1120                1125
Pro Met Val Leu Pro Arg Thr Ser Pro Cys Asp Asn Phe Asp Cys
    1130                1135                1140
Gln Asn Gly Ala Gln Cys Ile Ile Arg Ile Asn Glu Pro Ile Cys
    1145                1150                1155
Gln Cys Leu Pro Gly Tyr Leu Gly Glu Lys Cys Glu Lys Leu Val
    1160                1165                1170
Ser Val Asn Phe Val Asn Lys Glu Ser Tyr Leu Gln Ile Pro Ser
    1175                1180                1185
Ala Lys Val Arg Pro Gln Thr Asn Ile Thr Leu Gln Ile Ala Thr
    1190                1195                1200
Asp Glu Asp Ser Gly Ile Leu Leu Tyr Lys Gly Asp Lys Asp His
    1205                1210                1215
Ile Ala Val Glu Leu Tyr Arg Gly Arg Val Arg Ala Ser Tyr Asp
    1220                1225                1230
Thr Gly Ser His Pro Ala Ser Ala Ile Tyr Ser Val Glu Thr Ile
    1235                1240                1245
Asn Asp Gly Asn Phe His Ile Val Glu Leu Leu Thr Leu Asp Ser
    1250                1255                1260
Ser Leu Ser Leu Ser Val Asp Gly Gly Ser Pro Lys Val Ile Thr
    1265                1270                1275
Asn Leu Ser Lys Gln Ser Thr Leu Asn Phe Asp Ser Pro Leu Tyr
    1280                1285                1290
Val Gly Gly Met Pro Gly Lys Asn Asn Val Ala Ser Leu Arg Gln
    1295                1300                1305
Ala Pro Gly Gln Asn Gly Thr Ser Phe His Gly Cys Ile Arg Asn
    1310                1315                1320
```

| | | | | | | | | | | |
|---|---|---|---|---|---|---|---|---|---|---|
| Leu | Tyr | Ile | Asn | Ser | Glu | Leu | Gln | Asp | Phe | Arg | Lys | Met | Pro | Met |
| 1325 | | | | | 1330 | | | | | 1335 | | | | |

Gln Thr Gly Ile Leu Pro Gly Cys Glu Pro Cys His Lys Lys Val
1340      1345      1350

Cys Ala His Gly Met Cys Gln Pro Ser Ser Gln Ser Gly Phe Thr
 1355      1360      1365

Cys Glu Cys Glu Glu Gly Trp Met Gly Pro Leu Cys Asp Gln Arg
1370      1375      1380

Thr Asn Asp Pro Cys Leu Gly Asn Lys Cys Val His Gly Thr Cys
 1385      1390      1395

Leu Pro Ile Asn Ala Phe Ser Tyr Ser Cys Lys Cys Leu Glu Gly
1400      1405      1410

His Gly Gly Val Leu Cys Asp Glu Glu Glu Asp Leu Phe Asn Pro
 1415      1420      1425

Cys Gln Met Ile Lys Cys Lys His Gly Lys Cys Arg Leu Ser Gly
1430      1435      1440

Val Gly Gln Pro Tyr Cys Glu Cys Asn Ser Gly Phe Thr Gly Asp
 1445      1450      1455

Ser Cys Asp Arg Glu Ile Ser Cys Arg Gly Glu Arg Ile Arg Asp
1460      1465      1470

Tyr Tyr Gln Lys Gln Gln Gly Tyr Ala Ala Cys Gln Thr Thr Lys
 1475      1480      1485

Lys Val Ser Arg Leu Glu Cys Arg Gly Gly Cys Ala Gly Gly Gln
1490      1495      1500

Cys Cys Gly Pro Leu Arg Ser Lys Arg Arg Lys Tyr Ser Phe Glu
 1505      1510      1515

Cys Thr Asp Gly Ser Ser Phe Val Asp Glu Val Glu Lys Val Val
1520      1525      1530

Lys Cys Gly Cys Ala Arg Cys Ala Ser
 1535      1540

<210> SEQ ID NO 9
<211> LENGTH: 4578
<212> TYPE: DNA
<213> ORGANISM: Mus musculus

<400> SEQUENCE: 9

```
atgagtggca ttggctggca gacactgtcc ctatcgctgg ggttagtgtt gtcgatcttg      60
aacaaggtgg cgccgcaggc gtgcccggcc cagtgctcct gttcaggcag cacggtggac     120
tgtcatgggc tggcactgcg cagtgtgccc aggaatatcc cccgcaacac cgagagactg     180
gatttgaatg gaaataacat cacgaggatc acgaagatag attttgctgg tctcaggcac     240
ctcagagttc ttcagctcat ggagaacaga atcagcacca tcgagagggg agcattccag     300
gatcttaagg agctggaaag actgcgttta acagaaata accttcagtt gtttcctgag      360
ctgctgtttc tcgggactgc gaagctctac cggcttgatc tcagtgaaaa tcaaattcaa     420
gcaattccaa ggaaggcttt ccgtgggca gttgacatta aaaacctgca actggattac      480
aaccagatca gctgcattga agatggggcg ttcagagctc tacgagatct ggaagtgctc     540
actctgaaca ataacaatat tactagactt tcagtggcaa gtttcaacca tatgcctaaa     600
cttaggacat ttcgactcca ctcgaacaac ttgtactgcg actgccacct agcctggctc     660
tcagactggc ttcgccaaag gccacgggtg ggcttgtaca ctcagtgtat gggcccatcc     720
cacctgaggg gccacaatgt agcagaggtt caaaaacgag agtttgtctg cagtgatgag     780
```

```
gaagaaggtc accagtcatt catggctccc tcctgcagtg tgctgcactg ccccgctgct    840
tgtacctgta gcaacaacat tgtagactgc cgagggaaag gtctcactga gatccccaca    900
aatctgcctg agaccatcac agaaatacgt ttggaacaga actccatcag ggtcatccct    960
ccaggagcct tctcaccata caaaaagctt agacgactag acctgagcaa caaccagatc   1020
tctgaacttg caccagatgc cttccaagga ctgcgctctc tgaattcact tgtcctgtat   1080
ggaaataaaa tcacagaact cccaaaaagt ttattcgaag gactattttc cttgcagcta   1140
ctattattga atgccaacaa gataaactgc cttcgggtag atgcttttca ggacctgcac   1200
aacttgaacc ttctctcctt atatgacaat aagcttcaga cggttgccaa gggcaccttc   1260
tcagccctca gagccatcca aactatgcat ttggcccaga atcctttcat ttgtgactgc   1320
catctcaagt ggctagcgga ttatctccac accaacccaa ttgagaccag cggtgcccgt   1380
tgcaccagcc ccgccgcct ggcaaacaaa agaattggac agatcaaaag caagaaattc    1440
cgttgttcag gtacagaaga ttatcgatca aaattaagtg gagactgctt tgcagacttg   1500
gcttgtcctg agaagtgtcg ctgtgaaggg accacagtag actgctccaa tcaaagactc   1560
aacaaaatcc ctgaccatat tccccagtac acagcagagc tgcgtctcaa taataatgaa   1620
ttcacagtgt tagaagccac gggaatattt aagaaacttc ctcagttacg taaaatcaac   1680
tttagcaaca ataagatcac ggatatcgag gagggtgcat ttgaaggcgc gtctggtgtg   1740
aatgaaattc ttctcaccag taccgtttg gaaaatgttc agcataagat gttcaaagga    1800
ctggagagcc tcaaaacatt gatgctgaga agtaatcgaa taagctgtgt tgggaacgac   1860
agtttcatag gactcggctc tgtgcgtctg ctctctttat atgacaatca aattaccaca   1920
gtggcaccag gagcatttga ttctctccat tcattatcca ctctaaacct cttggccaat   1980
cctttcaact gtaactgtca cctggcatgg ctggagaat ggctcagaag gaaaagaatt    2040
gtaacaggaa atcctcgatg ccaaaaaccc tacttcctga aggaaatccc aatccaggat   2100
gtagccattc aggacttcac ctgtgatgat ggaaatgatg acaatagttg ctctccactc   2160
tcccgttgtc cttctgaatg tacctgcttg gatacagtgg tacgatgtag caacaagggc   2220
ttgaaggttt tgcctaaagg tattccaaaa gatgtcacag agctgtatct ggatgggaac   2280
cagtttacgc tggtcccgaa ggaactctct aactacaaac atttaacact tatagactta   2340
agtaacaacc gaataagcac cctttccaat caaagcttca gcaacatgac ccagcttctc   2400
accttaatcc tcagttacaa ccgtctgaga tgtatccctc acgaaccctt tgatggattg   2460
aagtctcttc ggttactgtc tttacatgga atgacattt ctgttgtgcc tgaaggtgcc    2520
ttcaatgact tgtcagcctt gtcacactta gcgattggag ccaaccctct ttactgtgat   2580
tgtaacatgc agtggttatc cgactgggtg aagtcggaat ataaggaacc tggaattgca   2640
cgctgtgccg gccctggaga aatggcagat aaattattac tcactactcc ctccaaaaaa   2700
tttacatgtc aaggtcccgt ggatatcact attcaagcca agtgtaatcc ctgcttatca   2760
aatccatgta aaaatgatgg cacctgtaac aatgaccccg ttgattttta tcgatgtacc   2820
tgcccatatg gattcaaggg tcaggactgt gatgtcccca ttcatgcttg tatcagtaat   2880
ccatgtaaac atggaggaac ttgtcactta aggaaggag agaatgctgg attctggtgc    2940
acttgtgctg atgggtttga aggagaaaac tgtgaagtca atattgatga ttgtgaagat   3000
aatgattgtg aaaataattc tacatgcgtt gatggaatta caactacac atgtctttgc    3060
ccaccggaat acacaggtga actgtgtgag gaaaagctgg acttctgtgc acaagacttg   3120
aatccctgcc agcatgactc caagtgcatc ctgactccaa agggattcaa gtgtgactgc   3180
```

| | | | | |
|---|---|---|---|---|
| actccaggat | acattggtga | gcactgtgac | attgactttg | atgactgcca agataacaag | 3240 |
| tgtaaaaacg | gtgctcactg | cacagatgcc | gtgaacggat | acacgtgcgt ctgtcctgaa | 3300 |
| ggctacagtg | gcttgttctg | tgagttttct | ccacccatgg | tcctccctcg caccagcccc | 3360 |
| tgtgataatt | ttgattgcca | gaatggagcc | cagtgtatca | tcaggataaa tgaaccaata | 3420 |
| tgccagtgtt | tgcctggcta | cctgggagag | aagtgtgaga | aattggtcag tgtgaatttt | 3480 |
| gtaaacaaag | agtcctatct | tcagattcct | tcagccaagg | ttcggcctca gacaaacatc | 3540 |
| acacttcaga | ttgccacaga | tgaagacagc | ggcatcctct | tgtataaagg tgacaaagac | 3600 |
| cacattgccg | tggaactcta | tagagggcga | gttcgagcca | gctatgacac cggctctcat | 3660 |
| ccggcttctg | ccatttacag | tgtggagaca | atcaatgatg | aaacttcca cattgtggag | 3720 |
| ctactgaccc | tggattccag | tctttccctc | tctgtggatg | gaggaagccc taaagtcatc | 3780 |
| accaatttgt | caaaacaatc | tactctgaat | ttcgactctc | cactctatgt aggaggcatg | 3840 |
| cctgggaaaa | ataacgtggc | atccctgcgc | caggcccctg | gcaaaatgg caccagcttc | 3900 |
| catggctgta | tccggaacct | ttacattaac | agtgagctgc | aggacttccg gaaaatgcct | 3960 |
| atgcaaaccg | gaattctgcc | tggctgtgaa | ccatgccaca | agaaagtatg tgcccatggc | 4020 |
| atgtgccagc | ccagcagcca | atcaggcttc | acctgtgaat | gtgaggaagg gtggatgggg | 4080 |
| cccctctgtg | accagagaac | caatgatccc | tgcctcggaa | acaaatgtgt gcatgggacc | 4140 |
| tgcctgccca | tcaatgcctt | ctcctatagt | tgcaagtgcc | tggagggcca tggcggtgtc | 4200 |
| ctctgtgatg | aagaagaaga | tctctttaac | ccctgccaga | tgatcaagtg caagcatggg | 4260 |
| aagtgcaggc | tttctggagt | gggccagccc | tattgtgaat | gcaacagtgg attcaccggg | 4320 |
| gacagctgtg | atagagaaat | tcttgtcga | ggggaacgga | taagggacta ttaccagaag | 4380 |
| cagcagggtt | acgctgcctg | tcaaacaact | aagaaagtat | ctcgcttgga atgcagaggc | 4440 |
| gggtgcgctg | gaggccagtg | ctgtggacct | ctgagaagca | agaggcggaa atactctttc | 4500 |
| gaatgcacag | atggctcctc | atttgtggac | gaggttgaga | agtggtgaa gtgcggctgc | 4560 |
| gcgagatgtg | cctcctaa | | | | 4578 |

<210> SEQ ID NO 10
<211> LENGTH: 1525
<212> TYPE: PRT
<213> ORGANISM: Mus musculus

<400> SEQUENCE: 10

Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
                20                  25                  30

Ser Cys Ser Gly Ser Thr Val Asp Cys His Gly Leu Ala Leu Arg Ser
            35                  40                  45

Val Pro Arg Asn Ile Pro Arg Asn Thr Glu Arg Leu Asp Leu Asn Gly
        50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110

```
Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Ser Ile Arg Val Ile Pro
305                 310                 315                 320

Pro Gly Ala Phe Ser Pro Tyr Lys Lys Leu Arg Arg Leu Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Val Ala
                405                 410                 415

Lys Gly Thr Phe Ser Ala Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Arg Leu Asn Lys Ile Pro Asp His Ile Pro
        515                 520                 525
```

```
Gln Tyr Thr Ala Glu Leu Arg Leu Asn Asn Asn Glu Phe Thr Val Leu
    530                 535                 540

Glu Ala Thr Gly Ile Phe Lys Lys Leu Pro Gln Leu Arg Lys Ile Asn
545                 550                 555                 560

Phe Ser Asn Asn Lys Ile Thr Asp Ile Glu Glu Gly Ala Phe Glu Gly
                    565                 570                 575

Ala Ser Gly Val Asn Glu Ile Leu Leu Thr Ser Asn Arg Leu Glu Asn
                580                 585                 590

Val Gln His Lys Met Phe Lys Gly Leu Glu Ser Leu Lys Thr Leu Met
        595                 600                 605

Leu Arg Ser Asn Arg Ile Ser Cys Val Gly Asn Asp Ser Phe Ile Gly
    610                 615                 620

Leu Gly Ser Val Arg Leu Leu Ser Leu Tyr Asp Asn Gln Ile Thr Thr
625                 630                 635                 640

Val Ala Pro Gly Ala Phe Asp Ser Leu His Ser Leu Ser Thr Leu Asn
                    645                 650                 655

Leu Leu Ala Asn Pro Phe Asn Cys Asn Cys His Leu Ala Trp Leu Gly
                660                 665                 670

Glu Trp Leu Arg Arg Lys Arg Ile Val Thr Gly Asn Pro Arg Cys Gln
        675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Ser Glu Cys Thr Cys Leu Asp Thr Val Val Arg Cys
                    725                 730                 735

Ser Asn Lys Gly Leu Lys Val Leu Pro Lys Gly Ile Pro Lys Asp Val
                740                 745                 750

Thr Glu Leu Tyr Leu Asp Gly Asn Gln Phe Thr Leu Val Pro Lys Glu
        755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                    805                 810                 815

Phe Asp Gly Leu Lys Ser Leu Arg Leu Leu Ser Leu His Gly Asn Asp
                820                 825                 830

Ile Ser Val Val Pro Glu Gly Ala Phe Asn Asp Leu Ser Ala Leu Ser
        835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                    885                 890                 895

Pro Ser Lys Lys Phe Thr Cys Gln Gly Pro Val Asp Ile Thr Ile Gln
                900                 905                 910

Ala Lys Cys Asn Pro Cys Leu Ser Asn Pro Cys Lys Asn Asp Gly Thr
        915                 920                 925

Cys Asn Asn Asp Pro Val Asp Phe Tyr Arg Cys Thr Cys Pro Tyr Gly
    930                 935                 940
```

-continued

```
Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Asn Ala
                965                 970                 975

Gly Phe Trp Cys Thr Cys Ala Asp Gly Phe Glu Gly Glu Asn Cys Glu
                980                 985                 990

Val Asn Ile Asp Asp Cys Glu Asp  Asn Asp Cys Glu Asn  Asn Ser Thr
            995                 1000                1005

Cys Val  Asp Gly Ile Asn Asn  Tyr Thr Cys Leu Cys  Pro Pro Glu
    1010                1015                1020

Tyr Thr  Gly Glu Leu Cys Glu  Glu Lys Leu Asp Phe  Cys Ala Gln
    1025                1030                1035

Asp Leu  Asn Pro Cys Gln His  Asp Ser Lys Cys Ile  Leu Thr Pro
    1040                1045                1050

Lys Gly  Phe Lys Cys Asp Cys  Thr Pro Gly Tyr Ile  Gly Glu His
    1055                1060                1065

Cys Asp  Ile Asp Phe Asp Asp  Cys Gln Asp Asn Lys  Cys Lys Asn
    1070                1075                1080

Gly Ala  His Cys Thr Asp Ala  Val Asn Gly Tyr Thr  Cys Val Cys
    1085                1090                1095

Pro Glu  Gly Tyr Ser Gly Leu  Phe Cys Glu Phe Ser  Pro Pro Met
    1100                1105                1110

Val Leu  Pro Arg Thr Ser Pro  Cys Asp Asn Phe Asp  Cys Gln Asn
    1115                1120                1125

Gly Ala  Gln Cys Ile Ile Arg  Ile Asn Glu Pro Ile  Cys Gln Cys
    1130                1135                1140

Leu Pro  Gly Tyr Leu Gly Glu  Lys Cys Glu Lys Leu  Val Ser Val
    1145                1150                1155

Asn Phe  Val Asn Lys Glu Ser  Tyr Leu Gln Ile Pro  Ser Ala Lys
    1160                1165                1170

Val Arg  Pro Gln Thr Asn Ile  Thr Leu Gln Ile Ala  Thr Asp Glu
    1175                1180                1185

Asp Ser  Gly Ile Leu Leu Tyr  Lys Gly Asp Lys Asp  His Ile Ala
    1190                1195                1200

Val Glu  Leu Tyr Arg Gly Arg  Val Arg Ala Ser Tyr  Asp Thr Gly
    1205                1210                1215

Ser His  Pro Ala Ser Ala Ile  Tyr Ser Val Glu Thr  Ile Asn Asp
    1220                1225                1230

Gly Asn  Phe His Ile Val Glu  Leu Leu Thr Leu Asp  Ser Ser Leu
    1235                1240                1245

Ser Leu  Ser Val Asp Gly Gly  Ser Pro Lys Val Ile  Thr Asn Leu
    1250                1255                1260

Ser Lys  Gln Ser Thr Leu Asn  Phe Asp Ser Pro Leu  Tyr Val Gly
    1265                1270                1275

Gly Met  Pro Gly Lys Asn Asn  Val Ala Ser Leu Arg  Gln Ala Pro
    1280                1285                1290

Gly Gln  Asn Gly Thr Ser Phe  His Gly Cys Ile Arg  Asn Leu Tyr
    1295                1300                1305

Ile Asn  Ser Glu Leu Gln Asp  Phe Arg Lys Met Pro  Met Gln Thr
    1310                1315                1320

Gly Ile  Leu Pro Gly Cys Glu  Pro Cys His Lys Lys  Val Cys Ala
    1325                1330                1335
```

| | | | | | | | | | | |
|---|---|---|---|---|---|---|---|---|---|---|
| His | Gly | Met | Cys | Gln | Pro | Ser | Ser | Gln | Ser | Gly | Phe | Thr | Cys | Glu |
| 1340 | | | | | 1345 | | | | | 1350 | | | | |
| Cys | Glu | Glu | Gly | Trp | Met | Gly | Pro | Leu | Cys | Asp | Gln | Arg | Thr | Asn |
| 1355 | | | | | 1360 | | | | | 1365 | | | | |
| Asp | Pro | Cys | Leu | Gly | Asn | Lys | Cys | Val | His | Gly | Thr | Cys | Leu | Pro |
| 1370 | | | | | 1375 | | | | | 1380 | | | | |
| Ile | Asn | Ala | Phe | Ser | Tyr | Ser | Cys | Lys | Cys | Leu | Glu | Gly | His | Gly |
| 1385 | | | | | 1390 | | | | | 1395 | | | | |
| Gly | Val | Leu | Cys | Asp | Glu | Glu | Asp | Leu | Phe | Asn | Pro | Cys | Gln |
| 1400 | | | | | 1405 | | | | | 1410 | | | | |
| Met | Ile | Lys | Cys | Lys | His | Gly | Lys | Cys | Arg | Leu | Ser | Gly | Val | Gly |
| 1415 | | | | | 1420 | | | | | 1425 | | | | |
| Gln | Pro | Tyr | Cys | Glu | Cys | Asn | Ser | Gly | Phe | Thr | Gly | Asp | Ser | Cys |
| 1430 | | | | | 1435 | | | | | 1440 | | | | |
| Asp | Arg | Glu | Ile | Ser | Cys | Arg | Gly | Glu | Arg | Ile | Arg | Asp | Tyr | Tyr |
| 1445 | | | | | 1450 | | | | | 1455 | | | | |
| Gln | Lys | Gln | Gln | Gly | Tyr | Ala | Ala | Cys | Gln | Thr | Thr | Lys | Lys | Val |
| 1460 | | | | | 1465 | | | | | 1470 | | | | |
| Ser | Arg | Leu | Glu | Cys | Arg | Gly | Gly | Cys | Ala | Gly | Gly | Gln | Cys | Cys |
| 1475 | | | | | 1480 | | | | | 1485 | | | | |
| Gly | Pro | Leu | Arg | Ser | Lys | Arg | Arg | Lys | Tyr | Ser | Phe | Glu | Cys | Thr |
| 1490 | | | | | 1495 | | | | | 1500 | | | | |
| Asp | Gly | Ser | Ser | Phe | Val | Asp | Glu | Val | Glu | Lys | Val | Val | Lys | Cys |
| 1505 | | | | | 1510 | | | | | 1515 | | | | |
| Gly | Cys | Ala | Arg | Cys | Ala | Ser |
| 1520 | | | | | 1525 | |

<210> SEQ ID NO 11
<211> LENGTH: 4566
<212> TYPE: DNA
<213> ORGANISM: Mus musculus

<400> SEQUENCE: 11

```
atgagtggca ttggctggca gacactgtcc ctatcgctgg ggttagtgtt gtcgatcttg     60
aacaaggtgg cgccgcaggc gtgcccggcc cagtgctcct gttcaggcag cacggtggac    120
tgtcatgggc tggcactgcg cagtgtgccc aggaatatcc cccgcaacac cgagagactg    180
gatttgaatg gaataacat cacgaggatc acgaagatag attttgctgg tctcaggcac    240
ctcagagttc ttcagctcat ggagaacaga atcagcacca tcgagagggg agcattccag    300
gatcttaagg agctggaaag actgcgttta aacagaaata accttcagtt gtttcctgag    360
ctgctgtttc tcgggactgc gaagctctac cggcttgatc tcagtgaaaa tcaaattcaa    420
gcaattccaa ggaaggcttt ccgtggggca gttgacatta aaaacctgca actggattac    480
aaccagatca gctgcattga gatggggcg ttcagagctc tacgagatct ggaagtgctc    540
actctgaaca ataacaatat tactagactt tcagtggcaa gtttcaacca tatgcctaaa    600
cttaggacat ttcgactcca ctcgaacaac ttgtactgcg actgccacct agcctggctc    660
tcagactggc ttcgccaaag gccacgggtg ggcttgtaca ctcagtgtat gggcccatcc    720
cacctgaggg gccacaatgt agcagaggtt caaaaacgag agtttgtctg cagtggtcac    780
cagtcattca tggctccctc ctgcagtgtg ctgcactgcc ccgctgcttg tacctgtagc    840
aacaacattg tagactgccg agggaaaggt ctcactgaga tccccacaaa tctgcctgag    900
accatcacag aaatacgttt ggaacagaac tccatcaggg tcatccctcc aggagccttc    960
```

-continued

```
tcaccataca aaaagcttag acgactagac ctgagcaaca accagatctc tgaacttgca    1020
ccagatgcct tccaaggact gcgctctctg aattcacttg tcctgtatgg aaataaaatc    1080
acagaactcc caaaaagttt attcgaagga ctattttcct tgcagctact attattgaat    1140
gccaacaaga taaactgcct tcgggtagat gcttttcagg acctgcacaa cttgaacctt    1200
ctctccttat atgacaataa gcttcagacg gttgccaagg gcaccttctc agccctcaga    1260
gccatccaaa ctatgcattt ggcccagaat cctttcattt gtgactgcca tctcaagtgg    1320
ctagcggatt atctccacac caacccaatt gagaccagcg gtgcccgttg caccagcccc    1380
cgccgcctgg caaacaaaag aattggacag atcaaaagca agaaattccg ttgttcaggt    1440
acagaagatt atcgatcaaa attaagtgga gactgctttg cagacttggc ttgtcctgag    1500
aagtgtcgct gtgaagggac cacagtagac tgctccaatc aaagactcaa caaaatccct    1560
gaccatattc cccagtacac agcagagctg cgtctcaata taatgaatt cacagtgtta    1620 gaagccacgg gaatatttaa gaaacttcct cagttacgta aaatcaactt tagcaacaat    1680
aagatcacgg atatcgagga gggtgcattt gaaggcgcgt ctggtgtgaa tgaaattctt    1740
ctcaccagta accgtttgga aaatgttcag cataagatgt tcaaaggact ggagagcctc    1800
aaaacattga tgctgagaag taatcgaata agctgtgttg ggaacgacag tttcatagga    1860
ctcggctctg tgcgtctgct ctctttatat gacaatcaaa ttaccacagt ggcaccagga    1920
gcatttgatt ctctccattc attatccact ctaaacctct tggccaatcc tttcaactgt    1980
aactgtcacc tggcatggct gggagaatgg ctcagaagga aaagaattgt aacaggaaat    2040
cctcgatgcc aaaaaccta cttcctgaag gaaatcccaa tccaggatgt agccattcag    2100
gacttcacct gtgatgatgg aaatgatgac aatagttgct ctccactctc ccgttgtcct    2160
tctgaatgta cctgcttgga tacagtggta cgatgtagca acaagggctt gaaggttttg    2220
cctaaaggta ttccaaaaga tgtcacagag ctgtatctgg atgggaacca gtttacgctg    2280
gtcccgaagg aactctctaa ctacaaacat ttaacactta tagacttaag taacaaccga    2340
ataagcaccc tttccaatca aagcttcagc aacatgaccc agcttctcac cttaatcctc    2400
agttacaacc gtctgagatg tatccctcca cgaacctttg atggattgaa gtctcttcgg    2460
ttactgtctt tacatggaaa tgacatttct gttgtgcctg aaggtgcctt caatgacttg    2520
tcagccttgt cacacttagc gattggagcc aaccctcttt actgtgattg taacatgcag    2580
tggttatccg actgggtgaa gtcggaatat aaggaacctg gaattgcacg ctgtgccggc    2640 cctgagaaa tggcagataa attattactc actactccct ccaaaaaatt tacatgtcaa    2700
ggtcccgtgg atatcactat tcaagccaag tgtaatccct gcttatcaaa tccatgtaaa    2760
aatgatggca cctgtaacaa tgaccccgtt gatttttatc gatgtacctg cccatatgga    2820
ttcaagggtc aggactgtga tgtccccatt catgcttgta tcagtaatcc atgtaaacat    2880
ggaggaactt gtcacttaaa ggaaggagag aatgctggat tctggtgcac ttgtgctgat    2940
gggtttgaag gagaaaactg tgaagtcaat attgatgatt gtgaagataa tgattgtgaa    3000
aataattcta catgcgttga tggaattaac aactacacat gtctttgccc accggaatac    3060
acaggtgaac tgtgtgagga aaagctggac ttctgtgcac aagacttgaa tccctgccag    3120
catgactcca gtgcatcct gactccaaag ggattcaagt gtgactgcac tccaggatac    3180
attggtgagc actgtgacat tgactttgat gactgccaag ataacaagtg taaaaacggt    3240
gctcactgca cagatgccgt gaacggatac acgtgcgtct gtcctgaagg ctacagtggc    3300
ttgttctgtg agttttctcc acccatggtc ctccctcgca ccagcccctg tgataatttt    3360
```

```
gattgccaga atggagccca gtgtatcatc aggataaatg aaccaatatg ccagtgtttg    3420
cctggctacc tgggagagaa gtgtgagaaa ttggtcagtg tgaattttgt aaacaaagag    3480
tcctatcttc agattccttc agccaaggtt cggcctcaga caaacatcac acttcagatt    3540
gccacagatg aagacagcgg catcctcttg tataaaggtg acaaagacca cattgccgtg    3600
gaactctata gagggcgagt tcgagccagc tatgacaccg gctctcatcc ggcttctgcc    3660
atttacagtg tggagacaat caatgatgga aacttccaca ttgtggagct actgaccctg    3720
gattccagtc tttccctctc tgtggatgga ggaagcccta agtcatcac caatttgtca    3780 aaacaatcta ctctgaattt cgactctcca ctctatgtag gaggcatgcc tgggaaaaat    3840
aacgtggcat ccctgcgcca ggcccctggg caaaatggca ccagcttcca tggctgtatc    3900
cggaaccttt acattaacag tgagctgcag gacttccgga aaatgcctat gcaaaccgga    3960
attctgcctg gctgtgaacc atgccacaag aaagtatgtg cccatggcat gtgccagccc    4020
agcagccaat caggcttcac ctgtgaatgt gaggaagggt ggatgggcc cctctgtgac    4080 cagagaacca atgatccctg cctcggaaac aaatgtgtgc atgggacctg cctgcccatc    4140
aatgccttct cctatagttg caagtgcctg gagggccatg gcggtgtcct ctgtgatgaa    4200
gaagaagatc tctttaaccc ctgccagatg atcaagtgca agcatgggaa gtgcaggctt    4260
tctggagtgg gccagcccta ttgtgaatgc aacagtggat tcaccgggga cagctgtgat    4320
agagaaattt cttgtcgagg ggaacggata agggactatt accagaagca gcagggttac    4380
gctgcctgtc aaacaactaa gaaagtatct cgcttggaat gcagaggcgg gtgcgctgga    4440
ggccagtgct gtggacctct gagaagcaag aggcggaaat actctttcga atgcacagat    4500
ggctcctcat ttgtggacga ggttgagaaa gtggtgaagt gcggctgcgc gagatgtgcc    4560
tcctaa                                                              4566
```

<210> SEQ ID NO 12
<211> LENGTH: 1521
<212> TYPE: PRT
<213> ORGANISM: Mus musculus

<400> SEQUENCE: 12

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140
```

-continued

```
Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Ile Thr Arg Leu Ser Val
            180                 185                 190

Ala Ser Phe Asn His Met Pro Lys Leu Arg Thr Phe Arg Leu His Ser
            195                 200                 205

Asn Asn Leu Tyr Cys Asp Cys His Leu Ala Trp Leu Ser Asp Trp Leu
        210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
                260                 265                 270

Cys Pro Ala Ala Cys Thr Cys Ser Asn Asn Ile Val Asp Cys Arg Gly
            275                 280                 285

Lys Gly Leu Thr Glu Ile Pro Thr Asn Leu Pro Glu Thr Ile Thr Glu
290                 295                 300

Ile Arg Leu Glu Gln Asn Ser Ile Arg Val Ile Pro Pro Gly Ala Phe
305                 310                 315                 320

Ser Pro Tyr Lys Lys Leu Arg Arg Leu Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Asn Ala Asn Lys Ile
370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Val Ala Lys Gly Thr Phe
                405                 410                 415

Ser Ala Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
        435                 440                 445

Pro Ile Glu Thr Ser Gly Ala Arg Cys Thr Ser Pro Arg Arg Leu Ala
450                 455                 460

Asn Lys Arg Ile Gly Gln Ile Lys Ser Lys Phe Arg Cys Ser Gly
465                 470                 475                 480

Thr Glu Asp Tyr Arg Ser Lys Leu Ser Gly Asp Cys Phe Ala Asp Leu
                485                 490                 495

Ala Cys Pro Glu Lys Cys Arg Cys Glu Gly Thr Thr Val Asp Cys Ser
            500                 505                 510

Asn Gln Arg Leu Asn Lys Ile Pro Asp His Ile Pro Gln Tyr Thr Ala
        515                 520                 525

Glu Leu Arg Leu Asn Asn Asn Glu Phe Thr Val Leu Glu Ala Thr Gly
530                 535                 540

Ile Phe Lys Lys Leu Pro Gln Leu Arg Lys Ile Asn Phe Ser Asn Asn
545                 550                 555                 560
```

```
Lys Ile Thr Asp Ile Glu Glu Gly Ala Phe Glu Gly Ala Ser Gly Val
                565                 570                 575
Asn Glu Ile Leu Leu Thr Ser Asn Arg Leu Glu Asn Val Gln His Lys
            580                 585                 590
Met Phe Lys Gly Leu Glu Ser Leu Lys Thr Leu Met Leu Arg Ser Asn
        595                 600                 605
Arg Ile Ser Cys Val Gly Asn Asp Ser Phe Ile Gly Leu Gly Ser Val
    610                 615                 620
Arg Leu Leu Ser Leu Tyr Asp Asn Gln Ile Thr Thr Val Ala Pro Gly
625                 630                 635                 640
Ala Phe Asp Ser Leu His Ser Leu Ser Thr Leu Asn Leu Leu Ala Asn
                645                 650                 655
Pro Phe Asn Cys Asn Cys His Leu Ala Trp Leu Gly Glu Trp Leu Arg
            660                 665                 670
Arg Lys Arg Ile Val Thr Gly Asn Pro Arg Cys Gln Lys Pro Tyr Phe
        675                 680                 685
Leu Lys Glu Ile Pro Ile Gln Asp Val Ala Ile Gln Asp Phe Thr Cys
    690                 695                 700
Asp Asp Gly Asn Asp Asp Asn Ser Cys Ser Pro Leu Ser Arg Cys Pro
705                 710                 715                 720
Ser Glu Cys Thr Cys Leu Asp Thr Val Val Arg Cys Ser Asn Lys Gly
                725                 730                 735
Leu Lys Val Leu Pro Lys Gly Ile Pro Lys Asp Val Thr Glu Leu Tyr
            740                 745                 750
Leu Asp Gly Asn Gln Phe Thr Leu Val Pro Lys Glu Leu Ser Asn Tyr
        755                 760                 765
Lys His Leu Thr Leu Ile Asp Leu Ser Asn Asn Arg Ile Ser Thr Leu
    770                 775                 780
Ser Asn Gln Ser Phe Ser Asn Met Thr Gln Leu Leu Thr Leu Ile Leu
785                 790                 795                 800
Ser Tyr Asn Arg Leu Arg Cys Ile Pro Pro Arg Thr Phe Asp Gly Leu
                805                 810                 815
Lys Ser Leu Arg Leu Leu Ser Leu His Gly Asn Asp Ile Ser Val Val
            820                 825                 830
Pro Glu Gly Ala Phe Asn Asp Leu Ser Ala Leu Ser His Leu Ala Ile
        835                 840                 845
Gly Ala Asn Pro Leu Tyr Cys Asp Cys Asn Met Gln Trp Leu Ser Asp
    850                 855                 860
Trp Val Lys Ser Glu Tyr Lys Glu Pro Gly Ile Ala Arg Cys Ala Gly
865                 870                 875                 880
Pro Gly Glu Met Ala Asp Lys Leu Leu Leu Thr Thr Pro Ser Lys Lys
                885                 890                 895
Phe Thr Cys Gln Gly Pro Val Asp Ile Thr Ile Gln Ala Lys Cys Asn
            900                 905                 910
Pro Cys Leu Ser Asn Pro Cys Lys Asn Asp Gly Thr Cys Asn Asn Asp
        915                 920                 925
Pro Val Asp Phe Tyr Arg Cys Thr Cys Pro Tyr Gly Phe Lys Gly Gln
    930                 935                 940
Asp Cys Asp Val Pro Ile His Ala Cys Ile Ser Asn Pro Cys Lys His
945                 950                 955                 960
Gly Gly Thr Cys His Leu Lys Glu Gly Glu Asn Ala Gly Phe Trp Cys
                965                 970                 975
```

Thr Cys Ala Asp Gly Phe Glu Gly Glu Asn Cys Glu Val Asn Ile Asp
            980             985                 990

Asp Cys Glu Asp Asn Asp Cys Glu  Asn Asn Ser Thr Cys  Val Asp Gly
           995              1000                 1005

Ile Asn Asn Tyr Thr Cys Leu  Cys Pro Pro Glu Tyr  Thr Gly Glu
   1010             1015                 1020

Leu Cys Glu Glu Lys Leu Asp  Phe Cys Ala Gln Asp  Leu Asn Pro
   1025             1030                 1035

Cys Gln His Asp Ser Lys Cys  Ile Leu Thr Pro Lys  Gly Phe Lys
   1040             1045                 1050

Cys Asp Cys Thr Pro Gly Tyr  Ile Gly Glu His Cys  Asp Ile Asp
   1055             1060                 1065

Phe Asp Asp Cys Gln Asp Asn  Lys Cys Lys Asn Gly  Ala His Cys
   1070             1075                 1080

Thr Asp Ala Val Asn Gly Tyr  Thr Cys Val Cys Pro  Glu Gly Tyr
   1085             1090                 1095

Ser Gly Leu Phe Cys Glu Phe  Ser Pro Pro Met Val  Leu Pro Arg
   1100             1105                 1110

Thr Ser Pro Cys Asp Asn Phe  Asp Cys Gln Asn Gly  Ala Gln Cys
   1115             1120                 1125

Ile Ile Arg Ile Asn Glu Pro  Ile Cys Gln Cys Leu  Pro Gly Tyr
   1130             1135                 1140

Leu Gly Glu Lys Cys Glu Lys  Leu Val Ser Val Asn  Phe Val Asn
   1145             1150                 1155

Lys Glu Ser Tyr Leu Gln Ile  Pro Ser Ala Lys Val  Arg Pro Gln
   1160             1165                 1170

Thr Asn Ile Thr Leu Gln Ile  Ala Thr Asp Glu Asp  Ser Gly Ile
   1175             1180                 1185

Leu Leu Tyr Lys Gly Asp Lys  Asp His Ile Ala Val  Glu Leu Tyr
   1190             1195                 1200

Arg Gly Arg Val Arg Ala Ser  Tyr Asp Thr Gly Ser  His Pro Ala
   1205             1210                 1215

Ser Ala Ile Tyr Ser Val Glu  Thr Ile Asn Asp Gly  Asn Phe His
   1220             1225                 1230

Ile Val Glu Leu Leu Thr Leu  Asp Ser Ser Leu Ser  Leu Ser Val
   1235             1240                 1245

Asp Gly Gly Ser Pro Lys Val  Ile Thr Asn Leu Ser  Lys Gln Ser
   1250             1255                 1260

Thr Leu Asn Phe Asp Ser Pro  Leu Tyr Val Gly Gly  Met Pro Gly
   1265             1270                 1275

Lys Asn Asn Val Ala Ser Leu  Arg Gln Ala Pro Gly  Gln Asn Gly
   1280             1285                 1290

Thr Ser Phe His Gly Cys Ile  Arg Asn Leu Tyr Ile  Asn Ser Glu
   1295             1300                 1305

Leu Gln Asp Phe Arg Lys Met  Pro Met Gln Thr Gly  Ile Leu Pro
   1310             1315                 1320

Gly Cys Glu Pro Cys His Lys  Lys Val Cys Ala His  Gly Met Cys
   1325             1330                 1335

Gln Pro Ser Ser Gln Ser Gly  Phe Thr Cys Glu Cys  Glu Glu Gly
   1340             1345                 1350

Trp Met Gly Pro Leu Cys Asp  Gln Arg Thr Asn Asp  Pro Cys Leu
   1355             1360                 1365

| Gly | Asn | Lys | Cys | Val | His | Gly | Thr | Cys | Leu | Pro | Ile | Asn | Ala | Phe |
| | 1370 | | | | 1375 | | | | | 1380 | | | | |

| Ser | Tyr | Ser | Cys | Lys | Cys | Leu | Glu | Gly | His | Gly | Gly | Val | Leu | Cys |
| 1385 | | | | | 1390 | | | | | 1395 | | | | |

| Asp | Glu | Glu | Glu | Asp | Leu | Phe | Asn | Pro | Cys | Gln | Met | Ile | Lys | Cys |
| 1400 | | | | | 1405 | | | | | 1410 | | | | |

| Lys | His | Gly | Lys | Cys | Arg | Leu | Ser | Gly | Val | Gly | Gln | Pro | Tyr | Cys |
| 1415 | | | | | 1420 | | | | | 1425 | | | | |

| Glu | Cys | Asn | Ser | Gly | Phe | Thr | Gly | Asp | Ser | Cys | Asp | Arg | Glu | Ile |
| | 1430 | | | | 1435 | | | | | 1440 | | | | |

| Ser | Cys | Arg | Gly | Glu | Arg | Ile | Arg | Asp | Tyr | Tyr | Gln | Lys | Gln | Gln |
| 1445 | | | | | 1450 | | | | | 1455 | | | | |

| Gly | Tyr | Ala | Ala | Cys | Gln | Thr | Thr | Lys | Lys | Val | Ser | Arg | Leu | Glu |
| 1460 | | | | | 1465 | | | | | 1470 | | | | |

| Cys | Arg | Gly | Gly | Cys | Ala | Gly | Gly | Gln | Cys | Cys | Gly | Pro | Leu | Arg |
| 1475 | | | | | 1480 | | | | | 1485 | | | | |

| Ser | Lys | Arg | Arg | Lys | Tyr | Ser | Phe | Glu | Cys | Thr | Asp | Gly | Ser | Ser |
| 1490 | | | | | 1495 | | | | | 1500 | | | | |

| Phe | Val | Asp | Glu | Val | Glu | Lys | Val | Val | Lys | Cys | Gly | Cys | Ala | Arg |
| 1505 | | | | | 1510 | | | | | 1515 | | | | |

| Cys | Ala | Ser |
| 1520 | | |

<210> SEQ ID NO 13
<211> LENGTH: 4519
<212> TYPE: DNA
<213> ORGANISM: Rattus norvegicus

<400> SEQUENCE: 13

```
atgagtggca ttggctggca gacactgtcc ctatctctgg cgttagtgtt gtcgatcttg      60
aaccaggtgg cgcctcaggc gtgcccggcc cagtgctcct gttcaggcag cacagtggac     120
tgtcatgggc tggcactgcg cagtgtgccc aggaatatcc cccgcaacac ggagagactg     180
gatttgaatg gaaataacat cacaaggatc acgaagacag attttgcggg tctcagacac     240
ctcagagttc ttcagctcat ggagaacaag atcagcacca tcgagagggg agcattccag     300
gatcttaagg agctagaaag actgcgttta aacagaaata accttcagtt gtttcctgag     360
ctgctgtttc ttgggactgc gaagctctac cggcttgatc tcagtgaaaa tcagattcaa     420
gcaattccaa ggaaggcttt ccgtggtgca gttgacatta aaatctgca gttggattac     480 aaccagatca gctgcattga agatgggggca ttccgagctc tgcgagatct ggaagtgctc     540
actctgaaca ataacaatat tactagactt tcagtggcaa gtttcaacca tatgcctaaa     600
cttaggacat ttcgactcca ctccaacaac ctatactgcg actgccacct ggcctggctc     660
tcggactggc ttcgccaaag gccacgggtg ggcttgtaca ctcagtgtat gggcccatcc     720
cacctgaggg gccataatgt agcagaggtt caaaaacgag agtttgtctg cagtgatgag     780
gaagaaggtc accagtcatt catggctccc tcctgcagtg tgctgcactg cccgattgct     840
tgtacctgta gcaacaacat tgtagactgc cgagggaaag gtctcactga tcccccaca     900 aatctgcctg agaccatcac agaaatacgt ttggaacaga actccataag ggtcatccct     960
ccaggagcat tctcaccata caaaagcttt cgacgactag acctgagtaa taaccagatc    1020
tcggaacttg ctccagatgc cttccaagga ctgcgttctc tgaattccct tgtcctgtat    1080
ggaaataaaa tcacagaact cccaaaaagt ttatttgaag gactgttttc cttacagcta    1140
```

```
ctattattga atgccaacaa gataaactgc cttcgggtag atgcttttca ggacctgcac   1200
aacttgaacc ttctctcctt atacgacaat aagcttcaga ctgttgccaa gggcaccttc   1260
tcagctctca gagccatcca aactatgcat ttggcccaga atcctttcat ttgtgactgc   1320
catctcaagt ggctagcgga ttatctccac accaacccaa ttgagaccag cggtgcccgt   1380
tgcaccagtc cccgccgcct ggctaacaaa agaattggac agatcaaaag caagaaattc   1440
cgttgttcag gtacagaaga ttatcgatca aaattaagtg gagactgctt tgcagacttg   1500
gcttgtcctg aaaaatgtcg ctgtgaaggg accacagtag actgctccaa tcaaaaactc   1560
aacaaaatcc cagaccatat tccccagtac acagcagagc tgcgtctcaa taataatgaa   1620
ttcacagtgt tagaagccac gggaatattt aagaaacttc ctcaattgcg taaaatcaac   1680
cttagcaaca ataagatcac tgatatcgag gaggggcat tcgaaggtgc gtctggtgtg   1740
aatgagattc tgcttaccag taaccgtttg gaaaatgttc agcataagat gttcaaagga   1800
ttggagagcc tcaaaacatt gatgctgaga agtaatcgaa taagctgtgt gggaaacgac   1860
agtttcacag gactcggttc tgtgcgtctg ctctctttat atgacaatca aattaccaca   1920
gttgcaccag gagcatttgg tactctccat tcattatcta cactaaacct cttggccaat   1980
cctttcaact gtaactgtca cctggcatgg cttggagaat ggctcagaag gaaagaatt   2040 gtaacaggaa atcctcgatg ccaaaaaccc tacttcttga aggaaatacc aatccaggat   2100
gtagccattg aggacttcac ctgtgatgac ggaaacgatg ataatagctg ctctccactc   2160
tcccgttgtc cttcggaatg tacttgcttg gatacagtag tacgatgtag caacaagggc   2220
ttgaaggtct tacctaaagg cattccaaga gatgtcacag aactgtatct ggatgggaac   2280
cagtttacac tggtcccgaa ggaactctcc aactacaaac atttaacact tatagactta   2340
agtaacaaca gaataagcac cctttccaac caaagcttca gcaacatgac ccaacttctc   2400
accttaattc tcagttacaa ccgtctgaga tgtatccctc cacggacctt tgatggattg   2460
aaatctcttc gtttactgtc tctacatgga atgacattt ctgtcgtgcc tgaaggtgcc   2520
tttggtgacc tttcagcctt gtcacactta gcaattggag ccaaccctct ttactgtgat   2580
tgtaacatgc agtggttatc cgactgggtg aagtcggaat ataaggaacc tggaattgcc   2640
cgctgtgccg gtcccggaga aatggcagat aaattgttac tcacaactcc ctccaaaaaa   2700
tttacatgtc aaggtcctgt ggatgttact attcaagcca agtgtaaccc ctgcttgtca   2760
aatccatgta aaaatgatgg cacctgtaac aatgacccgg tggatttta tcgatgcacc   2820 tgcccatatg gtttcaaggg ccaggactgt gatgtcccca ttcatgcctg tatcagtaat   2880
ccatgtaaac atggaggaac ttgccacta aaagaaggag agaatgatgg attctggtgt   2940
acttgtgctg atgggtttga aggagaaagc tgtgacatca atattgatga ttgcgaagat   3000
aatgattgtg aaaataattc tacatgcgtt gatggaatta caactacac gtgtctttgc   3060 ccaccggaat acacaggcga actgtgtgag gaaaaactgg acttctgtgc acaagacctg   3120
aatccctgcc agcatgactc caagtgcatc ctgacgccaa agggattcaa gtgtgactgc   3180
actccgggat acattggtga gcactgtgac atcgactttg atgactgcca agataacaag   3240
tgcaaaaacg tgctcattg cacagatgca gtgaacggat acacatgtgt ctgtcctgaa   3300
ggctacagtg gcttgttctg tgagttttct ccacccatgg tcctccctcg caccagcccc   3360
tgtgataatt ttgattgtca gaatggagcc cagtgtatca tcagggtgaa tgaaccaata   3420
tgccagtgtt tgcctggcta cttggggagag aagtgtgaga aattggtcag tgtgaatttt   3480
gtaaacaaag agtcctatct tcagattcct tcagccaagg ttcgacctca gacaaacatc   3540
```

```
acacttcaga ttgccacaga tgaagacagc ggcatcctct tgtacaaggg tgacaaggac    3600
cacattgctg tggaactcta tcgagggcga gttcgagcca gctatgacac cggctctcac    3660
ccggcttctg ccatttacag tgtggagaca atcaatgatg gaaacttcca cattgtagag    3720
ctactgaccc tggattcgag tctttccctc tctgtggatg gaggaagccc taaaatcatc    3780
accaatttgt caaaacaatc tactctgaat ttcgactctc cactttacgt aggaggtatg    3840
cctgggaaaa ataacgtggc ttcgctgcgc caggcccctg gcagaacgg caccagcttc    3900 catggctgta tccggaacct ttacattaac agtgaactgc aggacttccg gaaagtgcct    3960
atgcaaaccg gaattctgcc tggctgtgaa ccatgccaca agaaagtgtg tgcccatggc    4020
acatgccagc ccagcagcca atcaggcttc acctgtgaat gtgaggaagg gtggatgggg    4080
cccctctgtg accagagaac caatgatccc tgtctcggaa acaaatgtgt acatgggacc    4140
tgcttgccca tcaacgcctt ctcctacagc tgcaagtgcc tggagggcca cggcggggtc    4200
ctctgtgatg aagaagaaga tctgtttaac ccctgccagg tgatcaagtg caagcacggg    4260
aagtgcaggc tctctgggct cgggcagccc tattgtgaat gcagcagtgg attcaccggg    4320
gacagctgtg acagagaaat tcttgtcga ggggaacgga taaggattta ttaccaaaag    4380
cagcagggtt acgctgcctg tcaaacgact aagaaagtat ctcgcttgga gtgcagaggc    4440
gggtgtgctg gggggcagtg ctgtggacct ctgagaagca agaggcggaa atactctttc    4500
gaatgcacag atggatctt                                                 4519
```

<210> SEQ ID NO 14
<211> LENGTH: 1525
<212> TYPE: PRT
<213> ORGANISM: Rattus norvegicus

<400> SEQUENCE: 14

```
Met Ser Gly Ile Gly Trp Gln Thr Leu Ser Leu Ser Leu Ala Leu Val
1               5                   10                  15

Leu Ser Ile Leu Asn Gln Val Ala Pro Gln Ala Cys Pro Ala Gln Cys
                20                  25                  30

Ser Cys Ser Gly Ser Thr Val Asp Cys His Gly Leu Ala Leu Arg Ser
            35                  40                  45

Val Pro Arg Asn Ile Pro Arg Asn Thr Glu Arg Leu Asp Leu Asn Gly
        50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190
```

```
Ala Ser Phe Asn His Met Pro Lys Leu Arg Thr Phe Arg Leu His Ser
            195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Gly His Gln Ser Phe Met Ala Pro Ser Cys
            260                 265                 270

Ser Val Leu His Cys Pro Ile Ala Cys Thr Cys Ser Asn Asn Ile Val
            275                 280                 285

Asp Cys Arg Gly Lys Gly Leu Thr Glu Ile Pro Thr Asn Leu Pro Glu
        290                 295                 300

Thr Ile Thr Glu Ile Arg Leu Glu Gln Asn Ser Ile Arg Val Ile Pro
305                 310                 315                 320

Pro Gly Ala Phe Ser Pro Tyr Lys Lys Leu Arg Arg Leu Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Val Ala
                405                 410                 415

Lys Gly Thr Phe Ser Ala Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480

Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Lys Leu Asn Lys Ile Pro Asp His Ile Pro
        515                 520                 525

Gln Tyr Thr Ala Glu Leu Arg Leu Asn Asn Glu Phe Thr Val Leu
    530                 535                 540

Glu Ala Thr Gly Ile Phe Lys Lys Leu Pro Gln Leu Arg Lys Ile Asn
545                 550                 555                 560

Leu Ser Asn Asn Lys Ile Thr Asp Ile Glu Glu Gly Ala Phe Glu Gly
                565                 570                 575

Ala Ser Gly Val Asn Glu Ile Leu Leu Thr Ser Asn Arg Leu Glu Asn
            580                 585                 590

Val Gln His Lys Met Phe Lys Gly Leu Glu Ser Leu Lys Thr Leu Met
        595                 600                 605
```

```
Leu Arg Ser Asn Arg Ile Ser Cys Val Gly Asn Asp Ser Phe Thr Gly
    610                 615                 620

Leu Gly Ser Val Arg Leu Ser Leu Tyr Asp Asn Gln Ile Thr Thr
625                 630                 635                 640

Val Ala Pro Gly Ala Phe Gly Thr Leu His Ser Leu Ser Thr Leu Asn
                645                 650                 655

Leu Leu Ala Asn Pro Phe Asn Cys Asn Cys His Leu Ala Trp Leu Gly
                660                 665                 670

Glu Trp Leu Arg Arg Lys Arg Ile Val Thr Gly Asn Pro Arg Cys Gln
            675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Ser Glu Cys Thr Cys Leu Asp Thr Val Val Arg Cys
                725                 730                 735

Ser Asn Lys Gly Leu Lys Val Leu Pro Lys Gly Ile Pro Arg Asp Val
                740                 745                 750

Thr Glu Leu Tyr Leu Asp Gly Asn Gln Phe Thr Leu Val Pro Lys Glu
            755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
                820                 825                 830

Ile Ser Val Val Pro Glu Gly Ala Phe Gly Asp Leu Ser Ala Leu Ser
            835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895

Pro Ser Lys Lys Phe Thr Cys Gln Gly Pro Val Asp Val Thr Ile Gln
                900                 905                 910

Ala Lys Cys Asn Pro Cys Leu Ser Asn Pro Cys Lys Asn Asp Gly Thr
            915                 920                 925

Cys Asn Asn Asp Pro Val Asp Phe Tyr Arg Cys Thr Cys Pro Tyr Gly
    930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Asn Asp
                965                 970                 975

Gly Phe Trp Cys Thr Cys Ala Asp Gly Phe Glu Gly Glu Ser Cys Asp
                980                 985                 990

Ile Asn Ile Asp Asp Cys Glu Asp  Asn Asp Cys Glu Asn  Asn Ser Thr
            995                 1000                1005

Cys Val  Asp Gly Ile Asn Asn  Tyr Thr Cys Leu Cys  Pro Pro Glu
    1010                1015                1020
```

| | | | | | | | | | | |
|---|---|---|---|---|---|---|---|---|---|---|
|Tyr|Thr|Gly|Glu|Leu|Cys|Glu|Glu|Lys|Leu|Asp|Phe|Cys|Ala|Gln|
| |1025| | | | |1030| | | |1035| | | | |

Asp Leu Asn Pro Cys Gln His Asp Ser Lys Cys Ile Leu Thr Pro
    1040            1045                1050

Lys Gly Phe Lys Cys Asp Cys Thr Pro Gly Tyr Ile Gly Glu His
    1055            1060                1065

Cys Asp Ile Asp Phe Asp Asp Cys Gln Asp Asn Lys Cys Lys Asn
    1070            1075                1080

Gly Ala His Cys Thr Asp Ala Val Asn Gly Tyr Thr Cys Val Cys
    1085            1090                1095

Pro Glu Gly Tyr Ser Gly Leu Phe Cys Glu Phe Ser Pro Pro Met
    1100            1105                1110

Val Leu Pro Arg Thr Ser Pro Cys Asp Asn Phe Asp Cys Gln Asn
    1115            1120                1125

Gly Ala Gln Cys Ile Ile Arg Val Asn Glu Pro Ile Cys Gln Cys
    1130            1135                1140

Leu Pro Gly Tyr Leu Gly Glu Lys Cys Glu Lys Leu Val Ser Val
    1145            1150                1155

Asn Phe Val Asn Lys Glu Ser Tyr Leu Gln Ile Pro Ser Ala Lys
    1160            1165                1170

Val Arg Pro Gln Thr Asn Ile Thr Leu Gln Ile Ala Thr Asp Glu
    1175            1180                1185

Asp Ser Gly Ile Leu Leu Tyr Lys Gly Asp Lys Asp His Ile Ala
    1190            1195                1200

Val Glu Leu Tyr Arg Gly Arg Val Arg Ala Ser Tyr Asp Thr Gly
    1205            1210                1215

Ser His Pro Ala Ser Ala Ile Tyr Ser Val Glu Thr Ile Asn Asp
    1220            1225                1230

Gly Asn Phe His Ile Val Glu Leu Leu Thr Leu Asp Ser Ser Leu
    1235            1240                1245

Ser Leu Ser Val Asp Gly Gly Ser Pro Lys Ile Ile Thr Asn Leu
    1250            1255                1260

Ser Lys Gln Ser Thr Leu Asn Phe Asp Ser Pro Leu Tyr Val Gly
    1265            1270                1275

Gly Met Pro Gly Lys Asn Asn Val Ala Ser Leu Arg Gln Ala Pro
    1280            1285                1290

Gly Gln Asn Gly Thr Ser Phe His Gly Cys Ile Arg Asn Leu Tyr
    1295            1300                1305

Ile Asn Ser Glu Leu Gln Asp Phe Arg Lys Val Pro Met Gln Thr
    1310            1315                1320

Gly Ile Leu Pro Gly Cys Glu Pro Cys His Lys Lys Val Cys Ala
    1325            1330                1335

His Gly Thr Cys Gln Pro Ser Ser Gln Ser Gly Phe Thr Cys Glu
    1340            1345                1350

Cys Glu Glu Gly Trp Met Gly Pro Leu Cys Asp Gln Arg Thr Asn
    1355            1360                1365

Asp Pro Cys Leu Gly Asn Lys Cys Val His Gly Thr Cys Leu Pro
    1370            1375                1380

Ile Asn Ala Phe Ser Tyr Ser Cys Lys Cys Leu Glu Gly His Gly
    1385            1390                1395

Gly Val Leu Cys Asp Glu Glu Asp Leu Phe Asn Pro Cys Gln
    1400            1405                1410

```
Val Ile Lys Cys Lys His Gly Lys Cys Arg Leu Ser Gly Leu Gly
    1415                1420                1425

Gln Pro Tyr Cys Glu Cys Ser Ser Gly Phe Thr Gly Asp Ser Cys
    1430                1435                1440

Asp Arg Glu Ile Ser Cys Arg Gly Glu Arg Ile Arg Asp Tyr Tyr
    1445                1450                1455

Gln Lys Gln Gln Gly Tyr Ala Ala Cys Gln Thr Thr Lys Lys Val
    1460                1465                1470

Ser Arg Leu Glu Cys Arg Gly Gly Cys Ala Gly Gly Gln Cys Cys
    1475                1480                1485

Gly Pro Leu Arg Ser Lys Arg Arg Lys Tyr Ser Phe Glu Cys Thr
    1490                1495                1500

Asp Gly Ser Ser Phe Val Asp Glu Val Glu Lys Val Val Lys Cys
    1505                1510                1515

Gly Cys Thr Arg Cys Ala Ser
    1520                1525

<210> SEQ ID NO 15
<211> LENGTH: 4641
<212> TYPE: DNA
<213> ORGANISM: Canis familiaris

<400> SEQUENCE: 15
atgcgcgggg ccggccggcg ggcgctgccc gtgtcgctgg ggctcgtgct gctgatcctg      60
ggcgaggcgg cgccgcaggc gtgcccggcg cagtgctcct gctcgggcag caccgtggac     120
tgtcacgggc tggcgctgcg cagcgtgccc aggagcatcc cccgcaacac cgagaggctg     180
gatttgaatg caataacat cacacggatt accaagacag atttcgctgg tcttcgacac      240
ctaagagttc ttcagcttat ggagaataag attagcacca ttgaaagagg agcattccag     300
gatcttaagg aactggagag actgcgttta aacagaaatc accttcagct gtttcctgag     360
ttgctgtttc ttgggacttc gaagctgtac aggcttgatc tcagtgaaaa ccaaattcag     420
gcaattccaa ggaaggcttt ccgtggggca gttgacatta aaaatttgca actggattac     480
aaccagatca gctgtattga agatgggca tttagagctc tgcgggacct ggaagtgctc     540
actctcaaca ataacaacat tactagactt tctgtggcaa gtttcaacca tatgcctaaa     600
cttaggactt ttcggctgca ttcaaacaat ctgtattgcg actgccacct ggcctggctt     660
tctgactggc tgcgccaaag gccccgggtt ggtctctaca ctcagtgtat gggcccatcc     720
cacctgaggg tcataacgt agccgaggtt caaaaacgcg aatttgtctg cagtggtaag     780
ggagaaagaa cctttctgtt gtcctattat cttatgctac tttgccacca gtccttcatg     840
gctccttctt gcagcgtcct gcattgtcca gccgcttgta cctgtagcaa caatatcgta     900
gactgtcgtg ggaaaggtct cactgagatc cccacgaacc tgccagagac catcacagaa     960
atacgtttgg aacagaactc aatcaaggtc atccctcctg agctttctc accatataaa     1020 aagcttagaa gaattgacct gagcaataat cagatctctg aactagcacc ggacgctttc     1080
caaggactac gctctctgaa ttcacttgtc ctctatggaa ataaaatcac ggaactccca     1140
aaaagtttat ttgaaggact gttttcctta cagctgctat tattgaatgc aacaagata      1200 aactgccttc gggtagatgc tttcaggat ctgcacaacc tgaatcttct ctccctgtac      1260
gacaacaagc tgcagaccat cgccaagggg accttctcac ctctccgggc cattcagacc     1320
atgcacctgg cccagaaccc ctttatttgt gactgccatc tcaagtggct ggcggactat     1380
```

-continued

```
ctccacacca accccatcga gaccagtggt gcccggtgca ccagcccccg gcgcctggca    1440
aacaaaagaa tcggacagat caaaagcaag aaattccgtt gttcagctaa agaacagtat    1500
ttcattccag gtacagaaga ttatcgatca aaattaagcg gggactgctt tgcagatctg    1560
gcttgccctg aaaagtgccg ctgtgaagga accacagtag attgctccaa tcaaaaactc    1620
accaaaatcc cagaccacat cccccagtac actgcagagc tgcgtctcaa taataatgaa    1680
ttcacagtgc tggaagctac aggaatcttc aagaaacttc cgcagttacg taaaataaac    1740
ttcagcaaca acaagatcac agacattgaa gaaggagcat ttgaaggagc agctggtgta    1800
aacgaaatcc ttctcacgag taaccgtttg gaaaatgttc agcataagat gttcaaggga    1860
ttggaaagcc tgaaaacgtt gatgttgcga agcaatcgca taagctgcgt tggcaacgat    1920
agcttcatag gcctgagctc tgtgcggttg ctttcgctgt acgataatca gatcgccacc    1980
atcgcgccgg gggcgttcga caccctgcac tcgttgtcca ccctaaacct gttggccaac    2040
ccttttaact gcaactgcta cctgcttggg ctgggcgagt ggctcaggaa gaaaagaatt    2100
gtaaccggaa atcctcgctg tcaaaaacca tacttcctca aagaaatccc catccaggac    2160
gtcgccattc aagacttcac gtgtgacgac ggaaatgacg acagtagctg ttctccactc    2220
tcgcgctgtc ccacggaatg cacgtgcttg gatacagttg tccgatgtag caacaagggc    2280
ctgaaggtct tgcccaaagg tattcccaga gacgtcactg aactgtatct ggatgggaac    2340
cactttacct tggttcccaa ggagctctat aactacaaac atctaacgct tatagacctg    2400
agcaacaacc gcataagcac tctttctaat cagagcttca gcaacatgac ccagctcctc    2460
accctaattc tcagttacaa ccgtttgaga tgtattcctc ctcgaacctt cgatggactc    2520
aagtctctcc gattactttc attacatgga aatgacattt ctgttgtgcc tgaaggtgct    2580
ttcagtgatc tctctgcatt atcacaccta gcaatcggag ccaaccccct ttactgtgat    2640
tgcaacatgc agtggttatc ggactgggta agtcggaat acaaagaacc cgggattgct    2700
cgctgtgccg gccccggaga atggcagat aaattattac tcacgactcc ctccaaaaaa    2760
tttacatgtc aaggtcctgt ggatatcaat attctagcta atgtaatcc ctgcttatca    2820 aacccatgta agaatgatgg cacctgtaac aatgatccag tcgactttta tcgctgtacc    2880
tgtccgtatg gtttcaaggg gcaggactgt gatgtcccaa tccacgcatg catcagtaac    2940
ccgtgtacac atggaggaac ttgccactta aaggagggag aaaaagatgg attctggtgt    3000
atttgtgccg atggatttga aggagaaaat tgtgaagtca atgttgatga ctgtgaagat    3060
aatgactgtg aaaataactc tacgtgtgtc gatggaatta ataactacac atgcctttgt    3120
ccgcctgagt acacaggcga gttgtgtgag gagaagctgg acttctgcgc tcaggacctg    3180 aaccctgcc agcacgactc caagtgcatc ctgatgccca aaggattcaa atgcgactgc    3240
acgccggggt acgtgggcga gcactgcgac atcgacttcg acgactgcca ggatcacaag    3300
tgtaaaaacg gagcgcactg cacggacgcg gtgaacggct acacgtgcac ctgccccgaa    3360
ggctacagcg gcttgttctg tgaattctcc ccgcccatgg tcctcccacg caccagcccc    3420
tgtgacaact tcgactgtca gaacggggcg cagtgcatcg tcagggcggg cgagccaatc    3480
tgccagtgtc tgcccggcta ccaggggac aagtgtgaga agttggtcag cgtgaacttc    3540
gtgaacaaag agtcgtatct tcaaattcct tcagccaagg tccggcccca acgaacatc    3600 acccctgcaga ttgccaccga cgaagacagc gggatcctcc tgtacaaggg cgacaaggac    3660
cacattgccg tggagctgta tcggggacgg gtgcgcgcca gctacgacac cggctcgcac    3720
cccgcttctg ccatttacag cgtggagacg atcaatgatg gaaactttca cattgtggaa    3780
```

-continued

```
ctacttgccc tggatcagag cctgtccctc tccgtggatg gagggagccc caaaatcatc    3840
accaacttgt caaagcagtc cactctgaat tttgactctc cactctatgt aggaggcatg    3900
cccgggagga caacgtggc cgcggccctg cgccaggccc cggggcacaa cggcaccagc     3960
ttccacggct gcatccggaa cctgtatatc aacagcgagc tccaggactt ccgccaggtg    4020
cccatgcaga ccggcatcct gcccggctgc gagccgtgcc acaggaaggt gtgtgcccac    4080
ggcgcgtgcc agcccagcag ccagtcgggc ttcacctgcg agtgcgagga gggctggacg    4140
gggcccctgt gtgaccagag gaccaacgac ccctgtctcg ggaacaaatg tgtgcacggc    4200
acctgcttgc ccatcaacgc cttctcctac agctgtaagt gtctggaggg ccacggggc    4260
gtcctctgcg acgaagagga ggacctgttc aaccctgcc aggccatcag gtgcaagcac    4320
gggaaatgca ggctctcggg cctgggccag ccctactgcg aatgcagcag cgggtacacg    4380
ggggatagct gcgaccgaga agtgtcctgt cggggcgagc gcgtccggga ctactaccca    4440
aagcagcagg gctacgcggc ctgccagacc accaagaagg tgtcgcggct ggagtgcagg    4500
ggcggctgcg cggccgggca gtgctgcggg ccgctgcgga gcaagcggcg gaaatactcc    4560
ttcgagtgca cggacggctc gtcgttcgtg gacgaggtgg agaaggtggt caagtgcggc    4620
tgcagcaggt gcgccgcctg a                                              4641
```

<210> SEQ ID NO 16
<211> LENGTH: 1546
<212> TYPE: PRT
<213> ORGANISM: Canis familiaris

<400> SEQUENCE: 16

```
Met Arg Gly Ala Gly Arg Arg Ala Leu Pro Val Ser Leu Gly Leu Val
1               5                   10                  15

Leu Leu Ile Leu Gly Glu Ala Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Ser Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ser Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205
```

-continued

```
Asn Asn Leu Tyr Cys Asp Cys His Leu Ala Trp Leu Ser Asp Trp Leu
    210                 215                 220
Arg Gln Arg Pro Arg Val Gly Leu Tyr Thr Gln Cys Met Gly Pro Ser
225                 230                 235                 240
His Leu Arg Gly His Asn Val Ala Glu Val Gln Lys Arg Glu Phe Val
                245                 250                 255
Cys Ser Gly Lys Gly Glu Arg Thr Phe Leu Leu Ser Tyr Tyr Leu Met
                260                 265                 270
Leu Leu Cys His Gln Ser Phe Met Ala Pro Ser Cys Ser Val Leu His
        275                 280                 285
Cys Pro Ala Ala Cys Thr Cys Ser Asn Asn Ile Val Asp Cys Arg Gly
290                 295                 300
Lys Gly Leu Thr Glu Ile Pro Thr Asn Leu Pro Glu Thr Ile Thr Glu
305                 310                 315                 320
Ile Arg Leu Glu Gln Asn Ser Ile Lys Val Ile Pro Pro Gly Ala Phe
                325                 330                 335
Ser Pro Tyr Lys Lys Leu Arg Arg Ile Asp Leu Ser Asn Asn Gln Ile
                340                 345                 350
Ser Glu Leu Ala Pro Asp Ala Phe Gln Gly Leu Arg Ser Leu Asn Ser
        355                 360                 365
Leu Val Leu Tyr Gly Asn Lys Ile Thr Glu Leu Pro Lys Ser Leu Phe
    370                 375                 380
Glu Gly Leu Phe Ser Leu Gln Leu Leu Leu Leu Asn Ala Asn Lys Ile
385                 390                 395                 400
Asn Cys Leu Arg Val Asp Ala Phe Gln Asp Leu His Asn Leu Asn Leu
                405                 410                 415
Leu Ser Leu Tyr Asp Asn Lys Leu Gln Thr Ile Ala Lys Gly Thr Phe
                420                 425                 430
Ser Pro Leu Arg Ala Ile Gln Thr Met His Leu Ala Gln Asn Pro Phe
        435                 440                 445
Ile Cys Asp Cys His Leu Lys Trp Leu Ala Asp Tyr Leu His Thr Asn
    450                 455                 460
Pro Ile Glu Thr Ser Gly Ala Arg Cys Thr Ser Pro Arg Arg Leu Ala
465                 470                 475                 480
Asn Lys Arg Ile Gly Gln Ile Lys Ser Lys Lys Phe Arg Cys Ser Ala
                485                 490                 495
Lys Glu Gln Tyr Phe Ile Pro Gly Thr Glu Asp Tyr Arg Ser Lys Leu
                500                 505                 510
Ser Gly Asp Cys Phe Ala Asp Leu Ala Cys Pro Glu Lys Cys Arg Cys
        515                 520                 525
Glu Gly Thr Thr Val Asp Cys Ser Asn Gln Lys Leu Thr Lys Ile Pro
    530                 535                 540
Asp His Ile Pro Gln Tyr Thr Ala Glu Leu Arg Leu Asn Asn Asn Glu
545                 550                 555                 560
Phe Thr Val Leu Glu Ala Thr Gly Ile Phe Lys Lys Leu Pro Gln Leu
                565                 570                 575
Arg Lys Ile Asn Phe Ser Asn Asn Lys Ile Thr Asp Ile Glu Glu Gly
                580                 585                 590
Ala Phe Glu Gly Ala Ala Gly Val Asn Glu Ile Leu Leu Thr Ser Asn
        595                 600                 605
Arg Leu Glu Asn Val Gln His Lys Met Phe Lys Gly Leu Glu Ser Leu
    610                 615                 620
```

-continued

Lys Thr Leu Met Leu Arg Ser Asn Arg Ile Ser Cys Val Gly Asn Asp
625                 630                 635                 640

Ser Phe Ile Gly Leu Ser Ser Val Arg Leu Leu Ser Leu Tyr Asp Asn
            645                 650                 655

Gln Ile Ala Thr Ile Ala Pro Gly Ala Phe Asp Thr Leu His Ser Leu
            660                 665                 670

Ser Thr Leu Asn Leu Leu Ala Asn Pro Phe Asn Cys Asn Cys Tyr Leu
            675                 680                 685

Ala Trp Leu Gly Glu Trp Leu Arg Lys Lys Arg Ile Val Thr Gly Asn
            690                 695                 700

Pro Arg Cys Gln Lys Pro Tyr Phe Leu Lys Glu Ile Pro Ile Gln Asp
705                 710                 715                 720

Val Ala Ile Gln Asp Phe Thr Cys Asp Asp Gly Asn Asp Asp Ser Ser
            725                 730                 735

Cys Ser Pro Leu Ser Arg Cys Pro Thr Glu Cys Thr Cys Leu Asp Thr
            740                 745                 750

Val Val Arg Cys Ser Asn Lys Gly Leu Lys Val Leu Pro Lys Gly Ile
            755                 760                 765

Pro Arg Asp Val Thr Glu Leu Tyr Leu Asp Gly Asn His Phe Thr Leu
770                 775                 780

Val Pro Lys Glu Leu Tyr Asn Tyr Lys His Leu Thr Leu Ile Asp Leu
785                 790                 795                 800

Ser Asn Asn Arg Ile Ser Thr Leu Ser Asn Gln Ser Phe Ser Asn Met
            805                 810                 815

Thr Gln Leu Leu Thr Leu Ile Leu Ser Tyr Asn Arg Leu Arg Cys Ile
            820                 825                 830

Pro Pro Arg Thr Phe Asp Gly Leu Lys Ser Leu Arg Leu Leu Ser Leu
            835                 840                 845

His Gly Asn Asp Ile Ser Val Val Pro Glu Gly Ala Phe Ser Asp Leu
            850                 855                 860

Ser Ala Leu Ser His Leu Ala Ile Gly Ala Asn Pro Leu Tyr Cys Asp
865                 870                 875                 880

Cys Asn Met Gln Trp Leu Ser Asp Trp Val Lys Ser Glu Tyr Lys Glu
            885                 890                 895

Pro Gly Ile Ala Arg Cys Ala Gly Pro Gly Glu Met Ala Asp Lys Leu
            900                 905                 910

Leu Leu Thr Thr Pro Ser Lys Lys Phe Thr Cys Gln Gly Pro Val Asp
            915                 920                 925

Ile Asn Ile Leu Ala Lys Cys Asn Pro Cys Leu Ser Asn Pro Cys Lys
930                 935                 940

Asn Asp Gly Thr Cys Asn Asn Asp Pro Val Asp Phe Tyr Arg Cys Thr
945                 950                 955                 960

Cys Pro Tyr Gly Phe Lys Gly Gln Asp Cys Asp Val Pro Ile His Ala
            965                 970                 975

Cys Ile Ser Asn Pro Cys Thr His Gly Gly Thr Cys His Leu Lys Glu
            980                 985                 990

Gly Glu Lys Asp Gly Phe Trp Cys Ile Cys Ala Asp Gly Phe Glu Gly
            995                 1000                1005

Glu Asn Cys Glu Val Asn Val Asp Asp Cys Glu Asp Asn Asp Cys
    1010                1015                1020

Glu Asn Asn Ser Thr Cys Val Asp Gly Ile Asn Asn Tyr Thr Cys
    1025                1030                1035

-continued

```
Leu Cys Pro Pro Glu Tyr Thr Gly Glu Leu Cys Glu Glu Lys Leu
    1040                1045                1050

Asp Phe Cys Ala Gln Asp Leu Asn Pro Cys Gln His Asp Ser Lys
    1055                1060                1065

Cys Ile Leu Met Pro Lys Gly Phe Lys Cys Asp Cys Thr Pro Gly
    1070                1075                1080

Tyr Val Gly Glu His Cys Asp Ile Asp Phe Asp Cys Gln Asp
    1085                1090                1095

His Lys Cys Lys Asn Gly Ala His Cys Thr Asp Ala Val Asn Gly
    1100                1105                1110

Tyr Thr Cys Thr Cys Pro Glu Gly Tyr Ser Gly Leu Phe Cys Glu
    1115                1120                1125

Phe Ser Pro Pro Met Val Leu Pro Arg Thr Ser Pro Cys Asp Asn
    1130                1135                1140

Phe Asp Cys Gln Asn Gly Ala Gln Cys Ile Val Arg Ala Gly Glu
    1145                1150                1155

Pro Ile Cys Gln Cys Leu Pro Gly Tyr Gln Gly Asp Lys Cys Glu
    1160                1165                1170

Lys Leu Val Ser Val Asn Phe Val Asn Lys Glu Ser Tyr Leu Gln
    1175                1180                1185

Ile Pro Ser Ala Lys Val Arg Pro Gln Thr Asn Ile Thr Leu Gln
    1190                1195                1200

Ile Ala Thr Asp Glu Asp Ser Gly Ile Leu Leu Tyr Lys Gly Asp
    1205                1210                1215

Lys Asp His Ile Ala Val Glu Leu Tyr Arg Gly Arg Val Arg Ala
    1220                1225                1230

Ser Tyr Asp Thr Gly Ser His Pro Ala Ser Ala Ile Tyr Ser Val
    1235                1240                1245

Glu Thr Ile Asn Asp Gly Asn Phe His Ile Val Glu Leu Leu Ala
    1250                1255                1260

Leu Asp Gln Ser Leu Ser Leu Ser Val Asp Gly Gly Ser Pro Lys
    1265                1270                1275

Ile Ile Thr Asn Leu Ser Lys Gln Ser Thr Leu Asn Phe Asp Ser
    1280                1285                1290

Pro Leu Tyr Val Gly Gly Met Pro Gly Arg Asn Asn Val Ala Ala
    1295                1300                1305

Ala Leu Arg Gln Ala Pro Gly His Asn Gly Thr Ser Phe His Gly
    1310                1315                1320

Cys Ile Arg Asn Leu Tyr Ile Asn Ser Glu Leu Gln Asp Phe Arg
    1325                1330                1335

Gln Val Pro Met Gln Thr Gly Ile Leu Pro Gly Cys Glu Pro Cys
    1340                1345                1350

His Arg Lys Val Cys Ala His Gly Ala Cys Gln Pro Ser Ser Gln
    1355                1360                1365

Ser Gly Phe Thr Cys Glu Cys Glu Glu Gly Trp Thr Gly Pro Leu
    1370                1375                1380

Cys Asp Gln Arg Thr Asn Asp Pro Cys Leu Gly Asn Lys Cys Val
    1385                1390                1395

His Gly Thr Cys Leu Pro Ile Asn Ala Phe Ser Tyr Ser Cys Lys
    1400                1405                1410

Cys Leu Glu Gly His Gly Gly Val Leu Cys Asp Glu Glu Asp
    1415                1420                1425
```

| | | | | | | | | | | |
|---|---|---|---|---|---|---|---|---|---|---|
| Leu | Phe | Asn | Pro | Cys | Gln | Ala | Ile | Arg | Cys | Lys | His | Gly | Lys | Cys |
| | 1430 | | | | 1435 | | | | 1440 | |

Arg Leu Ser Gly Leu Gly Gln Pro Tyr Cys Glu Cys Ser Ser Gly
1445                1450                1455

Tyr Thr Gly Asp Ser Cys Asp Arg Glu Val Ser Cys Arg Gly Glu
1460                1465                1470

Arg Val Arg Asp Tyr Tyr Pro Lys Gln Gln Gly Tyr Ala Ala Cys
1475                1480                1485

Gln Thr Thr Lys Lys Val Ser Arg Leu Glu Cys Arg Gly Gly Cys
1490                1495                1500

Ala Ala Gly Gln Cys Cys Gly Pro Leu Arg Ser Lys Arg Arg Lys
1505                1510                1515

Tyr Ser Phe Glu Cys Thr Asp Gly Ser Ser Phe Val Asp Glu Val
1520                1525                1530

Glu Lys Val Val Lys Cys Gly Cys Ser Arg Cys Ala Ala
1535                1540                1545

```
<210> SEQ ID NO 17
<211> LENGTH: 4605
<212> TYPE: DNA
<213> ORGANISM: Bos taurus

<400> SEQUENCE: 17
atgcacggcg tcggctggca gacgctgtcc ctgtctctgg ggttagtgct ggcgatcctg     60
aacgaggtgg cgccgcaagc gtgtccggcg cagtgctcct gctccgggag cacagtggac    120
tgtcacgggc tggcgttgcg cagtgtgccc aggaatatcc cccgcaacac cgagagattg    180
gatttgaatg gaaataacat cacaaggatt accaagacag attttgctgg tcttcgacac    240
ctaagagttc ttcagcttat ggagaataag attaccacca ttgaaagagg agcattccag    300
gatcttaaag aactggagag actgcgttta acagaaatc  accttcagct gtttcctgag    360
ttgctgtttc ttgggacttc gaagctatac aggcttgacc tcagtgaaaa ccagattcag    420
gcaattccaa ggaaagcttt tcgtggggca gttgatatta aaaatctgca actggattac    480
aaccacatca gctgtattga agatgggca ttcagggctc tccgggacct ggaagtgctc    540
actctcaaca ataacaacat tactagactt tctgtggcaa gtttcaacca tatgcctaaa    600
cttaggactt ttcgactcca ttcgaacaac ctatattgtg actgccacct ggcctggctc    660
tcggactggc tgcgccaaag gcctcgggtg ggcctctaca ctcagtgtat ggggccatct    720
cacctgaggg gccacaatgt agctgaggtt caaaaacgag aatttgtctg cagcgatgag    780
gaagaaggtc accagtcatt tatggctcct tcttgcagtg ttttgcactg cccagctgct    840
tgtacctgta gcaacaacat cgtagattgc cgtgggaaag gtctcactga gatcccacg     900 aatctgccag agaccatcac agaaatacgt ttggaacaga actcaatcaa ggtcatccct    960
cctggagctt tctcaccata taaaaagctt agaagaatcg acctgagcaa taatcagatc   1020
tctgagctag caccagatgc tttccaagga ctacgctctc tgaattcact tgtcctctat   1080
ggaaataaaa tcacagaact cccaaaaagt ttatttgaag gactgttttc cttacagtta   1140
ctattactga atgccaacaa gataaactgc ctccgggtag atgcttttca ggatctgcac   1200
aacctgaacc ttctctcctt atatgacaac aagcttcaga ccatcgccaa ggggaccttt   1260
tcacctctcc gggccattca aaccatgcat ttggcccaga ccccttatt tgtgactgc     1320 catctcaagt ggctggcgga ttatctccat accaacccaa tcgagaccag tggtgcccgc   1380
tgcaccagtc cccggcgact ggcaaacaaa agaatcggac agatcaaaag caagaaattc   1440
```

| | |
|---|---|
| cgttgttcag ctaaagaaca gtatttcatt ccaggtacag aagattatcg atcaaaatta | 1500 |
| agtggggact gctttgccga tttggcttgc cctgaaaagt gccgctgcga agggaccaca | 1560 |
| gtagactgct ccaatcaaaa actcaccaaa atcccagatc acattcccca gtacactgca | 1620 |
| gagctgcgcc tcaacaataa tgaatttaca gtgttggaag ctaccgggat cttcaagaaa | 1680 |
| cttcctcagt tacgtaaaat aaactttagc aacaataaga tcacagacat gaagaggga | 1740 |
| gcgtttgaag gagcatctgg tgtgaatgaa atacttctca cgagtaatcg tttggaaaat | 1800 |
| gttcagcata agatgttcaa gggcttggaa agcctcaaga ctttgatgtt gagaagtaat | 1860 |
| cgcataagct gtgtagggaa tgacagtttc ataggactca gctctgtgcg tttgcttttct | 1920 |
| ttatatgata atcagattac taccattgca ccaggagctt ttgatactct ccattcttta | 1980 |
| tctactctaa acctcttggc caatccttc aactgtaact gctacctggc ttggttggga | 2040 |
| gaatggctta ggaagaaaag aattgtaaca ggaaatcctc gatgtcagaa accctatttc | 2100 |
| ctcaaagaaa tccccatcca ggatgtggcc attcaagact tcacttgtga tgatggaaat | 2160 |
| gatgacaata gctgttcccc actctctcgc tgtcctgccg agtgtacctg cttggacaca | 2220 |
| gtggttcgat gtagcaacaa agccttgaag gtcttgccca aaggaattcc aagagatgtc | 2280 |
| actgaattgt atctggatgg gaaccagttt accttggttc ctaaggaact ctctaactac | 2340 |
| aaacatttaa cacttataga cttaagtaac aacagaataa gcaccctctc taatcagagc | 2400 |
| ttcagcaaca tgacccagct cctcacttta attcttagtt acaaccgttt gagatgtatt | 2460 |
| cctcctcgaa ccttcgatgg actgaagtct cttcggttac tttctttaca tggaaacgac | 2520 |
| atttctgttg tgcctgaagg tgctttcaat gatcttgctg cattatcaca cctagcaatt | 2580 |
| ggagccaacc ctcttactg tgattgtaac atgcagtggt tatccgactg ggtaaagtcg | 2640 |
| gaatacaaag agccgggaat tgctcgctgt gctggtcctg gagaaatggc agataaacta | 2700 |
| cttctcacaa ctccctccaa aaaatttaca tgtcaaggtc ctgtggatgt caatattcta | 2760 |
| gctaaatgta atccctgctt atcaaatcca tgtaaaaatg atggcacctg taacaatgac | 2820 |
| ccagttgact tttatcgctg cacctgtcca tatggtttca aggggcagga ttgtgatgtt | 2880 |
| ccaattcatg cgtgcatcag caacccatgt aaacatggag gaacttgcca cttaaaagaa | 2940 |
| ggagaaaaag atggattctg tgtgtatttgt gctgatggat ttgaaggaga aaattgtgaa | 3000 |
| atcaatgttg atgactgtga agataatgac tgtgaaaata actctacatg tgtcgatgga | 3060 |
| attaataact acacatgcct ttgcccacct gagtacacag gagagttgtg tgaggagaaa | 3120 |
| ctggacttct gtgcccagga cttgaaccc tgccagcatg actccaagtg catcctgacg | 3180 |
| ccaaagggat acaaatgtga ctgcactcca ggatacatag gcgaacattg tgacattgac | 3240 |
| ttcgatgact gccaagataa caagtgtaag aacggagccc actgcaccga tgcagtgaac | 3300 |
| ggttacacat gcacctgtcc tgaaggctac agtggcttgt tttgtgaatt ttctccacct | 3360 |
| atggttctcc ctcgtaccag cccctgtgat aattttgatt gtcagaatgg agctcaatgc | 3420 |
| atcatcagga tcaatgagcc aatatgccag tgtttgcctg gctaccaggg agaaaagtgt | 3480 |
| gaaaaactgg tcagtgtgaa ttttgtaaac aaagagtctt atcttcagat cccttccgcc | 3540 |
| aaggtccggc tcaaacaaa catcactctt cagatcgcca cagatgaaga cagtggaatc | 3600 |
| ctcctgtata agggtgataa agaccatatt gctgtagaac tctaccgagg acgtgttcgt | 3660 |
| gccagctatg acaccggctc ccacccggct tctgccattt acagtgtgga gacaatcaat | 3720 |
| gacggaaatt ttcacattgt ggaactactt gccctggatc aaagtctctc cctctcagtg | 3780 |

```
gatggaggga gccccaaaat cattaccaac ttgtcaaaac agtccactct gaattttgac    3840
tccccactct atgttggagg catgcccggg aagaacaacg tggccgcagc tctgcgccag    3900
gcccctgggc agaatggcac cagcttccac ggttgcatcc ggaaccttta catcaacagc    3960
gaacttcagg acttcggaa ggtgcccatg cagaccggca tcctgcctgg ctgtgaacca    4020
tgccacaaga aggtgtgtgc ccacggcaca tgccagccca gcagccaggc cggcttcacc    4080
tgcgagtgcg aggaaggatg gacagggccc ctctgtgatc agaggaccaa tgaccctgt     4140 cttggaaata aatgcgtcca cggcacctgc ctgcccatca atgcgttctc ctacagctgc    4200
aaatgcctag agggccatgg gggcgtcctc tgtgatgaag aggaggatct gtttaaccca    4260
tgccaggcga tcaagtgcaa gcatgggaaa tgcaggctct caggactggg gcagccctac    4320
tgtgaatgca gcagtggata caccggggac agctgtgatc gagaaatctc ttgtcgaggg    4380
gaacggataa agattatta ccaaaagcag cagggctacg ccgcttgcca gacgaccaag    4440
aaggtgtctc ggttggaatg cagagggggc tgtgcaggcg ggcagtgctg cggacctctg    4500
aggagcaaga aaggaaata ctctttcgaa tgcactgatg ggtcctcgtt tgtggacgag    4560
gtggagaagg tggtaaagtg tggctgtacc cgctgcgctt cctaa                    4605
```

<210> SEQ ID NO 18
<211> LENGTH: 1534
<212> TYPE: PRT
<213> ORGANISM: Bos taurus

<400> SEQUENCE: 18

```
Met His Gly Val Gly Trp Gln Thr Leu Ser Leu Ser Leu Gly Leu Val
1               5                   10                  15

Leu Ala Ile Leu Asn Glu Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Thr Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ser Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn His Ile Ser Cys Ile Glu Asp Gly Ala Phe Arg Ala Leu Arg Asp
                165                 170                 175

Leu Glu Val Leu Thr Leu Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220
```

```
Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
            245                 250                 255

Cys Ser Asp Glu Glu Gly His Gln Ser Phe Met Ala Pro Ser Cys
        260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
        290                 295                 300

Thr Ile Thr Glu Ile Arg Leu Glu Gln Asn Ser Ile Lys Val Ile Pro
305                 310                 315                 320

Pro Gly Ala Phe Ser Pro Tyr Lys Lys Leu Arg Arg Ile Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Ile Ala
                405                 410                 415

Lys Gly Thr Phe Ser Pro Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
        450                 455                 460

Arg Arg Leu Ala Asn Lys Arg Ile Gly Gln Ile Lys Ser Lys Lys Phe
465                 470                 475                 480

Arg Cys Ser Ala Lys Glu Gln Tyr Phe Ile Pro Gly Thr Glu Asp Tyr
                485                 490                 495

Arg Ser Lys Leu Ser Gly Asp Cys Phe Ala Asp Leu Ala Cys Pro Glu
            500                 505                 510

Lys Cys Arg Cys Glu Gly Thr Thr Val Asp Cys Ser Asn Gln Lys Leu
        515                 520                 525

Thr Lys Ile Pro Asp His Ile Pro Gln Tyr Thr Ala Glu Leu Arg Leu
530                 535                 540

Asn Asn Asn Glu Phe Thr Val Leu Glu Ala Thr Gly Ile Phe Lys Lys
545                 550                 555                 560

Leu Pro Gln Leu Arg Lys Ile Asn Phe Ser Asn Asn Lys Ile Thr Asp
                565                 570                 575

Ile Glu Glu Gly Ala Phe Glu Gly Ala Ser Gly Val Asn Glu Ile Leu
            580                 585                 590

Leu Thr Ser Asn Arg Leu Glu Asn Val Gln His Lys Met Phe Lys Gly
        595                 600                 605

Leu Glu Ser Leu Lys Thr Leu Met Leu Arg Ser Asn Arg Ile Ser Cys
        610                 615                 620

Val Gly Asn Asp Ser Phe Ile Gly Leu Ser Ser Val Arg Leu Leu Ser
625                 630                 635                 640
```

-continued

Leu Tyr Asp Asn Gln Ile Thr Thr Ile Ala Pro Gly Ala Phe Asp Thr
            645                 650                 655

Leu His Ser Leu Ser Thr Leu Asn Leu Leu Ala Asn Pro Phe Asn Cys
        660                 665                 670

Asn Cys Tyr Leu Ala Trp Leu Gly Glu Trp Leu Arg Lys Lys Arg Ile
        675                 680                 685

Val Thr Gly Asn Pro Arg Cys Gln Lys Pro Tyr Phe Leu Lys Glu Ile
    690                 695                 700

Pro Ile Gln Asp Val Ala Ile Gln Asp Phe Thr Cys Asp Asp Gly Asn
705                 710                 715                 720

Asp Asp Asn Ser Cys Ser Pro Leu Ser Arg Cys Pro Ala Glu Cys Thr
            725                 730                 735

Cys Leu Asp Thr Val Val Arg Cys Ser Asn Lys Ala Leu Lys Val Leu
            740                 745                 750

Pro Lys Gly Ile Pro Arg Asp Val Thr Glu Leu Tyr Leu Asp Gly Asn
        755                 760                 765

Gln Phe Thr Leu Val Pro Lys Glu Leu Ser Asn Tyr Lys His Leu Thr
    770                 775                 780

Leu Ile Asp Leu Ser Asn Asn Arg Ile Ser Thr Leu Ser Asn Gln Ser
785                 790                 795                 800

Phe Ser Asn Met Thr Gln Leu Leu Thr Leu Ile Leu Ser Tyr Asn Arg
            805                 810                 815

Leu Arg Cys Ile Pro Pro Arg Thr Phe Asp Gly Leu Lys Ser Leu Arg
            820                 825                 830

Leu Leu Ser Leu His Gly Asn Asp Ile Ser Val Val Pro Glu Gly Ala
        835                 840                 845

Phe Asn Asp Leu Ala Ala Leu Ser His Leu Ala Ile Gly Ala Asn Pro
    850                 855                 860

Leu Tyr Cys Asp Cys Asn Met Gln Trp Leu Ser Asp Trp Val Lys Ser
865                 870                 875                 880

Glu Tyr Lys Glu Pro Gly Ile Ala Arg Cys Ala Gly Pro Gly Glu Met
            885                 890                 895

Ala Asp Lys Leu Leu Leu Thr Thr Pro Ser Lys Lys Phe Thr Cys Gln
        900                 905                 910

Gly Pro Val Asp Val Asn Ile Leu Ala Lys Cys Asn Pro Cys Leu Ser
    915                 920                 925

Asn Pro Cys Lys Asn Asp Gly Thr Cys Asn Asn Asp Pro Val Asp Phe
    930                 935                 940

Tyr Arg Cys Thr Cys Pro Tyr Gly Phe Lys Gly Gln Asp Cys Asp Val
945                 950                 955                 960

Pro Ile His Ala Cys Ile Ser Asn Pro Cys Lys His Gly Gly Thr Cys
            965                 970                 975

His Leu Lys Glu Gly Glu Lys Asp Gly Phe Trp Cys Ile Cys Ala Asp
            980                 985                 990

Gly Phe Glu Gly Glu Asn Cys Glu Ile Asn Val Asp Asp Cys Glu Asp
        995                 1000                1005

Asn Asp Cys Glu Asn Asn Ser Thr Cys Val Asp Gly Ile Asn Asn
    1010                1015                1020

Tyr Thr Cys Leu Cys Pro Pro Glu Tyr Thr Gly Glu Leu Cys Glu
    1025                1030                1035

Glu Lys Leu Asp Phe Cys Ala Gln Asp Leu Asn Pro Cys Gln His
    1040                1045                1050

```
Asp Ser Lys Cys Ile Leu Thr Pro Lys Gly Tyr Lys Cys Asp Cys
    1055                1060                1065

Thr Pro Gly Tyr Ile Gly Glu His Cys Asp Ile Asp Phe Asp Asp
    1070                1075                1080

Cys Gln Asp Asn Lys Cys Lys Asn Gly Ala His Cys Thr Asp Ala
    1085                1090                1095

Val Asn Gly Tyr Thr Cys Thr Cys Pro Glu Gly Tyr Ser Gly Leu
    1100                1105                1110

Phe Cys Glu Phe Ser Pro Pro Met Val Leu Pro Arg Thr Ser Pro
    1115                1120                1125

Cys Asp Asn Phe Asp Cys Gln Asn Gly Ala Gln Cys Ile Ile Arg
    1130                1135                1140

Ile Asn Glu Pro Ile Cys Gln Cys Leu Pro Gly Tyr Gln Gly Glu
    1145                1150                1155

Lys Cys Glu Lys Leu Val Ser Val Asn Phe Val Asn Lys Glu Ser
    1160                1165                1170

Tyr Leu Gln Ile Pro Ser Ala Lys Val Arg Pro Gln Thr Asn Ile
    1175                1180                1185

Thr Leu Gln Ile Ala Thr Asp Glu Asp Ser Gly Ile Leu Leu Tyr
    1190                1195                1200

Lys Gly Asp Lys Asp His Ile Ala Val Glu Leu Tyr Arg Gly Arg
    1205                1210                1215

Val Arg Ala Ser Tyr Asp Thr Gly Ser His Pro Ala Ser Ala Ile
    1220                1225                1230

Tyr Ser Val Glu Thr Ile Asn Asp Gly Asn Phe His Ile Val Glu
    1235                1240                1245

Leu Leu Ala Leu Asp Gln Ser Leu Ser Leu Ser Val Asp Gly Gly
    1250                1255                1260

Ser Pro Lys Ile Ile Thr Asn Leu Ser Lys Gln Ser Thr Leu Asn
    1265                1270                1275

Phe Asp Ser Pro Leu Tyr Val Gly Gly Met Pro Gly Lys Asn Asn
    1280                1285                1290

Val Ala Ala Ala Leu Arg Gln Ala Pro Gly Gln Asn Gly Thr Ser
    1295                1300                1305

Phe His Gly Cys Ile Arg Asn Leu Tyr Ile Asn Ser Glu Leu Gln
    1310                1315                1320

Asp Phe Arg Lys Val Pro Met Gln Thr Gly Ile Leu Pro Gly Cys
    1325                1330                1335

Glu Pro Cys His Lys Lys Val Cys Ala His Gly Thr Cys Gln Pro
    1340                1345                1350

Ser Ser Gln Ala Gly Phe Thr Cys Glu Cys Glu Glu Gly Trp Thr
    1355                1360                1365

Gly Pro Leu Cys Asp Gln Arg Thr Asn Asp Pro Cys Leu Gly Asn
    1370                1375                1380

Lys Cys Val His Gly Thr Cys Leu Pro Ile Asn Ala Phe Ser Tyr
    1385                1390                1395

Ser Cys Lys Cys Leu Glu Gly His Gly Gly Val Leu Cys Asp Glu
    1400                1405                1410

Glu Glu Asp Leu Phe Asn Pro Cys Gln Ala Ile Lys Cys Lys His
    1415                1420                1425

Gly Lys Cys Arg Leu Ser Gly Leu Gly Gln Pro Tyr Cys Glu Cys
    1430                1435                1440
```

| | | | | | | | | | | | |
|---|---|---|---|---|---|---|---|---|---|---|---|
| Ser | Ser | Gly | Tyr | Thr | Gly | Asp | Ser | Cys | Asp | Arg | Glu | Ile | Ser | Cys |
| | 1445 | | | | 1450 | | | | 1455 | | |
| Arg | Gly | Glu | Arg | Ile | Arg | Asp | Tyr | Tyr | Gln | Lys | Gln | Gln | Gly | Tyr |
| 1460 | | | | | 1465 | | | | 1470 | | |
| Ala | Ala | Cys | Gln | Thr | Thr | Lys | Lys | Val | Ser | Arg | Leu | Glu | Cys | Arg |
| 1475 | | | | | 1480 | | | | 1485 | | |
| Gly | Gly | Cys | Ala | Gly | Gly | Gln | Cys | Cys | Gly | Pro | Leu | Arg | Ser | Lys |
| 1490 | | | | | 1495 | | | | 1500 | | |
| Arg | Arg | Lys | Tyr | Ser | Phe | Glu | Cys | Thr | Asp | Gly | Ser | Ser | Phe | Val |
| 1505 | | | | | 1510 | | | | 1515 | | |
| Asp | Glu | Val | Glu | Lys | Val | Val | Lys | Cys | Gly | Cys | Thr | Arg | Cys | Ala |
| 1520 | | | | | 1525 | | | | 1530 | | |
| Ser |

<210> SEQ ID NO 19
<211> LENGTH: 4587
<212> TYPE: DNA
<213> ORGANISM: Gallus gallus

<400> SEQUENCE: 19

| | |
|---|---|
| atgatgtgcg cctgggggag gctcccctg gccctggggc tgctgctggt gctggcgggc | 60 |
| gaggcggcgc cgcagccgtg cccggcgcag tgctcctgct caggaagcac ggtggactgt | 120 |
| cacgggctgg cgctgcgcgg cgtcccgagg aacatccccc gcaacactga gcggctggac | 180 |
| cttaatggaa ataacatcac cagaatcacc aagaccgact tgctggtct aaggcacctt | 240 |
| cgagttcttc agctcatgga gaacaagatt agcactattg agagaggagc attccaggat | 300 |
| ttaaaagaac tggagaggct gcgcctaaac agaaataacc tccagttgct ttctgaactg | 360 |
| ctctttctgg gacgccgaa gttatacagg cttgatctta gtgaaaatca gattcaagcc | 420 |
| atacccagga aggcatttcg tggagcagta gacataaaaa atctgcaact ggattacaac | 480 |
| cagatcagct gtattgaaga tggggcattt agggctctac gcgacctgga agtgctcact | 540 |
| ctcaacaaca ataacattac tcgactgtcc gtcgcaagtt tcaatcatat gcccaaactc | 600 |
| agaacttttc gcctgcactc caacaacctc tactgtgact gccacctggc ctggctgtcg | 660 |
| gactggctgc ggcagcggcc acgtgtaggc ctctacactc agtgcatggg cccagcacac | 720 |
| ctgcggggcc ataacgtggc tgaggtccag aagcgggagt tcgtctgcag tggtcaccaa | 780 |
| tcatttatgg ctccatcctg cagtgtcttg cattgtcctg ctgcatgcac ctgtagtaac | 840 |
| aacattgtgg actgtcgtgg gaaaggcctt actgaaattc aacaaatct tccagaaacc | 900 |
| attactgaaa tacggttaga acaaaattca atcaaagtca tacctcctgg agctttctca | 960 |
| ccctataaaa agcttcgaag aattgacctg agcaataacc agatctctga agcagctcca | 1020 |
| gatgctttcc agggcttacg ttctctcaat tcacttgtcc tctatggcaa taaaattaca | 1080 |
| gaacttccaa aaggcctatt tgaaggactg ttttctctgc aattgctatt attaaatgcc | 1140 |
| aacaagatca attgcctgcg tgttgatgct tttcaagatc tgcacaactt gaatctccta | 1200 |
| tctttatatg acaacaagct tcagaccatt gcaaaggca cctttcacc tctacgtgca | 1260 |
| attcagacct tgcatttggc tcagaaccca tttatctgtg actgccatct gaagtggctg | 1320 |
| gcggattatc ttcatacaaa ccccattgag accagtggtg cccgctgcac cagcccccgc | 1380 |
| cgtctggcaa acaaaaggat cggccagatc aaaagcaaga attccgctg ctcagctaaa | 1440 |
| gagcagtatt tcattccagg cactgaagat tacagatcca aattaagtgg tgactgcttt | 1500 |
| gcagatttgg cttgccctga gaaatgtcgc tgtgaaggga ccacagtgga ctgctccaat | 1560 |

```
cagaaactca acaaaattcc tgatcacatc ccacagtaca cagcagagtt gcgactcaat    1620
aacaatgaat tttcagtcct ggaagctact gggatcttta agaagcttcc tcaactgcga    1680
aaaataaacc tgagcaataa caagattaca gatattgaag aaggtgcatt tgatggagcc    1740
tctggtgtca atgaactatt gctcactagc aatcgtttgg aaactgttag agacaaaatg    1800
ttcaaaggac tggaaagtct taaaacactg atgctgagga gtaaccgtgt gagctgtgtg    1860
gggaacgaca gtttcacagg cctgagctct gtccgtctgc tctcactata tgacaaccag    1920
atcaccaccg tggcacccgg ctccttcgat accctgcatt cactctctac attaaacctc    1980
ttggccaatc ctttcaactg caactgccat cttgcatggc ttggagattg gctaaggaag    2040
aaacgcattg tgacgggaaa ccctcgctgt cagaaacctt atttcctcaa agagattcct    2100
atccaggatg tggcaattca ggattttaca tgtgatgatg aaatgatgaa caatagctgc    2160
tctccgctgt cccgctgtcc tgcagaatgt acttgtctag acacagttgt tcgctgcagc    2220
aacaaaggcc taaagctttt gcctaaaggc atcccaaaag atgtaactga actatatttg    2280
gatggaaacc agtttactct tgttcctaaa gagctctcca actacaaaca tttaacactt    2340
atagatttaa gtaacaacag aatcagcact ctttctaatc agagcttcag caacatgact    2400
cagctgctca ccttaattct tagttacaac cgcctgaggt gtatccctgc acggactttt    2460
gatgggttga atcacttag gttgctgtct ttacatggca atgatatttc tgtggttcct    2520
gaaggagcct ttaatgatct ttcagcgtta tcacacctgg ctattggagc aaatcctctt    2580
tattgtgatt gtaacatgca atggctgtct gactgggtaa atcagaata caaagaacct    2640 ggtattgcac gatgtgctgg ccctggagaa atggcagata aacttctact tacaactcca    2700
tctaaaaaat ttacttgcca agggcccgtg gatgtcaata ttcttgctaa gtgtaacccc    2760
tgcttatcaa atccatgtaa aaatgatgga acctgcaata atgatccagt tgacttctat    2820
agatgtactt gcccatatgg tttcaagggt caagactgtg atattcccat tcatgcctgc    2880
attagtaacc cttgcaacca tggtggaact tgtcatttga agaaggaga aaagatggt    2940 ttctggtgca cttgtgcaga tggatttgaa ggagaaaatt gtgaaataaa tgttgatgac    3000
tgtgaagaca atgactgtga aaataactct acttgtgtgg atggaattaa taattatact    3060
tgcctttgtc cacctgaata tacaggtgag ctctgtgagg agaaactaga tttctgtgct    3120
caaaacctga acccttgcca gcacgactca aagtgtatct tgactcccaa aggttacaag    3180
tgtgattgca cacctggata tgtaggtgaa cactgcgata ttgacttcga tgactgccag    3240
gacaataaat gtaaaacgg agcacagtgt acggatgcag ttaacgggta acttgtatt    3300 tgcccagagg gatacagtgg cttgttttgt gagttttcgc caccaatggt tttacctcgc    3360
accagcccct tgtgataatta tgaatgccaa aatggagccc agtgtattgt aaaggagagt    3420
gaaccaatct gccagtgttt atcaggctac caggtgagaa atgtgaaaa gctgatcagt    3480 ataaactttg tcaacaaaga atcctatcta caaatccctt cagctaagat acactcccaa    3540
accaatatca ctcttcagat tgccacagac gaagacagtg ggatcctgct ctacaaaggc    3600
gataaggatc atatagcagt agagctgtac cgtggtagag tgagggtcag ttatgacaca    3660
ggatcttatc cagcctctgc tatttacagt gtggaaacta ttaatgatgg caatttccac    3720
attgtggagc tgcttgccat ggatcagatt ctgtctttgt ctattgatgg aggaagcccc    3780
aagataatta ccaatttgtc caagcagtcc actttgaatt ttgattctcc actgtatgtc    3840
ggaggcatgc ctgtgaaaaa taacattgca gctctacgtc agtctccagg acagaatggc    3900
```

```
acaagcttcc atggctgcat ccgtaatctg tatatcaaca gcgaactcca ggacttcaga    3960
aatgtgccac tgcaagtggg aattctgcca ggttgcgagc cttgtcacaa gaaagtttgt    4020
gtgcatggaa catgccatgc taccagccag tcaagcttta cctgtgagtg tgaaggagga    4080
tggactggac ccctctgtga tcaacaaact aatgacccgt gtctcggaaa taaatgtgtg    4140
catggtacct gcttgccgat caatgcattt tcatacagtt gtaaatgcct gcagggacat    4200 ggggagtcc tctgtgatga agaggaaatg ctgtttaacc cctgccaatc catcaggtgt    4260
aaacatggca aatgcaggct ttcaggactt gggaaaccat attgcgaatg cagcagcgga    4320 tacacgggg acagctgtga taagaaaatc tcttgtcgag gggaacgaat ccgagattac    4380
taccaaaagc agcaagggta tgctgcgtgc cagacgacca agaaggtatc gagactagaa    4440
tgtaaaggag gatgttcaac cgggcagtgc tgtggaccac taaggagcaa gagacggaaa    4500
tactcttttg aatgcactga tgggtcgtca tttgtggacg agattgaaaa agtggtgaag    4560
tgtggctgta caaattgtcc ctcctaa                                       4587
```

<210> SEQ ID NO 20
<211> LENGTH: 1528
<212> TYPE: PRT
<213> ORGANISM: Gallus gallus

<400> SEQUENCE: 20

```
Met Met Cys Ala Trp Gly Arg Leu Pro Leu Ala Leu Gly Leu Leu Leu
1               5                   10                  15

Val Leu Ala Gly Glu Ala Ala Pro Gln Pro Cys Pro Ala Gln Cys Ser
            20                  25                  30

Cys Ser Gly Ser Thr Val Asp Cys His Gly Leu Ala Leu Arg Gly Val
        35                  40                  45

Pro Arg Asn Ile Pro Arg Asn Thr Glu Arg Leu Asp Leu Asn Gly Asn
    50                  55                  60

Asn Ile Thr Arg Ile Thr Lys Thr Asp Phe Ala Gly Leu Arg His Leu
65                  70                  75                  80

Arg Val Leu Gln Leu Met Glu Asn Lys Ile Ser Thr Ile Glu Arg Gly
                85                  90                  95

Ala Phe Gln Asp Leu Lys Glu Leu Glu Arg Leu Arg Leu Asn Arg Asn
            100                 105                 110

Asn Leu Gln Leu Leu Ser Glu Leu Leu Phe Leu Gly Thr Pro Lys Leu
        115                 120                 125

Tyr Arg Leu Asp Leu Ser Glu Asn Gln Ile Gln Ala Ile Pro Arg Lys
    130                 135                 140

Ala Phe Arg Gly Ala Val Asp Ile Lys Asn Leu Gln Leu Asp Tyr Asn
145                 150                 155                 160

Gln Ile Ser Cys Ile Glu Asp Gly Ala Phe Arg Ala Leu Arg Asp Leu
                165                 170                 175

Glu Val Leu Thr Leu Asn Asn Asn Asn Ile Thr Arg Leu Ser Val Ala
            180                 185                 190

Ser Phe Asn His Met Pro Lys Leu Arg Thr Phe Arg Leu His Ser Asn
        195                 200                 205

Asn Leu Tyr Cys Asp Cys His Leu Ala Trp Leu Ser Asp Trp Leu Arg
    210                 215                 220

Gln Arg Pro Arg Val Gly Leu Tyr Thr Gln Cys Met Gly Pro Ala His
225                 230                 235                 240

Leu Arg Gly His Asn Val Ala Glu Val Gln Lys Arg Glu Phe Val Cys
                245                 250                 255
```

```
Ser Gly His Gln Ser Phe Met Ala Pro Ser Cys Ser Val Leu His Cys
            260                 265                 270

Pro Ala Ala Cys Thr Cys Ser Asn Asn Ile Val Asp Cys Arg Gly Lys
                275                 280                 285

Gly Leu Thr Glu Ile Pro Thr Asn Leu Pro Glu Thr Ile Thr Glu Ile
        290                 295                 300

Arg Leu Glu Gln Asn Ser Ile Lys Val Ile Pro Pro Gly Ala Phe Ser
305                 310                 315                 320

Pro Tyr Lys Lys Leu Arg Arg Ile Asp Leu Ser Asn Asn Gln Ile Ser
                325                 330                 335

Glu Ala Ala Pro Asp Ala Phe Gln Gly Leu Arg Ser Leu Asn Ser Leu
                340                 345                 350

Val Leu Tyr Gly Asn Lys Ile Thr Glu Leu Pro Lys Gly Leu Phe Glu
                355                 360                 365

Gly Leu Phe Ser Leu Gln Leu Leu Leu Leu Asn Ala Asn Lys Ile Asn
        370                 375                 380

Cys Leu Arg Val Asp Ala Phe Gln Asp Leu His Asn Leu Asn Leu Leu
385                 390                 395                 400

Ser Leu Tyr Asp Asn Lys Leu Gln Thr Ile Ala Lys Gly Thr Phe Ser
                405                 410                 415

Pro Leu Arg Ala Ile Gln Thr Leu His Leu Ala Gln Asn Pro Phe Ile
                420                 425                 430

Cys Asp Cys His Leu Lys Trp Leu Ala Asp Tyr Leu His Thr Asn Pro
                435                 440                 445

Ile Glu Thr Ser Gly Ala Arg Cys Thr Ser Pro Arg Arg Leu Ala Asn
                450                 455                 460

Lys Arg Ile Gly Gln Ile Lys Ser Lys Lys Phe Arg Cys Ser Ala Lys
465                 470                 475                 480

Glu Gln Tyr Phe Ile Pro Gly Thr Glu Asp Tyr Arg Ser Lys Leu Ser
                485                 490                 495

Gly Asp Cys Phe Ala Asp Leu Ala Cys Pro Glu Lys Cys Arg Cys Glu
                500                 505                 510

Gly Thr Thr Val Asp Cys Ser Asn Gln Lys Leu Asn Lys Ile Pro Asp
                515                 520                 525

His Ile Pro Gln Tyr Thr Ala Glu Leu Arg Leu Asn Asn Asn Glu Phe
                530                 535                 540

Ser Val Leu Glu Ala Thr Gly Ile Phe Lys Lys Leu Pro Gln Leu Arg
545                 550                 555                 560

Lys Ile Asn Leu Ser Asn Asn Lys Ile Thr Asp Ile Glu Glu Gly Ala
                565                 570                 575

Phe Asp Gly Ala Ser Gly Val Asn Glu Leu Leu Leu Thr Ser Asn Arg
                580                 585                 590

Leu Glu Thr Val Arg Asp Lys Met Phe Lys Gly Leu Glu Ser Leu Lys
                595                 600                 605

Thr Leu Met Leu Arg Ser Asn Arg Val Ser Cys Val Gly Asn Asp Ser
                610                 615                 620

Phe Thr Gly Leu Ser Ser Val Arg Leu Leu Ser Leu Tyr Asp Asn Gln
625                 630                 635                 640

Ile Thr Thr Val Ala Pro Gly Ser Phe Asp Thr Leu His Ser Leu Ser
                645                 650                 655

Thr Leu Asn Leu Leu Ala Asn Pro Phe Asn Cys Asn Cys His Leu Ala
                660                 665                 670
```

-continued

```
Trp Leu Gly Asp Trp Leu Arg Lys Lys Arg Ile Val Thr Gly Asn Pro
            675                 680                 685
Arg Cys Gln Lys Pro Tyr Phe Leu Lys Glu Ile Pro Ile Gln Asp Val
690                 695                 700
Ala Ile Gln Asp Phe Thr Cys Asp Asp Gly Asn Asp Asp Asn Ser Cys
705                 710                 715                 720
Ser Pro Leu Ser Arg Cys Pro Ala Glu Cys Thr Cys Leu Asp Thr Val
                725                 730                 735
Val Arg Cys Ser Asn Lys Gly Leu Lys Ala Leu Pro Lys Gly Ile Pro
            740                 745                 750
Lys Asp Val Thr Glu Leu Tyr Leu Asp Gly Asn Gln Phe Thr Leu Val
            755                 760                 765
Pro Lys Glu Leu Ser Asn Tyr Lys His Leu Thr Leu Ile Asp Leu Ser
770                 775                 780
Asn Asn Arg Ile Ser Thr Leu Ser Asn Gln Ser Phe Ser Asn Met Thr
785                 790                 795                 800
Gln Leu Leu Thr Leu Ile Leu Ser Tyr Asn Arg Leu Arg Cys Ile Pro
                805                 810                 815
Ala Arg Thr Phe Asp Gly Leu Lys Ser Leu Arg Leu Leu Ser Leu His
            820                 825                 830
Gly Asn Asp Ile Ser Val Val Pro Glu Gly Ala Phe Asn Asp Leu Ser
            835                 840                 845
Ala Leu Ser His Leu Ala Ile Gly Ala Asn Pro Leu Tyr Cys Asp Cys
850                 855                 860
Asn Met Gln Trp Leu Ser Asp Trp Val Lys Ser Glu Tyr Lys Glu Pro
865                 870                 875                 880
Gly Ile Ala Arg Cys Ala Gly Pro Gly Glu Met Ala Asp Lys Leu Leu
                885                 890                 895
Leu Thr Thr Pro Ser Lys Lys Phe Thr Cys Gln Gly Pro Val Asp Val
            900                 905                 910
Asn Ile Leu Ala Lys Cys Asn Pro Cys Leu Ser Asn Pro Cys Lys Asn
            915                 920                 925
Asp Gly Thr Cys Asn Asn Asp Pro Val Asp Phe Tyr Arg Cys Thr Cys
930                 935                 940
Pro Tyr Gly Phe Lys Gly Gln Asp Cys Asp Ile Pro Ile His Ala Cys
945                 950                 955                 960
Ile Ser Asn Pro Cys Asn His Gly Gly Thr Cys His Leu Lys Glu Gly
                965                 970                 975
Glu Lys Asp Gly Phe Trp Cys Thr Cys Ala Asp Gly Phe Glu Gly Glu
            980                 985                 990
Asn Cys Glu Ile Asn Val Asp Asp  Cys Glu Asp Asn Asp  Cys Glu Asn
            995                 1000                1005
Asn Ser  Thr Cys Val Asp Gly  Ile Asn Asn Tyr Thr  Cys Leu Cys
1010                1015                1020
Pro Pro Glu Tyr Thr Gly Glu  Leu Cys Glu Glu Lys  Leu Asp Phe
1025                1030                1035
Cys Ala  Gln Asn Leu Asn Pro  Cys Gln His Asp Ser  Lys Cys Ile
1040                1045                1050
Leu Thr  Pro Lys Gly Tyr Lys  Cys Asp Cys Thr Pro  Gly Tyr Val
1055                1060                1065
Gly Glu  His Cys Asp Ile Asp  Phe Asp Asp Cys Gln  Asp Asn Lys
1070                1075                1080
```

-continued

Cys Lys Asn Gly Ala Gln Cys Thr Asp Ala Val Asn Gly Tyr Thr
1085                1090                1095

Cys Ile Cys Pro Glu Gly Tyr Ser Gly Leu Phe Cys Glu Phe Ser
1100                1105                1110

Pro Pro Met Val Leu Pro Arg Thr Ser Pro Cys Asp Asn Tyr Glu
1115                1120                1125

Cys Gln Asn Gly Ala Gln Cys Ile Val Lys Glu Ser Glu Pro Ile
1130                1135                1140

Cys Gln Cys Leu Ser Gly Tyr Gln Gly Glu Lys Cys Glu Lys Leu
1145                1150                1155

Ile Ser Ile Asn Phe Val Asn Lys Glu Ser Tyr Leu Gln Ile Pro
1160                1165                1170

Ser Ala Lys Ile His Ser Gln Thr Asn Ile Thr Leu Gln Ile Ala
1175                1180                1185

Thr Asp Glu Asp Ser Gly Ile Leu Leu Tyr Lys Gly Asp Lys Asp
1190                1195                1200

His Ile Ala Val Glu Leu Tyr Arg Gly Arg Val Arg Val Ser Tyr
1205                1210                1215

Asp Thr Gly Ser Tyr Pro Ala Ser Ala Ile Tyr Ser Val Glu Thr
1220                1225                1230

Ile Asn Asp Gly Asn Phe His Ile Val Glu Leu Leu Ala Met Asp
1235                1240                1245

Gln Ile Leu Ser Leu Ser Ile Asp Gly Gly Ser Pro Lys Ile Ile
1250                1255                1260

Thr Asn Leu Ser Lys Gln Ser Thr Leu Asn Phe Asp Ser Pro Leu
1265                1270                1275

Tyr Val Gly Gly Met Pro Val Lys Asn Asn Ile Ala Ala Leu Arg
1280                1285                1290

Gln Ser Pro Gly Gln Asn Gly Thr Ser Phe His Gly Cys Ile Arg
1295                1300                1305

Asn Leu Tyr Ile Asn Ser Glu Leu Gln Asp Phe Arg Asn Val Pro
1310                1315                1320

Leu Gln Val Gly Ile Leu Pro Gly Cys Glu Pro Cys His Lys Lys
1325                1330                1335

Val Cys Val His Gly Thr Cys His Ala Thr Ser Gln Ser Ser Phe
1340                1345                1350

Thr Cys Glu Cys Glu Gly Gly Trp Thr Gly Pro Leu Cys Asp Gln
1355                1360                1365

Gln Thr Asn Asp Pro Cys Leu Gly Asn Lys Cys Val His Gly Thr
1370                1375                1380

Cys Leu Pro Ile Asn Ala Phe Ser Tyr Ser Cys Lys Cys Leu Gln
1385                1390                1395

Gly His Gly Gly Val Leu Cys Asp Glu Glu Met Leu Phe Asn
1400                1405                1410

Pro Cys Gln Ser Ile Arg Cys Lys His Gly Lys Cys Arg Leu Ser
1415                1420                1425

Gly Leu Gly Lys Pro Tyr Cys Glu Cys Ser Ser Gly Tyr Thr Gly
1430                1435                1440

Asp Ser Cys Asp Lys Glu Ile Ser Cys Arg Gly Glu Arg Ile Arg
1445                1450                1455

Asp Tyr Tyr Gln Lys Gln Gln Gly Tyr Ala Ala Cys Gln Thr Thr
1460                1465                1470

```
Lys Lys Val Ser Arg Leu Glu Cys Lys Gly Gly Cys Ser Thr Gly
    1475                1480                1485

Gln Cys Cys Gly Pro Leu Arg Ser Lys Arg Arg Lys Tyr Ser Phe
    1490                1495                1500

Glu Cys Thr Asp Gly Ser Ser Phe Val Asp Glu Ile Glu Lys Val
    1505                1510                1515

Val Lys Cys Gly Cys Thr Asn Cys Pro Ser
    1520                1525

<210> SEQ ID NO 21
<211> LENGTH: 1088
<212> TYPE: PRT
<213> ORGANISM: Homo sapiens

<400> SEQUENCE: 21

Gln Ala Cys Pro Ala Gln Cys Ser Cys Ser Gly Ser Thr Val Asp Cys
1               5                   10                  15

His Gly Leu Ala Leu Arg Ser Val Pro Arg Asn Ile Pro Arg Asn Thr
            20                  25                  30

Glu Arg Leu Asp Leu Asn Gly Asn Asn Ile Thr Arg Ile Thr Lys Ile
        35                  40                  45

Asp Phe Ala Gly Leu Arg His Leu Arg Val Leu Gln Leu Met Glu Asn
    50                  55                  60

Arg Ile Ser Thr Ile Glu Arg Gly Ala Phe Gln Asp Leu Lys Glu Leu
65                  70                  75                  80

Glu Arg Leu Arg Leu Asn Arg Asn Asn Leu Gln Leu Phe Pro Glu Leu
                85                  90                  95

Leu Phe Leu Gly Thr Ala Lys Leu Tyr Arg Leu Asp Leu Ser Glu Asn
            100                 105                 110

Gln Ile Gln Ala Ile Pro Arg Lys Ala Phe Arg Gly Ala Val Asp Ile
        115                 120                 125

Lys Asn Leu Gln Leu Asp Tyr Asn Gln Ile Ser Cys Ile Glu Asp Gly
    130                 135                 140

Ala Phe Arg Ala Leu Arg Asp Leu Glu Val Leu Thr Leu Asn Asn Asn
145                 150                 155                 160

Asn Ile Thr Arg Leu Ser Val Ala Ser Phe Asn His Met Pro Lys Leu
                165                 170                 175

Arg Thr Phe Arg Leu His Ser Asn Asn Leu Tyr Cys Asp Cys His Leu
            180                 185                 190

Ala Trp Leu Ser Asp Trp Leu Arg Gln Arg Pro Arg Val Gly Leu Tyr
        195                 200                 205

Thr Gln Cys Met Gly Pro Ser His Leu Arg Gly His Asn Val Ala Glu
    210                 215                 220

Val Gln Lys Arg Glu Phe Val Cys Ser Gly His Gln Ser Phe Met Ala
225                 230                 235                 240

Pro Ser Cys Ser Val Leu His Cys Pro Ala Ala Cys Thr Cys Ser Asn
                245                 250                 255

Asn Ile Val Asp Cys Arg Gly Lys Gly Leu Thr Glu Ile Pro Thr Asn
            260                 265                 270

Leu Pro Glu Thr Ile Thr Glu Ile Arg Leu Glu Gln Asn Ser Ile Arg
        275                 280                 285

Val Ile Pro Pro Gly Ala Phe Ser Pro Tyr Lys Lys Leu Arg Arg Leu
    290                 295                 300

Asp Leu Ser Asn Asn Gln Ile Ser Glu Leu Ala Pro Asp Ala Phe Gln
305                 310                 315                 320
```

```
Gly Leu Arg Ser Leu Asn Ser Leu Val Leu Tyr Gly Asn Lys Ile Thr
                325                 330                 335
Glu Leu Pro Lys Ser Leu Phe Glu Gly Leu Phe Ser Leu Gln Leu Leu
                340                 345                 350
Leu Leu Asn Ala Asn Lys Ile Asn Cys Leu Arg Val Asp Ala Phe Gln
                355                 360                 365
Asp Leu His Asn Leu Asn Leu Leu Ser Leu Tyr Asp Asn Lys Leu Gln
            370                 375                 380
Thr Val Ala Lys Gly Thr Phe Ser Ala Leu Arg Ala Ile Gln Thr Met
385                 390                 395                 400
His Leu Ala Gln Asn Pro Phe Ile Cys Asp Cys His Leu Lys Trp Leu
                405                 410                 415
Ala Asp Tyr Leu His Thr Asn Pro Ile Glu Thr Ser Gly Ala Arg Cys
                420                 425                 430
Thr Ser Pro Arg Arg Leu Ala Asn Lys Arg Ile Gly Gln Ile Lys Ser
            435                 440                 445
Lys Lys Phe Arg Cys Ser Gly Thr Glu Asp Tyr Arg Ser Lys Leu Ser
            450                 455                 460
Gly Asp Cys Phe Ala Asp Leu Ala Cys Pro Glu Lys Cys Arg Cys Glu
465                 470                 475                 480
Gly Thr Thr Val Asp Cys Ser Asn Gln Arg Leu Asn Lys Ile Pro Asp
                485                 490                 495
His Ile Pro Gln Tyr Thr Ala Glu Leu Arg Leu Asn Asn Asn Glu Phe
            500                 505                 510
Thr Val Leu Glu Ala Thr Gly Ile Phe Lys Lys Leu Pro Gln Leu Arg
                515                 520                 525
Lys Ile Asn Phe Ser Asn Asn Lys Ile Thr Asp Ile Glu Glu Gly Ala
            530                 535                 540
Phe Glu Gly Ala Ser Gly Val Asn Glu Ile Leu Leu Thr Ser Asn Arg
545                 550                 555                 560
Leu Glu Asn Val Gln His Lys Met Phe Lys Gly Leu Glu Ser Leu Lys
                565                 570                 575
Thr Leu Met Leu Arg Ser Asn Arg Ile Ser Cys Val Gly Asn Asp Ser
                580                 585                 590
Phe Ile Gly Leu Gly Ser Val Arg Leu Leu Ser Leu Tyr Asp Asn Gln
            595                 600                 605
Ile Thr Thr Val Ala Pro Gly Ala Phe Asp Ser Leu His Ser Leu Ser
            610                 615                 620
Thr Leu Asn Leu Leu Ala Asn Pro Phe Asn Cys Asn Cys His Leu Ala
625                 630                 635                 640
Trp Leu Gly Glu Trp Leu Arg Arg Lys Arg Ile Val Thr Gly Asn Pro
                645                 650                 655
Arg Cys Gln Lys Pro Tyr Phe Leu Lys Glu Ile Pro Ile Gln Asp Val
            660                 665                 670
Ala Ile Gln Asp Phe Thr Cys Asp Asp Gly Asn Asp Asn Ser Cys
            675                 680                 685
Ser Pro Leu Ser Arg Cys Pro Ser Glu Cys Thr Cys Leu Asp Thr Val
            690                 695                 700
Val Arg Cys Ser Asn Lys Gly Leu Lys Val Leu Pro Lys Gly Ile Pro
705                 710                 715                 720
Lys Asp Val Thr Glu Leu Tyr Leu Asp Gly Asn Gln Phe Thr Leu Val
                725                 730                 735
```

-continued

```
Pro Lys Glu Leu Ser Asn Tyr Lys His Leu Thr Leu Ile Asp Leu Ser
            740                 745                 750

Asn Asn Arg Ile Ser Thr Leu Ser Asn Gln Ser Phe Ser Asn Met Thr
        755                 760                 765

Gln Leu Leu Thr Leu Ile Leu Ser Tyr Asn Arg Leu Arg Cys Ile Pro
    770                 775                 780

Pro Arg Thr Phe Asp Gly Leu Lys Ser Leu Arg Leu Leu Ser Leu His
785                 790                 795                 800

Gly Asn Asp Ile Ser Val Val Pro Glu Gly Ala Phe Asn Asp Leu Ser
                805                 810                 815

Ala Leu Ser His Leu Ala Ile Gly Ala Asn Pro Leu Tyr Cys Asp Cys
            820                 825                 830

Asn Met Gln Trp Leu Ser Asp Trp Val Lys Ser Glu Tyr Lys Glu Pro
        835                 840                 845

Gly Ile Ala Arg Cys Ala Gly Pro Gly Glu Met Ala Asp Lys Leu Leu
    850                 855                 860

Leu Thr Thr Pro Ser Lys Lys Phe Thr Cys Gln Gly Pro Val Asp Ile
865                 870                 875                 880

Thr Ile Gln Ala Lys Cys Asn Pro Cys Leu Ser Asn Pro Cys Lys Asn
                885                 890                 895

Asp Gly Thr Cys Asn Asn Asp Pro Val Asp Phe Tyr Arg Cys Thr Cys
            900                 905                 910

Pro Tyr Gly Phe Lys Gly Gln Asp Cys Asp Val Pro Ile His Ala Cys
        915                 920                 925

Ile Ser Asn Pro Cys Lys His Gly Gly Thr Cys His Leu Lys Glu Gly
    930                 935                 940

Glu Asn Ala Gly Phe Trp Cys Thr Cys Ala Asp Gly Phe Glu Gly Glu
945                 950                 955                 960

Asn Cys Glu Val Asn Ile Asp Asp Cys Glu Asp Asn Asp Cys Glu Asn
                965                 970                 975

Asn Ser Thr Cys Val Asp Gly Ile Asn Asn Tyr Thr Cys Leu Cys Pro
            980                 985                 990

Pro Glu Tyr Thr Gly Glu Leu Cys Glu Glu Lys Leu Asp Phe Cys Ala
        995                 1000                1005

Gln Asp Leu Asn Pro Cys Gln His Asp Ser Lys Cys Ile Leu Thr
    1010                1015                1020

Pro Lys Gly Phe Lys Cys Asp Cys Thr Pro Gly Tyr Ile Gly Glu
    1025                1030                1035

His Cys Asp Ile Asp Phe Asp Asp Cys Gln Asp Asn Lys Cys Lys
    1040                1045                1050

Asn Gly Ala His Cys Thr Asp Ala Val Asn Gly Tyr Thr Cys Val
    1055                1060                1065

Cys Pro Glu Gly Tyr Ser Gly Leu Phe Cys Glu Phe Ser Pro Pro
    1070                1075                1080

Met Val Leu Pro Arg
    1085

<210> SEQ ID NO 22
<211> LENGTH: 408
<212> TYPE: PRT
<213> ORGANISM: Homo sapiens

<400> SEQUENCE: 22

Thr Ser Pro Cys Asp Asn Phe Asp Cys Gln Asn Gly Ala Gln Cys Ile
1               5                   10                  15
```

Ile Arg Ile Asn Glu Pro Ile Cys Gln Cys Leu Pro Gly Tyr Leu Gly
            20                  25                  30

Glu Lys Cys Glu Lys Leu Val Ser Val Asn Phe Val Asn Lys Glu Ser
        35                  40                  45

Tyr Leu Gln Ile Pro Ser Ala Lys Val Arg Pro Gln Thr Asn Ile Thr
    50                  55                  60

Leu Gln Ile Ala Thr Asp Glu Asp Ser Gly Ile Leu Leu Tyr Lys Gly
65                  70                  75                  80

Asp Lys Asp His Ile Ala Val Glu Leu Tyr Arg Gly Arg Val Arg Ala
                85                  90                  95

Ser Tyr Asp Thr Gly Ser His Pro Ala Ser Ala Ile Tyr Ser Val Glu
            100                 105                 110

Thr Ile Asn Asp Gly Asn Phe His Ile Val Glu Leu Leu Thr Leu Asp
            115                 120                 125

Ser Ser Leu Ser Leu Ser Val Asp Gly Gly Ser Pro Lys Val Ile Thr
130                 135                 140

Asn Leu Ser Lys Gln Ser Thr Leu Asn Phe Asp Ser Pro Leu Tyr Val
145                 150                 155                 160

Gly Gly Met Pro Gly Lys Asn Asn Val Ala Ser Leu Arg Gln Ala Pro
                165                 170                 175

Gly Gln Asn Gly Thr Ser Phe His Gly Cys Ile Arg Asn Leu Tyr Ile
            180                 185                 190

Asn Ser Glu Leu Gln Asp Phe Arg Lys Met Pro Met Gln Thr Gly Ile
            195                 200                 205

Leu Pro Gly Cys Glu Pro Cys His Lys Lys Val Cys Ala His Gly Met
        210                 215                 220

Cys Gln Pro Ser Ser Gln Ser Gly Phe Thr Cys Glu Cys Glu Glu Gly
225                 230                 235                 240

Trp Met Gly Pro Leu Cys Asp Gln Arg Thr Asn Asp Pro Cys Leu Gly
                245                 250                 255

Asn Lys Cys Val His Gly Thr Cys Leu Pro Ile Asn Ala Phe Ser Tyr
            260                 265                 270

Ser Cys Lys Cys Leu Glu Gly His Gly Gly Val Leu Cys Asp Glu Glu
        275                 280                 285

Glu Asp Leu Phe Asn Pro Cys Gln Met Ile Lys Cys Lys His Gly Lys
    290                 295                 300

Cys Arg Leu Ser Gly Val Gly Gln Pro Tyr Cys Glu Cys Asn Ser Gly
305                 310                 315                 320

Phe Thr Gly Asp Ser Cys Asp Arg Glu Ile Ser Cys Arg Gly Glu Arg
                325                 330                 335

Ile Arg Asp Tyr Tyr Gln Lys Gln Gln Gly Tyr Ala Ala Cys Gln Thr
            340                 345                 350

Thr Lys Lys Val Ser Arg Leu Glu Cys Arg Gly Gly Cys Ala Gly Gly
            355                 360                 365

Gln Cys Cys Gly Pro Leu Arg Ser Lys Arg Arg Lys Tyr Ser Phe Glu
370                 375                 380

Cys Thr Asp Gly Ser Ser Phe Val Asp Glu Val Glu Lys Val Val Lys
385                 390                 395                 400

Cys Gly Cys Ala Arg Cys Ala Ser
                405

<210> SEQ ID NO 23
<211> LENGTH: 9

```
<212> TYPE: PRT
<213> ORGANISM: Artificial Sequence
<220> FEATURE:
<223> OTHER INFORMATION: /note="Description of Artificial Sequence:
      (Gly)4Ala(Gly)4 linker"

<400> SEQUENCE: 23

Gly Gly Gly Gly Ala Gly Gly Gly Gly
1               5

<210> SEQ ID NO 24
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 24
tgttcctctt aatcctgccc a                                              21

<210> SEQ ID NO 25
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 25
ccaacctgca caagttccct t                                              21

<210> SEQ ID NO 26
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 26
gatctggtgg aacgaggcaa                                                20

<210> SEQ ID NO 27
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 27
cttcgggttc tggaggcttg                                                20

<210> SEQ ID NO 28
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 28
gcccaactgt gacttccatt aa                                             22

<210> SEQ ID NO 29
<211> LENGTH: 21
```

```
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 29
gtagcactcc cctcgagtga t                                         21

<210> SEQ ID NO 30
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 30
aaggtgaaga gcatcataac cct                                       23

<210> SEQ ID NO 31
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 31
tcacgccttt cataacacat tcc                                       23

<210> SEQ ID NO 32
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 32
cagcacattt atcccggtgt ac                                        22

<210> SEQ ID NO 33
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 33
aaatgccgcc atccacatag                                           20

<210> SEQ ID NO 34
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 34
cacaatgcag gaaaggatca                                           20

<210> SEQ ID NO 35
<211> LENGTH: 20
<212> TYPE: DNA
```

```
<213> ORGANISM: Artificial Sequence
<220> FEATURE:
<223> OTHER INFORMATION: /note="Description of Artificial Sequence:
      Synthetic primer"

<400> SEQUENCE: 35
ggtcatcagc aggcacatag                                              20

<210> SEQ ID NO 36
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 36
acttttggtg ttgttctggg aa                                           22

<210> SEQ ID NO 37
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 37
gcatgaacag gatctcaggc                                              20

<210> SEQ ID NO 38
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 38
tctggtagtg tcctgctcac ag                                           22

<210> SEQ ID NO 39
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 39
tcgtaacggc caaaacaaat                                              20

<210> SEQ ID NO 40
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 40
acgctggtgc tctatgcaag                                              20

<210> SEQ ID NO 41
<211> LENGTH: 21
<212> TYPE: DNA
<213> ORGANISM: Artificial Sequence
```

```
<220> FEATURE:
<223> OTHER INFORMATION: /note="Description of Artificial Sequence:
      Synthetic primer"

<400> SEQUENCE: 41
tcagttgctg cccattcatc a                                              21

<210> SEQ ID NO 42
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 42
aaggctgggt gaagaccctt a                                              21

<210> SEQ ID NO 43
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 43
tgaatggccg tttctggaag t                                              21

<210> SEQ ID NO 44
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 44
tgctcttctg tatcgcccag t                                              21

<210> SEQ ID NO 45
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 45
gccgtgttaa ggaatctgct g                                              21

<210> SEQ ID NO 46
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 46
gccgactaaa tcaagcaaca                                                20

<210> SEQ ID NO 47
<211> LENGTH: 20
<212> TYPE: DNA
<213> ORGANISM: Artificial Sequence
<220> FEATURE:
```

```
<223> OTHER INFORMATION: /note="Description of Artificial Sequence:
      Synthetic primer"

<400> SEQUENCE: 47
caatgggcat aaagctatgg                                               20

<210> SEQ ID NO 48
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 48
gcacatggga gtgttgtga                                                19

<210> SEQ ID NO 49
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 49
ccttctcctt ctccttcagc                                               20

<210> SEQ ID NO 50
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 50
gggtcacacg agacagatga                                               20

<210> SEQ ID NO 51
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 51
ggaaccagat catagccaac a                                             21

<210> SEQ ID NO 52
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 52
gaaccatgaa gtcaacgact                                               20

<210> SEQ ID NO 53
<211> LENGTH: 20
<212> TYPE: DNA
<213> ORGANISM: Artificial Sequence
```

```
<220> FEATURE:
<223> OTHER INFORMATION: /note="Description of Artificial Sequence:
      Synthetic primer"

<400> SEQUENCE: 53
gcgaagttca cagtggttcc                                                 20

<210> SEQ ID NO 54
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 54
catttattat cgcggcccta                                                 20

<210> SEQ ID NO 55
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 55
tgttgggttg tttgatcctg                                                 20

<210> SEQ ID NO 56
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 56
ggagatggca caggaggaa                                                  19

<210> SEQ ID NO 57
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 57
gcccgtagtg cttcagctt                                                  19

<210> SEQ ID NO 58
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 58
cagtgtggtg cacgtctcca atc                                             23

<210> SEQ ID NO 59
<211> LENGTH: 21
<212> TYPE: DNA
<213> ORGANISM: Artificial Sequence
<220> FEATURE:
```

```
<223> OTHER INFORMATION: /note="Description of Artificial Sequence:
      Synthetic primer"

<400> SEQUENCE: 59
tgaaccaaag ttgaccacca g                                              21

<210> SEQ ID NO 60
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 60
cctgtaaccc cagaactcca                                                20

<210> SEQ ID NO 61
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 61
cagatgagca aaggtgcaaa                                                20

<210> SEQ ID NO 62
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 62
tccgcgttct catgtaggtc t                                              21

<210> SEQ ID NO 63
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 63
ggacctgatg caaccctatg a                                              21

<210> SEQ ID NO 64
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 64
gcagggcagt gggaagcta                                                 19

<210> SEQ ID NO 65
<211> LENGTH: 21
<212> TYPE: DNA
<213> ORGANISM: Artificial Sequence
<220> FEATURE:
```

-continued

<223> OTHER INFORMATION: /note="Description of Artificial Sequence:
Synthetic primer"

<400> SEQUENCE: 65
cctcttgaag aaggctttgc a                                              21

<210> SEQ ID NO 66
<211> LENGTH: 22
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 66
ccacttctcc tgagtttaca gc                                             22

<210> SEQ ID NO 67
<211> LENGTH: 23
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 67
gcattttaac cgaacatctg tcc                                            23

<210> SEQ ID NO 68
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 68
aggtggtgat agccggtatg t                                              21

<210> SEQ ID NO 69
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 69
tgggtaatcc atagagccca g                                              21

<210> SEQ ID NO 70
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 70
gacctggtct tgtgctctcc                                                20

<210> SEQ ID NO 71
<211> LENGTH: 20
<212> TYPE: DNA
<213> ORGANISM: Artificial Sequence

```
<220> FEATURE:
<223> OTHER INFORMATION: /note="Description of Artificial Sequence:
      Synthetic primer"

<400> SEQUENCE: 71
gggatgactg gtgttggagg                                                    20

<210> SEQ ID NO 72
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 72
gggctgccag gttctagtc                                                     19

<210> SEQ ID NO 73
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 73
cctccgaggt ccttctca                                                      18

<210> SEQ ID NO 74
<211> LENGTH: 16
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 74
agagtctaaa gcgcct                                                        16

<210> SEQ ID NO 75
<211> LENGTH: 16
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 75
ccgagaccaa cgtgaa                                                        16

<210> SEQ ID NO 76
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 76
gctggaggag tgtttttttg c                                                  21

<210> SEQ ID NO 77
<211> LENGTH: 21
<212> TYPE: DNA
<213> ORGANISM: Artificial Sequence
<220> FEATURE:
```

```
<223> OTHER INFORMATION: /note="Description of Artificial Sequence:
      Synthetic primer"

<400> SEQUENCE: 77
agttgaacca agcaggtcac a                                             21

<210> SEQ ID NO 78
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 78
gagacccctg tgtcggttc                                                19

<210> SEQ ID NO 79
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 79
ctgcgtgtgt gaaatgtcat tg                                            22

<210> SEQ ID NO 80
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 80
aggagtgtcg acttcgcaaa                                               20

<210> SEQ ID NO 81
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 81
ctcttcttgc cgcttcagtt t                                             21

<210> SEQ ID NO 82
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 82
ctcccaccca cgcttacac                                                19

<210> SEQ ID NO 83
<211> LENGTH: 21
<212> TYPE: DNA
<213> ORGANISM: Artificial Sequence
```

<220> FEATURE:
<223> OTHER INFORMATION: /note="Description of Artificial Sequence: Synthetic primer"

<400> SEQUENCE: 83
gccctaacct ctctccactc a                                              21

<210> SEQ ID NO 84
<211> LENGTH: 19
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 84
gggctgtgct gtctgttga                                                 19

<210> SEQ ID NO 85
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 85
tgattccctt caggtaaggc a                                              21

<210> SEQ ID NO 86
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 86
ttacagcttt gggtccagac a                                              21

<210> SEQ ID NO 87
<211> LENGTH: 21
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 87
ggagttctcc ctttacagca c                                              21

<210> SEQ ID NO 88
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 88
gaactgccaa ccacagtcac                                                20

<210> SEQ ID NO 89
<211> LENGTH: 20
<212> TYPE: DNA
<213> ORGANISM: Artificial Sequence
<220> FEATURE:

<223> OTHER INFORMATION: /note="Description of Artificial Sequence:
      Synthetic primer"

<400> SEQUENCE: 89
tttgttccac ctctccatca                                                  20

<210> SEQ ID NO 90
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 90
gtgtgtactg ggaaggcatt ga                                               22

<210> SEQ ID NO 91
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 91
gccacgaggt tatggtgaca                                                  20

<210> SEQ ID NO 92
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 92
caggatcgaa agcaagacag t                                                21

<210> SEQ ID NO 93
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 93
aagtcctctt ccgacatcca g                                                21

<210> SEQ ID NO 94
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 94
tgatgtgaat gacttggata cagaca                                           26

<210> SEQ ID NO 95
<211> LENGTH: 26
<212> TYPE: DNA

```
<213> ORGANISM: Artificial Sequence
<220> FEATURE:
<223> OTHER INFORMATION: /note="Description of Artificial Sequence:
      Synthetic primer"

<400> SEQUENCE: 95
gctcattgtt gtactggttg gatatg                                      26

<210> SEQ ID NO 96
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 96
cagcacggtg aagccattc                                              19

<210> SEQ ID NO 97
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 97
gcgtgcatcc gcttgtg                                                17

<210> SEQ ID NO 98
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 98
gtgagtgtgc ccaggtatgc                                             20

<210> SEQ ID NO 99
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 99
cgacaggttg caccacttc                                              19

<210> SEQ ID NO 100
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 100
ccagaaggca cagcagtctt                                             20

<210> SEQ ID NO 101
<211> LENGTH: 19
<212> TYPE: DNA
<213> ORGANISM: Artificial Sequence
```

```
<220> FEATURE:
<223> OTHER INFORMATION: /note="Description of Artificial Sequence:
      Synthetic primer"

<400> SEQUENCE: 101
ccgacatcag gaagcgacc                                                    19

<210> SEQ ID NO 102
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 102
ctgctccccg gatatgaacc                                                   20

<210> SEQ ID NO 103
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 103
tagcatgcac tcacacctgg                                                   20

<210> SEQ ID NO 104
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 104
gattctggtg cacttgtgct g                                                 21

<210> SEQ ID NO 105
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 105
tgtgtattcc ggtgggcaaa                                                   20

<210> SEQ ID NO 106
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 106
gctgtgaacc atgccacaag                                                   20

<210> SEQ ID NO 107
<211> LENGTH: 21
<212> TYPE: DNA
<213> ORGANISM: Artificial Sequence
<220> FEATURE:
```

<223> OTHER INFORMATION: /note="Description of Artificial Sequence:
      Synthetic primer"

<400> SEQUENCE: 107
cacacatttg tttccgaggc a                                        21

<210> SEQ ID NO 108
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 108
gcaacaccga gagactggat t                                        21

<210> SEQ ID NO 109
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 109
agatcctgga atgctcccct                                          20

<210> SEQ ID NO 110
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 110
ccacgctgat cctgagctac                                          20

<210> SEQ ID NO 111
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 111
gcactcggag ggatcttagc                                          20

<210> SEQ ID NO 112
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 112
ccacctgcaa gaccatcgac                                          20

-continued

<210> SEQ ID NO 113
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 113
ctggcgagcc ttagtttgga c                                              21

<210> SEQ ID NO 114
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 114
caggcggtgc ctatgtctc                                                 19

<210> SEQ ID NO 115
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 115
cgatcacccc gaagttcagt ag                                             22

<210> SEQ ID NO 116
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 116
gtctcagagc aggataccaa gc                                             22

<210> SEQ ID NO 117
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 117
ctctcctcga ataccacagc c                                              21

<210> SEQ ID NO 118
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 118
cactgctttg ggagccttc                                                 19

```
<210> SEQ ID NO 119
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 119
ggggcagcga ttcatttttc t                                           21

<210> SEQ ID NO 120
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 120
aagctgtgcg atgtccatgt                                             20

<210> SEQ ID NO 121
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 121
aagccacaaa ccctttgaaa a                                           21

<210> SEQ ID NO 122
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 122
aggcttcctg aggaccttta                                             20

<210> SEQ ID NO 123
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 123
tccttaggca agatctgatg c                                           21

<210> SEQ ID NO 124
<211> LENGTH: 25
<212> TYPE: PRT
<213> ORGANISM: Mus musculus

<400> SEQUENCE: 124

Met Ser Gly Ile Gly Trp Gln Thr Leu Ser Leu Ser Leu Gly Leu Val
1               5                   10                  15

Leu Ser Ile Leu Asn Lys Val Ala Pro
            20                  25
```

<210> SEQ ID NO 125
<211> LENGTH: 1521
<212> TYPE: PRT
<213> ORGANISM: Mus musculus

<400> SEQUENCE: 125

```
Met Ser Gly Ile Gly Trp Gln Thr Leu Ser Leu Ser Leu Gly Leu Val
1               5                   10                  15

Leu Ser Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Ile Asp Phe Ala Gly Leu Arg His
65                  70                  75                  80

Leu Arg Val Leu Gln Leu Met Glu Asn Arg Ile Ser Thr Ile Glu Arg
                85                  90                  95

Gly Ala Phe Gln Asp Leu Lys Glu Leu Glu Arg Leu Arg Leu Asn Arg
            100                 105                 110

Asn Asn Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Ser Ile Arg Val Ile Pro Pro Gly Ala Phe
305                 310                 315                 320

Ser Pro Tyr Lys Lys Leu Arg Arg Leu Asp Leu Ser Asn Asn Gln Ile
                325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
        355                 360                 365

Glu Gly Leu Phe Ser Leu Gln Leu Leu Leu Leu Asn Ala Asn Lys Ile
    370                 375                 380
```

-continued

```
Asn Cys Leu Arg Val Asp Ala Phe Gln Asp Leu His Asn Leu Asn Leu
385                 390                 395                 400

Leu Ser Leu Tyr Asp Asn Lys Leu Gln Thr Val Ala Lys Gly Thr Phe
                405                 410                 415

Ser Ala Leu Arg Ala Ile Gln Thr Met His Leu Ala Gln Asn Pro Phe
            420                 425                 430

Ile Cys Asp Cys His Leu Lys Trp Leu Ala Asp Tyr Leu His Thr Asn
                435                 440                 445

Pro Ile Glu Thr Ser Gly Ala Arg Cys Thr Ser Pro Arg Arg Leu Ala
            450                 455                 460

Asn Lys Arg Ile Gly Gln Ile Lys Ser Lys Phe Arg Cys Ser Gly
465                 470                 475                 480

Thr Glu Asp Tyr Arg Ser Lys Leu Ser Gly Asp Cys Phe Ala Asp Leu
                485                 490                 495

Ala Cys Pro Glu Lys Cys Arg Cys Glu Gly Thr Thr Val Asp Cys Ser
            500                 505                 510

Asn Gln Arg Leu Asn Lys Ile Pro Asp His Ile Pro Gln Tyr Thr Ala
                515                 520                 525

Glu Leu Arg Leu Asn Asn Asn Glu Phe Thr Val Leu Glu Ala Thr Gly
530                 535                 540

Ile Phe Lys Lys Leu Pro Gln Leu Arg Lys Ile Asn Phe Ser Asn Asn
545                 550                 555                 560

Lys Ile Thr Asp Ile Glu Gly Ala Phe Glu Gly Ala Ser Gly Val
                565                 570                 575

Asn Glu Ile Leu Leu Thr Ser Asn Arg Leu Glu Asn Val Gln His Lys
                580                 585                 590

Met Phe Lys Gly Leu Glu Ser Leu Lys Thr Leu Met Leu Arg Ser Asn
                595                 600                 605

Arg Ile Ser Cys Val Gly Asn Asp Ser Phe Ile Gly Leu Gly Ser Val
610                 615                 620

Arg Leu Leu Ser Leu Tyr Asp Asn Gln Ile Thr Thr Val Ala Pro Gly
625                 630                 635                 640

Ala Phe Asp Ser Leu His Ser Leu Ser Thr Leu Asn Leu Leu Ala Asn
                645                 650                 655

Pro Phe Asn Cys Asn Cys His Leu Ala Trp Leu Gly Glu Trp Leu Arg
                660                 665                 670

Arg Lys Arg Ile Val Thr Gly Asn Pro Arg Cys Gln Lys Pro Tyr Phe
                675                 680                 685

Leu Lys Glu Ile Pro Ile Gln Asp Val Ala Ile Gln Asp Phe Thr Cys
                690                 695                 700

Asp Asp Gly Asn Asp Asp Asn Ser Cys Ser Pro Leu Ser Arg Cys Pro
705                 710                 715                 720

Ser Glu Cys Thr Cys Leu Asp Thr Val Val Arg Cys Ser Asn Lys Gly
                725                 730                 735

Leu Lys Val Leu Pro Lys Gly Ile Pro Lys Asp Val Thr Glu Leu Tyr
                740                 745                 750

Leu Asp Gly Asn Gln Phe Thr Leu Val Pro Lys Glu Leu Ser Asn Tyr
                755                 760                 765

Lys His Leu Thr Leu Ile Asp Leu Ser Asn Asn Arg Ile Ser Thr Leu
                770                 775                 780

Ser Asn Gln Ser Phe Ser Asn Met Thr Gln Leu Leu Thr Leu Ile Leu
785                 790                 795                 800
```

-continued

```
Ser Tyr Asn Arg Leu Arg Cys Ile Pro Pro Arg Thr Phe Asp Gly Leu
            805                 810                 815

Lys Ser Leu Arg Leu Leu Ser Leu His Gly Asn Asp Ile Ser Val Val
        820                 825                 830

Pro Glu Gly Ala Phe Asn Asp Leu Ser Ala Leu Ser His Leu Ala Ile
        835                 840                 845

Gly Ala Asn Pro Leu Tyr Cys Asp Cys Asn Met Gln Trp Leu Ser Asp
850                 855                 860

Trp Val Lys Ser Glu Tyr Lys Glu Pro Gly Ile Ala Arg Cys Ala Gly
865                 870                 875                 880

Pro Gly Glu Met Ala Asp Lys Leu Leu Leu Thr Thr Pro Ser Lys Lys
                885                 890                 895

Phe Thr Cys Gln Gly Pro Val Asp Ile Thr Ile Gln Ala Lys Cys Asn
            900                 905                 910

Pro Cys Leu Ser Asn Pro Cys Lys Asn Asp Gly Thr Cys Asn Asn Asp
        915                 920                 925

Pro Val Asp Phe Tyr Arg Cys Thr Cys Pro Tyr Gly Phe Lys Gly Gln
        930                 935                 940

Asp Cys Asp Val Pro Ile His Ala Cys Ile Ser Asn Pro Cys Lys His
945                 950                 955                 960

Gly Gly Thr Cys His Leu Lys Glu Gly Glu Asn Ala Gly Phe Trp Cys
                965                 970                 975

Thr Cys Ala Asp Gly Phe Glu Gly Glu Asn Cys Glu Val Asn Ile Asp
            980                 985                 990

Asp Cys Glu Asp Asn Asp Cys Glu  Asn Asn Ser Thr Cys  Val Asp Gly
        995                 1000                1005

Ile Asn  Asn Tyr Thr Cys  Leu  Cys Pro Pro Glu Tyr  Thr Gly Glu
       1010                1015                1020

Leu Cys  Glu Glu Lys Leu Asp  Phe Cys Ala Gln Asp  Leu Asn Pro
       1025                1030                1035

Cys Gln  His Asp Ser Lys Cys  Ile Leu Thr Pro Lys  Gly Phe Lys
       1040                1045                1050

Cys Asp  Cys Thr Pro Gly Tyr  Ile Gly Glu His Cys  Asp Ile Asp
       1055                1060                1065

Phe Asp  Asp Cys Gln Asp Asn  Lys Cys Lys Asn Gly  Ala His Cys
       1070                1075                1080

Thr Asp  Ala Val Asn Gly Tyr  Thr Cys Val Cys Pro  Glu Gly Tyr
       1085                1090                1095

Ser Gly  Leu Phe Cys Glu Phe  Ser Pro Pro Met Val  Leu Pro Arg
       1100                1105                1110

Thr Ser  Pro Cys Asp Asn Phe  Asp Cys Gln Asn Gly  Ala Gln Cys
       1115                1120                1125

Ile Ile  Arg Ile Asn Glu Pro  Ile Cys Gln Cys Leu  Pro Gly Tyr
       1130                1135                1140

Leu Gly  Glu Lys Cys Glu Lys  Leu Val Ser Val Asn  Phe Val Asn
       1145                1150                1155

Lys Glu  Ser Tyr Leu Gln Ile  Pro Ser Ala Lys Val  Arg Pro Gln
       1160                1165                1170

Thr Asn  Ile Thr Leu Gln Ile  Ala Thr Asp Glu Asp  Ser Gly Ile
       1175                1180                1185

Leu Leu  Tyr Lys Gly Asp Lys  Asp His Ile Ala Val  Glu Leu Tyr
       1190                1195                1200
```

```
Arg Gly Arg Val Arg Ala Ser Tyr Asp Thr Gly Ser His Pro Ala
        1205                1210                1215

Ser Ala Ile Tyr Ser Val Glu Thr Ile Asn Asp Gly Asn Phe His
        1220                1225                1230

Ile Val Glu Leu Leu Thr Leu Asp Ser Ser Leu Ser Leu Ser Val
        1235                1240                1245

Asp Gly Gly Ser Pro Lys Val Ile Thr Asn Leu Ser Lys Gln Ser
        1250                1255                1260

Thr Leu Asn Phe Asp Ser Pro Leu Tyr Val Gly Gly Met Pro Gly
        1265                1270                1275

Lys Asn Asn Val Ala Ser Leu Arg Gln Ala Pro Gly Gln Asn Gly
        1280                1285                1290

Thr Ser Phe His Gly Cys Ile Arg Asn Leu Tyr Ile Asn Ser Glu
        1295                1300                1305

Leu Gln Asp Phe Arg Lys Met Pro Met Gln Thr Gly Ile Leu Pro
        1310                1315                1320

Gly Cys Glu Pro Cys His Lys Lys Val Cys Ala His Gly Met Cys
        1325                1330                1335

Gln Pro Ser Ser Gln Ser Gly Phe Thr Cys Glu Cys Glu Glu Gly
        1340                1345                1350

Trp Met Gly Pro Leu Cys Asp Gln Arg Thr Asn Asp Pro Cys Leu
        1355                1360                1365

Gly Asn Lys Cys Val His Gly Thr Cys Leu Pro Ile Asn Ala Phe
        1370                1375                1380

Ser Tyr Ser Cys Lys Cys Leu Glu Gly His Gly Gly Val Leu Cys
        1385                1390                1395

Asp Glu Glu Glu Asp Leu Phe Asn Pro Cys Gln Met Ile Lys Cys
        1400                1405                1410

Lys His Gly Lys Cys Arg Leu Ser Gly Val Gly Gln Pro Tyr Cys
        1415                1420                1425

Glu Cys Asn Ser Gly Phe Thr Gly Asp Ser Cys Asp Arg Glu Ile
        1430                1435                1440

Ser Cys Arg Gly Glu Arg Ile Arg Asp Tyr Tyr Gln Lys Gln Gln
        1445                1450                1455

Gly Tyr Ala Ala Cys Gln Thr Thr Lys Lys Val Ser Arg Leu Glu
        1460                1465                1470

Cys Arg Gly Gly Cys Ala Gly Gly Gln Cys Cys Gly Pro Leu Arg
        1475                1480                1485

Ser Lys Arg Arg Lys Tyr Ser Phe Glu Cys Thr Asp Gly Ser Ser
        1490                1495                1500

Phe Val Asp Glu Val Glu Lys Val Val Lys Cys Gly Cys Ala Arg
        1505                1510                1515

Cys Ala Ser
        1520

<210> SEQ ID NO 126
<211> LENGTH: 1523
<212> TYPE: PRT
<213> ORGANISM: Mus musculus

<400> SEQUENCE: 126

Met Ala Leu Gly Arg Thr Gly Ala Gly Ala Ala Val Arg Ala Arg Leu
1               5                   10                  15
```

```
Ala Leu Gly Leu Ala Leu Ala Ser Ile Leu Ser Gly Pro Pro Ala Ala
            20                  25                  30

Ala Cys Pro Thr Lys Cys Thr Cys Ser Ala Ala Ser Val Asp Cys His
            35                  40                  45

Gly Leu Gly Leu Arg Ala Val Pro Arg Gly Ile Pro Arg Asn Ala Glu
 50                  55                  60

Arg Leu Asp Leu Asp Arg Asn Asn Ile Thr Arg Ile Thr Lys Met Asp
 65                  70                  75                  80

Phe Ala Gly Leu Lys Asn Leu Arg Val Leu His Leu Glu Asp Asn Gln
                85                  90                  95

Val Ser Ile Ile Glu Arg Gly Ala Phe Gln Asp Leu Lys Gln Leu Glu
                100                 105                 110

Arg Leu Arg Leu Asn Lys Asn Lys Leu Gln Val Leu Pro Glu Leu Leu
            115                 120                 125

Phe Gln Ser Thr Pro Lys Leu Thr Arg Leu Asp Leu Ser Glu Asn Gln
130                 135                 140

Ile Gln Gly Ile Pro Arg Lys Ala Phe Arg Gly Val Thr Gly Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
            195                 200                 205

Thr Leu Arg Leu His Ser Asn His Leu Tyr Cys Asp Cys His Leu Ala
210                 215                 220

Trp Leu Ser Asp Trp Leu Arg Gln Arg Thr Ile Gly Gln Phe Thr
225                 230                 235                 240

Leu Cys Met Ala Pro Val His Leu Arg Gly Phe Ser Val Ala Asp Val
            245                 250                 255

Gln Lys Lys Glu Tyr Val Cys Pro Gly Pro His Ser Glu Ala Pro Ala
            260                 265                 270

Cys Asn Ala Asn Ser Leu Ser Cys Pro Ser Ala Cys Ser Cys Ser Asn
            275                 280                 285

Asn Ile Val Asp Cys Arg Gly Lys Gly Leu Thr Glu Ile Pro Ala Asn
290                 295                 300

Leu Pro Glu Gly Ile Val Glu Ile Arg Leu Glu Gln Asn Ser Ile Lys
305                 310                 315                 320

Ser Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
            355                 360                 365

Glu Ile Pro Lys Gly Leu Phe Asp Gly Leu Val Ser Leu Gln Leu Leu
            370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Val Pro Leu Gln Ser Ile Gln Thr Leu
            420                 425                 430
```

```
His Leu Ala Gln Asn Pro Phe Val Cys Asp Cys His Leu Lys Trp Leu
            435                 440                 445

Ala Asp Tyr Leu Gln Asp Asn Pro Ile Glu Thr Ser Gly Ala Arg Cys
    450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Asn Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Ala Arg Ile Pro Ser
            515                 520                 525

His Leu Pro Glu Tyr Thr Thr Asp Leu Arg Leu Asn Asp Asn Asp Ile
            530                 535                 540

Ser Val Leu Glu Ala Thr Gly Ile Phe Lys Lys Leu Pro Asn Leu Arg
545                 550                 555                 560

Lys Ile Asn Leu Ser Asn Asn Arg Ile Lys Glu Val Arg Glu Gly Ala
                565                 570                 575

Phe Asp Gly Ala Ala Gly Val Gln Glu Leu Met Leu Thr Gly Asn Gln
            580                 585                 590

Leu Glu Thr Met His Gly Arg Met Phe Arg Gly Leu Ser Ser Leu Lys
            595                 600                 605

Thr Leu Met Leu Arg Ser Asn Leu Ile Ser Cys Val Ser Asn Asp Thr
            610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
                645                 650                 655

Thr Ile Asn Leu Leu Ser Asn Pro Phe Asn Cys Asn Cys His Met Ala
                660                 665                 670

Trp Leu Gly Arg Trp Leu Arg Lys Arg Arg Ile Val Ser Gly Asn Pro
            675                 680                 685

Arg Cys Gln Lys Pro Phe Phe Leu Lys Glu Ile Pro Ile Gln Asp Val
            690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Val Glu Thr Val Val
                725                 730                 735

Arg Cys Ser Asn Arg Gly Leu His Ala Leu Pro Lys Gly Met Pro Lys
            740                 745                 750

Asp Val Thr Glu Leu Tyr Leu Glu Gly Asn His Leu Thr Ala Val Pro
            755                 760                 765

Lys Glu Leu Ser Ala Phe Arg Gln Leu Thr Leu Ile Asp Leu Ser Asn
770                 775                 780

Asn Ser Ile Ser Met Leu Thr Asn His Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
            820                 825                 830

Asn Asp Ile Ser Ser Val Pro Glu Gly Ser Phe Asn Asp Leu Thr Ser
            835                 840                 845
```

-continued

```
Leu Ser His Leu Ala Leu Gly Thr Asn Pro Leu His Cys Asp Cys Ser
850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Ser Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
        915                 920                 925

Gly Thr Cys Ser Gln Asp Pro Val Glu Gln Tyr Arg Cys Thr Cys Pro
    930                 935                 940

Tyr Ser Tyr Lys Gly Lys Asp Cys Thr Val Pro Ile Asn Thr Cys Val
945                 950                 955                 960

Gln Asn Pro Cys Glu His Gly Gly Thr Cys His Leu Ser Glu Asn Leu
                965                 970                 975

Arg Asp Gly Phe Ser Cys Ser Cys Pro Leu Gly Phe Glu Gly Gln Arg
            980                 985                 990

Cys Glu Ile Asn Pro Asp Asp Cys Glu Asp Asn Asp Cys Glu Asn Ser
        995                 1000                1005

Ala Thr Cys Val Asp Gly Ile Asn Asn Tyr Ala Cys Leu Cys Pro
    1010                1015                1020

Pro Asn Tyr Thr Gly Glu Leu Cys Asp Glu Val Ile Asp Tyr Cys
    1025                1030                1035

Val Pro Glu Met Asn Leu Cys Gln His Glu Ala Lys Cys Ile Ser
    1040                1045                1050

Leu Asp Lys Gly Phe Arg Cys Glu Cys Val Pro Gly Tyr Ser Gly
    1055                1060                1065

Lys Leu Cys Glu Thr Asn Asn Asp Asp Cys Val Ala His Lys Cys
    1070                1075                1080

Arg His Gly Ala Gln Cys Val Asp Glu Val Asn Gly Tyr Thr Cys
    1085                1090                1095

Ile Cys Pro Gln Gly Phe Ser Gly Leu Phe Cys Glu His Pro Pro
    1100                1105                1110

Pro Met Val Leu Leu Gln Thr Ser Pro Cys Asp Gln Tyr Glu Cys
    1115                1120                1125

Gln Asn Gly Ala Gln Cys Ile Val Val Gln Glu Pro Thr Cys
    1130                1135                1140

Arg Cys Pro Pro Gly Phe Ala Gly Pro Arg Cys Glu Lys Leu Ile
    1145                1150                1155

Thr Val Asn Phe Val Gly Lys Asp Ser Tyr Val Glu Leu Ala Ser
    1160                1165                1170

Ala Lys Val Arg Pro Gln Ala Asn Ile Ser Leu Gln Val Ala Thr
    1175                1180                1185

Asp Lys Asp Asn Gly Ile Leu Leu Tyr Lys Gly Asp Asn Asp Pro
    1190                1195                1200

Leu Ala Leu Glu Leu Tyr Gln Gly His Val Arg Leu Val Tyr Asp
    1205                1210                1215

Ser Leu Ser Ser Pro Pro Thr Thr Val Tyr Ser Val Glu Thr Val
    1220                1225                1230

Asn Asp Gly Gln Phe His Ser Val Glu Leu Val Met Leu Asn Gln
    1235                1240                1245
```

```
Thr Leu Asn Leu Val Val Asp Lys Gly Ala Pro Lys Ser Leu Gly
    1250                1255                1260

Lys Leu Gln Lys Gln Pro Ala Val Gly Ser Asn Ser Pro Leu Tyr
    1265                1270                1275

Leu Gly Gly Ile Pro Thr Ser Thr Gly Leu Ser Ala Leu Arg Gln
    1280                1285                1290

Gly Ala Asp Arg Pro Leu Gly Gly Phe His Gly Cys Ile His Glu
    1295                1300                1305

Val Arg Ile Asn Asn Glu Leu Gln Asp Phe Lys Ala Leu Pro Pro
    1310                1315                1320

Gln Ser Leu Gly Val Ser Pro Gly Cys Lys Ser Cys Thr Val Cys
    1325                1330                1335

Arg His Gly Leu Cys Arg Ser Val Glu Lys Asp Ser Val Val Cys
    1340                1345                1350

Glu Cys His Pro Gly Trp Thr Gly Pro Leu Cys Asp Gln Glu Ala
    1355                1360                1365

Arg Asp Pro Cys Leu Gly His Ser Cys Arg His Gly Thr Cys Met
    1370                1375                1380

Ala Thr Gly Asp Ser Tyr Val Cys Lys Cys Ala Glu Gly Tyr Gly
    1385                1390                1395

Gly Ala Leu Cys Asp Gln Lys Asn Asp Ser Ala Ser Ala Cys Ser
    1400                1405                1410

Ala Phe Lys Cys His His Gly Gln Cys His Ile Ser Asp Arg Gly
    1415                1420                1425

Glu Pro Tyr Cys Leu Cys Gln Pro Gly Phe Ser Gly His His Cys
    1430                1435                1440

Glu Gln Glu Asn Pro Cys Met Gly Glu Ile Val Arg Glu Ala Ile
    1445                1450                1455

Arg Arg Gln Lys Asp Tyr Ala Ser Cys Ala Thr Ala Ser Lys Val
    1460                1465                1470

Pro Ile Met Glu Cys Arg Gly Gly Cys Gly Ser Gln Cys Cys Gln
    1475                1480                1485

Pro Ile Arg Ser Lys Arg Arg Lys Tyr Val Phe Gln Cys Thr Asp
    1490                1495                1500

Gly Ser Ser Phe Val Glu Glu Val Glu Arg His Leu Glu Cys Gly
    1505                1510                1515

Cys Arg Ala Cys Ser
    1520

<210> SEQ ID NO 127
<211> LENGTH: 4
<212> TYPE: PRT
<213> ORGANISM: Artificial Sequence
<220> FEATURE:
<223> OTHER INFORMATION: /note="Description of Artificial Sequence:
      RRX(S/T) motif"
<220> FEATURE:
<221> NAME/KEY: misc_feature
<222> LOCATION: (3)..(3)
<223> OTHER INFORMATION: Xaa = any amino acid
<220> FEATURE:
<221> NAME/KEY: misc_feature
<222> LOCATION: (4)..(4)
<223> OTHER INFORMATION: Xaa = S or T

<400> SEQUENCE: 127

Arg Arg Xaa Xaa
1
```

METHODS FOR IDENTIFICATION, ASSESSMENT, PREVENTION, AND TREATMENT OF METABOLIC DISORDERS USING SLIT2

CROSS-REFERENCE TO RELATED APPLICATIONS

This application claims the benefit of priority to U.S. Provisional Application No. 62/193,359, filed 16 Jul. 2015, the entire contents of said application is incorporated herein in its entirety by this reference.

STATEMENT OF RIGHTS

This invention was made with government support under Grant DK031405 awarded by the National Institutes of Health. The U.S. government has certain rights in the invention.

BACKGROUND OF THE INVENTION

Metabolic disorders comprise a collection of health disorders or risks that increase the risk of morbidity and loss of qualify of life. For example, diabetes, obesity, including central obesity (disproportionate fat tissue in and around the abdomen), atherogenic dyslipidemia (including a family of blood fat disorders, e.g., high triglycerides, low HDL cholesterol, and high LDL cholesterol that can foster plaque buildups in the vascular system, including artery walls), high blood pressure (130/85 mmHg or higher), insulin resistance or glucose intolerance (the inability to properly use insulin or blood sugar), a chronic prothrombotic state (e.g., characterized by high fibrinogen or plasminogen activator inhibitor-1 levels in the blood), and a chronic proinflammatory state (e.g., characterized by higher than normal levels of high-sensitivity C-reactive protein in the blood), are all metabolic disorders collectively afflicting greater than 50 million people in the United States.

Brown fat has attracted significant interest as an antidiabetic tissue owing to its ability to dissipate energy as heat (Cannon and Nedergaard (2004) *Physiol. Rev.* 84:277-359; Lowell and Spiegelman (2000) Nature 404:652-660). Activation of brown fat thermogenesis involves the induction of a program of genes, including uncoupling protein 1 (UCP1), which uncouples respiration and increases heat production in fat cells (Kozak and Harper (2000) *Annu. Rev. Nutr.* 20:339-363). Other non-UCP1 pathways may also contribute to non-shivering thermogenesis (Kazak et al. (2015) *Cell* 163:643-655). It is now recognized that at least two types of thermogenic fat cells exist—classical interscapular brown fat, as well as inducible brown-like adipocytes in white fat (also known as beige fat), which tends to be dispersed among white fat depots (Wu et al. (2012) *Cell* 150:366-376; Shinoda et al. (2015) *Nat. Med.* 4:389-394). BAT has high basal levels of UCP1, whereas beige fat has low basal levels that are highly inducible upon stimulation with cold or other agents (Wu et al. (2012) *Cell* 150:366-376). Despite their common ability to exhibit adaptive thermogenesis, brown and beige cells do not derive from the same lineage precursors (Lepper and Fan (2010) *Genesis* 48:424-436; Long et al. (2014) *Cell Metabolism* 19:810-820; Seale et al. (2008) *Nature* 454:961-967) and express different molecular signatures (Long et al. (2014) *Cell Metabolism* 19:810-820; Sharp et al. (2012) *PLoS One* 7:e49452; Wu et al. (2012) *Cell* 150:366-376; Harms and Seale (2013) *Nat. Med.* 19:1252-1263). Mouse models resistant to weight gain through enhanced brown and beige fat content or activity have demonstrated that activation of thermogenesis in fat can be a powerful strategy to improve metabolic health and prevent weight gain (Cederberg and Enerback (2003) *Curr. Mol. Med.* 3:107-125; Fisher et al. (2012) *Genes Dev.* 26:271-281; Vegiopoulos et al. (2010) *Science* 328:1158-1161; Ye et al. (2012) *Cell* 151:96-110). Ablation of UCP1+ cells in transgenic mice have an increased propensity toward obesity and diabetes (Lowell et al. (1993) *Nature* 366:740-742), whereas UCP1 knockout mice develop obesity under thermoneutrality conditions when fed a high fat diet (Feldmann et al. (2009) *Cell Metabolism* 9:203-209).

A physiological stimulus for inducing active thermogenic fat in mice and humans is a cold environment, which causes the release of neurotransmitters, such as catecholamines, from nerve terminals or M2 macrophages (Morrison et al. (2012) *Front. Endocrinol.* 3:5; Nguyen et al. (2011) *Nature* 480:103-108). Brown fat has relatively recently been found to exist and be functional in adult humans based on studies observing increased symmetrical glucose uptake in supraclavicular regions upon exposure to cold environment (Cypess et al. (2009) *N. Engl. J. Med.* 360:1509-1517; Virtanen et al. (2009) *N. Engl. J. Med.* 360:1518-1525; Yoneshiro et al. (2011) *Obesity* 19:13-16). Brown fat has also been shown to be activated by the β3-agonist, mirabegron, illustrating that the canonical cAMP pathway for adipose thermogenesis is likely to be function in humans and raising the possibility of additional, yet unknown pathways of activation (Cypess et al. (2014) *Cell Metab.* 21:33-38). The functional characteristics of human BAT has yet to be determined, but several papers have shown that supraclavicular human brown fat is most similar to the beige fat of rodents (Wu et al. (2012) *Cell* 150:366-376; Sharp et al. (2012) *PLoS ONE* 7:e49452; Shinoda et al. (2015) *Nat. Med.* 4:389-394). Thus, it is believed that brown and beige fat likely have complementary and overlapping functions in the maintenance of whole body energy homeostasis.

The transcriptional regulator PRDM16 is critical to the development of both brown and beige fat (Seale et al. (2007) *Cell Metabolism* 6:38-54; Seale et al. (2008) *Nature* 454:961-967; Kajimura et al. (2009) *Nature* 460:1154-1158; Seale et al. (2011) *J. Clin. Invest.* 121:96-105). Mice with fat-specific ablation of PRDM16 demonstrate significantly lower basal thermogenic gene expression in the subcutaneous fat: these animals are also resistant to browning of the white fat when stimulated with a cold environment or β3-agonism (Cohen et al. (2014) *Cell* 156:304-316). Conversely, aP2-PRDM16 transgenic mice show enhanced "browning" of their subcutaneous adipose depots, leading to augmented energy expenditure, reduced weight gain on high fat diet, and improved glucose and insulin homeostasis (Seale et al. (2011) *J Clin. Invest.* 121:96-105). As the classical brown fat in this model was found to be relatively unaffected, adiponectin (aP)-driven deletion of PRDM16 mice provide the opportunity to specifically study beige fat function. These mice develop a moderate obese phenotype compared to littermate controls, which is accompanied by an expansion of the subcutaneous depots with increased infiltration of inflammatory immune cells.

Despite decades of scientific research, such factors have not been identified and few effective therapies have emerged to treat metabolic disorders. The various metabolic benefits of activating brown or beige fat have raised interest in the discovery of hormones and secreted proteins that can act on fat tissue locally or systemically to induce browning. Beige fat development occurs in distinct pockets of cells, consistent with the possibility of a paracrine regulatory factor at work. White adipose tissues secrete many proteins factors (adipokines) that influence local and systemic metabolism, including adipsin, adiponectin, leptin and TNFα (Rosen and Spiegelman (2014) *Cell.* 156:20-44; Blither and Mantzoros (2015) *Metabolism.* 64:131.45). However, there is a great need to identify molecular regulators of metabolic disorders, especially those unknown secretory proteins from brown and/or beige fat. Such molecular regulators would also be useful in the generation of diagnostic, prognostic, and therapeutic agents to effectively control metabolic disorders in subjects.

SUMMARY OF THE INVENTION

The present invention is based in part on the discovery that Slit2 and biologically active fragments thereof are polypeptides secreted by beige fat cells that have the ability to modulate many metabolic processes, including modulating adipose thermogenesis, energy expenditure, and glucose homeostasis. Expression of Slit2 and its biologically active fragments is regulated by thermogenic stimuli (e.g., Prdm16 and cold exposure), their expression is downregulated in the white adipose tissue of obese animals, and they induce activation of PKA signaling, which is required for its pro-thermogenic activity. Slit2 and its biologically active fragments protect against diet-induced insulin resistance when circulating levels of Slit2 are increased in the blood, as it induces a thermogenic gene expression program in the subcutaneous white fat. Slit2 and its biologically active fragments act in a cell-autonomous manner to induce a cAMP cellular signaling program, induce thermogenic gene expression, and increase whole body energy expenditure. Based on this role in peripheral tissue for Slit and its biologically active fragments to modulate adipose tissue homeostasis and glucose metabolism, they have the therapeutic ability to treat metabolic disorders, especially obesity-induced metabolic disorders.

In one aspect, a use of an agent that modulates expression and/or activity of Slit2 or a biologically active fragment thereof in a subject for the preparation of a medicament for modulating a metabolic response in the subject is provided.

(S/T) residue is a serine or threonine, HSL; and k) modified expression of UCP1 protein. In still another embodiment, the metabolic response is upregulated. In yet another embodiment, the metabolic response is downregulated.

As described above, the compositions and methods of the present invention are characterized by many embodiments and each such embodiment can be applied to any combination of embodiments described herein. For example, in one embodiment, expression and/or activity of Slit2 or the biologically active fragment thereof is upregulated. In another embodiment, expression and/or activity of Slit2 or the biologically active fragment thereof is upregulated using an agent selected from the group consisting of a nucleic acid molecule encoding a Slit2 polypeptide or fragment thereof, and a Slit2 polypeptide or fragment thereof. In still another embodiment, the method further comprises contacting the cell with an additional agent that increases the metabolic response. In yet another embodiment, expression and/or activity of Slit2 or the biologically active fragment thereof is downregulated. In another embodiment, expression and/or activity of Slit2 or the biologically active fragment thereof is downregulated using an agent selected from the group consisting of an anti-Slit2 antisense nucleic acid molecule, an anti-Slit2 RNA interference molecule, a blocking anti-Slit2 antibody, a non-activating form of Slit2 polypeptide or fragment thereof, and a small molecule that binds to Slit2. In still another embodiment, the method further comprises contacting the cell with an additional agent that decreases the metabolic response. In yet another embodiment, the step of contacting occurs in vivo. In another embodiment, the step of contacting occurs in vitro. In still another embodiment, the cell is selected from the group consisting of fibroblasts, adipoblasts, preadipocytes, adipocytes, white adipocytes, brown adipocytes, and beige adipocytes. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein. In another embodiment, the metabolic response is upregulated. In still another embodiment, the metabolic response is downregulated.

In another aspect, a method for modulating a metabolic response comprising contacting a cell with an agent that modulates expression and/or activity of Slit2 or a biologically active fragment thereof to thereby modulate the metabolic response is provided.

In still another aspect, a method of preventing or treating a metabolic disorder in a subject comprising administering to the subject an agent that promotes expression and/or activity of Slit2 or a biologically active fragment thereof in the subject, thereby preventing or treating the metabolic disorder in the subject is provided. In one embodiment, the agent is selected from the group consisting of a nucleic acid molecule encoding a Slit2 polypeptide or fragment thereof, and a Slit2 polypeptide or fragment thereof. In another embodiment, the agent is administered by intravenous or subcutaneous injection. In still another embodiment, the agent is administered in a pharmaceutically acceptable formulation. In yet another embodiment, the metabolic disorder is selected from the group consisting of insulin resistance, hyperinsulinemia, hypoinsulinemia, type II diabetes, hypertension, hyperhepatosteatosis, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, and Prader-Labhart-Willi syndrome. In another embodiment, the subject is a non-human animal or a human.

In yet another aspect, a method for preventing or treating a metabolic disorder in a subject comprising administering to the subject an agent that inhibits Slit2 expression and/or activity in the subject, thereby preventing or treating the metabolic disorder in the subject is provided. In one embodiment, the agent is selected from the group consisting of an anti-Slit2 antisense nucleic acid molecule, an anti-Slit2 RNA interference molecule, a blocking anti-Slit2 antibody, a non-activating form of Slit2 polypeptide or fragment thereof, and a small molecule that binds to Slit2. In another embodiment, the agent is administered by intravenous or subcutaneous injection. In still another embodiment, the agent is administered in a pharmaceutically acceptable formulation. In yet another embodiment, the metabolic disorder is selected from the group consisting of obesity-associated cancer, anorexia, and cachexia. In another embodiment, the subject is a non-human animal or a human.

In another aspect, a cell-based assay for screening for agents that modulate a metabolic response in a cell by modulating the expression and/or activity of Slit2 or a biologically active fragment comprising contacting the cell expressing Slit2 or the biologically active fragment thereof with a test agent the modulates the expression and/or activity of Slit2 and determining the ability of the test agent to modulate a metabolic response in the cell is provided.

In still another aspect, a method for assessing the efficacy of an agent that modulates Slit2 expression and/or activity for modulating a metabolic response in a subject, comprising a) detecting in a subject sample at a first point in time, the expression and/or activity of Slit2; b) repeating step a) during at least one subsequent point in time after administration of the agent; and c) comparing the expression and/or activity detected in steps a) and b), wherein a significantly lower expression and/or activity of a marker listed in Table 1 or 2 in the first subject sample relative to at least one subsequent subject sample, indicates that the agent increases the metabolic response in the subject and/or wherein a significantly higher expression and/or activity of a marker listed in Table 1 or 2 in the first subject sample relative to at least one subsequent subject sample, indicates that the test agent decreases the metabolic response in the subject is provided.

As described above, the compositions, assays, and methods of the present invention are characterized by many embodiments and each such embodiment can be applied to any combination of embodiments described herein. For example, in one embodiment, expression and/or activity of Slit2 or the biologically active fragment thereof is upregulated. In another embodiment, expression and/or activity of Slit2 or the biologically active fragment thereof is downregulated. In still another embodiment, the agent is selected from the group consisting of a nucleic acid molecule encoding a Slit2 polypeptide or fragment thereof, a Slit2 polypeptide or fragment thereof, a small molecule that binds to Slit2, an anti-Slit2 antisense nucleic acid molecule, an anti-Slit2 RNA interference molecule, an anti-Slit2 siRNA molecule, a blocking anti-Slit2 antibody, and a non-activating form of Slit2 polypeptide or fragment thereof. In yet another embodiment, the subject has undergone treatment for the metabolic disorder, has completed treatment for the metabolic disorder, and/or is in remission from the metabolic disorder between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of a metabolic disorder. In yet another embodiment, the first and/or at least one subsequent sample is selected from the group consisting of tissue, whole blood, serum, plasma, buccal scrape, saliva, cerebrospinal fluid, urine, stool, and bone marrow. In another embodiment, the first and/or at least one subsequent sample is a portion of a single sample or pooled samples obtained from the subject. In still another embodiment, a significantly higher expression and/or activity comprises upregulating the expression and/or activity by at least 25% relative to the second sample. In yet another embodiment, a significantly lower expression and/or activity comprises downregulating the expression and/or activity by at least 25% relative to the second sample. In another embodiment, the amount of the marker is compared. In still another embodiment, the amount of the marker is determined by determining the level of protein expression of the marker. In yet another embodiment, the presence of the protein is detected using a reagent which specifically binds with the protein. In another embodiment, the reagent is selected from the group consisting of an antibody, an antibody derivative, and an antibody fragment. In still another embodiment, the level of expression of the marker in the sample is assessed by detecting the presence in the sample of a transcribed polynucleotide or portion thereof. In yet another embodiment, the transcribed polynucleotide is an mRNA or a cDNA. In another embodiment, the step of detecting further comprises amplifying the transcribed polynucleotide. In still another embodiment, the level of expression of the marker in the sample is assessed by detecting the presence in the sample of a transcribed polynucleotide which anneals with the marker or anneals with a portion of a polynucleotide under stringent hybridization conditions. In yet another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein. In another embodiment, the metabolic response is upregulated. In still another embodiment, the metabolic response is downregulated. In yet another embodiment, Slit2 is selected from the group of Slit2 sequences shown in Table 1.

BRIEF DESCRIPTION OF FIGURES

FIG. 12 includes 6 panels, identified as panels A, B, C, D, E, and F, which show that Slit2 promotes a thermogenesis program in cells and in mice. Panels A and B show normalized thermogenic mRNA expression (Panel A) and (Panel B) oxygen consumption measured by Seahorse in primary brown fat cells from $Slit2^{flox/flox}$ mice transduced with adenovirus expressing LacZ ($Slit2^{flox/flox}$) or CRE)($Slit2^{KO}$). Panel C shows total body weight in $Slit2^{flox/flox}$ mice infected with with AAV8-GFP ($Slit2^{flox/flox}$-AAV8-GFP) or CRE virus ($Slit2^{flox/flox}$-AAV8-CRE) (n=8). Panels D-F show normalized mRNA expression of vascular and neuronal markers in BAT (Panel D), iWAT (Panel E) and quadriceps muscle (Panel F) 7 days postinjection with LacZ or Slit2-FL adenovirus.

Figures 1D, 1E:
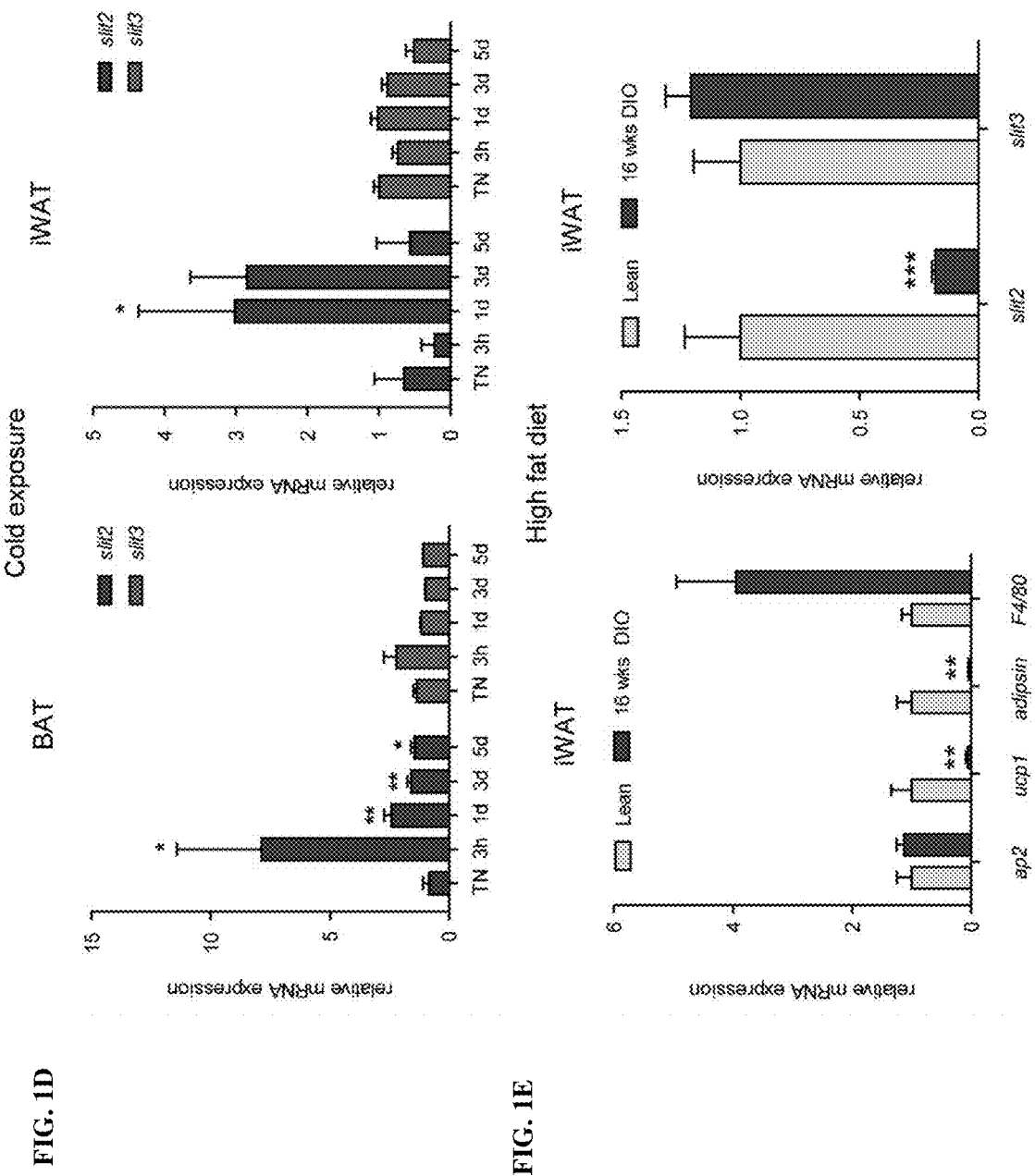
FIG. 1 includes 7 panels, identified as panels A, B, C, D, E, F, and G which show that Slit2 is a PRDM16-regulated secreted protein in adipose cells. Panel A representative images from UCP1 immunohistochemistry on sections of inguinal subcutaneous adipose tissue from aP2-PRDM16 and wild type mice. Images are shown at 10× magnification. Scale bar, 100 µm. Panel B shows normalized thermogenic gene expression in primary inguinal cells from aP2-PRDM16 and wild type mice at day 7 of differentiation. Panel C shows a heat map of relative protein levels in conditioned medium from wild type or ap2-PRDM16 primary inguinal cells (n=2 per group) as determined by TMT labeling and mass spectrometry. Shown is a short list of detected secreted proteins. The fold change for each individual sample is shade-coded according to the key. Panel D shows the normalized mRNA expression of Slit1, Slit2 and Slit3 in BAT and iWAT from 6 week-old mice chronically housed at 30° C. thermoneutrality (TN) or exposed to a 4° C. cold challenge for the indicated time points (n=3 per group). Gene expression of Apt, Ucp1, Adipsin, F4/80, Slit2 and Slit3 in iWAT (Panel E) and Slit2 and Slit3 in eWAT (Panel F) from C57/b6 mice fed a chow diet or a high fat diet for 16 weeks is shown. Panel G shows primary inguinal cells treated with forskolin for 4 h before gene expression analysis of Adiponectin, Ucp1, Slit2 and Slit3. Data are presented as mean±SEM. *$p<0.05$, $p<0.01$, *$p<0.001$.

Note that for every figure containing a histogram, the bars from left to right for each discreet measurement correspond to the figure boxes from top to bottom in the figure legend as indicated.

DETAILED DESCRIPTION OF THE INVENTION

The present invention is based in part on the discovery that Slit2 and biologically active fragments thereof are secreted polypeptides that have the ability to modulate adipose thermogenesis and related metabolic activity (e.g., modulate one or more biological activities of a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein.

It is demonstrated herein that Slit2 and its biologically active cleavage products are secreted by beige fat cells and can act systemically on cells in culture and in vivo to stimulate a broad program of brown fat-like development. Slit2 and its biologically active cleavage products is induced by natural stimuli, such as at the cold and Prdm16 gene expression, and they can cause an increase in energy expenditure in mice with no change in movement or food intake. This results in improvement in metabolic disorders (e.g., obesity and glucose homeostasis).

In order that the present invention may be more readily understood, certain terms are first defined. Additional definitions are set forth throughout the detailed description.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarity, or, for example, in the case of binding to DNA duplexes, through specific interactions in the major groove of the double helix.

The terms "beige fat" or "brite (brown in white) fat" or "iBAT (induced brown adipose tissue)" or "recruitable BAT (brown adipose tissue)" or "wBAT (white adipose BAT)" refer to clusters of UCP1-expressing adipocytes having thermogenic capacity that develop in white adipose tissue (WAT). Beige fat can develop in subcutaneous WAT, such as in inguinal WAT, or in intra-abdominal WAT such as in epididymal WAT. Similar to adipocytes in brown adipose tissue (BAT), beige cells are characterized by a) multilocular lipid droplet morphology, b), high mitochondrial content, and/or c) expression of a core set of brown fat-specific genes, such as Ucp1, Cidea, Pgc1a, and other listed in Table 2. BAT and beige fat both are able to undergo thermogenesis, but these are distinct cell types since beige cells do not derive from Myf5 precursor cells like BAT cells, beige fat express thermogenic genes only in response to activators like beta-adrenergic receptor or PPARgamma agonists unlike constitutive expression in BAT cells (Harms and Seale (2013) *Nat. Med.* 19:1252-1263).

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The terms "metabolic disorder" and "obesity related disorders" are used interchangeably herein and include a disorder, disease or condition which is caused or characterized by an abnormal or unwanted metabolism (i.e., the chemical changes in living cells by which energy is provided for vital processes and activities) in a subject. Metabolic disorders include diseases, disorders, or conditions associated with aberrant or unwanted (higher or lower) thermogenesis or aberrant or unwanted levels (high or low) adipose cell (e.g., brown or white adipose cell) content or function. Metabolic disorders can be characterized by a misregulation (e.g., downregulation or upregulation) of PGC-1 activity. Metabolic disorders can detrimentally affect cellular functions such as cellular proliferation, growth, differentiation, or migration, cellular regulation of homeostasis, inter- or intracellular communication; tissue function, such as liver function, muscle function, or adipocyte function; systemic responses in an organism, such as hormonal responses (e.g., insulin response). Examples of metabolic disorders include obesity, insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, Lawrence-Moon syndrome, Prader-Labhart-Willi syndrome, anorexia, and cachexia.

As used herein, the term "Slit2" refers to the Slit2 family member of the slit family of secreted proteins and is intended to include fragments, variants (e.g., allelic variants) and derivatives thereof unless otherwise specified. Slit proteins are secreted extracellular matrix proteins bound to the cell surface by the extracellular matrix (e.g., heparan sulfates) (Liang et al. (1999) J. Biol. Chem. 274:17885-17892; Ronca et al. (2001) J. Biol. Chem. 276:29141-29147). Slit proteins have four leucine-rich repeat (LRR) domains connected by disulfide bonds, followed by six epidermal growth factor (EGF) repeats, a beta-sandwich domain similar to that of laminin G called a LamG domain, one to three additional EGF repeats, and a C-terminal cysteine knot (Holmes et al. (1998) Mech. Dev. 79:57-72; Itoh et al. (1998) Brain Res. Mol. Brain Res. 62:175-186; Brose et al. (1999) Cell 96:795-806; Rothberg and Artavanis-Tsakonas (1992) J. Mol. Biol. 227:367-370; Hohenester et al. (1999) Mol. Cell 4:783-792; Nguyen-Ba-Carvet and Chedotal (2002) Neuron 22:463-473). Slit2 is proteolytically cleaved within the EGF domain region (Brose et al. (1999) Cell 96:795-806; Patel et al. (2001) Development 128:5031-5037; Condac et al. (2012) Glycobiol. 22:1183-1192. Following proteolytic cleavage of Slit2, the canonical 140 kDa N-terminal fragment remains associated with the cell surface, whereas the 50-60 kDa C-terminal fragment can be detected in conditioned cell media (Brose et al. (1999) Cell 96:795-806; Wang et al. (1999) Cell 96:771-784. Slit2 protein is known to interact with the transmembrane receptor Roundabout, also known as Robo, and is known to be involved in neuronal guidance, kidney development, blood cell migration, and osteoblast differentiation. However, Slit2 has not heretofore been implicated in the regulation of cellular metabolism. Mature slit proteins lack a signal sequence and Slit2 sequences of the present invention can comprise a signal sequence, as well as lack a signal sequence. The Slit2 signal sequence is generally the most N-terminal 20, 21, 22, 23, 24, 25, 26, 27, 28, 29, or 30 amino acids. In one embodiment, the Slit2 signal sequence is MSGIGWQTLSLSLGLVLSILNKVAP (SEQ ID NO: 124).

At least three splice variants encoding distinct human Slit2 isoforms exist. Slit2 isoform 1 (NM_004787.2 and NP_004778.1), also referred to as Slit2A, is the longest human Slit2 protein and is encoded by the longest transcript. Slit2 isoform 2 (NM_001289135.1 and NP_001276064.1), also referred to as Slit2C, lacks an alternate in-frame exon in the 5' coding region relative to the Slit2 transcript variant 1 and therefore encodes a smaller isoform relative to the Slit2 isoform 1. Slit2 isoform 3 (NM_001289136.1 and NP_001276065.1), also referred to as Slit2B, also lacks an alternate in-frame exon in the 5' coding region relative to the Slit2 transcript variant 1 and therefore encodes a smaller isoform relative to the Slit2 isoform 1. The nucleic acid and polypeptide sequences for each transcript variant and isoform is provided herein as SEQ ID NOs:1-6, respectively. Nucleic acid and polypeptide sequences of Slit2 orthologs in organisms other than humans are well known and include, for example, *Mus musculus* Slit2 (NM_001291227.1, NP_001278156.1, NM_001291228.1, NP_001278157.1, NM_178804.4, and NP_848919.3); *Rattus norvegicus* Slit2 (NM_022632.2 and NP_072154.2); *Canis lupus familiaris* Slit2 (XM_005618749.1 and XP_005618806.1); *Bos taurus* Slit2 (NM_001191516.2 and NP_001178445.2); and *Gallus gallus* Slit2 (NM_001267075.1 and NP_001254004.1).

In some embodiments, fragments of Slit2 having one or more biological activities of the full-length Slit2 protein are described and employed. Such fragments can comprise or consist of at least one domain of a Slit2 protein without containing the full-length Slit2 protein sequence. In some embodiments, Slit2 fragments can comprise, or consist of, an N-terminal signal peptide sequence (SS) domain, a leucine-rich repeat (LRR) domain, an EGF domain, a LamG domain, and a C-terminal cysteine knot domain, without containing the full-length Slit2 protein sequence. As further indicated in the Examples, Slit2 orthologs are highly homologous and retain common structural domains well known in the art. Biologically active fragments, such as Slit2-N and Slit2-C, are also described herein.

TABLE 1

```
SEQ ID NO: 1 Human Slit2 Transcript Variant 1 cDNA Sequence
    1    atgcgcggcg ttggctggca gatgctgtcc ctgtcgctgg ggttagtgct ggcgatcctg 61    aacaaggtgg caccgcaggc gtgcccggcg cagtgctctt gctcgggcag cacagtggac 121    tgtcacgggc tggcgctgcg cagcgtgccc aggaatatcc cccgcaacac cgagagactg 181    gatttaaatg gaaataacat cacaagaatt acgaagacag attttgctgg tcttagacat 241    ctaagagttc ttcagcttat ggagaataag attagcacca ttgaaagagg agcattccag 301    gatcttaaag aactagagag actgcgttta aacagaaatc accttcagct gtttcctgag 361    ttgctgtttc ttgggactgc gaagctatac aggcttgatc tcagtgaaaa ccaaattcag 421    gcaatcccaa ggaaagcttt ccgtggggca gttgacataa aaaatttgca actggattac 481    aaccagatca gctgtattga agatgggggca ttcagggctc tccgggacct ggaagtgctc 541    actctcaaca ataacaacat tactagactt tctgtggcaa gtttcaacca tatgcctaaa 601    cttaggactt ttcgactgca ttcaaacaac ctgtattgtg actgccacct ggcctggctc 661    tccgactggc ttcgccaaag gcctcgggtt ggtctgtaca ctcagtgtat gggccctcc 721    cacctgagag gccataatgt agccgaggtt caaaaacgag aatttgtctg cagtggtcac 781    cagtcattta tggctccttc ttgtagtgtt ttgcactgcc ctgccgcctg tacctgtagc 841    aacaatatcg tagactgtcg tgggaaaggt ctcactgaga tccccacaaa tcttccagag 901    accatcacag aaatacgttt ggaacagaac acaatcaaag tcatccctcc tggagctttc 961    tcaccatata aaaagcttag acgaattgac ctgagcaata atcagatctc tgaacttgca
```

TABLE 1-continued

```
1021  ccagatgctt tccaaggact acgctctctg aattcacttg tcctctatgg aaataaaatc
1081  acagaactcc ccaaaagttt atttgaagga ctgttttcct tacagctcct attattgaat
1141  gccaacaaga taaactgcct tcgggtagat gcttttcagg atctccacaa cttgaacctt
1201  ctctccctat atgacaacaa gcttcagacc atcgccaagg ggacctttc acctcttcgg
1261  gccattcaaa ctatgcattt ggcccagaac cccttttattt gtgactgcca tctcaagtgg
1321  ctagcggatt atctccatac caacccgatt gagaccagtg gtgcccgttg caccagcccc
1381  cgccgcctgg caaacaaaag aattggacag atcaaaagca agaaattccg ttgttcagct
1441  aaagaacagt atttcattcc aggtacagaa gattatcgat caaaattaag tggagactgc
1501  tttgcggatc tggcttgccc tgaaaagtgt cgctgtgaag gaaccacagt agattgctct
1561  aatcaaaagc tcaacaaaat cccggagcac attccccagt acactgcaga gttgcgtctc
1621  aataataatg aatttaccgt gttggaagcc acaggaatct ttaagaaact tcctcaatta
1681  cgtaaaataa actttagcaa caataagatc acagatattg aggagggagc atttgaagga
1741  gcatctggtg taaatgaaat acttcttacg agtaatcgtt tggaaaatgt gcagcataag
1801  atgttcaagg gattggaaag cctcaaaact ttgatgttga gaagcaatcg aataacctgt
1861  gtggggaatg acagtttcat aggactcagt tctgtgcgtt tgctttcttt gtatgataat
1921  caaattacta cagttgcacc agggcatt gatactctcc attctttatc tactctaaac
1981  ctcttggcca atccttttaa ctgtaactgc tacctggctt ggttgggaga gtggctgaga
2041  aagaagagaa ttgtcacggg aaatcctaga tgtcaaaaac catacttcct gaaagaaata
2101  cccatccagg atgtggccat tcaggacttc acttgtgatg acggaaatga tgacaatagt
2161  tgctccccac tttctcgctg tcctactgaa tgtacttgct tggatacagt cgtccgatgt
2221  agcaacaagg gtttgaaggt cttgccgaaa ggtattccaa gagatgtcac agagttgtat
2281  ctggatggaa accaatttac actggttccc aaggaactct ccaactacaa acatttaaca
2341  cttatagact taagtaacaa cagaataagc acgctttcta atcagagctt cagcaacatg
2401  acccagctcc tcaccttaat tcttagttac aaccgtctga gatgtattcc tcctcgcacc
2461  tttgatggat taaagtctct tcgattactt tctctacatg gaaatgacat ttctgttgtg
2521  cctgaaggtg ctttcaatga tctttctgca ttatcacatc tagcaattgg agccaaccct
2581  ctttactgtg attgtaacat gcagtggtta tccgactggg tgaagtcgga atataaggag
2641  cctggaattg ctcgttgtgc tggtcctgga gaaatggcag ataaacttt actcacaact
2701  ccctccaaaa aatttacctg tcaaggtcct gtggatgtca atattctagc taagtgtaac
2761  ccctgcctat caaatccgtg taaaaatgat ggcacatgta atagtgatcc agttgacttt
2821  taccgatgca cctgtccata tggtttcaag gggcaggact gtgatgtccc aattcatgcc
2881  tgcatcagta acccatgtaa acatggagga acttgccact taaaggaagg agaagaagat
2941  ggattctggt gtatttgtgc tgatggattt gaaggagaaa attgtgaagt caacgttgat
3001  gattgtgaag ataatgactg tgaaaataat tctacatgtg tcgatggcat taataactac
3061  acatgccttt gcccacctga gtataagg gagttgtgtg aggagaagct ggacttctgt
3121  gcccaggacc tgaaccctg ccagcacgat tcaaagtgca tcctaactcc aaagggattc
3181  aaatgtgact gcacaccagg gtacgtaggt gaacactgcg acatcgattt tgacgactgc
3241  caagacaaca agtgtaaaa cggagcccac tgcacagatg cagtgaacgg ctatacgtgc
3301  atatgccccg aaggttacag tggcttgttc tgtgagttt ctccacccat ggtcctccct
3361  cgtaccagcc cctgtgataa ttttgattgt cagaatggag ctcagtgtat cgtcagaata
```

TABLE 1-continued

```
3421  aatgagccaa tatgtcagtg tttgcctggc tatcagggag aaaagtgtga aaaattggtt
3481  agtgtgaatt ttataaacaa agagtcttat cttcagattc cttcagccaa ggttcggcct
3541  cagacgaaca taacacttca gattgccaca gatgaagaca gcggaatcct cctgtataag
3601  ggtgacaaag accatatcgc ggtagaactc tatcggggc gtgttcgtgc cagctatgac
3661  accggctctc atccagcttc tgccatttac agtgtggaga caatcaatga tggaaacttc
3721  cacattgtgg aactacttgc cttggatcag agtctctctt tgtccgtgga tggtgggaac
3781  cccaaaatca tcactaactt gtcaaagcag tccactctga attttgactc tccactctat
3841  gtaggaggca tgccagggaa gagtaacgtg gcatctctgc ccaggcccc tgggcagaac
3901  ggaaccagct ccacggctg catccggaac ctttacatca acagtgagct gcaggacttc
3961  cagaaggtgc cgatgcaaac aggcattttg cctggctgtg agccatgcca caagaaggtg
4021  tgtgcccatg gcacatgcca gcccagcagc caggcaggct tcacctgcga gtgccaggaa
4081  ggatggatgg ggcccctctg tgaccaacgg accaatgacc cttgccttgg aaataaatgc
4141  gtacatggca cctgcttgcc catcaatgcg ttctcctaca gctgtaagtg cttggagggc
4201  catggaggtg tcctctgtga tgaagaggag gatctgtttta acccatgcca ggcgatcaag
4261  tgcaagcatg ggaagtgcag gctttcaggt ctggggcagc cctactgtga atgcagcagt
4321  ggatacacgg gggacagctg tgatcgagaa atctcttgtc gaggggaaag gataagagat
4381  tattaccaaa agcagcaggg ctatgctgct tgccaaacaa ccaagaaggt gtcccgatta
4441  gagtgcagag gtgggtgtgc aggagggcag tgctgtggac cgctgaggag caagcggcgg
4501  aaatactctt tcgaatgcac tgacggctcc tcctttgtgg acgaggttga gaaagtggtg
4561  aagtgcggct gtacgaggtg tgtgtcctaa
```

SEQ ID NO: 2 Human Slit Isoform 1 Amino Acid Sequence

```
   1  mrgvgwqmls lslglvlail nkvapqacpa qcscsgstvd chglalrsvp rniprnterl
  61  dlngnnitri tktdfaglrh lrvlqlmenk istiergafq dlkelerlrl nrnhlqlfpe
 121  llflgtakly rldlsengiq aiprkafrga vdiknlqldy nqisciedga fralrdlevl
 181  tlnnnnitrl svasfnhmpk lrtfrlhsnn lycdchlawl sdwlrqrpry glytqcmgps
 241  hlrghnvaev qkrefvcsgh qsfmapscsv lhcpaactcs nnivdcrgkg lteiptnlpe
 301  titeirleqn tikvippgaf spykklrrid lsnnqisela pdafgglrsl nslvlygnki
 361  telpkslfeg lfslqlllln ankinclrvd afqdlhnlnl lslydnklqt iakgtfsplr
 421  aigtmhlagn pficdchlkw ladylhtnpi etsgarctsp rrlankrigq ikskkfrcsa
 481  keqyfipgte dyrsklsgdc fadlacpekc rcegttvdcs nqklnkipeh ipqytaelrl
 541  nnneftvlea tgifkklpql rkinfsnnki tdieegafeg asgvneillt snrlenvqhk
 601  mfkgleslkt lmlrsnritc vgndsfigls svrllslydn qittvapgaf dtlhslstln
 661  llanpfncnc ylawlgewlr kkrivtgnpr cqkpyflkei piqdvaiqdf tcddgndddns
 721  csplsrcpte ctcldtvvrc snkglkvlpk giprdvtely ldgnqftivp kelsnykhlt
 781  lidlsnnris tlsnqsfsnm tqlltlilsy nrlcipprt fdglkslrll slhgndisvv
 841  pegafndlsa lshlaiganp lycdcnmqwl sdwvkseyke pgiarcagpg emadkllltt
 901  pskkftcqgp vdvnilakcn pclsnpcknd gtcnsdpvdf yrctcpygfk gqdcdvpiha
 961  cisnpckhgg tchlkegeed gfwcicadgf egencevnvd dcedndcenn stcvdginny
1021  tcicppeytg elceeklfdc aqdlnpcqhd skciltpkgf kcdctpgyvg ehcdidfddc
1081  qdnkckngah ctdavngytc icpegysglf cefsppmvlp rtspcdnfdc qngaqcivri
```

TABLE 1-continued

```
1141  nepicqclpg yggekceklv svnfinkesy lqipsakvrp qtnitlqiat dedsgillyk
1201  gdkdhiavel yrgrvrasyd tgshpasaiy svetindgnf hivellaldq slslsvdggn
1261  pkiitnlskq stlnfdsply vggmpgksnv aslrqapgqn gtsfhgcirn lyinselqdf
1321  qkvpmqtgil pgcepchkkv cahgtcqpss gagftcecqe gwmgplcdqr tndpclgnkc
1381  vhgtclpina fsysckcleg hggvlcdeee dlfnpcgaik ckhgkcrlsg lgqpycecss
1441  gytgdscdre iscrgerird yyqkqqgyaa cqttkkvsrl ecrggcaggq ccgplrskrr
1501  kysfectdgs sfvdevekvv kcgctrcvs
```

SEQ ID NO: 3 Human Slit2 Transcript Variant 2 cDNA Sequence

```
   1  atgcgcggcg ttggctggca gatgctgtcc ctgtcgctgg ggttagtgct ggcgatcctg
  61  aacaaggtgg caccgcaggc gtgcccggcg cagtgctctt gctcgggcag cacagtggac
 121  tgtcacgggc tggcgctgcg cagcgtgccc aggaatatcc cccgcaacac cgagagactg
 181  gatttaaatg aaataacat cacaagaatt acgaagacag attttgctgg tcttagacat
 241  ctaagagttc ttcagcttat ggagaataag attagcacca ttgaaagagg agcattccag
 301  gatcttaaag aactagagag actgcgttta aacagaaatc accttcagct gtttcctgag
 361  ttgctgtttc ttgggactgc gaagctatac aggcttgatc tcagtgaaaa ccaaattcag
 421  gcaatcccaa ggaaagcttt ccgtggggca gttgacataa aaatttgca actggattac
 481  aaccagatca gctgtattga agatgggca ttcagggctc tccgggacct ggaagtgctc
 541  actctcaaca ataacaacat tactagactt tctgtggcaa gtttcaacca tatgcctaaa
 601  cttaggactt ttcgactgca ttcaaacaac ctgtattgtg actgccacct ggcctggctc
 661  tccgactggc ttcgccaaag gcctcgggtt ggtctgtaca ctcagtgtat gggcccctcc
 721  cacctgagag ccataatgt agccgaggtt caaaaacgag aatttgtctg cagtgatgag
 781  gaagaaggtc accagtcatt tatggctcct tcttgtagtg ttttgcactg ccctgccgcc
 841  tgtacctgta gcaacaatat cgtagactgt cgtgggaaag gtctcactga tccccaca
 901  aatcttccag agaccatcac agaaatacgt ttggaacaga cacaatcaa agtcatccct
 961  cctggagctt tctcaccata taaaaagctt agacgaattg acctgagcaa taatcagatc
1021  tctgaacttg caccagatgc tttccaagga ctacgctctc tgaattcact tgtcctctat
1081  ggaaataaaa tcacagaact ccccaaaagt ttatttgaag actgttttc cttacagctc
1141  ctattattga atgccaacaa gataaactgc cttcgggtag atgcttttca ggatctccac
1201  aacttgaacc ttctctccct atatgacaac aagcttcaga ccatcgccaa ggggaccttt
1261  tcacctcttc gggccattca aactatgcat ttgcccaga accctttat ttgtgactgc
1321  catctcaagt ggctagcgga ttatctccat accaacccga ttgagaccag tggtgcccgt
1381  tgcaccagcc ccgccgcct ggcaaacaaa agaattggac agatcaaaag caagaaattc
1441  cgttgttcag gtacagaaga ttatcgatca aaattaagtg gagactgctt tgcggatctg
1501  gcttgccctg aaaagtgtcg ctgtgaagga accacagtag attgctctaa tcaaaagctc
1561  aacaaaatcc cggagcacat tccccagtac actgcagagt tgcgtctcaa taataatgaa
1621  tttaccgtgt tggaagccac aggaatcttt aagaaacttc ctcaattacg taaaataaac
1681  tttagcaaca ataagatcac agatattgag gagggagcat tgaaggagc atctggtgta
1741  aatgaaatac ttcttacgag taatcgtttg gaaaatgtgc agcataagat gttcaaggga
1801  ttggaaagcc tcaaaacttt gatgttgaga agcaatcgaa taacctgtgt ggggaatgac
1861  agtttcatag gactcagttc tgtgcgtttg ctttctttgt atgataatca aattactaca
1921  gttgcaccag gggcatttga tactctccat tctttatcta ctctaaacct cttggccaat
```

TABLE 1-continued

```
1981  ccttttaact gtaactgcta cctggcttgg ttgggagagt ggctgagaaa gaagagaatt
2041  gtcacgggaa atcctagatg tcaaaaacca tacttcctga agaaatacc  catccaggat
2101  gtggccattc aggacttcac ttgtgatgac ggaaatgatg acaatagttg ctccccactt
2161  tctcgctgtc ctactgaatg tacttgcttg gatacagtcg tccgatgtag caacaagggt
2221  ttgaaggtct tgccgaaagg tattccaaga gatgtcacag agttgtatct ggatgaaac
2281  caatttacac tggttcccaa ggaactctcc aactacaaac atttaacact tatagactta
2341  agtaacaaca gaataagcac gctttctaat cagagcttca gcaacatgac ccagctcctc
2401  accttaattc ttagttacaa ccgtctgaga tgtattcctc ctcgcacctt tgatggatta
2461  aagtctcttc gattactttc tctacatgga aatgacattt ctgttgtgcc tgaaggtgct
2521  ttcaatgatc tttctgcatt atcacatcta gcaattggag ccaaccctct ttactgtgat
2581  tgtaacatgc agtggttatc cgactgggtg aagtcggaat ataaggagcc tggaattgct
2641  cgttgtgctg gtcctggaga aatggcagat aaacttttac tcacaactcc ctccaaaaaa
2701  tttacctgtc aaggtcctgt ggatgtcaat attctagcta agtgtaaccc ctgcctatca
2761  aatccgtgta aaaatgatgg cacatgtaat agtgatccag ttgacttta ccgatgcacc
2821  tgtccatatg gtttcaaggg gcaggactgt gatgtcccaa ttcatgcctg catcagtaac
2881  ccatgtaaac atggaggaac ttgccactta aaggaaggag aagaagatgg attctggtgt
2941  atttgtgctg atggatttga aggagaaaat tgtgaagtca cgttgatga  ttgtgaagat
3001  aatgactgtg aaaataattc tacatgtgtc gatggcatta ataactacac atgcctttgc
3061  ccacctgagt atacaggtga gttgtgtgag gagaagctgg acttctgtgc caggacctg
3121  aaccctgcc  agcacgattc aaagtgcatc ctaactccaa agggattcaa atgtgactgc
3181  acaccagggt acgtaggtga acactgcgac atcgattttg acgactgcca agacaacaag
3241  tgtaaaaacg gagcccactg cacagatgca gtgaacggct atacgtgcat atgccccgaa
3301  ggttacagtg gcttgttctg tgagttttct ccacccatgg tcctccctcg taccagcccc
3361  tgtgataatt ttgattgtca gaatggagct cagtgtatcg tcagaataaa tgagccaata
3421  tgtcagtgtt tgcctggcta tcagggagaa aagtgtgaaa aattggttag tgtgaatttt
3481  ataaacaaag agtcttatct tcagattcct tcagccaagg ttcggcctca gacgaacata
3541  acacttcaga ttgccacaga tgaagacagc ggaatcctcc tgtataaggg tgacaaagac
3601  catatcgcgg tagaactcta tcgggggcgt gttcgtgcca gctatgacac cggctctcat
3661  ccagcttctg ccatttacag tgtggagaca atcaatgatg gaaacttcca cattgtggaa
3721  ctacttgcct tggatcagag tctctctttg tccgtggatg gtgggaaccc caaaatcatc
3781  actaacttgt caaagcagtc cactctgaat tttgactctc cactctatgt aggaggcatg
3841  ccaggaaga  gtaacgtggc atctctgcgc caggcccctg ggcagaacga accagcttc
3901  cacggctgca tccggaacct ttacatcaac agtgagctgc aggacttcca gaaggtgccg
3961  atgcaaacag gcattttgcc tggctgtgag ccatgccaca gaaggtgtg  tgcccatggc
4021  acatgccagc ccagcagcca ggcaggcttc acctgcgagt gccaggaagg atggatgggg
4081  cccctctgtg accaacggac caatgacct  tgccttggaa ataaatgcgt acatggcacc
4141  tgcttgccca tcaatgcgtt ctcctacagc tgtaagtgct tggagggcca tggaggtgtc
4201  ctctgtgatg aagaggagga tctgttaac ccatgccagg cgatcaagtg caagcatggg
4261  aagtgcaggc tttcaggtct ggggcagccc tactgtgaat gcagcagtgg atacacgggg
4321  gacagctgtg atcgagaaat ctcttgtcga ggggaaagga taagagatta ttaccaaaag
```

TABLE 1-continued

```
4381    cagcagggct atgctgcttg ccaaacaacc aagaaggtgt cccgattaga gtgcagaggt
4441    gggtgtgcag gagggcagtg ctgtggaccg ctgaggagca agcggcggaa atactctttc
4501    gaatgcactg acggctcctc ctttgtggac gaggttgaga aagtggtgaa gtgcggctgt
4561    acgaggtgtg tgtcctaa
```

SEQ ID NO: 4 Human Slit2 Isoform 2 Amino Acid Sequence
```
   1    mrgvgwqmls lslglvlail nkvapqacpa qcscsgstvd chglalrsvp rniprnterl
  61    dlngnnitri tktdfaglrh lrvlqlmenk istiergafq dlkelerlrl nrnhlqlfpe
 121    llflgtakly rldlsengiq aiprkafrga vdiknlqldy nqisciedga fralrdlevl
 181    tlnnnnitrl svasfnhmpk lrtfrlhsnn lycdchlawl sdwlrqrpry glytqcmgps
 241    hlrghnvaev qkrefvcsde eeghqsfmap scsvlhcpaa ctcsnnivdc rgkglteipt
 301    nlpetiteir leqntikvip pgafspykkl rridlsnnqi selapdafqg lrslnslvly
 361    gnkitelpks lfeglfslql lllnankinc lrvdafqdlh nlnllslydn klqtiakgtf
 421    splraiqtmh laqnpficdc hlkwladylh tnpietsgar ctsprrlank rigqikskkf
 481    rcsgtedyrs klsgdcfadl acpekcrceg ttvdcsnqkl nkipehipqy taelrinnne
 541    ftvleatgif kklpqlrkin fsnnkitdie egafegasgv neilltsnrl envqhkmfkg
 601    leslktlmlr snritcvgnd sfiglssvrl lslydngitt vapgafdtlh slstlnllan
 661    pfncncylaw lgewlrkkri vtgnprcqkp yflkeipiqd vaiqdftcdd gnddnscspl
 721    srcptectcl dtvvrcsnkg lkvlpkgipr dvtelyldgn qftivpkels nykhltlidl
 781    snnristlsn gsfsnmtqll tlilsynrlr cipprtfdgl kslrllslhg ndisvvpega
 841    fndlsalshl aiganplycd cnmqwlsdwv kseykepgia rcagpgemad klllttpskk
 901    ftcqgpvdvn ilakcnpcls npckndgtcn sdpvdfyrct cpygfkgqdc dvpihacisn
 961    pckhggtchl kegeedgfwc icadgfegen cevnvddced ndcennstcv dginnytcic
1021    ppeytgelce ekldfcaqdl npcqhdskci ltpkgfkcdc tpgyvgehcd idfddcgdnk
1081    ckngahctda vngytcicpe gysglfcefs ppmvlprtsp cdnfdcqnga qcivrinepi
1141    cgclpgygge kceklvsvnf inkesylqip sakvrpqtni tlqiatdeds gillykgdkd
1201    hiavelyrgr vrasydtgsh pasaiysvet indgnfhive llaldqslsl svdggnpkii
1261    tnlskqstln fdsplyvggm pgksnvaslr qapgqngtsf hgcirnlyin selqdfqkvp
1321    mqtgilpgce pchkkvcahg tcussgagf tcecgegwmg plcdqrtndp clgnkcvhgt
1381    clpinafsys ckcleghggv lcdeeedlfn pcgaikckhg kcrlsglgqp ycecssgytg
1441    dscdreiscr gerirdyyqk qqgyaacqtt kkvsrlecrg gcaggqccgp lrskrrkysf
1501    ectdgssfvd evekvvkcgc trcvs
```

SEQ ID NO: 5 Human Slit2 Transcript Variant 3 cDNA Sequence
```
   1    atgcgcggcg ttggctggca gatgctgtcc ctgtcgctgg ggttagtgct ggcgatcctg
  61    aacaaggtgg caccgcaggc gtgcccggcg cagtgctctt gctcgggcag cacagtggac
 121    tgtcacgggc tggcgctgcg cagcgtgccc aggaatatcc cccgcaacac cgagagactg
 181    gatttaaatg gaaataacat cacaagaatt acgaagacag attttgctgg tcttagacat
 241    ctaagagttc ttcagcttat ggagaataag attagcacca ttgaagagg agcattccag
 301    gatcttaaag aactagagag actgcgttta aacagaaatc accttcagct gtttcctgag
 361    ttgctgtttc ttgggactgc gaagctatac aggcttgatc tcagtgaaaa ccaaattcag
 421    gcaatcccaa ggaaagcttt ccgtggggca gttgacataa aaaatttgca actggattac
 481    aaccagatca gctgtattga agatgggca ttcagggctc tccggacct ggaagtgctc
```

TABLE 1-continued

```
 541   actctcaaca ataacaacat tactagactt tctgtggcaa gtttcaacca tatgcctaaa
 601   cttaggactt ttcgactgca ttcaaacaac ctgtattgtg actgccacct ggcctggctc
 661   tccgactggc ttcgccaaag gcctcgggtt ggtctgtaca ctcagtgtat gggcccctcc
 721   cacctgagag gccataatgt agccgaggtt caaaaacgag aatttgtctg cagtggtcac
 781   cagtcattta tggctccttc ttgtagtgtt ttgcactgcc ctgccgcctg tacctgtagc
 841   aacaatatcg tagactgtcg tgggaaaggt ctcactgaga tccccacaaa tcttccagag
 901   accatcacag aaatacgttt ggaacagaac acaatcaaag tcatccctcc tggagctttc
 961   tcaccatata aaaagcttag acgaattgac ctgagcaata atcagatctc tgaacttgca
1021   ccagatgctt tccaaggact acgctctctg aattcacttg tcctctatgg aaataaaatc
1081   acagaactcc ccaaaagttt atttgaagga ctgttttcct tacagctcct attattgaat
1141   gccaacaaga taaactgcct tcgggtagat gcttttcagg atctccacaa cttgaacctt
1201   ctctccctat atgacaacaa gcttcagacc atcgccaagg ggacctttc acctcttcgg
1261   gccattcaaa ctatgcattt ggcccagaac ccctttattt gtgactgcca tctcaagtgg
1321   ctagcggatt atctccatac caacccgatt gagaccagtg gtgcccgttg caccagcccc
1381   cgccgcctgg caaacaaaag aattggacag atcaaaagca agaaattccg ttgttcaggt
1441   acagaagatt atcgatcaaa attaagtgga gactgctttg cggatctggc ttgccctgaa
1501   aagtgtcgct gtgaaggaac cacagtagat tgctctaatc aaaagctcaa caaaatcccg
1561   gagcacattc cccagtacac tgcagagttg cgtctcaata ataatgaatt taccgtgttg
1621   gaagccacag gaatctttaa gaaacttcct caattacgta aaataaactt tagcaacaat
1681   aagatcacag atattgagga gggagcattt gaaggagcat ctggtgtaaa tgaaatactt
1741   cttacgagta atcgtttgga aaatgtgcag cataagatgt tcaagggatt ggaaagcctc
1801   aaaactttga tgttgagaag caatcgaata acctgtgtgg ggaatgacag tttcatagga
1861   ctcagttctg tgcgtttgct ttctttgtat gataatcaaa ttactacagt tgcaccaggg
1921   gcatttgata ctctccattc tttatctact ctaaacctct ggccaatcc ttttaactgt
1981   aactgctacc tggcttggtt gggagagtgg ctgagaaaga agagaattgt cacgggaaat
2041   cctagatgtc aaaaaccata cttcctgaaa gaaatacca tccaggatgt ggccattcag
2101   gacttcactt gtgatgacgg aaatgatgac aatagttgct ccccactttc tcgctgtcct
2161   actgaatgta cttgcttgga tacagtcgtc cgatgtagca acaagggttt gaaggtcttg
2221   ccgaaaggta ttccaagaga tgtcacagag ttgtatctgg atggaaacca atttacactg
2281   gttcccaagg aactctccaa ctacaaacat ttaacactta tagacttaag taacaacaga
2341   ataagcacgc tttctaatca gagcttcagc aacatgaccc agctcctcac cttaattctt
2401   agttacaacc gtctgagatg tattcctcct cgcaccttg atggattaaa gtctcttcga
2461   ttactttctc tacatggaaa tgacatttct gttgtgcctg aaggtgcttt caatgatctt
2521   tctgcattat cacatctagc aattggagcc aaccctcttt actgtgattg taacatgcag
2581   tggttatccg actgggtgaa gtcggaatat aaggagcctg gaattgctcg ttgtgctggt
2641   cctggagaaa tggcagataa acttttactc acaactccct ccaaaaaatt tacctgtcaa
2701   ggtcctgtgg atgtcaatat tctagctaag tgtaaccct gcctatcaaa tccgtgtaaa
2761   aatgatggca catgtaatag tgatccagtt gacttttacc gatgcacctg tccatatggt
2821   ttcaagggc aggactgtga tgtcccaatt catgcctgca tcagtaaccc atgtaaacat
2881   ggaggaactt gccacttaaa ggaaggagaa gaagatggat tctggtgtat ttgtgctgat
```

TABLE 1-continued

```
2941    ggatttgaag gagaaaattg tgaagtcaac gttgatgatt gtgaagataa tgactgtgaa
3001    aataattcta catgtgtcga tggcattaat aactacacat gcctttgccc acctgagtat
3061    acaggtgagt tgtgtgagga gaagctggac ttctgtgccc aggacctgaa cccctgccag
3121    cacgattcaa agtgcatcct aactccaaag ggattcaaat gtgactgcac accagggtac
3181    gtaggtgaac actgcgacat cgattttgac gactgccaag acaacaagtg taaaaacgga
3241    gcccactgca cagatgcagt gaacggctat acgtgcatat gccccgaagg ttacagtggc
3301    ttgttctgtg agttttctcc acccatggtc ctccctcgta ccagcccctg tgataatttt
3361    gattgtcaga atggagctca gtgtatcgtc agaataaatg agccaatatg tcagtgtttg
3421    cctggctatc agggagaaaa gtgtgaaaaa ttggttagtg tgaattttat aaacaaagag
3481    tcttatcttc agattccttc agccaaggtt cggcctcaga cgaacataac acttcagatt
3541    gccacagatg aagacagcgg aatcctcctg tataagggtg acaaagacca tatcgcggta
3601    gaactctatc gggggcgtgt tcgtgccagc tatgacaccg gctctcatcc agcttctgcc
3661    atttacagtg tggagacaat caatgatgga aacttccaca ttgtggaact acttgccttg
3721    gatcagagtc tctctttgtc cgtggatggt gggaaccccca aaatcatcac taacttgtca
3781    aagcagtcca ctctgaattt tgactctcca ctctatgtag gaggcatgcc agggaagagt
3841    aacgtggcat ctctgcgcca ggcccctggg cagaacggaa ccagcttcca cggctgcatc
3901    cggaaccttt acatcaacag tgagctgcag gacttccaga aggtgccgat gcaaacaggc
3961    attttgcctg gctgtgagcc atgccacaag aaggtgtgtg cccatggcac atgccagccc
4021    agcagccagg caggcttcac ctgcgagtgc caggaaggat ggatggggcc cctctgtgac
4081    caacggacca atgacccttg ccttggaaat aaatgcgtac atggcacctg cttgcccatc
4141    aatgcgttct cctacagctg taagtgcttg gagggccatg gaggtgtcct ctgtgatgaa
4201    gaggaggatc tgtttaaccc atgccaggcg atcaagtgca agcatgggaa gtgcaggctt
4261    tcaggtctgg ggcagcccta ctgtgaatgc agcagtggat acacgggga cagctgtgat
4321    cgagaaatct cttgtcgagg ggaaaggata agagattatt accaaaagca gcagggctat
4381    gctgcttgcc aaacaaccaa gaaggtgtcc cgattagagt gcagaggtgg gtgtgcagga
4441    gggcagtgct gtggaccgct gaggagcaag cggcggaaat actctttcga atgcactgac
4501    ggctcctcct ttgtgggacga ggttgagaaa gtggtgaagt gcggctgtac gaggtgtgtg
4561    tcctaa
```

SEQ ID NO: 6 Human Slit2 Isoform 3 Amino Acid Sequence

```
  1    mrgvgwqmls lslglvlail nkvapqacpa qcscsgstvd chglalrsvp rniprnterl
 61    dlngnnitri tktdfaglrh lrvlqlmenk istiergafq dlkelerlrl nrnhlqlfpe
121    llflgtakly rldlsengiq aiprkafrga vdiknlqldy nqisciedga fralrdlevl
181    tlnnnnitrl svasfnhmpk lrtfrlhsnn lycdchlawl sdwlrqrpry glytqcmgps
241    hlrghnvaev qkrefvcsgh qsfmapscsv lhcpaactcs nnivdcrgkg lteiptnlpe
301    titeirleqn tikvippgaf spykklrrid lsnnqisela pdafgglrsl nslvlygnki
361    telpkslfeg lfslqlllln ankinclrvd afqdlhnlnl lslydnklqt iakgtfsplr
421    aigtmhlagn pficdchlkw ladylhtnpi etsgarctsp rrlankrigq ikskkfrcsg
481    tedyrsklsg dcfadlacpe kcrcegttvd csnqklnkip ehipqytael rinnneftvl
541    eatgifkklp qlrkinfsnn kitdieegaf egasgvneil ltsnrlenvq hkmfkglesl
601    ktlmlrsnri tcvgndsfig lssvrllsly dngittvapg afdtlhslst lnllanpfnc
```

TABLE 1-continued

```
 661  ncylawlgew lrkkrivtgn prcqkpyflk eipiqdvaiq dftcddgndd nscsplsrcp
 721  tectcldtvv rcsnkglkvl pkgiprdvte lyldgnqftl vpkelsnykh ltlidlsnnr
 781  istlsnqsfs nmtqlltlil synrlrcipp rtfdglkslr llslhgndis vvpegafndl
 841  salshlaiga nplycdcnmq wlsdwvksey kepgiarcag pgemadklll ttpskkftcq
 901  gpvdvnilak cnpclsnpck ndgtcnsdpv dfyrctcpyg fkgqdcdvpi hacisnpckh
 961  ggtchlkege edgfwcicad gfegencevn vddcedndce nnstcvdgin nytcicppey
1021  tgelceekld fcaqdlnpcq hdskciltpk gfkcdctpgy vgehcdidfd dcgdnkckng
1081  ahctdavngy tcicpegysg lfcefsppmv lprtspcdnf dcqngaqciv rinepicgcl
1141  pgyqgekcek lvsvnfinke sylqipsakv rpqtnitlqi atdedsgill ykgdkdhiav
1201  elyrgrvras ydtgshpasa iysvetindg nfhivellal dqslslsvdg gnpkiitnls
1261  kgstlnfdsp lyvggmpgks nvaslrqapg qngtsfhgci rnlyinselq dfqkvpmqtg
1321  ilpgcepchk kvcahgtcqp ssgagftcec qegwmgplcd grtndpolgn kcvhgtclpi
1381  nafsysckcl eghggvlcde eedlfnpcqa ikckhgkcrl sglgqpycec ssgytgdscd
1441  reiscrgeri rdyyqkqqgy aacqttkkvs rlecrggcag gqccgplrsk rrkysfectd
1501  gssfvdevek vvkcgctrcv s
```
SEQ ID NO: 7 Mouse Slit2 Transcript Variant 1 cDNA Sequence
```
   1  atgagtggca ttggctggca gacactgtcc ctatcgctgg ggttagtgtt gtcgatcttg
  61  aacaaggtgg cgccgcaggc gtgcccggcc cagtgctcct gttcaggcag cacggtggac
 121  tgtcatgggc tggcactgcg cagtgtgccc aggaatatcc cccgcaacac cgagagactg
 181  gatttgaatg gaaataacat cacgaggatc acgaagatag attttgctgg tctcaggcac
 241  ctcagagttc ttcagctcat ggagaacaga atcagcacca tcgagagggg agcattccag
 301  gatcttaagg agctggaaag actgcgttta aacagaaata accttcagtt gtttcctgag
 361  ctgctgtttc tcgggactgc gaagctctac cggcttgatc tcagtgaaaa tcaaattcaa
 421  gcaattccaa ggaaggcttt ccgtgggca gttgacatta aaaacctgca actggattac
 481  aaccagatca gctgcattga agatggggcg ttcagagctc tacgagatct ggaagtgctc
 541  actctgaaca ataacaatat tactagactt tcagtggcaa gtttcaacca tatgcctaaa
 601  cttaggacat ttcgactcca ctcgaacaac ttgtactgcg actgccacct agcctggctc
 661  tcagactggc ttcgccaaag gccacgggtg ggcttgtaca ctcagtgtat gggcccatcc
 721  cacctgaggg ccacaatgt agcagaggtt caaaaacgag agtttgtctg cagtgatgag
 781  gaagaaggtc accagtcatt catggctccc tcctgcagtg tgctgcactg ccccgctgct
 841  tgtacctgta gcaacaacat tgtagactgc cgagggaaag gtctcactga gatccccaca
 901  aatctgcctg agaccatcac agaaatacgt ttgaacaga actccatcag ggtcatccct
 961  ccaggagcct tctcaccata caaaaagctt agacgactag acctgagcaa caaccagatc
1021  tctgaacttg caccagatgc cttccaagga ctgcgctctc tgaattcact tgtcctgtat
1081  ggaaataaaa tcacagaact cccaaaaagt ttattcgaag gactattttc cttgcagcta
1141  ctattattga atgccaacaa gataaactgc cttcgggtag atgcttttca ggacctgcac
1201  aacttgaacc ttctctcctt atatgacaat aagcttcaga cggttgccaa gggcaccttc
1261  tcagccctca gagccatcca actatgcat ttggcccaga tcctttcat ttgtgactgc
1321  catctcaagt ggctagcgga ttatctccac accaacccaa ttgagaccag cggtgcccgt
1381  tgcaccagcc cccgccgcct ggcaaacaaa gaattggac agatcaaaag caagaaattc
1441  cgttgttcag ctaaagaaca gtatttcatt ccaggtacag aagattatcg atcaaaatta
```

TABLE 1-continued

```
1501  agtggagact gctttgcaga cttggcttgt cctgagaagt gtcgctgtga agggaccaca
1561  gtagactgct ccaatcaaag actcaacaaa atccctgacc atattcccca gtacacagca
1621  gagctgcgtc tcaataataa tgaattcaca gtgttagaag ccacgggaat atttaagaaa
1681  cttcctcagt tacgtaaaat caactttagc aacaataaga tcacggatat cgaggagggt
1741  gcatttgaag gcgcgtctgg tgtgaatgaa attcttctca ccagtaaccg tttggaaaat
1801  gttcagcata agatgttcaa aggactggag agcctcaaaa cattgatgct gagaagtaat
1861  cgaataagct gtgttgggaa cgacagtttc ataggactcg gctctgtgcg tctgctctct
1921  ttatatgaca atcaaattac cacagtggca ccaggagcat ttgattctct ccattcatta
1981  tccactctaa acctcttggc caatccttc aactgtaact gtcacctggc atggctggga
2041  gaatggctca gaaggaaaag aattgtaaca ggaaatcctc gatgccaaaa accctacttc
2101  ctgaaggaaa tcccaatcca ggatgtagcc attcaggact tcacctgtga tgatggaaat
2161  gatgacaata gttgctctcc actctcccgt tgtccttctg aatgtacctg cttggataca
2221  gtggtacgat gtagcaacaa gggcttgaag gttttgccta aaggtattcc aaaagatgtc
2281  acagagctgt atctggatgg gaaccagttt acgctggtcc cgaaggaact ctctaactac
2341  aaacatttaa cacttataga cttaagtaac aaccgaataa gcacccttc caatcaaagc
2401  ttcagcaaca tgacccagct tctcaccta atcctcagtt acaaccgtct gagatgtatc
2461  cctccacgaa cctttgatgg attgaagtct cttcggttac tgtctttaca tggaaatgac
2521  atttctgttg tgcctgaagg tgccttcaat gacttgtcag ccttgtcaca cttagcgatt
2581  ggagccaacc ctctttactg tgattgtaac atgcagtggt tatccgactg ggtgaagtcg
2641  gaatataagg aacctggaat tgcacgctgt gccggccctg agaaatggc agataaatta
2701  ttactcacta ctccctccaa aaaatttaca tgtcaaggtc cgtggatat cactattcaa
2761  gccaagtgta atcctgctt atcaaatcca tgtaaaaatg atggcacctg taacaatgac
2821  cccgttgatt tttatcgatg tacctgccca tatggattca agggtcagga ctgtgatgtc
2881  cccattcatg cttgtatcag taatccatgt aaacatggag gaacttgtca cttaaaggaa
2941  ggagagaatg ctggattctg gtgcacttgt gctgatgggt ttgaaggaga aaactgtgaa
3001  gtcaatattg atgattgtga agataatgat tgtgaaaata attctacatg cgttgatgga
3061  attaacaact acacatgtct ttgcccaccg gaatacacag ctgctaatct gaatgaggtg
3121  gaaaaggtg aactgtgtga ggaaaagctg gacttctgtg cacaagactt gaatccctgc
3181  cagcatgact ccaagtgcat cctgactcca aagggattca agtgtgactg cactccagga
3241  tacattggtg agcactgtga cattgacttt gatgactgcc aagataacaa gtgtaaaaac
3301  ggtgctcact gcacagatgc cgtgaacgga tacacgtgcg tctgtcctga aggctacagt
3361  ggcttgttct gtgagtttc tccacccatg gtcctccctc gcaccagccc ctgtgataat
3421  tttgattgcc agaatggagc ccagtgtatc atcaggataa atgaaccaat gccagtgt
3481  ttgcctggct acctgggaga gaagtgtgag aaattggtca gtgtgaattt tgtaaacaaa
3541  gagtcctatc ttcagattcc ttcagccaag gttcggcctc agacaaacat cacacttcag
3601  attgccacag atgaagacag cggcatcctc ttgtataaag gtgacaaaga ccacattgcc
3661  gtggaactct atagggggcg agttcgagcc agctatgaca ccggctctca tccggcttct
3721  gccatttaca gtgtggagac aatcaatgat ggaaacttcc acattgtgga gctactgacc
3781  ctggattcca gtcttcccct ctctgtggat ggaggaagcc ctaaagtcat caccaatttg
3841  tcaaaacaat ctactctgaa tttcgactct ccactctatg taggaggcat gcctgggaaa
```

TABLE 1-continued

```
3901  aataacgtgg catccctgcg ccaggcccct gggcaaaatg gcaccagctt ccatggctgt
3961  atccggaacc tttacattaa cagtgagctg caggacttcc ggaaaatgcc tatgcaaacc
4021  ggaattctgc ctggctgtga accatgccac aagaaagtat gtgcccatgg catgtgccag
4081  cccagcagcc aatcaggctt cacctgtgaa tgtgaggaag ggtggatggg gccccctctgt
4141  gaccagagaa ccaatgatcc ctgcctcgga aacaaatgtg tgcatgggac ctgcctgccc
4201  atcaatgcct tctcctatag ttgcaagtgc ctggagggcc atggcggtgt cctctgtgat
4261  gaagaagaag atctctttaa cccctgccag atgatcaagt gcaagcatgg aagtgcagg
4321  ctttctggag tgggccagcc ctattgtgaa tgcaacagtg gattcaccgg ggacagctgt
4381  gatagagaaa tttcttgtcg aggggaacgg ataagggact attaccagaa gcagcagggg
4441  tacgctgcct gtcaaacaac taagaaagta tctcgcttgg aatgcagagg cgggtgcgct
4501  ggaggccagt gctgtggacc tctgagaagc aagaggcgga aatactcttt cgaatgcaca
4561  gatggctcct catttgtgga cgaggttgag aaagtggtga agtgcggctg cgcgagatgt
4621  gcctcctaa
```

SEQ ID NO: 8 Mouse Slit2 Isoform 1 Amino Acid Sequence

```
   1  msgigwqtls lslglvlsil nkvapqacpa qcscsgstvd chglalrsvp rniprnterl
  61  dlngnnitri tkidfaglrh lrvlqlmenr istiergafq dlkelerlrl nrnnlqlfpe
 121  llflgtakly rldlsengiq aiprkafrga vdiknlqldy nqisciedga fralrdlevl
 181  tlnnnnitrl svasfnhmpk lrtfrlhsnn lycdchlawl sdwlrqrpry glytqcmgps
 241  hlrghnvaev qkrefvcsde eeghqsfmap scsvlhcpaa ctcsnnivdc rgkglteipt
 301  nlpetiteir leqnsirvip pgafspykkl rrldlsnnqi selapdafqg lrslnslvly
 361  gnkitelpks lfeglfslql lllnankinc lrvdafqdlh nlnllslydn klqtvakgtf
 421  salraiqtmh laqnpficdc hlkwladylh tnpietsgar ctsprrlank rigqikskkf
 481  rcsakegyfi pgtedyrskl sgdcfadlac pekcrcegtt vdcsnqrink ipdhipqyta
 541  elrinnneft vleatgifkk lpqlrkinfs nnkitdieeg afegasgvne illtsnrlen
 601  vqhkmfkgle slktlmlrsn riscvgndsf iglgsvrlls lydnqittva pgafdslhsl
 661  stlnllanpf ncnchlawlg ewlrrkrivt gnprcqkpyf lkeipiqdva iqdftcddgn
 721  ddnscsplsr cpsectcldt vvrcsnkglk vlpkgipkdv telyldgnqf tivpkelsny
 781  khltlidlsn nristlsnqs fsnmtqlltl ilsynrlrci pprtfdglks lrllslhgnd
 841  isvvpegafn dlsalshlai ganplycdcn mqwlsdwvks eykepgiarc agpgemadkl
 901  llttpskkft cqgpvditiq akcnpclsnp ckndgtcnnd pvdfyrctcp ygfkgqdcdv
 961  pihacisnpc khggtchlke genagfwctc adgfegence vniddcednd cennstcvdg
1021  innytcicpp eytaanlnev ekgelceekl dfcaqdlnpc qhdskciltp kgfkcdctpg
1081  yigehcdidf ddcgdnkckn gahctdavng ytcvcpegys glfcefsppm vlprtspcdn
1141  fdcqngaqci irinepicqc lpgylgekce klvsvnfvnk esylqipsak vrpqtnitlq
1201  iatdedsgil lykgdkdhia velyrgrvra sydtgshpas aiysvetind gnfhivellt
1261  ldsslslsvd ggspkvitnl skgstlnfds plyvggmpgk nnvaslrqap gqngtsfhgc
1321  irnlyinsel qdfrkmpmqt gilpgcepch kkvcahgmcq pssqsgftce ceegwmgplc
1381  dqrtndpclg nkcvhgtclp inafsysckc leghggvlcd eeedlfnpcq mikckhgkcr
1441  lsgvgqpyce cnsgftgdsc dreiscrger irdyyqkqqg yaacqttkkv srlecrggca
1501  ggqccgplrs krrkysfect dgssfvdeve kvvkcgcarc as
```

TABLE 1-continued

SEQ ID NO: 9 Mouse Slit2 Transcript Variant 2 cDNA Sequence

```
   1  atgagtggca ttggctggca gacactgtcc ctatcgctgg ggttagtgtt gtcgatcttg
  61  aacaaggtgg cgccgcaggc gtgcccggcc cagtgctcct gttcaggcag cacggtggac
 121  tgtcatgggc tggcactgcg cagtgtgccc aggaatatcc cccgcaacac cgagagactg
 181  gatttgaatg gaaataacat cacgaggatc acgaagatag attttgctgg tctcaggcac
 241  ctcagagttc ttcagctcat ggagaacaga atcagcacca tcgagagggg agcattccag
 301  gatcttaagg agctggaaag actgcgttta aacagaaata accttcagtt gtttcctgag
 361  ctgctgtttc tcgggactgc gaagctctac cggcttgatc tcagtgaaaa tcaaattcaa
 421  gcaattccaa ggaaggcttt ccgtggggca gttgacatta aaacctgca actggattac
 481  aaccagatca gctgcattga agatggggcg ttcagagctc tacgagatct ggaagtgctc
 541  actctgaaca ataacaatat tactagactt tcagtggcaa gtttcaacca tatgcctaaa
 601  cttaggacat ttcgactcca ctcgaacaac ttgtactgcg actgccacct agcctggctc
 661  tcagactggc ttcgccaaag gccacgggtg ggcttgtaca ctcagtgtat gggcccatcc
 721  cacctgaggg gccacaatgt agcagaggtt caaaaacgag agtttgtctg cagtgatgag
 781  gaagaaggtc accagtcatt catggctccc tcctgcagtg tgctgcactg ccccgctgct
 841  tgtacctgta gcaacaacat tgtagactgc cgagggaaag gtctcactga tcccccaca
 901  aatctgcctg agaccatcac agaaatacgt ttggaacaga actccatcag ggtcatccct
 961  ccaggagcct tctcaccata caaaaagctt agacgactag acctgagcaa caaccagatc
1021  tctgaacttg caccagatgc cttccaagga ctgcgctctc tgaattcact tgtcctgtat
1081  ggaaataaaa tcacagaact cccaaaaagt ttattcgaag gactattttc cttgcagcta
1141  ctattattga atgccaacaa gataaactgc cttcgggtag atgcttttca ggacctgcac
1201  aacttgaacc ttctctcctt atatgacaat aagcttcaga cggttgccaa gggcaccttc
1261  tcagccctca gagccatcca actatgcat ttggcccaga tcctttcat ttgtgactgc
1321  catctcaagt ggctagcgga ttatctccac accaacccaa ttgagaccag cggtgcccgt
1381  tgcaccagcc cccgccgcct ggcaaaacaaa agaattggac agatcaaaag caagaaattc
1441  cgttgttcag gtacagaaga ttatcgatca aaattaagtg gagactgctt tgcagacttg
1501  gcttgtcctg agaagtgtcg ctgtgaaggg accacagtag actgctcaa tcaaagactc
1561  aacaaaatcc ctgaccatat tccccagtac acagcagagc tgcgtctcaa taataatgaa
1621  ttcacagtgt tagaagccac gggaatattt aagaaacttc ctcagttacg taaaatcaac
1681  tttagcaaca ataagatcac ggatatcgag gagggtgcat ttgaaggcgc gtctggtgtg
1741  aatgaaattc ttctcaccag taaccgtttg gaaaatgttc agcataagat gttcaaagga
1801  ctggagagcc tcaaaacatt gatgctgaga agtaatcgaa taagctgtgt tgggaacgac
1861  agtttcatag gactcggctc tgtgcgtctg ctctctttat atgacaatca aattaccaca
1921  gtggcaccag gagcatttga ttctctccat tcattatcca ctctaaacct cttggccaat
1981  cctttcaact gtaactgtca cctggcatgg ctgggagaat ggctcagaag gaaaagaatt
2041  gtaacaggaa atcctcgatg ccaaaaaccc tacttcctga ggaaatccc aatccaggat
2101  gtagccattc aggacttcac ctgtgatgat ggaaatgatg acaatagttg ctctccactc
2161  tcccgttgtc cttctgaatg tacctgcttg gatacagtgg tacgatgtag caacaagggc
2221  ttgaaggttt tgcctaaagg tattccaaaa gatgtcacag agctgtatct ggatgggaac
2281  cagtttacgc tggtcccgaa ggaactctct aactacaaac atttaacact tatagactta
2341  agtaacaacc gaataagcac cctttccaat caaagcttca gcaacatgac ccagcttctc
```

TABLE 1-continued

```
2401  accttaatcc tcagttacaa ccgtctgaga tgtatccctc cacgaacctt tgatggattg
2461  aagtctcttc ggttactgtc tttacatgga aatgacattt ctgttgtgcc tgaaggtgcc
2521  ttcaatgact tgtcagcctt gtcacactta gcgattggag ccaaccctct ttactgtgat
2581  tgtaacatgc agtggttatc cgactgggtg aagtcggaat ataaggaacc tggaattgca
2641  cgctgtgccg gccctggaga aatggcagat aaattattac tcactactcc ctccaaaaaa
2701  tttacatgtc aaggtcccgt ggatatcact attcaagcca agtgtaatcc ctgcttatca
2761  aatccatgta aaatgatgg cacctgtaac aatgaccccg ttgattttta tcgatgtacc
2821  tgcccatatg gattcaaggg tcaggactgt gatgtcccca ttcatgcttg tatcagtaat
2881  ccatgtaaac atggaggaac ttgtcactta aaggaaggag agaatgctgg attctggtgc
2941  acttgtgctg atgggtttga aggagaaaac tgtgaagtca atattgatga ttgtgaagat
3001  aatgattgtg aaaataattc tacatgcgtt gatggaatta caactacac atgtctttgc
3061  ccaccggaat acacaggtga actgtgtgag gaaaagctgg acttctgtgc acaagacttg
3121  aatccctgcc agcatgactc caagtgcatc ctgactccaa agggattcaa gtgtgactgc
3181  actccaggat acattggtga gcactgtgac attgactttg atgactgcca agataacaag
3241  tgtaaaaacg gtgctcactg cacagatgcc gtgaacggat acacgtgcgt ctgtcctgaa
3301  ggctacagtg gcttgttctg tgagttttct ccacccatgg tcctccctcg caccagcccc
3361  tgtgataatt ttgattgcca gaatggagcc cagtgtatca tcaggataaa tgaaccaata
3421  tgccagtgtt tgcctggcta cctgggagag aagtgtgaga aattggtcag tgtgaatttt
3481  gtaaacaaag agtcctatct tcagattcct tcagccaagg ttcggcctca gacaaacatc
3541  acacttcaga ttgccacaga tgaagacagg ggcatcctct tgtataaagg tgacaaagac
3601  cacattgccg tggaactcta tagagggcga gttcgagcca gctatgacac cggctctcat
3661  ccggcttctg ccatttacag tgtggagaca atcaatgatg gaaacttcca cattgtggag
3721  ctactgaccc tggattccag tctttccctc tctgtggatg gaggaagccc taaagtcatc
3781  accaatttgt caaaacaatc tactctgaat ttcgactctc cactctatgt aggaggcatg
3841  cctgggaaaa ataacgtggc atccctgcgc caggcccctg gcaaaatgg caccagcttc
3901  catggctgta tccggaacct ttacattaac agtgagctgc aggacttccg gaaaatgcct
3961  atgcaaaccg gaattctgcc tggctgtgaa ccatgccaca gaaagtatg tgcccatggc
4021  atgtgccagc ccagcagcca atcaggcttc acctgtgaat gtgaggaagg gtggatgggg
4081  cccctctgtg accagagaac caatgatccc tgcctcggaa acaaatgtgt gcatgggacc
4141  tgcctgccca tcaatgcctt tcctatagt tgcaagtgcc tggagggcca tggcggtgtc
4201  ctctgtgatg aagaagaaga tctctttaac ccctgccaga tgatcaagtg caagcatggg
4261  aagtgcaggc tttctggagt gggccagccc tattgtgaat gcaacagtgg attcaccggg
4321  gacagctgtg atagagaaat ttcttgtcga ggggaacgga taagggacta ttaccagaag
4381  cagcagggtt acgctgcctg tcaaacaact aagaaagtat ctcgcttgga atgcagaggc
4441  gggtgcgctg gaggccagtg ctgtggacct ctgagaagca agaggcggaa atactctttc
4501  gaatgcacag atggctcctc atttgtggac gaggttgaga agtggtgaa gtgcggctgc
4561  gcgagatgtg cctcctaa
```

SEQ ID NO: 10 Mouse Slit2 Isoform 2 Amino Acid Sequence
```
  1  msgigwqtls lslglvlsil nkvapqacpa qcscsgstvd chglalrsvp rniprnterl
 61  dlngnnitri tkidfaglrh lrvlqlmenr istiergafq dlkelerlrl nrnnlqlfpe
```

TABLE 1-continued

```
 121  llflgtakly rldlsengiq aiprkafrga vdiknlqldy nqisciedga fralrdlevl
 181  tlnnnnitrl svasfnhmpk lrtfrlhsnn lycdchlawl sdwlrqrpry glytqcmgps
 241  hlrghnvaev qkrefvcsde eeghqsfmap scsvlhcpaa ctcsnnivdc rgkglteipt
 301  nlpetiteir leqnsirvip pgafspykkl rrldlsnnqi selapdafqg lrslnslvly
 361  gnkitelpks lfeglfslql lllnankinc lrvdafqdlh nlnllslydn klqtvakgtf
 421  salraiqtmh laqnpficdc hlkwladylh tnpietsgar ctsprrlank rigqikskkf
 481  rcsgtedyrs klsgdcfadl acpekcrceg ttvdcsnqrl nkipdhipqy taelrinnne
 541  ftvleatgif kklpqlrkin fsnnkitdie egafegasgv neilltsnrl envqhkmfkg
 601  leslktlmlr snriscvgnd sfiglgsvrl lslydngitt vapgafdslh slstlnllan
 661  pfncnchlaw lgewlrrkri vtgnprcqkp yflkeipiqd vaiqdftcdd gnddnscspl
 721  srcpsectcl dtvvrcsnkg lkvlpkgipk dvtelyldgn qftivpkels nykhltlidl
 781  snnristlsn gsfsnmtqll tlilsynrlr cipprtfdgl kslrllslhg ndisvvpega
 841  fndlsalshl aiganplycd cnmqwlsdwv kseykepgia rcagpgemad kllltttpskk
 901  ftcqgpvdit igakcnpols npckndgtcn ndpvdfyrct cpygfkgqdc dvpihacisn
 961  pckhggtchl kegenagfwc tcadgfegen cevniddced ndcennstcv dginnytcic
1021  ppeytgelce ekldfcaqdl npcqhdskci ltpkgfkcdc tpgyigehcd idfddcgdnk
1081  ckngahctda vngytcvcpe gysglfcefs ppmvlprtsp cdnfdcqnga qciirinepi
1141  cqclpgylge kceklvsvnf vnkesylqip sakvrpqtni tlqiatdeds gillykgdkd
1201  hiavelyrgr vrasydtgsh pasaiysvet indgnfhive lltldsslsl svdggspkvi
1261  tnlskqstln fdsplyvggm pgknnvaslr qapgqngtsf hgcirnlyin selqdfrkmp
1321  mqtgilpgce pchkkvcahg mcussgsgf tceceegwmg plcdqrtndp clgnkcvhgt
1381  clpinafsys ckcleghggv lcdeeedlfn pcqmikckhg korlsgvgqp ycecnsgftg
1441  dscdreiscr gerirdyyqk qqgyaacqtt kkvsrlecrg gcaggqccgp lrskrrkysf
1501  ectdgssfvd evekvvkcgc arcas
```

SEQ ID NO: 11 Mouse Slit2 Transcript Variant 3 cDNA Sequence
```
   1  atgagtggca ttggctggca gacactgtcc ctatcgctgg ggttagtgtt gtcgatcttg
  61  aacaaggtgg cgccgcaggc gtgcccggcc cagtgctcct gttcaggcag cacggtggac
 121  tgtcatgggc tggcactgcg cagtgtgccc aggaatatcc cccgcaacac cgagagactg
 181  gatttgaatg gaaataacat cacgaggatc acgaagatag attttgctgg tctcaggcac
 241  ctcagagttc ttcagctcat ggagaacaga atcagcacca tcgagagggg agcattccag
 301  gatcttaagg agctggaaag actgcgttta acagaaaata accttcagtt gtttcctgag
 361  ctgctgtttc tcgggactgc gaagctctac cggcttgatc tcagtgaaaa tcaaattcaa
 421  gcaattccaa ggaaggcttt ccgtggggca gttgacatta aaaacctgca actggattac
 481  aaccagatca gctgcattga agatgggcg ttcagagctc tacgagatct ggaagtgctc
 541  actctgaaca ataacaatat tactagactt tcagtggcaa gtttcaacca tatgcctaaa
 601  cttaggacat ttcgactcca ctcgaacaac ttgtactgcg actgccacct agcctggctc
 661  tcagactggc ttcgccaaag gccacgggtg ggcttgtaca ctcagtgtat gggcccatcc
 721  cacctgaggg ccacaatgt agcagaggtt caaaaacgag agtttgtctg cagtggtcac
 781  cagtcattca tggctccctc ctgcagtgtg ctgcactgcc ccgctgcttg tacctgtagc
 841  aacaacattg tagactgccg agggaaaggt ctcactgaga tccccacaaa tctgcctgag
 901  accatcacag aaatacgttt ggaacagaac tccatcaggg tcatccctcc aggagccttc
```

TABLE 1-continued

```
 961  tcaccataca aaaagcttag acgactagac ctgagcaaca accagatctc tgaacttgca
1021  ccagatgcct tccaaggact gcgctctctg aattcacttg tcctgtatgg aaataaaatc
1081  acagaactcc caaaaagttt attcgaagga ctattttcct tgcagctact attattgaat
1141  gccaacaaga taaactgcct tcgggtagat gcttttcagg acctgcacaa cttgaacctt
1201  ctctccttat atgacaataa gcttcagacg gttgccaagg cacttctc agccctcaga
1261  gccatccaaa ctatgcattt ggcccagaat cctttcattt gtgactgcca tctcaagtgg
1321  ctagcggatt atctccacac caacccaatt gagaccagcg gtgcccgttg caccagcccc
1381  cgccgcctgg caaacaaaag aattggacag atcaaaagca agaaattccg ttgttcaggt
1441  acagaagatt atcgatcaaa attaagtgga gactgctttg cagacttggc ttgtcctgag
1501  aagtgtcgct gtgaagggac cacagtagac tgctccaatc aaagactcaa caaaatccct
1561  gaccatattc cccagtacac agcagagctg cgtctcaata ataatgaatt cacagtgtta
1621  gaagccacgg gaatatttaa gaaacttcct cagttacgta aaatcaactt tagcaacaat
1681  aagatcacgg atatcgagga gggtgcattt gaaggcgcgt ctggtgtgaa tgaaattctt
1741  ctcaccagta accgtttgga aaatgttcag cataagatgt tcaaaggact ggagagcctc
1801  aaaacattga tgctgagaag taatcgaata agctgtgttg ggaacgacag tttcatagga
1861  ctcggctctg tgcgtctgct ctctttatat gacaatcaaa ttaccacagt ggcaccagga
1921  gcatttgatt ctctccattc attatccact ctaaacctct ggccaatcc tttcaactgt
1981  aactgtcacc tggcatggct gggagaatgg ctcagaagga aaagaattgt aacaggaaat
2041  cctcgatgcc aaaaaccta cttcctgaag gaaatcccaa tccaggatgt agccattcag
2101  gacttcacct gtgatgatgg aaatgatgac aatagttgct ctccactctc ccgttgtcct
2161  tctgaatgta cctgcttgga tacagtggta cgatgtagca caagggctt gaaggttttg
2221  cctaaaggta ttccaaaaga tgtcacagag ctgtatctgg atgggaacca gtttacgctg
2281  gtcccgaagg aactctctaa ctacaaacat ttaacactta tagacttaag taacaaccga
2341  ataagcaccc tttccaatca aagcttcagc aacatgaccc agcttctcac cttaatcctc
2401  agttacaacc gtctgagatg tatccctcca cgaacctttg atggattgaa gtctcttcgg
2461  ttactgtctt tacatggaaa tgacatttct gttgtgcctg aaggtgcctt caatgacttg
2521  tcagccttgt cacacttagc gattggagcc aaccctcttt actgtgattg taacatgcag
2581  tggttatccg actgggtgaa gtcggaatat aaggaacctg gaattgcacg ctgtgccggc
2641  cctggagaaa tggcagataa attattactc actactccct ccaaaaaatt tacatgtcaa
2701  ggtcccgtgg atatcactat tcaagccaag tgtaatccct gcttatcaaa tccatgtaaa
2761  aatgatggca cctgtaacaa tgaccccgtt gatttttatc gatgtacctg cccatatgga
2821  ttcaagggtc aggactgtga tgtcccccatt catgcttgta tcagtaatcc atgtaaacat
2881  ggaggaactt gtcacttaaa ggaaggagag aatgctggat tctggtgcac ttgtgctgat
2941  gggtttgaag gagaaaactg tgaagtcaat attgatgatt gtgaagataa tgattgtgaa
3001  ataattccta catgcgttga tggaattaac aactacacat gtctttgccc accggaatac
3061  acaggtgaac tgtgtgagga aaagctggac ttctgtgcac aagacttgaa tccctgccag
3121  catgactcca gtgcatcct gactccaaag ggattcaagt gtgactgcac tccaggatac
3181  attggtgagc actgtgacat tgactttgat gactgccaag ataacaagtg taaaaacggt
3241  gctcactgca cagatgccgt gaacggatac acgtgcgtct gtcctgaagg ctacagtggc
3301  ttgttctgtg agttttctcc acccatggtc ctccctcgca ccagcccctg tgataatttt
```

TABLE 1-continued

```
3361   gattgccaga atggagccca gtgtatcatc aggataaatg aaccaatatg ccagtgtttg
3421   cctggctacc tgggagagaa gtgtgagaaa ttggtcagtg tgaatttttgt aaacaaagag
3481   tcctatcttc agattccttc agccaaggtt cggcctcaga caaacatcac acttcagatt
3541   gccacagatg aagacagcgg catcctcttg tataaaggtg acaaagacca cattgccgtg
3601   gaactctata gagggcgagt tcgagccagc tatgacaccg gctctcatcc ggcttctgcc
3661   atttacagtg tggagacaat caatgatgga aacttccaca ttgtggagct actgaccctg
3721   gattccagtc tttccctctc tgtggatgga ggaagcccta aagtcatcac caatttgtca
3781   aaacaatcta ctctgaattt cgactctcca ctctatgtag gaggcatgcc tgggaaaaat
3841   aacgtggcat ccctgcgcca ggcccctggg caaaatggca ccagcttcca tggctgtatc
3901   cggaaccttt acattaacag tgagctgcag gacttccgga aaatgcctat gcaaaccgga
3961   attctgcctg gctgtgaacc atgccacaag aaagtatgtg cccatggcat gtgccagccc
4021   agcagccaat caggcttcac ctgtgaatgt gaggaagggt ggatggggcc cctctgtgac
4081   cagagaacca atgatccctg cctcggaaac aaatgtgtgc atgggacctg cctgcccatc
4141   aatgccttct cctatagttg caagtgcctg gagggccatg gcggtgtcct ctgtgatgaa
4201   gaagaagatc tctttaaccc ctgccagatg atcaagtgca agcatgggaa gtgcaggctt
4261   tctggagtgg gccagcccta ttgtgaatgc aacagtggat tcaccgggga cagctgtgat
4321   agagaaattt cttgtcgagg ggaacggata agggactatt accagaagca gcagggttac
4381   gctgcctgtc aaacaactaa gaaagtatct cgcttggaat gcagaggcgg gtgcgctgga
4441   ggccagtgct gtggacctct gagaagcaag aggcggaaat actcttttcga atgcacagat
4501   ggctcctcat tgtggacga ggttgagaaa gtggtgaagt gcggctgcgc gagatgtgcc
4561   tcctaa
```

SEQ ID NO: 12 Mouse Slit2 Isoform 3 Amino Acid Sequence
```
   1   msgigwqtls lslglvlsil nkvapqacpa qcscsgstvd chglalrsvp rniprnterl
  61   dlngnnitri tkidfaglrh lrvlqlmenr istiergafq dlkelerlrl nrnnlqlfpe
 121   llflgtakly rldlsengiq aiprkafrga vdiknlqldy nqisciedga fralrdlevl
 181   tlnnnnitrl svasfnhmpk lrtfrlhsnn lycdchlawl sdwlrqrpry glytqcmgps
 241   hlrghnvaev qkrefvcsgh qsfmapscsv lhcpaactcs nnivdcrgkg lteiptnlpe
 301   titeirleqn sirvippgaf spykklrrld lsnnqisela pdafgglrsl nslvlygnki
 361   telpkslfeg lfslqllllln ankinclrvd afqdlhnlnl lslydnklqt vakgtfsalr
 421   aigtmhlagn pficdchlkw ladylhtnpi etsgarctsp rrlankrigq ikskkfrcsg
 481   tedyrsklsg dcfadlacpe kcrcegttvd csnqrinkip dhipqytael rinnneftvl
 541   eatgifkklp qlrkinfsnn kitdieegaf egasgvneil ltsnrlenvq hkmfkglesl
 601   ktlmlrsnri scvgndsfig lgsvrllsly dngittvapg afdslhslst lnllanpfnc
 661   nchlawlgew lrrkrivtgn prcqkpyflk eipiqdvaiq dftcddgndd nscsplsrcp
 721   sectcldtvv rcsnkglkvl pkgipkdvte lyldgnqftl vpkelsnykh ltlidlsnnr
 781   istlsnqsfs nmtqlltlil synrlrcipp rtfdglkslr llslhgndis vvpegafndl
 841   salshlaiga nplycdcnmq wlsdwvksey kepgiarcag pgemadklll ttpskkftcq
 901   gpvditiqak cnpclsnpck ndgtcnndpv dfyrctcpyg fkgqdcdvpi hacisnpckh
 961   ggtchlkege nagfwctcad gfegencevn iddcedndce nnstcvdgin nytcicppey
1021   tgelceekld fcaqdlnpcq hdskciltpk gfkcdctpgy igehcdidfd dcgdnkckng
```

TABLE 1-continued

```
1081  ahctdavngy tcvcpegysg lfcefsppmv lprtspcdnf dcqngaqcii rinepicgcl
1141  pgylgekcek lvsvnfvnke sylqipsakv rpqtnitlqi atdedsgill ykgdkdhiav
1201  elyrgrvras ydtgshpasa iysvetindg nfhivelltl dsslslsvdg gspkvitnls
1261  kgstlnfdsp lyvggmpgkn nvaslrqapg qngtsfhgci rnlyinselq dfrkmpmqtg
1321  ilpgcephck kvcahgmcqp ssqsgftcec eegwmgplcd grtndpolgn kcvhgtclpi
1381  nafsysckcl eghggvlcde eedlfnpcqm ikckhgkcrl sgvgqpycec nsgftgdscd
1441  reiscrgeri rdyyqkqqgy aacqttkkvs rlecrggcag gqccgplrsk rrkysfectd
1501  gssfvdevek vvkcgcarca s
```

SEQ ID NO: 13 Rat Slit2 cDNA Sequence
```
   1  atgagtggca ttggctggca gacactgtcc ctatctctgg cgttagtgtt gtcgatcttg
  61  aaccaggtgg cgcctcaggc gtgcccggcc cagtgctcct gttcaggcag cacagtggac
 121  tgtcatgggc tggcactgcg cagtgtgccc aggaatatcc cccgcaacac ggagagactg
 181  gatttgaatg aaataacat cacaaggatc acgaagacag attttgcggg tctcagacac
 241  ctcagagttc ttcagctcat ggagaacaag atcagcacca tcgagagggg agcattccag
 301  gatcttaagg agctagaaag actgcgttta acagaaata accttcagtt gtttcctgag
 361  ctgctgtttc ttgggactgc gaagctctac cggcttgatc tcagtgaaaa tcagattcaa
 421  gcaattccaa ggaaggcttt ccgtggtgca gttgacatta aaaatctgca gttggattac
 481  aaccagatca gctgcattga agatgggca ttccgagctc tgcgagatct ggaagtgctc
 541  actctgaaca ataacaatat tactagactt tcagtggcaa gtttcaacca tatgcctaaa
 601  cttaggacat ttcgactcca ctccaacaac ctatactgcg actgccacct ggcctggctc
 661  tcggactggc ttcgccaaag gccacgggtg ggcttgtaca ctcagtgtat gggcccatcc
 721  cacctgaggg gccataatgt agcagaggtt caaaaacgag agtttgtctg cagtgatgag
 781  gaagaaggtc accagtcatt catggctccc tcctgcagtg tgctgcactg cccgattgct
 841  tgtacctgta gcaacaacat tgtagactgc cgagggaaag gtctcactga gatccccaca
 901  aatctgcctg agaccatcac agaaatacgt ttggaacaga actccataag ggtcatccct
 961  ccaggagcat tctcaccata caaaaagctt cgacgactag acctgagtaa taaccagatc
1021  tcggaacttg ctccagatgc cttccaagga ctgcgttctc tgaattccct tgtcctgtat
1081  ggaaataaaa tcacagaact cccaaaaagt ttatttgaag gactgttttc cttacagcta
1141  ctattattga atgccaacaa gataaactgc cttcgggtag atgcttttca ggacctgcac
1201  aacttgaacc ttctctcctt atacgacaat aagcttcaga ctgttgccaa gggcaccttc
1261  tcagctctca gagccatcca actatgcat ttggcccaga tcctttcat ttgtgactgc
1321  catctcaagt ggctagcgga ttatctccac accaacccaa ttgagaccag cggtgcccgt
1381  tgcaccagtc ccgcgcct ggctaacaaa agaattggac agatcaaaag caagaaattc
1441  cgttgttcag gtacagaaga ttatcgatca aaattaagtg agactgctt tgcagacttg
1501  gcttgtcctg aaaaatgtcg ctgtgaaggg accacagtag actgctcaa tcaaaaactc
1561  aacaaaatcc cagaccatat tccccagtac acagcagagc tgcgtctcaa taataatgaa
1621  ttcacagtgt tagaagccac gggaatattt aagaaacttc ctcaattgcg taaaatcaac
1681  cttagcaaca ataagatcac tgatatcgag gaggggcat tcgaaggtgc gtctggtgtg
1741  aatgagattc tgcttaccag taaccgtttg gaaatgttc agcataagat gttcaaagga
1801  ttggagagcc tcaaaacatt gatgctgaga agtaatcgaa taagctgtgt gggaaacgac
1861  agtttcacag gactcggttc tgtgcgtctg ctctctttat atgacaatca aattaccaca
```

TABLE 1-continued

```
1921  gttgcaccag gagcatttgg tactctccat tcattatcta cactaaacct cttggccaat
1981  cctttcaact gtaactgtca cctggcatgg cttggagaat ggctcagaag gaaaagaatt
2041  gtaacaggaa atcctcgatg ccaaaaaccc tacttcttga aggaaatacc aatccaggat
2101  gtagccattc aggacttcac ctgtgatgac ggaaacgatg ataatagctg ctctccactc
2161  tcccgttgtc cttcggaatg tacttgcttg gatacagtag tacgatgtag caacaagggc
2221  ttgaaggtct tacctaaagg cattccaaga gatgtcacag aactgtatct ggatgggaac
2281  cagtttacac tggtcccgaa ggaactctcc aactacaaac atttaacact tatagactta
2341  agtaacaaca gaataagcac cctttccaac caaagcttca gcaacatgac ccaacttctc
2401  accttaattc tcagttacaa ccgtctgaga tgtatccctc cacggacctt tgatggattg
2461  aaatctcttc gtttactgtc tctacatgga aatgacattt ctgtcgtgcc tgaaggtgcc
2521  tttggtgacc tttcagcctt gtcacactta gcaattggag ccaaccctct ttactgtgat
2581  tgtaacatgc agtggttatc cgactgggtg aagtcggaat ataaggaacc tggaattgcc
2641  cgctgtgccg gtcccggaga aatggcagat aaattgttac tcacaactcc ctccaaaaaa
2701  tttacatgtc aaggtcctgt ggatgttact attcaagcca agtgtaaccc ctgcttgtca
2761  aatccatgta aaatgatgg cacctgtaac aatgacccgg tggatttta tcgatgcacc
2821  tgcccatatg gtttcaaggg ccaggactgt gatgtcccca ttcatgccta tcagtaat
2881  ccatgtaaac atggaggaac ttgccactta aagaaggag agaatgatgg attctggtgt
2941  acttgtgctg atgggtttga aggagaaagc tgtgacatca atattgatga ttgcgaagat
3001  aatgattgtg aaaataattc tacatgcgtt gatggaatta caactacac gtgtctttgc
3061  ccaccggaat acacaggcga actgtgtgag gaaaaactgg acttctgtgc aagacctg
3121  aatccctgcc agcatgactc caagtgcatc ctgacgccaa agggattcaa gtgtgactgc
3181  actccgggat acattggtga gcactgtgac atcgactttg atgactgcca agataacaag
3241  tgcaaaaacg gtgctcattg cacagatgca gtgaacggat acacatgtgt ctgtcctgaa
3301  ggctacagtg gcttgttctg tgagttttct ccacccatgg tcctccctcg caccagcccc
3361  tgtgataatt ttgattgtca gaatggagcc cagtgtatca tcagggtgaa tgaaccaata
3421  tgccagtgtt tgcctggcta cttgggagag aagtgtgaga aattggtcag tgtgaattt
3481  gtaaacaaag agtcctatct tcagattcct tcagccaagg ttcgacctca gacaaacatc
3541  acacttcaga ttgccacaga tgaagacagc ggcatcctct tgtacaaggt tgacaaggac
3601  cacattgctg tggaactcta tcgagggcga gttcgagcca gctatgacac cggctctcac
3661  ccggcttctg ccattacag tgtggagaca atcaatgatg gaaacttcca cattgtagag
3721  ctactgaccc tggattcgag tctttccctc tctgtggatg gaggaagccc taaaatcatc
3781  accaatttgt caaaacaatc tactctgaat ttcgactctc cactttacgt aggaggtatg
3841  cctgggaaaa ataacgtggc ttcgctgcgc caggcccctg gcagaacgg caccagcttc
3901  catggctgta tccggaacct ttacattaac agtgaactgc aggacttccg gaaagtgcct
3961  atgcaaaccg gaattctgcc tggctgtgaa ccatgccaca gaaaagtgtg tgcccatggc
4021  acatgccagc ccagcagcca atcaggcttc acctgtgaat gtgaggaagg gtggatgggg
4081  cccctctgtg accagagaac caatgatccc gtgtctcggaa acaaatgtgt acatgggacc
4141  tgcttgccca tcaacgcctt ctcctacagc tgcaagtgcc tggagggcca cggcgggtc
4201  ctctgtgatg aagaagaaga tctgtttaac ccctgccagg tgatcaagtg caagcacggg
4261  aagtgcaggc tctctgggct cgggcagccc tattgtgaat gcagcagtgg attcaccggg
```

TABLE 1-continued

```
4321    gacagctgtg acagagaaat ttcttgtcga gggaacgga taagggatta ttaccaaaag
4381    cagcagggtt acgctgcctg tcaaacgact aagaaagtat ctcgcttgga gtgcagaggc
4441    gggtgtgctg gggggcagtg ctgtggacct ctgagaagca agaggcggaa atactctttc
4501    gaatgcacag atggatctt
```

SEQ ID NO: 14 Rat Slit2 Amino Acid Sequence
```
   1    msgigwqtls lslalvlsil nqvapqacpa qcscsgstvd chglalrsvp rniprnterl
  61    dlngnnitri tktdfaglrh lrvlqlmenk istiergafq dlkelerlrl nrnnlqlfpe
 121    llflgtakly rldlsengiq aiprkafrga vdiknlqldy nqisciedga fralrdlevl
 181    tlnnnnitrl svasfnhmpk lrtfrlhsnn lycdchlawl sdwlrqrpry glytqcmgps
 241    hlrghnvaev qkrefvcsde eeghqsfmap scsvlhopia ctcsnnivdc rgkglteipt
 301    nlpetiteir leqnsirvip pgafspykkl rrldlsnnqi selapdafqg lrslnslvly
 361    gnkitelpks lfeglfslql lllnankinc lrvdafqdlh nlnllslydn klqtvakgtf
 421    salraiqtmh laqnpficdc hlkwladylh tnpietsgar ctsprrlank rigqikskkf
 481    rcsgtedyrs klsgdcfadl acpekcrceg ttvdcsnqkl nkipdhipqy taelrinnne
 541    ftvleatgif kklpqlrkin lsnnkitdie egafegasgv neilltsnrl envqhkmfkg
 601    leslktlmlr snriscvgnd sftglgsvrl lslydngitt vapgafgtlh slstlnllan
 661    pfncnchlaw lgewlrrkri vtgnprcqkp yflkeipiqd vaiqdftcdd gnddnscspl
 721    srcpsectcl dtvvrcsnkg lkvlpkgipr dvtelyldgn qftivpkels nykhltlidl
 781    snnristlsn gsfsnmtqll tlilsynrlr cipprtfdgl kslrllslhg ndisvvpega
 841    fgdlsalshl aiganplycd cnmqwlsdwv kseykepgia rcagpgemad kllltttpskk
 901    ftcqgpvdvt igakcnpols npckndgtcn ndpvdfyrct cpygfkgqdc dvpihacisn
 961    pckhggtchl kegendgfwc tcadgfeges cdiniddced ndcennstcv dginnytcic
1021    ppeytgelce ekldfcaqdl npcqhdskci ltpkgfkcdc tpgyigehcd idfddcgdnk
1081    ckngahctda vngytcvcpe gysglfcefs ppmvlprtsp cdnfdcqnga qciirvnepi
1141    cqclpgylge kceklvsvnf vnkesylqip sakvrpqtni tlqiatdeds gillykgdkd
1201    hiavelyrgr vrasydtgsh pasaiysvet indgnfhive lltldsslsl svdggspkii
1261    tnlskqstln fdsplyvggm pgknnvaslr qapgqngtsf hgcirnlyin selqdfrkvp
1321    mqtgilpgce pchkkvcahg tcussgsgf tceceegwmg plcdqrtndp clgnkcvhgt
1381    clpinafsys ckcleghggv lcdeeedlfn pcqvikckhg kcrlsglgqp ycecssgftg
1441    dscdreiscr gerirdyyqk qqgyaacqtt kkvsrlecrg gcaggqccgp lrskrrkysf
1501    ectdgssfvd evekvvkcgc trcas
```

SEQ ID NO: 15 Dog Slit2 cDNA Sequence
```
   1    atgcgcgggg ccggccggcg ggcgctgccc gtgtcgctgg gctcgtgct gctgatcctg
  61    ggcgaggcgg cgccgcaggc gtgcccggcg cagtgctcct gctcgggcag caccgtggac
 121    tgtcacgggc tggcgctgcg cagcgtgccc aggagcatcc cccgcaacac cgagaggctg
 181    gatttgaatg caataacat cacacgcgatt accaagacag atttcgctgg tcttcgacac
 241    ctaagagttc ttcagcttat ggagaataag attagcacca ttgaagagg agcattccag
 301    gatcttaagg aactggagag actgcgttta aacagaaatc accttcagct gtttcctgag
 361    ttgctgtttc ttgggactte gaagctgtac aggcttgatc tcagtgaaaa ccaaattcag
 421    gcaattccaa ggaaggcttt ccgtggggca gttgacatta aaaatttgca actggattac
 481    aaccagatca gctgtattga agatggggca tttagagctc tgcgggacct ggaagtgctc
```

TABLE 1-continued

```
 541   actctcaaca ataacaacat tactagactt tctgtggcaa gtttcaacca tatgcctaaa
 601   cttaggactt ttcggctgca ttcaaacaat ctgtattgcg actgccacct ggcctggctt
 661   tctgactggc tgcgccaaag gccccgggtt ggtctctaca ctcagtgtat gggcccatcc
 721   cacctgaggg gtcataacgt agccgaggtt caaaaacgcg aatttgtctg cagtggtaag
 781   ggagaaagaa cctttctgtt gtcctattat cttatgctac tttgccacca gtccttcatg
 841   gctccttctt gcagcgtcct gcattgtcca gccgcttgta cctgtagcaa caatatcgta
 901   gactgtcgtg ggaaaggtct cactgagatc cccacgaacc tgccagagac catcacagaa
 961   atacgtttgg aacagaactc aatcaaggtc atccctcctg gagctttctc accatataaa
1021   aagcttagaa gaattgacct gagcaataat cagatctctg aactagcacc ggacgctttc
1081   caaggactac gctctctgaa ttcacttgtc ctctatggaa ataaaatcac ggaactccca
1141   aaaagtttat ttgaaggact gttttcctta cagctgctat tattgaatgc caacaagata
1201   aactgccttc gggtagatgc ttttcaggat ctgcacaacc tgaatcttct ctccctgtac
1261   gacaacaagc tgcagaccat cgccaagggg accttctcac ctctccgggc cattcagacc
1321   atgcacctgg cccagaaccc ctttatttgt gactgccatc tcaagtggct ggcggactat
1381   ctccacacca accccatcga gaccagtggt gcccggtgca ccagcccccg gcgcctggca
1441   aacaaaagaa tcggacagat caaaagcaag aaattccgtt gttcagctaa agaacagtat
1501   ttcattccag gtacagaaga ttatcgatca aaattaagcg gggactgctt tgcagatctg
1561   gcttgccctg aaaagtgccg ctgtgaagga accacagtag attgctccaa tcaaaaactc
1621   accaaaatcc cagaccacat cccccagtac actgcagagc tgcgtctcaa taataatgaa
1681   ttcacagtgc tggaagctac aggaatcttc aagaaacttc cgcagttacg taaaataaac
1741   ttcagcaaca acaagatcac agacattgaa gaaggagcat tgaaggagc agctggtgta
1801   aacgaaatcc ttctcacgag taaccgtttg gaaaatgttc agcataagat gttcaaggga
1861   ttggaaagcc tgaaaacgtt gatgttgcga agcaatcgca taagctgcgt tggcaacgat
1921   agcttcatag gcctgagctc tgtgcggttg ctttcgctgt acgataatca gatcgccacc
1981   atcgcgccgg ggcgttcga caccctgcac tcgttgtcca ccctaaacct gttggccaac
2041   cctttaact gcaactgcta cctggcttgg ctgggcgagt ggctcaggaa gaaaagaatt
2101   gtaaccggaa atcctcgctg tcaaaaacca tacttcctca agaaatccc catccaggac
2161   gtcgccattc aagacttcac gtgtgacgac ggaaatgacg acagtagctg ttctccactc
2221   tcgcgctgtc ccacggaatg cacgtgcttg gatacagttg tccgatgtag caacaagggc
2281   ctgaaggtct tgcccaaagg tattcccaga gacgtcactg aactgtatct ggatgggaac
2341   cactttacct tggttcccaa ggagctctat aactacaaac atctaacgct tatagacctg
2401   agcaacaacc gcataagcac tctttctaat cagagcttca gcaacatgac ccagctcctc
2461   accctaattc tcagttacaa ccgtttgaga tgtattcctc ctcgaacctt cgatggactc
2521   aagtctctcc gattactttc attacatgga aatgacattt ctgttgtgcc tgaaggtgct
2581   ttcagtgatc tctctgcatt atcacaccta gcaatcggag ccaacccct ttactgtgat
2641   tgcaacatgc agtggttatc ggactgggta agtcggaat acaaagaacc cgggattgct
2701   cgctgtgccg gccccggaga aatggcagat aaattattac tcacgactcc ctccaaaaaa
2761   tttacatgtc aaggtcctgt ggatatcaat attctagcta atgtaatcc ctgcttatca
2821   aacccatgta agaatgatgg cacctgtaac aatgatccag tcgacttta tcgctgtacc
2881   tgtccgtatg gtttcaaggg gcaggactgt gatgtcccaa tccacgcatg catcagtaac
```

TABLE 1-continued

```
2941  ccgtgtacac atggaggaac ttgccactta aaggagggag aaaaagatgg attctggtgt
3001  atttgtgccg atggatttga aggagaaaat tgtgaagtca atgttgatga ctgtgaagat
3061  aatgactgtg aaaataactc tacgtgtgtc gatggaatta ataactacac atgcctttgt
3121  ccgcctgagt acacaggcga gttgtgtgag gagaagctgg acttctgcgc tcaggacctg
3181  aaccctgcc agcacgactc caagtgcatc ctgatgccca aaggattcaa atgcgactgc
3241  acgccgggt acgtgggcga gcactgcgac atcgacttcg acgactgcca ggatcacaag
3301  tgtaaaaacg gagcgcactg cacggacgcg gtgaacggct acacgtgcac ctgccccgaa
3361  ggctacagcg gcttgttctg tgaattctcc ccgcccatgg tcctcccacg caccagcccc
3421  tgtgacaact tcgactgtca gaacgggcg cagtgcatcg tcagggcggg cgagccaatc
3481  tgccagtgtc tgcccggcta ccaggggac aagtgtgaga gttggtcag cgtgaacttc
3541  gtgaacaaag agtcgtatct tcaaattcct tcagccaagg tccggcccca aacgaacatc
3601  accctgcaga ttgccaccga cgaagacagc gggatcctcc tgtacaaggg cgacaaggac
3661  cacattgccg tggagctgta tcggggacgg gtgcgcgcca gctacgacac cggctcgcac
3721  cccgcttctg ccatttacag cgtggagacg atcaatgatg aaacttca cattgtggaa
3781  ctacttgccc tggatcagag cctgtccctc tccgtggatg agggagccc caaaatcatc
3841  accaacttgt caaagcagtc cactctgaat tttgactctc cactctatg aggaggcatg
3901  cccgggagga caacgtggc cgcggccctg cgccaggccc cggggcacaa cggcaccagc
3961  ttccacggct gcatccggaa cctgtatatc aacagcgagc tccaggactt ccgccaggtg
4021  cccatgcaga ccggcatcct gcccggctgc gagccgtgcc acaggaaggt gtgtgcccac
4081  ggcgcgtgcc agcccagcag ccagtcgggc ttcacctgcg agtgcgagga gggctggacg
4141  gggccctgt gtgaccagag gaccaacgac ccctgtctcg gaacaaatg tgtgcacggc
4201  acctgcttgc ccatcaacgc cttctcctac agctgtaagt gtctggaggg ccacggggc
4261  gtcctctgcg acgaagagga ggacctgttc aaccctgcc aggccatcag gtgcaagcac
4321  gggaaatgca ggctctcggg cctgggccag ccctactgcg aatgcagcag cgggtacacg
4381  ggggatagct gcgaccgaga agtgtcctgt cggggcgagc gcgtccggga ctactaccca
4441  aagcagcagg gctacgcggc ctgccagacc accaagaagg tgtcgcggct ggagtgcagg
4501  ggcggctgcg cggccgggca gtgctgcggg ccgctgcgga gcaagcggcg gaaatactcc
4561  ttcgagtgca cggacggctc gtcgttcgtg gacgaggtgg agaaggtggt caagtgcggc
4621  tgcagcaggt gcgccgcctg a
```

SEQ ID NO: 16 Dog Slit2 Amino Acid Sequence

```
  1  mrgagrralp vslglvllil geaapqacpa qcscsgstvd chglalrsvp rsiprnterl
 61  dlngnnitri tktdfaglrh lrvlqlmenk istiergafq dlkelerlrl nrnhlqlfpe
121  llflgtskly rldlsengiq aiprkafrga vdiknlqldy nqisciedga fralrdlevl
181  tlnnnnitrl svasfnhmpk lrtfrlhsnn lycdchlawl sdwlrqrpry glytqcmgps
241  hlrghnvaev qkrefvcsgk gertfllsyy lmllchqsfm apscsvlhcp aactcsnniv
301  dcrgkgltei ptnlpetite irleqnsikv ippgafspyk klrridlsnn qiselapdaf
361  qglrslnslv lygnkitelp kslfeglfsl qllllnanki nclrvdafqd lhnlnllsly
421  dnklqtiakg tfsplraiqt mhlaqnpfic dchlkwlady lhtnpietsg arctsprrla
481  nkriggqiksk kfrcsakegy fipgtedyrs klsgdcfadl acpekcrceg ttvdcsnqkl
541  tkipdhipqy taelrinnne ftvleatgif kklpqlrkin fsnnkitdie egafegaagv
```

TABLE 1-continued

```
 601  neilltsnrl envqhkmfkg leslktlmlr snriscvgnd sfiglssvrl lslydngiat
 661  iapgafdtlh slstlnllan pfncncylaw lgewlrkkri vtgnprcqkp yflkeipiqd
 721  vaiqdftcdd gnddsscspl srcptectcl dtvvrcsnkg lkvlpkgipr dvtelyldgn
 781  hftivpkely nykhltlidl snnristlsn gsfsnmtqll tlilsynrlr cipprrtfdgl
 841  kslrllslhg ndisvvpega fsdlsalshl aiganplycd cnmqwlsdwv kseykepgia
 901  rcagpgemad kllltttpskk ftcqgpvdin ilakcnpcls npckndgtcn ndpvdfyrct
 961  cpygfkgqdc dvpihacisn pcthggtchl kegekdgfwc icadgfegen cevnvddced
1021  ndcennstcv dginnytcic ppeytgelce ekldfcaqdl npcqhdskci lmpkgfkcdc
1081  tpgyvgehcd idfddcqdhk ckngahctda vngytctcpe gysglfcefs ppmvlprtsp
1141  cdnfdcqnga qcivragepi cgclpgyqgd kceklvsvnf vnkesylqip sakvrpqtni
1201  tlqiatdeds gillykgdkd hiavelyrgr vrasydtgsh pasaiysvet indgnfhive
1261  llaldqslsl svdggspkii tnlskqstln fdsplyvggm pgrnnvaaal rqapghngts
1321  fhgcirnlyi nselqdfrqv pmqtgilpgc epchrkvcah gacqpssqsg ftceceegwt
1381  gplcdqrtnd pclgnkcvhg tclpinafsy sckcleghgg vlcdeeedlf npcgairckh
1441  gkcrlsglgq pycecssgyt gdscdrevsc rgervrdyyp kqqgyaacqt tkkvsrlecr
1501  ggcaagqccg plrskrrkys fectdgssfv devekvvkcg csrcaa
```

SEQ ID NO: 17 Cow Slit2 cDNA Sequence
```
   1  atgcacggcg tcggctggca gacgctgtcc ctgtctctgg ggttagtgct ggcgatcctg
  61  aacgaggtgg cgccgcaagc gtgtccggcg cagtgctcct gctccgggag cacagtggac
 121  tgtcacgggc tggcgttgcg cagtgtgccc aggaatatcc cccgcaacac cgagagattg
 181  gatttgaatg gaaataacat cacaaggatt accaagacag attttgctgg tcttcgacac
 241  ctaagagttc ttcagcttat ggagaataag attaccacca ttgaaagagg agcattccag
 301  gatcttaaag aactggagag actgcgttta aacagaaatc accttcagct gtttcctgag
 361  ttgctgtttc ttgggacttc gaagctatac aggcttgacc tcagtgaaaa ccagattcag
 421  gcaattccaa ggaaagcttt tcgtggggca gttgatatta aaaatctgca actggattac
 481  aaccacatca gctgtattga agatggggca ttcagggctc tccgggacct ggaagtgctc
 541  actctcaaca taacaacat tactagactt tctgtggcaa gtttcaacca tatgcctaaa
 601  cttaggactt ttcgactcca ttcgaacaac ctatattgtg actgccacct ggcctggctc
 661  tcggactggc tgcgccaaag gcctcgggtg ggcctctaca ctcagtgtat gggggccatct
 721  cacctgaggg gccacaatgt agctgaggtt caaaaacgag aatttgtctg cagcgatgag
 781  gaagaaggtc accagtcatt tatggctcct tcttgcagtg ttttgcactg cccagctgct
 841  tgtacctgta gcaacaacat cgtagattgc cgtgggaaag gtctcactga gatccccacg
 901  aatctgccag agaccatcac agaaatacgt ttggaacaga actcaatcaa ggtcatccct
 961  cctggagctt tctcaccata taaaaagctt gaagaatcg acctgagcaa taatcagatc
1021  tctgagctag caccagatgc tttccaagga ctacgctctc tgaattcact tgtcctctat
1081  ggaaataaaa tcacagaact cccaaaaagt ttatttgaag actgttttc cttacagtta
1141  ctattactga atgccaacaa gataaactgc ctccgggtag atgctttca ggatctgcac
1201  aacctgaacc ttctctcctt atatgacaac aagcttcaga ccatcgccaa ggggaccttt
1261  tcacctctcc gggccattca aaccatgcat ttgggcccaga accccttat tgtgactgc
1321  catctcaagt ggctggcgga ttatctccat accaacccaa tcgagaccag tggtgcccgc
1381  tgcaccagtc cccggcgact ggcaaacaaa agaatcggac agatcaaaag caagaaattc
```

TABLE 1-continued

```
1441  cgttgttcag ctaaagaaca gtatttcatt ccaggtacag aagattatcg atcaaaatta
1501  agtggggact gctttgccga tttggcttgc cctgaaaagt gccgctgcga agggaccaca
1561  gtagactgct ccaatcaaaa actcaccaaa atcccagatc acattcccca gtacactgca
1621  gagctgcgcc tcaacaataa tgaatttaca gtgttggaag ctaccgggat cttcaagaaa
1681  cttcctcagt tacgtaaaat aaactttagc aacaataaga tcacagacat tgaagaggga
1741  gcgtttgaag gagcatctgg tgtgaatgaa atacttctca cgagtaatcg tttggaaaat
1801  gttcagcata agatgttcaa gggcttggaa agcctcaaga ctttgatgtt gagaagtaat
1861  cgcataagct gtgtagggaa tgacagtttc ataggactca gctctgtgcg tttgctttct
1921  ttatatgata atcagattac taccattgca ccaggagctt ttgatactct ccattcttta
1981  tctactctaa acctcttggc caatcctttc aactgtaact gctacctggc ttggttggga
2041  gaatggctta ggaagaaaag aattgtaaca ggaaatcctc gatgtcagaa accctatttc
2101  ctcaaagaaa tccccatcca ggatgtggcc attcaagact tcacttgtga tgatggaaat
2161  gatgacaata gctgttcccc actctctcgc tgtcctgccg agtgtacctg cttggacaca
2221  gtggttcgat gtagcaacaa agccttgaag gtcttgccca aaggaattcc aagagatgtc
2281  actgaattgt atctggatgg gaaccagttt accttggttc taaggaact ctctaactac
2341  aaacatttaa cacttataga cttaagtaac aacagaataa gcaccctctc taatcagagc
2401  ttcagcaaca tgacccagct cctcacttta attcttagtt acaaccgttt gagatgtatt
2461  cctcctcgaa ccttcgatgg actgaagtct cttcggttac tttctttaca tggaaacgac
2521  atttctgttg tgcctgaagg tgctttcaat gatcttgctg cattatcaca cctagcaatt
2581  ggagccaacc ctctttactg tgattgtaac atgcagtggt tatccgactg ggtaaagtcg
2641  gaatacaaag agccgggaat tgctcgctgt gctggtcctg agaaatggc agataaacta
2701  cttctcacaa ctccctccaa aaaatttaca tgtcaaggtc ctgtggatgt caatattcta
2761  gctaaatgta atccctgctt atcaaatcca tgtaaaaatg atggcacctg taacaatgac
2821  ccagttgact tttatcgctg cacctgtcca tatggtttca aggggcagga ttgtgatgtt
2881  ccaattcatg cgtgcatcag caacccatgt aaacatggag gaacttgcca cttaaaagaa
2941  ggagaaaaag atggattctg gtgtatttgt gctgatggat ttgaaggaga aaattgtgaa
3001  atcaatgttg atgactgtga agataatgac tgtgaaaata actctacatg tgtcgatgga
3061  attaataact acacatgcct ttgcccacct gagtcacag gagagttgtg tgaggagaaa
3121  ctggacttct gtgcccagga cttgaacccc tgccagcatg actccaagtg catcctgacg
3181  ccaaagggat acaaatgtga ctgcactcca ggatacatag cgaacattg tgacattgac
3241  ttcgatgact gccaagataa caagtgtaag aacggagccc actgcaccga tgcagtgaac
3301  ggttacacat gcacctgtcc tgaaggctac agtggcttgt tttgtgaatt ttctccacct
3361  atggttctcc ctcgtaccag cccctgtgat aattttgatt gtcagaatgg agctcaatgc
3421  atcatcagga tcaatgagcc aatatgccag tgtttgcctg gctaccaggg agaaaagtgt
3481  gaaaaactgg tcagtgtgaa ttttgtaaac aaagagtctt atcttcagat cccttccgcc
3541  aaggtccggc ctcaaacaaa catcactctt cagatcgcca cagatgaaga cagtggaatc
3601  ctcctgtata agggtgataa agaccatatt gctgtagaac tctaccgagg acgtgttcgt
3661  gccagctatg acaccggctc ccacccggct tctgccattt acagtgtgga gacaatcaat
3721  gacggaaatt ttcacattgt ggaactactt gccctggatc aaagtctctc cctctcagtg
3781  gatggaggga gccccaaaat cattaccaac ttgtcaaaac agtccactct gaattttgac
```

TABLE 1-continued

```
3841  tccccactct atgttggagg catgcccggg aagaacaacg tggccgcagc tctgcgccag
3901  gccctgggc  agaatggcac cagcttccac ggttgcatcc ggaaccttta catcaacagc
3961  gaacttcagg acttccggaa ggtgcccatg cagaccggca tcctgcctgg ctgtgaacca
4021  tgccacaaga aggtgtgtgc ccacggcaca tgccagccca gcagccaggc cggcttcacc
4081  tgcgagtgcg aggaaggatg acagggccc  ctctgtgatc agaggaccaa tgacccctgt
4141  cttggaaata atgcgtcca  cggcacctgc ctgcccatca atgcgttctc ctacagctgc
4201  aaatgcctag agggccatgg gggcgtcctc tgtgatgaag aggaggatct gtttaaccca
4261  tgccaggcga tcaagtgcaa gcatgggaaa tgcaggctct caggactggg gcagccctac
4321  tgtgaatgca gcagtggata caccggggac agctgtgatc gagaaatctc ttgtcgaggg
4381  gaacggataa gagattatta ccaaaagcag cagggctacg ccgcttgcca gacgaccaag
4441  aaggtgtctc ggttggaatg cagagggggc tgtgcaggcg ggcagtgctg cggacctctg
4501  aggagcaaga gaaggaaata ctctttcgaa tgcactgatg gtcctcgtt  tgtggacgag
4561  gtggagaagg tggtaaagtg tggctgtacc cgctgcgctt cctaa
```

SEQ ID NO: 18 Cow Slit2 Amino Acid Sequence

```
   1  mhgvgwqtls lslglvlail nevapqacpa qcscsgstvd chglalrsvp rniprnterl
  61  dlngnnitri tktdfaglrh lrvlqlmenk ittiergafq dlkelerlrl nrnhlqlfpe
 121  llflgtskly rldlsengiq aiprkafrga vdiknlqldy nhisciedga fralrdlevl
 181  tlnnnnitrl svasfnhmpk lrtfrlhsnn lycdchlawl sdwlrqrpry glytqcmgps
 241  hlrghnvaev qkrefvcsde eeghqsfmap scsvlhcpaa ctcsnnivdc rgkglteipt
 301  nlpetiteir leqnsikvip pgafspykkl rridlsnnqi selapdafqg lrslnslvly
 361  gnkitelpks lfeglfslql lllnankinc lrvdafqdlh nlnllslydn klqtiakgtf
 421  splraiqtmh laqnpficdc hlkwladylh tnpietsgar ctsprrlank rigqikskkf
 481  rcsakegyfi pgtedyrskl sgdcfadlac pekcrcegtt vdcsnqkltk ipdhipqyta
 541  elrinnneft vleatgifkk lpqlrkinfs nnkitdieeg afegasgvne illtsnrlen
 601  vqhkmfkgle slktlmlrsn riscvgndsf iglssvrlls lydnqittia pgafdtlhsl
 661  stlnllanpf ncncylawlg ewlrkkrivt gnprcqkpyf lkeipiqdva iqdftcddgn
 721  ddnscsplsr cpaectcldt vvrcsnkalk vlpkgiprdv telyldgnqf tivpkelsny
 781  khltlidlsn nristlsnqs fsnmtqllt  ilsynrlrci pprtfdglks lrllslhgnd
 841  isvvpegafn dlaalshlai ganplycdcn mqwlsdwvks eykepgiarc agpgemadkl
 901  llttpskkft cqgpvdvnil akcnpclsnp ckndgtcnnd pvdfyrctcp ygfkgqdcdv
 961  pihacisnpc khggtchlke gekdgfwcic adgfegence invddcednd cennstcvdg
1021  innytcicpp eytgelceek ldfcaqdlnp cqhdskcilt pkgykcdctp gyigehcdid
1081  fddcgdnkck ngahctdavn gytctcpegy sglfcefspp mvlprtspcd nfdcqngaqc
1141  iirinepicq clpgyqgekc eklvsvnfvn kesylqipsa kvrpqtnitl qiatdedsgi
1201  llykgdkdhi avelyrgrvr asydtgshpa saiysvetin dgnfhivell aldqslslsv
1261  dggspkiitn lskqstlnfd splyvggmpg knnvaaalrq apgqngtsfh gcirnlyins
1321  elqdfrkvpm qtgilpgcep chkkvcahgt cussgagft  ceceegwtgp lcdqrtndpc
1381  lgnkcvhgtc lpinafsysc kcleghggvl cdeeedlfnp cgaikckhgk crlsglgqpy
1441  cecssgytgd scdreiscrg erirdyyqkq qgyaacqttk kvsrlecrgg caggqccgpl
1501  rskrrkysfe ctdgssfvde vekvvkcgct rcas
```

TABLE 1-continued

SEQ ID NO: 19 Chicken Slit2 cDNA Sequence

```
   1  atgatgtgcg cctggggag gctcccctg gccctggggc tgctgctggt gctggcgggc
  61  gaggcggcgc cgcagccgtg cccggcgcag tgctcctgct caggaagcac ggtggactgt
 121  cacgggctgg cgctgcgcgg cgtcccgagg aacatccccc gcaacactga gcggctggac
 181  cttaatggaa ataacatcac cagaatcacc aagaccgact tgctggtct aaggcacctt
 241  cgagttcttc agctcatgga gaacaagatt agcactattg agagaggagc attccaggat
 301  ttaaaagaac tggagaggct gcgcctaaac agaaataacc tccagttgct ttctgaactg
 361  ctctttctgg ggacgccgaa gttatacagg cttgatctta gtgaaaatca gattcaagcc
 421  atacccagga aggcatttcg tggagcagta gacataaaaa atctgcaact ggattacaac
 481  cagatcagct gtattgaaga tggggcattt agggctctac gcgacctgga agtgctcact
 541  ctcaacaaca ataacattac tcgactgtcc gtcgcaagtt tcaatcatat gcccaaactc
 601  agaacttttc gcctgcactc caacaacctc tactgtgact gccacctggc ctggctgtcg
 661  gactggctgc ggcagcggcc acgtgtaggc ctctacactc agtgcatggg cccagcacac
 721  ctgcggggcc ataacgtggc tgaggtccag aagcgggagt tcgtctgcag tggtcaccaa
 781  tcatttatgg ctccatcctg cagtgtcttg cattgtcctg ctgcatgcac tgtagtaac
 841  aacattgtgg actgtcgtgg gaaaggcctt actgaaattc aacaaatct tccagaaacc
 901  attactgaaa tacggttaga acaaaattca atcaaagtca tacctcctgg agctttctca
 961  ccctataaaa agcttcgaag aattgacctg agcaataacc agatctctga agcagctcca
1021  gatgctttcc agggcttacg ttctctcaat tcacttgtcc tctatggcaa taaaattaca
1081  gaacttccaa aaggcctatt tgaaggactg ttttctctgc aattgctatt attaaatgcc
1141  aacaagatca attgcctgcg tgttgatgct tttcaagatc tgcacaactt gaatctccta
1201  tctttatatg acaacaagct tcagaccatt gcaaaggca cctttttcacc tctacgtgca
1261  attcagacct tgcatttggc tcagaaccca tttatctgtg actgccatct gaagtggctg
1321  gcggattatc ttcatacaaa ccccattgag accagtggtg cccgctgcac cagcccccgc
1381  cgtctggcaa acaaaaggat cggccagatc aaaagcaaga aattccgctg ctcagctaaa
1441  gagcagtatt tcattccagg cactgaagat tacagatcca aattaagtgg tgactgcttt
1501  gcagatttgg cttgccctga aaatgtcgc tgtgaaggga ccacagtgga ctgctccaat
1561  cagaaactca acaaaattcc tgatcacatc ccacagtaca cagcagagtt gcgactcaat
1621  aacaatgaat ttcagtcct ggaagctact gggatctta agaagcttcc tcaactgcga
1681  aaaataaacc tgagcaataa caagattaca gatattgaag aaggtgcatt tgatggagcc
1741  tctggtgtca atgaactatt gctcactagc aatcgtttgg aaactgttag agacaaaatg
1801  ttcaaaggac tggaaagtct taaaacactg atgctgagga gtaaccgtgt gagctgtgtg
1861  gggaacgaca gtttcacagg cctgagctct gtccgtctgc tctcactata tgacaaccag
1921  atcaccaccg tggcacccgg ctccttcgat accctgcatt cactctctac attaaacctc
1981  ttggccaatc ctttcaactg caactgccat cttgcatggc ttggagattg gctaaggaag
2041  aaacgcattg tgacgggaaa ccctcgctgt cagaaacctt atttcctcaa agagattcct
2101  atccaggatg tggcaattca ggatttaca tgtgatgatg gaaatgatga caatagctgc
2161  tctccgctgt cccgctgtcc tgcagaatgt acttgtctag acacagttgt tcgctgcagc
2221  aacaaaggcc taaagctttt gcctaaggc atcccaaaag atgtaactga actatatttg
2281  gatggaaacc agtttactct tgttcctaaa gagctctcca actacaaaca tttaacactt
2341  atagatttaa gtaacaacag aatcagcact ctttctaatc agagcttcag caacatgact
```

TABLE 1-continued

```
2401  cagctgctca ccttaattct tagttacaac cgcctgaggt gtatccctgc acggactttt
2461  gatgggttga aatcacttag gttgctgtct ttacatggca atgatatttc tgtggttcct
2521  gaaggagcct ttaatgatct ttcagcgtta tcacacctgg ctattggagc aaatcctctt
2581  tattgtgatt gtaacatgca atggctgtct gactgggtaa aatcagaata caaagaacct
2641  ggtattgcac gatgtgctgg ccctggagaa atggcagata aacttctact tacaactcca
2701  tctaaaaaat ttacttgcca agggcccgtg gatgtcaata ttcttgctaa gtgtaacccc
2761  tgcttatcaa atccatgtaa aaatgatgga acctgcaata atgatccagt tgacttctat
2821  agatgtactt gcccatatgg tttcaagggt caagactgtg atattcccat tcatgcctgc
2881  attagtaacc cttgcaacca tggtggaact tgtcatttga agaaggaga aaaagatggt
2941  ttctggtgca cttgtgcaga tggatttgaa ggagaaaatt gtgaaataaa tgttgatgac
3001  tgtgaagaca atgactgtga aaataactct acttgtgtgg atggaattaa taattatact
3061  tgcctttgtc cacctgaata tacaggtgag ctctgtgagg agaaactaga tttctgtgct
3121  caaaacctga acccttgcca gcacgactca aagtgtatct tgactcccaa aggttacaag
3181  tgtgattgca cacctggata tgtaggtgaa cactgcgata ttgacttcga tgactgccag
3241  gacaataaat gtaaaaacgg agcacagtgt acggatgcag ttaacgggta tacttgtatt
3301  tgcccagagg gatacagtgg cttgttttgt gagttttcgc caccaatggt tttacctcgc
3361  accagccctt gtgataatta tgaatgccaa aatggagccc agtgtattgt aaaggagagt
3421  gaaccaatct gccagtgttt atcaggctac cagggtgaga atgtgaaaa gctgatcagt
3481  ataaactttg tcaacaaaga atcctatcta caaatccctt cagctaagat acactcccaa
3541  accaatatca ctcttcagat tgccacagac gaagacagtg ggatcctgct ctacaaaggc
3601  gataaggatc atatagcagt agagctgtac cgtggtagag tgagggtcag ttatgacaca
3661  ggatcttatc cagcctctgc tatttacagt gtggaaacta ttaatgatgg caatttccac
3721  attgtggagc tgcttgccat ggatcagatt ctgtctttgt ctattgatgg aggaagcccc
3781  aagataatta ccaatttgtc caagcagtcc actttgaatt ttgattctcc actgtatgtc
3841  ggaggcatgc ctgtgaaaaa taacattgca gctctacgtc agtctccagg acagaatggc
3901  acaagcttcc atggctgcat ccgtaatctg tatatcaaca gcgaactcca ggacttcaga
3961  aatgtgccac tgcaagtggg aattctgcca ggttgcgagc ttgtcacaa gaaagtttgt
4021  gtgcatggaa catgccatgc taccagccag tcaagcttta cctgtgagtg tgaaggagga
4081  tggactggac ccctctgtga tcaacaaact aatgacccgt gtctcggaaa taaatgtgtg
4141  catggtacct gcttgccgat caatgcattt tcatacagtt gtaaatgcct gcagggacat
4201  gggggagtcc tctgtgatga agaggaaatg ctgtttaacc cctgccaatc catcaggtgt
4261  aaacatggca aatgcaggct ttcaggactt gggaaaccat attgcgaatg cagcagcgga
4321  tacacgggggg acagctgtga taaagaaatc tcttgtcgag gggaacgaat ccgagattac
4381  taccaaaagc agcaagggta tgctgcgtgc cagacgacca agaaggtatc gagactagaa
4441  tgtaaaggag gatgttcaac cgggcagtgc tgtggaccac taaggagcaa gagacggaaa
4501  tactctttttg aatgcactga tgggtcgtca tttgtggacg agattgaaaa agtggtgaag
4561  tgtggctgta caaattgtcc ctcctaa
```

SEQ ID NO: 20 Chicken Slit2 Amino Acid Sequence
```
  1  mmcawgrlpl alglllvlag eaapqpcpaq cscsgstvdc hglalrgvpr niprnterld
 61  lngnnitrit ktdfaglrhl rvlqlmenki stiergafqd lkelerlrin rnnlqllsel
```

| | |
|---|---|
| 121 | lflgtpklyr ldlsengiqa iprkafrgav diknlqldyn qisciedgaf ralrdlevlt |
| 181 | lnnnnitrls vasfnhmpkl rtfrlhsnnl ycdchlawls dwlrqrprvg lytqcmgpah |
| 241 | lrghnvaevq krefvcsghq sfmapscsvl hcpaactcsn nivdcrgkgl teiptnlpet |
| 301 | iteireqns ikvippgafs pykklrrridl snnqiseaap dafqglrsln slvlygnkit |
| 361 | elpkglfegl fslqllllna nkinclrvda fqdlhnlnll slydnklqti akgtfsplra |
| 421 | igtlhlagnp ficdchlkwl adylhtnpie tsgarctspr rlankrigqi kskkfrcsak |
| 481 | eqyfipgted yrsklsgdcf adlacpekcr cegttvdcsn qklnkipdhi pqytaelrin |
| 541 | nnefsvleat gifkklpqlr kinlsnnkit dieegafdga sgvnelllts nrletvrdkm |
| 601 | fkgleslktl mlrsnrvscv gndsftglss vrllslydnq ittvapgsfd tlhslstlnl |
| 661 | lanpfncnch lawlgdwlrk krivtgnprc qkpyflkeip iqdvaiqdft cddgnddnsc |
| 721 | splsrcpaec tcldtvvrcs nkglkalpkg ipkdvtelyl dgnqftivpk elsnykhltl |
| 781 | idlsnnrist lsnqsfsnmt qlltlilsyn rlrcipartf dglkslrlls lhgndisvvp |
| 841 | egafndlsal shlaiganpl ycdcnmqwls dwvkseykep giarcagpge madkllllttp |
| 901 | skkftcqgpv dvnilakcnp clsnpckndg tcnndpvdfy rctcpygfkg qdcdipihac |
| 961 | isnpcnhggt chlkegekdg fwctcadgfe genceinvdd cedndcenns tcvdginnyt |
| 1021 | cicppeytge lceekldfca qnlnpcqhds kciltpkgyk cdctpgyvge hcdidfddcq |
| 1081 | dnkckngaqc tdavngytci cpegysglfc efsppmvlpr tspcdnyecq ngaqcivkes |
| 1141 | epicgclsgy qgekceklis infvnkesyl qipsakihsq tnitlqiatd edsgillykg |
| 1201 | dkdhiavely rgrvrvsydt gsypasaiys vetindgnfh ivellamdqi lslsidggsp |
| 1261 | kiitnlskqs tlnfdsplyv ggmpvknnia alrqspgqng tsfhgcirnl yinselqdfr |
| 1321 | nvplqvgilp gcepchkkvc vhgtchatsq ssftcecegg wtgplcdqqt ndpclgnkcv |
| 1381 | hgtclpinaf sysckclqgh ggvlcdeeem lfnpcqsirc khgkcrlsgl gkpycecssg |
| 1441 | ytgdscdkei scrgerirdy yqkqqgyaac qttkkvsrle ckggcstgqc cgplrskrrk |
| 1501 | ysfectdgss fvdeiekvvk cgctncps |

SEQ ID NO: 21 Human Slit2-N Fragment Amino Acid Sequence
QACPAQCSCSGSTVDCHGLALRSVPRNIPRNTERLDLNGNNITRITKIDFAGLRHLR
VLQLMENRISTIERGAFQDLKELERLRLNRNNLQLFPELLFLGTAKLYRLDLSENQI
QAIPRKAFRGAVDIKNLQLDYNQISCIEDGAFRALRDLEVLTLNNNITRLSVASFN
HMPKLRTFRLHSNNLYCDCHLAWLSDWLRQRPRVGLYTQCMGPSHLRGHNVAEV
QKREFVCSGHQSFMAPSCSVLHCPAACTCSNNIVDCRGKGLTEIPTNLPETITEIRLE
QNSIRVIPPGAFSPYKKLRRLDLSNNQISELAPDAFQGLRSLNSLVLYGNKITELPKS
LFEGLFSLQLLLLNANKINCLRVDAFQDLHNLNLLSLYDNKLQTVAKGTFSALRAI
QTMHLAQNPFICDCHLKWLADYLHTNPIETSGARCTSPRRLANKRIGQIKSKKFRCS
GTEDYRSKLSGDCFADLACPEKCRCEGTTVDCSNQRLNKIPDHIPQYTAELRLNNN
EFTVLEATGIFKKKLPLRKINFSNNKITDIEEGAFEGASGVNEILLTSNRLENVQHKM
FKGLESLKTLMLRSNRISCVGNDSFIGLGSVRLLSLYDNQITTVAPGAFDSLHSLSTL
NLLANPFNCNCHLAWLGEWLRRKRIVTGNPRCQKPYFLKEIPIQDVAIQDFTCDDG
NDDNSCSPLSRCPSECTCLDTVVRCSNKGLKVLPKGIPKDVTELYLDGNQFTLVPK
ELSNYKHLTLIDLSNNRISTLSNQSFSNMTQLLTLILSYNRLRCIPPRTFDGLKSLRLL
SLHGNDISVVPEGAFNDLSALSHLAIGANPLYCDCNMQWLSDWVKSEYKEPGIAR
CAGPGEMADKLLLTTPSKKFTCQGPVDITIQAKCNPCLSNPCKNDGTCNNDPVDFY
RCTCPYGFKGQDCDVPIHACISNPCKHGGTCHLKEGENAGFWCTCADGFEGENCE
VNIDDCEDNDCENNSTCVDGINNYTCLCPPEYTGELCEEKLDFCAQDLNPCQHDSK
CILTPKGFKCDCTPGYIGEHCDIDFDDCQDNKCKNGAHCTDAVNGYTCVCPEGYS
GLFCEFSPPMVLPR SEQ ID NO: 22 Human Slit2-C Fragment Amino Acid Sequence
TSPCDNFDCQNGAQCIIRINEPICQCLPGYLGEKCEKLVSVNFVNKESYLQIPSAKVR
PQTNITLQIATDEDSGILLYKGDKDHIAVELYRGRVRASYDTGSHPASAIYSVETIND
GNFHIVELLTLDSSLSLSVDGGSPKVITNLSKQSTLNFDSPLYVGGMPGKNNVASLR
QAPGQNGTSFHGCIRNLYINSELQDFRKMPQTGILPGCEPCHKKVCAHGMCQPSS
QSGFTCECEEGWMGPLCDQRTNDPCLGNKCVHGTCLPINAFSYSCKCLEGHGGVL
CDEEEDLFNPCQMIKCKHGKCRLSGVGQPYCECNSGFTGDSCDREISCRGERIRDY
YQKQQGYAACQTTKKVSRLECRGGCAGGQCCGPLRSKRRKYSFECTDGSSFVDEV
EKVVKCGCARCAS Included in Table 1 are variations of 1, 2, 3, 4, 5, 6, 7, 8, 9, 10, 11, 12, 13, 14, 15, 16, 17, 18, 19, 20, or more nucleotides or amino acids on the 5' (N-terminal) end, on the 3' (C-terminal) end, or on both the 5' (N-terminal) and 3' (C-terminal) ends, of the domain sequences as long as the sequence variations encode or maintain the recited function and/or homology Included in Table 1 are nucleic acid and amino acid molecules comprising, consisting essentially of, or consisting of:

1) a nucleic acid or amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a sequence of SEQ ID NO:1-22, or a biologically active fragment thereof;

2) a nucleic acid or amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3500, 4000, 4500, 5000, 5500, 6000, 6500, 7000, 7500, 8000, 8500, 9000, 9500, 10000, or more nucleotides or amino acids, or any range in between, inclusive such as between 110 and 300 nucleotides;

3) a biologically active fragment of a nucleic acid or amino acid sequence of SEQ ID NO:1-22 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1510, 1515, 1520, 1521, 1522, 1523, 1524, 1525, 1526, 1527, 1528, 1529, 1530, or more nucleotides or amino acids, or any range in between, inclusive such as between 110 and 300 nucleotides;

4) a biologically active fragment of a nucleic acid or amino acid sequence sequence of SEQ ID NO:1-22 having 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1510, 1515, 1520, 1521, 1522, 1523, 1524, 1525, 1526, 1527, 1528, 1529, 1530, or fewer nucleotides or amino acids, or any range in between, inclusive such as between 110 and 300 nucleotides;

5) one or more domains selected from the group consisting of an N-terminal signal peptide sequence (SS) domain, a leucine-rich repeat (LRR) domain, an EGF domain, a LamG domain, and a C-terminal cysteine knot domain, in any combination, inclusive such as an EGF domain and a C-terminal cysteine knot domain;

6) the ability to modulate one or more biological activities of a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; and k) modified expression of UCP1 protein; and 7) any combination of 1) through 6), as well as those in the Examples and Figures and modified according to the descriptions provided herein, inclusive.

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein (e.g., cidea, adiponectin (adipoq), adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1)), are well known in the art and can be used in the embodiments of the invention.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |

-continued

GENETIC CODE

| | |
|---|---|
| Lysine (Lys, K) | AAA, AG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the present invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

I. Isolated Nucleic Acids

One aspect of the invention pertains to methods utilizing isolated nucleic acid molecules that encode Slit2 or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Slit2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of a sequence described in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous or identical to a nucleotide sequence described in Table 1 or a portion thereof (i.e., 100, 200, 300, 400, 450, 500, or more nucleotides), can be isolated using standard molecular biology techniques and the sequence information provided herein. For example, a human Slit2 cDNA can be isolated from a human beige fat cell line (from Stratagene, LaJolla, Calif., or Clontech, Palo Alto, Calif.) using all or portion of SEQ ID NOs: 1, 3, and 5, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989). Moreover, a nucleic acid molecule encompassing all or a portion of a sequence described in Table 1 or a nucleotide sequence which is at least about 50%, preferably at least about 60%, more preferably at least about 70%, yet more preferably at least about 80%, still more preferably at least about 90%, and most preferably at least about 95% or more homologous to a sequence described in Table 1, or fragment thereof, can be isolated by the polymerase chain reaction using oligonucleotide primers designed based upon the sequence described in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fl.). Synthetic oligonucleotide primers for PCR amplification can be designed based upon a sequence described in Table 1, or fragment thereof, or to the homologous nucleotide sequence. A nucleic acid of the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a Slit2 nucleotide sequence can be prepared by standard synthetic techniques, i.e., using an automated DNA synthesizer.

Probes based on the Slit2 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a Slit2 protein, such as by measuring a level of a Slit2-encoding nucleic acid in a sample of cells from a subject, i.e., detecting Slit2 mRNA levels.

Nucleic acid molecules encoding other Slit2 members and thus which have a nucleotide sequence which differs from the Slit2 sequences of SEQ ID NOs: 1, 3, 5, 7, 9, 11, 13, 15, 17, and 19, or fragment thereof, are contemplated. Moreover, nucleic acid molecules encoding Slit2 proteins from different species, and thus which have a nucleotide sequence which differs from the Slit2 sequences of SEQ ID NOs: 1, 3 5, 7, 9, 11, 13, 15, 17, and 19 are also intended to be within the scope of the present invention. For example, chimpanzee Slit2 cDNA can be identified based on the nucleotide sequence of a human and/or mouse Slit2.

In one embodiment, the nucleic acid molecule(s) of the invention encodes a protein or portion thereof which includes an amino acid sequence which is sufficiently homologous to an amino acid sequence of a sequence described in Table 1, or fragment thereof, such that the protein or portion thereof modulates (e.g., enhance), one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

As used herein, the language "sufficiently homologous" refers to proteins or portions thereof which have amino acid sequences which include a minimum number of identical or equivalent (e.g., an amino acid residue which has a similar side chain as an amino acid residue in an amino acid sequence described in Table 1, or fragment thereof) amino acid residues to an amino acid sequence of an amino acid sequence described in Table 1, or fragment thereof, such that the protein or portion thereof modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of an amino acid sequence described in Table 1, or a fragment thereof.

Portions of proteins encoded by the Slit2 nucleic acid molecule of the invention are preferably biologically active portions of the Slit2 protein. As used herein, the term "biologically active portion of Slit2" is intended to include a portion, e.g., a domain/motif, of Slit2 that has one or more of the biological activities of the full-length Slit2 protein.

Standard binding assays, e.g., immunoprecipitations and yeast two-hybrid assays, as described herein, or functional assays, e.g., RNAi or overexpression experiments, can be performed to determine the ability of a Slit2 protein or a biologically active fragment thereof to maintain a biological activity of the full-length Slit2 protein.

The invention further encompasses nucleic acid molecules that differ from a sequence described in Table 1, or fragment thereof, due to degeneracy of the genetic code and thus encode the same Slit2 protein as that encoded by a nucleotide sequence described in Table 1, or a fragment thereof. In another embodiment, an isolated nucleic acid molecule of the invention has a nucleotide sequence encoding a protein having an amino acid sequence described in Table 1, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to an amino acid sequence described in Table 1, or a fragment thereof, or differs by at least 1, 2, 3, 5 or 10 amino acids but not more than 30, 20, 15 amino acids from an amino acid sequence described in Table 1.

It will be appreciated by those skilled in the art that DNA sequence polymorphisms that lead to changes in the amino acid sequences of Slit2 may exist within a population (e.g., a mammalian population, e.g., a human population). Such genetic polymorphism in the Slit2 gene may exist among individuals within a population due to natural allelic variation. As used herein, the terms "gene" and "recombinant gene" refer to nucleic acid molecules comprising an open reading frame encoding a Slit2 protein, preferably a mammalian, e.g., human, Slit2 protein. Such natural allelic variations can typically result in 1-5% variance in the nucleotide sequence of the Slit2 gene. Any and all such nucleotide variations and resulting amino acid polymorphisms in Slit2 that are the result of natural allelic variation and that do not alter the functional activity of Slit2 are intended to be within the scope of the invention. Moreover, nucleic acid molecules encoding Slit2 proteins from other species, and thus which have a nucleotide sequence which differs from the human or mouse sequences of a sequence described in Table 1, are intended to be within the scope of the invention. Nucleic acid molecules corresponding to natural allelic variants and homologues of the human or mouse Slit2 cDNAs of the invention can be isolated based on their homology to the human or mouse Slit2 nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Slit2 sequence that may exist in the population, the skilled artisan will further appreciate that changes can be introduced by mutation into a sequence described in Table 1, or fragment thereof, thereby leading to changes in the amino acid sequence of the encoded Slit2 protein, without altering the functional ability of the Slit2 protein. For example, nucleotide substitutions leading to amino acid substitutions at "non-essential" amino acid residues can be made in a sequence described in Table 1, or fragment thereof. A "non-essential" amino acid residue is a residue that can be altered from the wild-type sequence of Slit2 (e.g., an amino acid sequence described in Table 1) without altering the activity of Slit2, whereas an "essential" amino acid residue is required for Slit2 activity. Other amino acid residues, however, (e.g., those that are not conserved or only semi-conserved between mouse and human) may not be essential for activity and thus are likely to be amenable to alteration without altering Slit2 activity. Furthermore, amino acid residues that are essential for Slit2 functions related to thermogenesis and/or adipogenesis, but not essential for Slit2 functions related to gluconeogenesis, are likely to be amenable to alteration.

Accordingly, another aspect of the invention pertains to nucleic acid molecules encoding Slit2 proteins that contain changes in amino acid residues that are not essential for Slit2 activity. Such Slit2 proteins differ in amino acid sequence from those amino acid sequences described in Table 1, or fragment thereof, yet retain at least one of the Slit2 activities described herein. In one embodiment, the isolated nucleic acid molecule comprises a nucleotide sequence encoding a protein, wherein the protein lacks one or more Slit2 domains.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared ×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a Slit2 protein homologous to an amino acid sequence described in Table 1, or fragment thereof, can be created by introducing one or more nucleotide substitutions, additions or deletions into a nucleotide sequence described in Table 1, or fragment thereof, or a homologous nucleotide sequence such that one or more amino acid substitutions, additions or deletions are introduced into the encoded protein. Mutations can be introduced into the sequence described in Table 1, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in Slit2 is preferably replaced with another amino acid residue from the same side chain family. Alternatively, in another embodiment, mutations can be introduced randomly along all or part of a Slit2 coding sequence, such as by saturation mutagenesis, and the resultant mutants can be screened for a Slit2 activity described herein to identify mutants that retain Slit2 activity. Following mutagenesis of a sequence described in Table 1, or fragment thereof, the encoded protein can be expressed recombinantly (as described herein) and the activity of the protein can be determined using, for example, assays described herein.

Slit2 levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Slit2 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Slit2 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding Slit2. Other suitable probes for use in the diagnostic assays of the invention are described herein. Hybridization of an mRNA with the probe indicates that Slit2 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the Slit2 mRNA expression levels.

An alternative method for determining the Slit2 mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the Slit2 mRNA.

As an alternative to making determinations based on the absolute Slit2 expression level, determinations may be based on the normalized Slit2 expression level. Expression levels are normalized by correcting the absolute Slit2 expression level by comparing its expression to the expression of a non-Slit2 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a Slit2 protein can also be detected and/or quantified by detecting or quantifying the expressed polypeptide. The Slit2 polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Slit2.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, piwiRNA, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the present invention, including one or more biomarkers listed in Table 1, the Figures, and the Examples, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g., cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the present invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, piwiRNA, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1, the Figures, and the Examples,). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-amino-hexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

It is to be understood that additional well known nucleic acid architecture or chemistry can be applied. Different modifications can be placed at different positions to prevent the oligonucleotide from activating RNase H and/or being capable of recruiting the RNAi machinery. In another embodiment, they may be placed such as to allow RNase H activation and/or recruitment of the RNAi machinery. The modifications can be non-natural bases, e.g. universal bases. It may be modifications on the backbone sugar or phosphate, e.g., 2'-O-modifications including LNA or phosphorothioate linkages. As used herein, it makes no difference whether the modifications are present on the nucleotide before incorporation into the oligonucleotide or whether the oligonucleotide is modified after synthesis.

Preferred modifications are those that increase the affinity of the oligonucleotide for complementary sequences, i.e. increases the tm (melting temperature) of the oligonucleotide base paired to a complementary sequence. Such modifications include 2'-O-flour, 2'-O-methyl, 2'-O-methoxyethyl. The use of LNA (locked nucleic acid) units, phosphoramidate, PNA (peptide nucleic acid) units or INA (intercalating nucleic acid) units is preferred. For shorter oligonucleotides, it is preferred that a higher percentage of affinity increasing modifications are present. If the oligonucleotide is less than 12 or 10 units long, it may be composed entirely of LNA units. A wide range of other non-natural units may also be build into the oligonucleotide, e.g., morpholino, 2'-deoxy-2'-fluoro-arabinonucleic acid (FANA) and arabinonucleic acid (ANA). In a preferred embodiment, the fraction of units modified at either the base or sugar relatively to the units not modified at either the base or sugar is selected from the group consisting of less than less than 99%, 95%, less than 90%, less than 85% or less than 75%, less than 70%, less than 65%, less than 60%, less than 50%, less than 45%, less than 40%, less than 35%, less than 30%, less than 25%, less than 20%, less than 15%, less than 10%, and less than 5%, less than 1%, more than 99%, more than 95%, more than 90%, more than 85% or more than 75%, more than 70%, more than 65%, more than 60%, more than 50%, more than 45%, more than 40%, more than 35%, more than 30%, more than 25%, more than 20%, more than 15%, more than 10%, and more than 5% and more than 1%.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g., mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, piwiRNA, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. Based on the genetic pathway analyses described herein, it is believed that such combinations of agents is especially effective in diagnosing, prognosing, preventing, and treating melanoma. Thus, "single active agents" described herein can be combined with other pharmacologically active compounds ("second active agents") known in the art according to the methods and compositions provided herein. It is believed that certain combinations work synergistically in the treatment of particular types of melanoma. Second active agents can be large molecules (e.g., proteins) or small molecules (e.g., synthetic inorganic, organometallic, or organic molecules).

II. Recombinant Expression Vectors and Host Cells

Another aspect of the invention pertains to the use of vectors, preferably expression vectors, containing a nucleic acid encoding Slit2 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a Slit2 nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals).

Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of Slit2 in prokaryotic or eukaryotic cells. For example, Slit2 can be expressed in bacterial cells such as *E. coli*, insect cells (using baculovirus expression vectors) yeast cells or mammalian cells. Suitable host cells are discussed further in Goeddel, *Gene Expression Technology*: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the Slit2 is cloned into a pGEX expression vector to create a vector encoding a fusion protein comprising, from the N-terminus to the C-terminus, and/or GST-thrombin cleavage site-Slit2. The fusion protein can be purified by affinity chromatography using glutathione-agarose resin. Recombinant Slit2 unfused to GST can be recovered by cleavage of the fusion protein with thrombin.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS174 (DE3) from a resident X prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the Slit2 expression vector is a yeast expression vector. Examples of vectors for expression in yeast *S. cerivisae* include pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, Slit2 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to Slit2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Slit2 protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. A Slit2 polypeptide or fragment thereof, may be secreted and isolated from a mixture of cells and medium containing the polypeptide. Alternatively, a Slit2 polypeptide or fragment thereof, may be retained cytoplasmically and the cells harvested, lysed and the protein or protein complex isolated. A Slit2 polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of Slit2 or a fragment thereof. In other embodiments, heterologous tags can be used for purification purposes (e.g., epitope tags and FC fusion tags), according to standards methods known in the art.

Thus, a nucleotide sequence encoding all or a selected portion of a Slit2 polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant Slit2 polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the Slit2 polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thio-ester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Slit2 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Slit2 protein. Accordingly, the invention further provides methods for producing Slit2 protein using the host cells of the invention. In one embodiment, the method comprises culturing the host cell of invention (into which a recombinant expression vector encoding Slit2 has been introduced) in a suitable medium until Slit2 is produced. In another embodiment, the method further comprises isolating Slit2 from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which Slit2 encoding sequences, or fragments thereof, have been introduced. Such host cells can then be used to create non-human transgenic animals in which exogenous Slit2 sequences have been introduced into their genome or homologous recombinant animals in which endogenous Slit2 sequences have been altered. Such animals are useful for studying the function and/or activity of Slit2, or fragments thereof, and for identifying and/or evaluating modulators of Slit2 activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Slit2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding Slit2, or a fragment thereof, into the male pronuclei of a fertilized oocyte, e.g., by microinjection, retroviral infection, and allowing the oocyte to develop in a pseudopregnant female foster animal. The huma Slit2 cDNA sequence can be introduced as a transgene into the genome of a nonhuman animal. Alternatively, a nonhuman homologue of the huma Slit2 gene can be used as a transgene. Intronic sequences and polyadenylation signals can also be included in the transgene to increase the efficiency of expression of the transgene. A tissue-specific regulatory sequence(s) can be operably linked to the Slit2 transgene to direct expression of Slit2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the Slit2 transgene in its genome and/or expression of Slit2 mRNA in tissues or cells of the animals. A transgenic founder animal can then be used to breed additional animals carrying the transgene. Moreover, transgenic animals carrying a transgene encoding Slit2 can further be bred to other transgenic animals carrying other transgenes.

To create a homologous recombinant animal, a vector is prepared which contains at least a portion of a Slit2 gene into which a deletion, addition or substitution has been introduced to thereby alter, e.g., functionally disrupt, the Slit2 gene. The Slit2 gene can be a human gene, but more preferably, is a nonhuman homologue of a huma Slit2 gene. For example, a mouse Slit2 gene can be used to construct a homologous recombination vector suitable for altering an endogenous Slit2 gene, respectively, in the mouse genome. In a preferred embodiment, the vector is designed such that, upon homologous recombination, the endogenous Slit2 gene is functionally disrupted (i.e., no longer encodes a functional protein; also referred to as a "knock out" vector). Alternatively, the vector can be designed such that, upon homologous recombination, the endogenous Slit2 gene is mutated or otherwise altered but still encodes functional protein (e.g., the upstream regulatory region can be altered to thereby alter the expression of the endogenous Slit2 protein). In the homologous recombination vector, the altered portion of the Slit2 gene is flanked at its 5' and 3' ends by additional nucleic acid of the Slit2 gene to allow for homologous recombination to occur between the exogenous Slit2 gene carried by the vector and an endogenous Slit2 gene in an embryonic stem cell. The additional flanking Slit2 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Slit2 gene has homologously recombined with the endogenous Slit2 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Slit2 Polypeptides and Anti-Slit2 Antibodies

The present invention provides soluble, purified and/or isolated forms of Slit2 polypeptides, or fragments thereof, for use in the present methods or as compositions.

In one aspect, a Slit2 polypeptide may comprise a full-length Slit2 amino acid sequence or a full-length Slit2 amino acid sequence with 1 to about 20 conservative amino acid substitutions. Amino acid sequence of any Slit2 polypeptide described herein can also be at least 50, 55, 60, 65, 70, 75, 80, 85, 90, 91, 92, 93, 94, 95, 96, 97, 98, 99, or 99.5% identical to a Slit2 polypeptide sequence of interest, described herein, well known in the art, or a fragment thereof. In addition, any Slit2 polypeptide, or fragment thereof, described herein has modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and 1) growth and effects of metabolic disorders, such as obesity-associated cancer, cachexia, anorexia, diabetes, and obesity.

In another aspect, the present invention contemplates a composition comprising an isolated Slit2 polypeptide and less than about 25%, or alternatively 15%, or alternatively 5%, contaminating biological macromolecules or polypeptides.

The present invention further provides compositions related to producing, detecting, or characterizing a Slit2 polypeptide, or fragment thereof, such as nucleic acids, vectors, host cells, and the like. Such compositions may serve as compounds that modulate a Slit2 polypeptide's expression and/or activity, such as antisense nucleic acids.

In certain embodiments, a Slit2 polypeptide of the invention may be a fusion protein containing a domain which increases its solubility and bioavailability and/or facilitates its purification, identification, detection, and/or structural characterization. Exemplary domains, include, for example, Fc, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a Slit2 polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 8, 9, 10, 15, 20 amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG (SEQ ID NO: 23). In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, Slit2 polypeptides, or fragments thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et.al., 2001 Immunity 14:123 133. Fusion to an Fc polypeptide offers the additional advantage of facilitating purification by affinity chromatography over Protein A or Protein G columns.

In still another embodiment, a Slit2 polypeptide may be labeled with a fluorescent label to facilitate their detection, purification, or structural characterization. In an exemplary embodiment, a Slit2 polypeptide of the invention may be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated Slit2 proteins, and biologically active portions thereof, as well as peptide fragments suitable for use as immunogens to raise anti-Slit2 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Slit2 protein in which the protein is separated from cellular components of the cells in which it is naturally or recombinantly produced. In one embodiment, the language "substantially free of cellular material" includes preparations of Slit2 protein having less than about 30% (by dry weight) of non-Slit2 protein (also referred to herein as a "contaminating protein"), more preferably less than about 20% of non-Slit2 protein, still more preferably less than about 10% of non-Slit2 protein, and most preferably less than about 5% non-Slit2 protein. When the Slit2 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Slit2 protein in which the protein is separated from chemical precursors or other chemicals which are involved in the synthesis of the protein. In one embodiment, the language "substantially free of chemical precursors or other chemicals" includes preparations of Slit2 protein having less than about 30% (by dry weight) of chemical precursors of non-Slit2 chemicals, more preferably less than about 20% chemical precursors of non-Slit2 chemicals, still more preferably less than about 10% chemical precursors of non-Slit2 chemicals, and most preferably less than about 5% chemical precursors of non-Slit2 chemicals. In preferred embodiments, isolated proteins or biologically active portions thereof lack contaminating proteins from the same animal from which the Slit2 protein is derived. Typically, such proteins are produced by recombinant expression of, for example, a huma Slit2 protein in a nonhuman cell.

In preferred embodiments, the protein or portion thereof comprises an amino acid sequence which is sufficiently homologous to an amino acid sequence described in Table 1, such that the protein or portion thereof maintains one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity. The portion of the protein is preferably a biologically active portion as described herein. In another preferred embodiment, the Slit2 protein has an amino acid sequence described in Table 1, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence described in Table 1, or fragment thereof. In yet another preferred embodiment, the Slit2 protein has an amino acid sequence which is encoded by a nucleotide sequence which hybridizes, e.g., hybridizes under stringent conditions, to a nucleotide sequence described in Table 1, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to a nucleotide sequence described in Table 1, or fragment thereof. The preferred Slit2 proteins of the present invention also preferably possess at least one of the Slit2 biological activities, or activities associated with the complex, described herein. For example, a preferred Slit2 protein of the present invention includes an amino acid sequence encoded by a nucleotide sequence which hybridizes, e.g., hybridizes under stringent conditions, to a nucleotide sequence described in Table 1, or fragment thereof, and which can maintain one or more of the following biological activities or, in complex, modulates (e.g., enhance) one or more of the following biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity.

Biologically active portions of the Slit2 protein include peptides comprising amino acid sequences derived from the amino acid sequence of the Slit2 protein, e.g., an amino acid sequence described in Table 1, or fragment thereof, or the amino acid sequence of a protein homologous to the Slit2 protein, which include fewer amino acids than the full length Slit2 protein or the full length protein which is homologous to the Slit2 protein, and exhibist at least one activity of the Slit2 protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., signal peptide, EGF repeat domain, C-terminal cysteine knot domain, etc.). In a preferred embodiment, the biologically active portion of the protein which includes one or more the domains/motifs described herein can modulate differentiation of adipocytes and/or thermogenesis in brown adipocytes. Moreover, other biologically active portions, in which other regions of the protein are deleted, can be prepared by recombinant techniques and evaluated for one or more of the activities described herein. Preferably, the biologically active portions of the Slit2 protein include one or more selected domains/motifs or portions thereof having biological activity. In an exemplary embodiment, a Slit2 fragment comprises and/or consists of about 408, 407, 406, 405, 404, 403, 402, 401, 400, 399, 398, 397, 396, 395, 394, 393, 392, 391, 390, 389, 388, 387, 386, 385, 384, 383, 382, 381, 380, 379, 378, 377, 376, 375, 374, 373, 372, 371, 370, 365, 360, 355, 350, 345, 340, 335, 330, 325, 320, 315, 310, 305, 300, 295, 290, 285, 280, 275, 270, 265, 260, 255, 250, 245, 240, 235, 230, 225, 220, 215, 210, 205, 200, or fewer residues of a sequence described in Table 1, or any range in between, inclusive, such as 275 to 408 amino acids in length.

Slit2 proteins can be produced by recombinant DNA techniques. For example, a nucleic acid molecule encoding the protein is cloned into an expression vector (as described above), the expression vector is introduced into a host cell (as described above) and the Slit2 protein is expressed in the host cell. The Slit2 protein can then be isolated from the cells by an appropriate purification scheme using standard protein purification techniques. Alternative to recombinant expression, a Slit2 protein, polypeptide, or peptide can be synthesized chemically using standard peptide synthesis techniques. Moreover, native Slit2 protein can be isolated from cells (e.g., brown adipocytes), for example using an anti-Slit2 antibody (described further below).

The invention also provides Slit2 chimeric or fusion proteins. As used herein, a Slit2 "chimeric protein" or "fusion protein" comprises a Slit2 polypeptide operatively linked to a non-Slit2 polypeptide. A "Slit2 polypeptide" refers to a polypeptide having an amino acid sequence corresponding to Slit2, whereas a "non-Slit2 polypeptide" refers to a polypeptide having an amino acid sequence corresponding to a protein which is not substantially homologous to the Slit2 protein, respectively, e.g., a protein which is different from the Slit2 protein and which is derived from the same or a different organism. Within the fusion protein, the term "operatively linked" is intended to indicate that the Slit2 polypeptide and the non-Slit2 polypeptide are fused in-frame to each other. The non-Slit2 polypeptide can be fused to the N-terminus or C-terminus of the Slit2 polypeptide, respectively. For example, in one embodiment the fusion protein is a Slit2-GST and/or Slit2-Fc fusion protein in which the Slit2 sequences, respectively, are fused to the N-terminus of the GST or Fc sequences. Such fusion proteins can facilitate the purification, expression, and/or bioavailbility of recombinant Slit2. In another embodiment, the fusion protein is a Slit2 protein containing a heterologous signal sequence at its C-terminus. In certain host cells (e.g., mammalian host cells), expression and/or secretion of Slit2 can be increased through use of a heterologous signal sequence.

Preferably, a Slit2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Slit2-encoding nucleic acid can be cloned into such an expression vector such that the fusion moiety is linked in-frame to the Slit2 protein.

The present invention also pertains to homologues of the Slit2 proteins which function as either a Slit2 agonist (mimetic) or a Slit2 antagonist. In a preferred embodiment, the Slit2 agonists and antagonists stimulate or inhibit, respectively, a subset of the biological activities of the naturally occurring form of the Slit2 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Slit2 protein.

Homologues of the Slit2 protein can be generated by mutagenesis, e.g., discrete point mutation or truncation of the Slit2 protein. As used herein, the term "homologue" refers to a variant form of the Slit2 protein which acts as an agonist or antagonist of the activity of the Slit2 protein. An agonist of the Slit2 protein can retain substantially the same, or a subset, of the biological activities of the Slit2 protein. An antagonist of the Slit2 protein can inhibit one or more of the activities of the naturally occurring form of the Slit2 protein, by, for example, competitively binding to a downstream or upstream member of the Slit2 cascade which includes the Slit2 protein. Thus, the mammalia Slit2 protein and homologues thereof of the present invention can be, for example, either positive or negative regulators of adipocyte differentiation and/or thermogenesis in brown adipocytes.

In an alternative embodiment, homologues of the Slit2 protein can be identified by screening combinatorial libraries of mutants, e.g., truncation mutants, of the Slit2 protein for Slit2 protein agonist or antagonist activity. In one embodiment, a variegated library of Slit2 variants is generated by combinatorial mutagenesis at the nucleic acid level and is encoded by a variegated gene library. A variegated library of Slit2 variants can be produced by, for example, enzymatically ligating a mixture of synthetic oligonucleotides into gene sequences such that a degenerate set of potential Slit2 sequences is expressible as individual polypeptides, or alternatively, as a set of larger fusion proteins (e.g., for phage display) containing the set of Slit2 sequences therein. There are a variety of methods which can be used to produce libraries of potential Slit2 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Slit2 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Slit2 protein coding can be used to generate a variegated population of Slit2 fragments for screening and subsequent selection of homologues of a Slit2 protein. In one embodiment, a library of coding sequence fragments can be generated by treating a double stranded PCR fragment of a Slit2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes N-terminal, C-terminal and internal fragments of various sizes of the Slit2 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Slit2 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Slit2 homologues (Arkin and Youvan (1992) *Proc. Natl. Acad. Sci. USA* 89:7811-7815; Delagrave et al. (1993) *Protein Engineering* 6(3):327-331).

In another aspect, an isolated Slit2 protein, or a a fragment thereof, can be used as an immunogen to generate antibodies that bind Slit2, or the complex thereof, using standard techniques for polyclonal and monoclonal antibody preparation. The full-length Slit2 protein can be used or, alternatively, antigenic peptide fragments of Slit2, or peptides in complex, can be used as immunogens. A Slit2 immunogen typically is used to prepare antibodies by immunizing a suitable subject, (e.g., rabbit, goat, mouse or other mammal) with the immunogen. An appropriate immunogenic preparation can contain, for example, recombinantly expressed Slit2 protein or a chemically synthesized Slit2 peptide. The preparation can further include an adjuvant, such as Freund's complete or incomplete adjuvant, or similar immunostimulatory agent. Immunization of a suitable subject with an immunogenic Slit2 preparation induces a polyclonal anti-Slit2 antibody response.

Accordingly, another aspect of the invention pertains to the use of anti-Slit2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as Slit2. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Slit2. The term "monoclonal antibody" or "monoclonal antibody composition", as used herein, refers to a population of antibody molecules that contain only one species of an antigen binding site capable of immunoreacting with a particular epitope of Slit2. A monoclonal antibody composition thus typically displays a single binding affinity for a particular Slit2 protein with which it immunoreacts.

Polyclonal anti-Slit2 antibodies can be prepared as described above by immunizing a suitable subject with a Slit2 immunogen, or fragment thereof. The anti-Slit2 antibody titer in the immunized subject can be monitored over time by standard techniques, such as with an enzyme linked immunosorbent assay (ELISA) using immobilized Slit2. If desired, the antibody molecules directed against Slit2 can be isolated from the mammal (e.g., from the blood) and further purified by well known techniques, such as protein A chromatography to obtain the IgG fraction. At an appropriate time after immunization, i.e., when the anti-Slit2 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a Slit2 immunogen as described above, and the culture supernatants of the resulting hybridoma cells are screened to identify a hybridoma producing a monoclonal antibody that binds Slit2.

Any of the many well-known protocols used for fusing lymphocytes and immortalized cell lines can be applied for the purpose of generating an anti-Slit2 monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, i.e., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Slit2, i.e., using a standard ELISA assay.

As an alternative to preparing monoclonal antibody-secreting hybridomas, a monoclonal anti-Slit2 antibody can be identified and isolated by screening a recombinant combinatorial immunoglobulin library (e.g., an antibody phage display library) with Slit2 to thereby isolate immunoglobulin library members that bind Slit2. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1369-1372; Hay et al. (1992) *Hum. Antibod. Hybridomas* 3:81-85; Huse et al. (1989) *Science* 246:1275-1281; Griffiths et al. (1993) *EMBO* 1 12:725-734; Hawkins et al. (1992) *J. Mol. Biol.* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-Slit2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-Slit2 antibody (e.g., monoclonal antibody) can be used to isolate Slit2 by standard techniques, such as affinity chromatography or immunoprecipitation. An anti-Slit2 antibody can facilitate the purification of natural Slit2 from cells and of recombinantly produced Slit2 expressed in host cells. Moreover, an anti-Slit2 antibody can be used to detect Slit2 protein (e.g., in a cellular lysate or cell supernatant) in order to evaluate the abundance and pattern of expression of the Slit2 protein. Anti-Slit2 antibodies can be used to monitor protein levels in a cell or tissue, e.g., adipose cells or tissue, as part of a clinical testing procedure, e.g., in order to monitor a safe dosage of an uncoupling agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In vivo techniques for detection of Slit2 protein include introducing into a subject a labeled antibody directed against the protein. For example, the antibody can be labeled with a radioactive marker whose presence and location in a subject can be detected by standard imaging techniques.

IV. Identification of Compounds that Modulate Slit2

The Slit2 nucleic acid and polypeptide molecules described herein may be used to design modulators of one or more of biological activities of the complex or complex polypeptides. In particular, information useful for the design of therapeutic and diagnostic molecules, including, for example, the protein domain, structural information, and the like for polypeptides of the invention is now available or attainable as a result of the ability to prepare, purify and characterize the complexes and complex polypeptides, and domains, fragments, variants and derivatives thereof.

In one aspect, modulators, inhibitors, or antagonists against the polypeptides of the invention, biological complexes containing them, or orthologues thereof, may be used to treat any disease or other treatable condition of a patient (including humans and animals), including, for example, metabolic disorders.

Modulators of Slit2 nucleic acid and polypeptide molecules, may be identified and developed as set forth below using techniques and methods known to those of skill in the art. The modulators of the invention may be employed, for instance, to inhibit and treat Slit2-mediated diseases or disorders. The modulators of the invention may elicit a change in one or more of the following activities: (a) a change in the level and/or rate of formation of a Slit2-receptor complex, (b) a change in the activity of a Slit2 nucleic acid and/or polypeptide, (c) a change in the stability of a Slit2 nucleic acid and/or polypeptide, (d) a change in the conformation of a Slit2 nucleic acid and/or polypeptide, or (e) a change in the activity of at least one polypeptide contained in a Slit2 complex. A number of methods for identifying a molecule which modulates a Slit2 nucleic acid and/or polypeptide are known in the art. For example, in one such method, a Slit2 nucleic acid and/or polypeptide, is contacted with a test compound, and the activity of the Slit2 nucleic acid and/or polypeptide is determined in the presence of the test compound, wherein a change in the activity of the Slit2 nucleic acid and/or polypeptide in the presence of the compound as compared to the activity in the absence of the compound (or in the presence of a control compound) indicates that the test compound modulates the activity of the Slit2 nucleic acid and/or polypeptide.

Compounds to be tested for their ability to act as modulators of Slit2 nucleic acids and/or polypeptides, can be produced, for example, by bacteria, yeast or other organisms (e.g. natural products), produced chemically (e.g. small molecules, including peptidomimetics), or produced recombinantly. Compounds for use with the above-described methods may be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In some embodiments, said polynucleotide is an antisense nucleic acid. In other embodiments, said polynucleotide is an siRNA. In certain embodiments, the compound comprises a biologically active fragment of a Slit2 polypeptide (e.g., a dominant negative form that binds to, but does not activate, a Slit2 receptor).

A variety of assay formats will suffice and, in light of the present disclosure, those not expressly described herein may nevertheless be comprehended by one of ordinary skill in the art based on the teachings herein. Assay formats for analyzing Slit2-receptor complex formation and/or activity of a Slit2 nucleic acid and/or polypeptide, may be generated in many different forms, and include assays based on cell-free systems, e.g. purified proteins or cell lysates, as well as cell-based assays which utilize intact cells. Simple binding assays can also be used to detect agents which modulate a Slit2, for example, by enhancing the formation of a Slit2, by enhancing the binding of a Slit2 to a substrate, and/or by enhancing the binding of a Slit2 polypeptide to a substrate. Another example of an assay useful for identifying a modulator of a Slit2 is a competitive assay that combines one or more Slit2 polypeptides with a potential modulator, such as, for example, polypeptides, nucleic acids, natural substrates or ligands, or substrate or ligand mimetics, under appropriate conditions for a competitive inhibition assay. Slit2 polypeptides can be labeled, such as by radioactivity or a colorimetric compound, such that Slit2-receptor complex formation and/or activity can be determined accurately to assess the effectiveness of the potential modulator.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays may also employ any of the methods for isolating, preparing and detecting Slit2es, or complex polypeptides, as described above.

Complex formation between a Slit2 polypeptide, or fragment thereof, and a binding partner (e.g., Slit2 receptor) may be detected by a variety of methods. Modulation of the complex's formation may be quantified using, for example, detectably labeled proteins such as radiolabeled, fluorescently labeled, or enzymatically labeled polypeptides or binding partners, by immunoassay, or by chromatographic detection. Methods of isolating and identifying Slit2-receptor complexes described above may be incorporated into the detection methods.

In certain embodiments, it may be desirable to immobilize a Slit2 polypeptide to facilitate separation of Slit2 complexes from uncomplexed forms of one or both of the proteins, as well as to accommodate automation of the assay. Binding of a Slit2 polypeptide to a binding partner may be accomplished in any vessel suitable for containing the reactants. Examples include microtitre plates, test tubes, and micro-centrifuge tubes. In one embodiment, a fusion protein may be provided which adds a domain that allows the protein to be bound to a matrix. For example, glutathione-S-transferase/polypeptide (GST/polypeptide) fusion proteins may be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes may be dissociated from the matrix, separated by SDS-PAGE, and the level of Slit2 polypeptides found in the bead fraction quantified from the gel using standard electrophoretic techniques such as described in the appended examples.

Other techniques for immobilizing proteins on matrices are also available for use in the subject assay. For instance, a Slit2 polypeptide may be immobilized utilizing conjugation of biotin and streptavidin. For instance, biotinylated polypeptide molecules may be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide may be derivatized to the wells of the plate, and polypeptide trapped in the wells by antibody conjugation. As above, preparations of a binding partner and a test compound are incubated in the polypeptide presenting wells of the plate, and the amount of complex trapped in the well may be quantified. Exemplary methods for detecting such complexes, in addition to those described above for the GST-immobilized complexes, include immunodetection of complexes using antibodies reactive with the binding partner, or which are reactive with the Slit2 polypeptide and compete with the binding partner; as well as enzyme-linked assays which rely on detecting an enzymatic activity associated with the binding partner, either intrinsic or extrinsic activity. In the instance of the latter, the enzyme may be chemically conjugated or provided as a fusion protein with the binding partner. To illustrate, the binding partner may be chemically cross-linked or genetically fused with horseradish peroxidase, and the amount of Slit2 polypeptide trapped in the Slit2 complex may be assessed with a chromogenic substrate of the enzyme, e.g. 3,3'-diaminobenzadine terahydrochloride or 4-chloro-1-napthol. Likewise, a fusion protein comprising the Slit2 polypeptide and glutathione-S-transferase may be provided, and Slit2 complex formation quantified by detecting the GST activity using 1-chloro-2,4-dinitrobenzene (Habig et al (1974) J Biol Chem 249:7130).

Antibodies against the Slit2 polypeptide can be used for immunodetection purposes. Alternatively, the Slit2 polypeptide to be detected may be "epitope-tagged" in the form of a fusion protein that includes, in addition to the polypeptide sequence, a second polypeptide for which antibodies are readily available (e.g. from commercial sources). For instance, the GST fusion proteins described above may also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system may be derived to favor discovery of modulators of particular intermediate states of the protein-protein interaction. For instance, a reconstituted protein assay may be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, may be accomplished in any vessel suitable for containing the reactants. Examples include microtitre plates, test tubes, and micro-centrifuge tubes.

In yet another embodiment, a Slit2 polypeptide may be used to generate a two-hybrid or interaction trap assay (see also, U.S. Pat. No. 5,283,317; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the interaction components to one another.

In particular, the method makes use of chimeric genes which express hybrid proteins. To illustrate, a first hybrid gene comprises the coding sequence for a binding domain of a transcriptional activator may be fused in frame to the coding sequence for a "bait" protein, e.g., a Slit2 polypeptide of sufficient length to bind to a potential interacting protein. The second hybrid protein encodes a transcriptional activation domain fused in frame to a gene encoding a "fish" protein, e.g., a potential interacting protein of sufficient length to interact with the protein-protein interaction component polypeptide portion of the bait fusion protein. If the bait and fish proteins are able to interact, e.g., form a protein-protein interaction component complex, they bring into close proximity the two domains of the transcriptional activator. This proximity causes transcription of a reporter gene which is operably linked to a transcriptional regulatory site responsive to the transcriptional activator, and expression of the reporter gene may be detected and used to score for the interaction of the bait and fish proteins. The host cell also contains a first chimeric gene which is capable of being expressed in the host cell. The gene encodes a chimeric protein, which comprises (a) a binding domain that recognizes the responsive element on the reporter gene in the host cell, and (b) a bait protein (e.g., a Slit2 polypeptide). A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The binding domain of the first hybrid protein and the transcriptional activation domain of the second hybrid protein may be derived from transcriptional activators having separable binding and transcriptional activation domains. For instance, these separate binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert binding domains may be used in the subject constructs; such as domains of ACE1, λcI, lac repressor, jun or fos. In another embodiment, the binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, formation of a complex between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a complex results in a detectable signal produced by the expression of the reporter gene.

In still further embodiments, the Slit2 polypeptide, or complex polypeptide, of interest may be generated in whole cells, taking advantage of cell culture techniques to support the subject assay. For example, the Slit2 polypeptide, or complex polypeptide, may be constituted in a prokaryotic or eukaryotic cell culture system. Advantages to generating the Slit2 polypeptide, or complex polypeptide, in an intact cell includes the ability to screen for modulators of the level and/or activity of the Slit2 polypeptide, or complex polypeptide, which are functional in an environment more closely approximating that which therapeutic use of the modulator would require, including the ability of the agent to gain entry into the cell. Furthermore, certain of the in vivo embodiments of the assay are amenable to high through-put analysis of candidate agents.

The Slit2 nucleic acids and/or polypeptide can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high throughput analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target. Accordingly, potential modulators of Slit2 may be detected in a cell-free assay generated by constitution of a functional Slit2 in a cell lysate. In an alternate format, the assay can be derived as a reconstituted protein mixture which, as described below, offers a number of benefits over lysate-based assays.

The activity of a Slit2 or a Slit2 polypeptide may be identified and/or assayed using a variety of methods well known to the skilled artisan. For example, the activity of a Slit2 nucleic acid and/or polypeptide may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

In other embodiments, the biological activity of a Slit2 nucleic acid and/or polypeptide may be assessed by monitoring changes in the phenotype of a targeted cell. For example, the detection means can include a reporter gene construct which includes a transcriptional regulatory element that is dependent in some form on the level and/or activity of a Slit2 nucleic acid and/or polypeptide. The Slit2 nucleic acid and/or polypeptide may be provided as a fusion protein with a domain that binds to a DNA element of a reporter gene construct. The added domain of the fusion protein can be one which, through its binding ability, increases or decreases transcription of the reporter gene. Whichever the case may be, its presence in the fusion protein renders it responsive to a Slit2 nucleic acid and/or polypeptide. Accordingly, the level of expression of the reporter gene will vary with the level of expression of a Slit2 nucleic acid and/or polypeptide.

Moreover, in the whole cell embodiments of the subject assay, the reporter gene construct can provide, upon expression, a selectable marker. A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of a Slit2 nucleic acid and/or polypeptide present in the cell. Such embodiments of the subject assay are particularly amenable to high through-put analysis in that proliferation of the cell can provide a simple measure of inhibition of the Slit2 nucleic acid and/or polypeptide.

Similarly, individual cells or analyses of phenotypes in organisms can be formed to determine effects of test agents on the modulation (e.g., upregulation) of one or more of the following Slit2-mediated biological activities: a) brown fat and/or beige fat gene expression, such as expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity.

V. Methods of the Invention

One aspect of the present invention relates to methods of selecting agents (e.g., antibodies, fusion constructs, peptides, small molecules, and small nucleic acids) which bind to, upregulate, downregulate, or modulate one or more biomarkers of the present invention listed in Table 1, the Figures, and the Examples, and/or a metabolic disorder. Such methods can use screening assays, including cell-based and non-cell based assays.

In one embodiment, the invention relates to assays for screening candidate or test compounds which bind to or modulate the expression or activity level of, one or more biomarkers of the present invention, including one or more biomarkers listed in Table 1, the Figures, and the Examples, or a fragment or ortholog thereof. Such compounds include, without limitation, antibodies, proteins, fusion proteins, nucleic acid molecules, and small molecules.

In one embodiment, an assay is a cell-based assay, comprising contacting a cell expressing one or more biomarkers of the present invention, including one or more biomarkers listed in Table 1, the Figures, and the Examples, or a fragment thereof, with a test compound and determining the ability of the test compound to modulate (e.g., stimulate or inhibit) the level of interaction between the biomarker and its natural binding partners as measured by direct binding or by measuring a parameter of cancer.

For example, in a direct binding assay, the biomarker polypeptide, a binding partner polypeptide of the biomarker, or a fragment(s) thereof, can be coupled with a radioisotope or enzymatic label such that binding of the biomarker polypeptide or a fragment thereof to its natural binding partner(s) or a fragment(s) thereof can be determined by detecting the labeled molecule in a complex. For example, the biomarker polypeptide, a binding partner polypeptide of the biomarker, or a fragment(s) thereof, can be labeled with $^{125}I$, $^{35}S$, $^{14}C$, or $^{3}H$, either directly or indirectly, and the radioisotope detected by direct counting of radioemmission or by scintillation counting. Alternatively, the polypeptides of interest a can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between one or more biomarkers of the present invention, including one or more biomarkers listed in Table 1, the Figures, and the Examples, or a fragment thereof, and its natural binding partner(s) or a fragment(s) thereof, without the labeling of any of the interactants (e.g., using a microphysiometer as described in McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g., antibodies, fusion proteins, peptides, nucleic acid molecules, or small molecules) to antagonize the interaction between a given set of nucleic acid molecules and/or polypeptides can be accomplished by determining the activity of one or more members of the set of interacting molecules. For example, the activity of one or more biomarkers of the present invention, including one or more biomarkers listed in Table 1, the Figures, and the Examples, or a fragment thereof, can be determined by detecting induction of cytokine or chemokine response, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the biomarker or a fragment thereof (e.g., modulations of biological pathways identified herein, such as modulated proliferation, apoptosis, cell cycle, and/or ligand-receptor binding activity). Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

In yet another embodiment, an assay of the present invention is a cell-free assay in which one or more biomarkers of the present invention, including one or more biomarkers listed in Table 1, the Figures, and the Examples, or a fragment thereof, e.g., a biologically active fragment thereof, is contacted with a test compound, and the ability of the test compound to bind to the polypeptide, or biologically active portion thereof, is determined. Binding of the test compound to the biomarker or a fragment thereof, can be determined either directly or indirectly as described above. Determining the ability of the biomarker or a fragment thereof to bind to its natural binding partner(s) or a fragment(s) thereof can also be accomplished using a technology such as real-time Biomolecular Interaction Analysis (BIA) (Sjolander, S. and Urbaniczky, C. (1990) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. One or more biomarkers polypeptide or a fragment thereof can be immobilized on a BIAcore chip and multiple agents, e.g., blocking antibodies, fusion proteins, peptides, or small molecules, can be tested for binding to the immobilized biomarker polypeptide or fragment thereof. An example of using the BIA technology is described by Fitz et al. (1997) *Oncogene* 15:613.

The cell-free assays of the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the biomarker nucleic acid and/or polypeptide, the natural binding partner(s) of the biomarker, or fragments thereof, to facilitate separation of complexed from uncomplexed forms of the reactants, as well as to accommodate automation of the assay. Binding of a test compound in the assay can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-base fusion proteins, can be adsorbed onto glutathione Sepharose® beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

In an alternative embodiment, determining the ability of the test compound to modulate the activity of one or more biomarkers of the present invention, including one or more biomarkers listed in Table 1, the Figures, and the Examples, or a fragment thereof, or of natural binding partner(s) thereof can be accomplished by determining the ability of the test compound to modulate the expression or activity of a gene, e.g., nucleic acid, or gene product, e.g., polypeptide, that functions downstream of the interaction. For example, cellular migration or invasion can be determined by monitoring cellular movement, matrigel assays, induction of invasion-related gene expression, and the like, as described further herein.

In another embodiment, modulators of one or more biomarkers of the present invention, including one or more biomarkers listed in Table 1, the Figures, and the Examples, or a fragment thereof, are identified in a method wherein a cell is contacted with a candidate compound and the expression or activity level of the biomarker is determined. The level of expression of biomarker RNA or polypeptide or fragments thereof in the presence of the candidate compound is compared to the level of expression of biomarker RNA or polypeptide or fragments thereof in the absence of the candidate compound. The candidate compound can then be identified as a modulator of biomarker expression based on this comparison. For example, when expression of biomarker RNA or polypeptide or fragments thereof is greater (statistically significantly greater) in the presence of the candidate compound than in its absence, the candidate compound is identified as a stimulator of biomarker expression. Alternatively, when expression of biomarker RNA or polypeptide or fragments thereof is reduced (statistically significantly less) in the presence of the candidate compound than in its absence, the candidate compound is identified as an inhibitor of biomarker expression. The expression level of biomarker RNA or polypeptide or fragments thereof in the cells can be determined by methods described herein for detecting biomarker mRNA or polypeptide or fragments thereof.

In yet another aspect of the present invention, a biomarker of the present invention, including one or more biomarkers listed in Table 1, the Figures, and the Examples, or a fragment thereof, can be used as "bait" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other nucleic acids and/or polypeptides which bind to or interact with the biomarker or fragments thereof and are involved in activity of the biomarkers. Such biomarker-binding proteins are also likely to be involved in the propagation of signals by the biomarker polypeptides or biomarker natural binding partner(s) as, for example, downstream elements of one or more biomarkers-mediated signaling pathway.

The two-hybrid system is based on the modular nature of most transcription factors, which consist of separable DNA-binding and activation domains. Briefly, the assay utilizes two different DNA constructs. In one construct, the gene that codes for one or more biomarkers polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming one or more biomarkers-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with one or more biomarkers polypeptide of the present invention, including one or more biomarkers listed in Table 1, the Figures, and the Examples, or a fragment thereof.

In another aspect, the invention pertains to a combination of two or more of the assays described herein. For example, a modulating agent can be identified using a cell-based or a cell-free assay, and the ability of the agent to modulate the activity of one or more biomarkers polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In other aspects of the present invention, the biomarkers described herein, including the biomarkers listed in Table 1, the Figures, and the Examples, or fragments thereof, can be used in one or more of the following methods: a) screening assays; b) predictive medicine (e.g., diagnostic assays, prognostic assays, and monitoring of clinical trials); and c) methods of treatment (e.g., therapeutic and prophylactic, e.g., by up- or down-modulating the copy number, level of expression, and/or level of activity of the one or more biomarkers).

The biomarkers described herein or agents that modulate the expression and/or activity of such biomarkers can be used, for example, to (a) express one or more biomarkers of the present invention, including one or more biomarkers listed in Table 1, the Figures, and the Examples, or a fragment thereof (e.g., via a recombinant expression vector in a host cell in gene therapy applications or synthetic nucleic acid molecule), (b) detect biomarker RNA or a fragment thereof (e.g., in a biological sample) or a genetic alteration in one or more biomarkers gene, and/or (c) modulate biomarker activity, as described further below. The biomarkers or modulatory agents thereof can be used to treat conditions or disorders characterized by insufficient or excessive production of one or more biomarkers polypeptide or fragment thereof or production of biomarker polypeptide inhibitors. In addition, the biomarker polypeptides or fragments thereof can be used to screen for naturally occurring biomarker binding partner(s), to screen for drugs or compounds which modulate biomarker activity, as well as to treat conditions or disorders characterized by insufficient or excessive production of biomarker polypeptide or a fragment thereof or production of biomarker polypeptide forms which have decreased, aberrant or unwanted activity compared to biomarker wild-type polypeptides or fragments thereof (e.g., melanoma).

A. Screening Assays

In one aspect, the present invention relates to a method for preventing in a subject, a disease or condition associated with an unwanted, more than desirable, or less than desirable, expression and/or activity of one or more biomarkers described herein. Subjects at risk for a disease that would benefit from treatment with the claimed agents or methods can be identified, for example, by any one or combination of diagnostic or prognostic assays known in the art and described herein (see, for example, agents and assays described above in the section describing methods of selecting agents and compositions).

B. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the expression and/or activity level of biomarkers of the present invention, including biomarkers listed in Table 1, the Figures, and the Examples, or fragments thereof, in the context of a biological sample (e.g., blood, serum, cells, or tissue) to thereby determine whether an individual is afflicted with a disease or disorder, or is at risk of developing a disorder, associated with aberrant or unwanted biomarker expression or activity. The present invention also provides for prognostic (or predictive) assays for determining whether an individual is at risk of developing a disorder associated with biomarker polypeptide, nucleic acid expression or activity. For example, mutations in one or more biomarkers gene can be assayed in a biological sample.

Such assays can be used for prognostic or predictive purpose to thereby prophylactically treat an individual prior to the onset of a disorder characterized by or associated with biomarker polypeptide, nucleic acid expression or activity. For example, Slit2 expression and activity is associated with increased thermogenesis and metabolism such that overexpression of Slit2 predicts treatment of metabolic disorders, either alone or in combination with additional agents, including nuclear receptor inhibitors.

Another aspect of the present invention pertains to monitoring the influence of agents (e.g., drugs, compounds, and small nucleic acid-based molecules) on the expression or activity of biomarkers of the present invention, including biomarkers listed in Table 1, the Figures, and the Examples, or fragments thereof, in clinical trials. These and other agents are described in further detail in the following sections.

The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker. In some embodiments, the amount of the marker in the subject can be considered "significantly" higher or lower than the normal amount if the amount is 10%, 15%, 20%, 25%, 30%, 35%, 40%, 45%, 50% or more, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered cellular localization" of a marker refers to the mislocalization of the marker within a cell relative to the normal localization within the cell e.g., within a healthy and/or wild-type cell. An indication of normal localization of the marker can be determined through an analysis of cellular localization motifs known in the field that are harbored by marker polypeptides. For example, SLNCR is a nuclear transcription factor coordinator and naturally functions to present combinations of nuclear transcription factors within the nucleus such that function is abrogated if nuclear import and/or export is inhibited.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal patient or the patient in need of metabolism modulation, cultured primary cells/tissues isolated from a subject such as a normal subject or the patient in need of metabolism modulation, adjacent normal cells/tissues obtained from the same organ or body location of the patient in need of metabolism modulation, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with a therapeutic and cells from patients having modulated metabolism. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-immune checkpoint inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

Outcome measures, such as overall survival, increased thermogenesis, and weight loss can be monitored over a period of time for subjects following therapy for whom the measurement values are known. In certain embodiments, the same doses of therapeutic agents are administered to each subject. In related embodiments, the doses administered are standard doses known in the art for therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months or longer. Biomarker threshold values that correlate to outcome of a therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a patient in need of modulated metabolism, comprising carrying out the methods for prognosing a patient according to the different aspects and embodiments of the present invention, and then weighing the results in light of other known clinical and pathological risk factors, in determining a course of treatment for the patient in need of modulated metabolism.

A "kit" is any manufacture (e.g., a package or container) comprising at least one reagent, e.g., a probe, for specifically detecting or modulating the expression of a marker of the present invention. The kit may be promoted, distributed, or sold as a unit for performing the methods of the present invention. Kits comprising compositions described herein are encompassed within the present invention.

1. Diagnostic Assays

The present invention provides, in part, methods, systems, and code for accurately classifying whether a biological sample is associated with a melanoma or a clinical subtype thereof. In some embodiments, the present invention is useful for classifying a sample (e.g., from a subject) as a sample that will respond to metabolic intervention using a statistical algorithm and/or empirical data (e.g., the presence or level of one or biomarkers described herein).

An exemplary method for detecting the level of expression or activity of one or more biomarkers of the present invention, including one or more biomarkers listed in Table 1, the Figures, and the Examples, or fragments thereof, and thus useful for classifying whether a sample is associated with melanoma or a clinical subtype thereof, involves obtaining a biological sample from a test subject and contacting the biological sample with a compound or an agent capable of detecting the biomarker (e.g., polypeptide or nucleic acid that encodes the biomarker or fragments thereof) such that the level of expression or activity of the biomarker is detected in the biological sample. In some embodiments, the presence or level of at least one, two, three, four, five, six, seven, eight, nine, ten, fifty, hundred, or more biomarkers of the present invention are determined in the individual's sample. In certain instances, the statistical algorithm is a single learning statistical classifier system. Exemplary statistical analyses are presented in the Examples and can be used in certain embodiments. In other embodiments, a single learning statistical classifier system can be used to classify a sample as a cancer sample, a cancer subtype sample, or a non-cancer sample based upon a prediction or probability value and the presence or level of one or more biomarkers described herein. The use of a single learning statistical classifier system typically classifies the sample as a cancer sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the cancer classification results to a clinician, e.g., an oncologist or hematologist.

In another embodiment, the method of the present invention further provides a diagnosis in the form of a probability that the individual has a cancer, such as melanoma, or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having cancer or a clinical subtype thereof. In yet another embodiment, the method of the present invention further provides a prognosis of cancer in the individual. For example, the prognosis can be surgery, development of melanoma or a clinical subtype thereof, development of one or more symptoms, development of malignant cancer, or recovery from the disease. In some instances, the method of classifying a sample as a cancer sample is further based on the symptoms (e.g., clinical factors) of the individual from which the sample is obtained. The symptoms or group of symptoms can be, for example, those associated with the IPI. In some embodiments, the diagnosis of an individual as having melanoma or a clinical subtype thereof is followed by administering to the individual a therapeutically effective amount of a drug useful for treating one or more symptoms associated with melanoma or a clinical subtype thereof.

In some embodiments, an agent for detecting biomarker RNA, genomic DNA, or fragments thereof is a labeled nucleic acid probe capable of hybridizing to biomarker RNA, genomic DNA, or fragments thereof. The nucleic acid probe can be, for example, full-length biomarker nucleic acid, or a portion thereof, such as an oligonucleotide of at least 15, 30, 50, 100, 250 or 500 nucleotides in length and sufficient to specifically hybridize under stringent conditions well known to a skilled artisan to biomarker mRNA or genomic DNA. Other suitable probes for use in the diagnostic assays of the present invention are described herein. In some embodiments, the nucleic acid probe is designed to detect transcript variants (i.e., different splice forms) of a gene.

A preferred agent for detecting Slit2 bioimarkers in complex with biomarker proteins is an antibody capable of binding to the biomarker, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the present invention can be used to detect biomarker mRNA, polypeptide, genomic DNA, or fragments thereof, in a biological sample in vitro as well as in vivo. For example, in vitro techniques for detection of biomarker mRNA or a fragment thereof include Northern hybridizations and in situ hybridizations. In vitro techniques for detection of biomarker polypeptide include enzyme linked immunosorbent assays (ELISAs), Western blots, immunoprecipitations and immunofluorescence. In vitro techniques for detection of biomarker genomic DNA or a fragment thereof include Southern hybridizations. Furthermore, in vivo techniques for detection of one or more biomarkers polypeptide or a fragment thereof include introducing into a subject a labeled anti-biomarker antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain RNA molecules from the test subject or genomic DNA molecules from the test subject. A preferred biological sample is a hematological tissue (e.g., a sample comprising blood, plasma, B cell, bone marrow, etc.) sample isolated by conventional means from a subject.

In another embodiment, the methods further involve obtaining a control biological sample from a control subject, contacting the control sample with a compound or agent capable of detecting polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof of one or more biomarkers listed in Table 1, the Figures, and the Examples, such that the presence of biomarker polypeptide, RNA, genomic DNA, or fragments thereof, is detected in the biological sample, and comparing the presence of biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof in the control sample with the presence of biomarker polypeptide, RNA, cDNA, small RNAs, mature miRNA, pre-miRNA, pri-miRNA, miRNA*, piwiRNA, piwiRNA, anti-miRNA, or a miRNA binding site, or a variant thereof, genomic DNA, or fragments thereof in the test sample.

The invention also encompasses kits for detecting the presence of a polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, of one or more biomarkers listed in Table 1, the Figures, and the Examples, in a biological sample. For example, the kit can comprise a labeled compound or agent capable of detecting one or more biomarkers polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in a biological sample; means for determining the amount of the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in the sample; and means for comparing the amount of the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof, in the sample with a standard. The compound or agent can be packaged in a suitable container. The kit can further comprise instructions for using the kit to detect the biomarker polypeptide, RNA, cDNA, small RNAs, mature miRNA, pre-miRNA, pri-miRNA, miRNA*, piwiRNA, anti-miRNA, or a miRNA binding site, or a variant thereof, genomic DNA, or fragments thereof.

In some embodiments, therapies tailored to treat stratified patient populations based on the described diagnostic assays are further administered, such as melanoma standards of treatment, immune therapy, and combinations thereof described herein.

2. Prognostic Assays

The diagnostic methods described herein can furthermore be utilized to identify subjects having or at risk of developing a disease or disorder associated with aberrant expression or activity of one or more biomarkers of the present invention, including one or more biomarkers listed in Table 1, the Figures, and the Examples, or a fragment thereof. As used herein, the term "aberrant" includes biomarker expression or activity levels which deviates from the normal expression or activity in a control.

The assays described herein, such as the preceding diagnostic assays or the following assays, can be used to identify a subject that would benefit from metabolic interventions (e.g., low levels of plasma Slit2 indicates that Slit2 administration would be differentially beneficial). Alternatively, the prognostic assays can be used to identify a subject having or at risk for developing a disorder associated with a misregulation of biomarker activity or expression. Thus, the present invention provides a method for identifying and/or classifying a disease associated with aberrant expression or activity of one or more biomarkers of the present invention, including one or more biomarkers listed in Table 1, the Figures, and the Examples, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. For example, such methods can be used to determine whether a subject can be effectively treated with an agent for a melanoma. Thus, the present invention provides methods for determining whether a subject can be effectively treated with an agent for a disease associated with aberrant biomarker expression or activity in which a test sample is obtained and biomarker polypeptide or nucleic acid expression or activity is detected (e.g., wherein a significant increase or decrease in biomarker polypeptide or nucleic acid expression or activity relative to a control is diagnostic for a subject that can be administered the agent to treat a disorder associated with aberrant biomarker expression or activity). In some embodiments, significant increase or decrease in biomarker expression or activity comprises at least 1.1, 1.2, 1.3, 1.4, 1.5, 1.6, 1.7, 1.8, 1.9, 2.0, 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

The methods of the present invention can also be used to detect genetic alterations in one or more biomarkers of the present invention, including one or more biomarkers listed in Table 1, the Figures, and the Examples, or a fragment thereof, thereby determining if a subject with the altered biomarker is at risk for melanoma characterized by aberrant biomarker activity or expression levels. In preferred embodiments, the methods include detecting, in a sample of cells from the subject, the presence or absence of a genetic alteration characterized by at least one alteration affecting the integrity of a gene encoding one or more biomarkers, or the mis-expression of the biomarker (e.g., mutations and/or splice variants). For example, such genetic alterations can be detected by ascertaining the existence of at least one of 1) a deletion of one or more nucleotides from one or more biomarkers gene, 2) an addition of one or more nucleotides to one or more biomarkers gene, 3) a substitution of one or more nucleotides of one or more biomarkers gene, 4) a chromosomal rearrangement of one or more biomarkers gene, 5) an alteration in the level of a messenger RNA transcript of one or more biomarkers gene, 6) aberrant modification of one or more biomarkers gene, such as of the methylation pattern of the genomic DNA, 7) the presence of a non-wild type splicing pattern of an RNA transcript of one or more biomarkers gene, 8) a non-wild type level of one or more biomarkers polypeptide, 9) allelic loss of one or more biomarkers gene, and 10) inappropriate post-translational modification of one or more biomarkers polypeptide. As described herein, there are a large number of assays known in the art which can be used for detecting alterations in one or more biomarkers gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in one or more biomarkers gene (see Abravaya et al. (1995) Nucleic Acids Res. 23:675-682). This method can include the steps of collecting a sample of cells from a subject, isolating nucleic acid (e.g., genomic DNA, mRNA, cDNA, small RNA, mature miRNA, pre-miRNA, pri-miRNA, miRNA*, piwiRNA, anti-miRNA, or a miRNA binding site, or a variant thereof) from the cells of the sample, contacting the nucleic acid sample with one or more primers which specifically hybridize to one or more biomarkers gene of the present invention, including the biomarker genes listed in Table 1, the Figures, and the Examples, or fragments thereof, under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more biomarkers gene of the present invention, including one or more biomarkers listed in Table 1, the Figures, and the Examples, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more biomarkers gene of the present invention, including a gene listed in Table 1, the Figures, and the Examples, or a fragment thereof, can be identified by hybridizing a sample and control nucleic acids, e.g., DNA, RNA, mRNA, small RNA, cDNA, mature miRNA, pre-miRNA, pri-miRNA, miRNA*, piwiRNA, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more biomarkers can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence one or more biomarkers gene of the present invention, including a gene listed in Table 1, the Figures, and the Examples, or a fragment thereof, and detect mutations by comparing the sequence of the sample biomarker gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in one or more biomarkers gene of the present invention, including a gene listed in Table 1, the Figures, and the Examples, or fragments thereof, include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker genes of the present invention, including genes listed in Table 1, the Figures, and the Examples, or fragments thereof, obtained from samples of cells. For example, the mutY enzyme of E. coli cleaves A at G/A mismatches and the thymidine DNA glycosylase from HeLa cells cleaves Tat G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in biomarker genes of the present invention, including genes listed in Table 1, the Figures, and the Examples, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well known in the art.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more biomarkers of the present invention, including one or more biomarkers listed in Table 1, the Figures, and the Examples, or fragments thereof.

3. Monitoring of Effects During Clinical Trials

Monitoring the influence of agents (e.g., drugs) on the expression or activity of one or more biomarkers of the present invention, including one or more biomarkers listed in Table 1, the Figures, and the Examples, or a fragment thereof (e.g., the modulation of a metabolic state) can be applied not only in basic drug screening, but also in clinical trials. For example, the effectiveness of an agent determined by a screening assay as described herein to increase expression and/or activity of one or more biomarkers of the present invention, including one or more biomarkers listed in Table 1, the Figures, and the Examples, or a fragment thereof, can be monitored in clinical trials of subjects exhibiting decreased expression and/or activity of one or more biomarkers of the present invention, including one or more biomarkers of the present invention, including one or more biomarkers listed in Table 1, the Figures, and the Examples, or a fragment thereof, relative to a control reference. Alternatively, the effectiveness of an agent determined by a screening assay to decrease expression and/or activity of one or more biomarkers of the present invention, including one or more biomarkers listed in Table 1, the Figures, and the Examples, or a fragment thereof, can be monitored in clinical trials of subjects exhibiting decreased expression and/or activity of the biomarker of the present invention, including one or more biomarkers listed in Table 1, the Figures, and the Examples, or a fragment thereof relative to a control reference. In such clinical trials, the expression and/or activity of the biomarker can be used as a "read out" or marker of the phenotype of a particular cell.

In some embodiments, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression and/or activity of one or more biomarkers of the present invention, including one or more biomarkers listed in Table 1, the Figures, and the Examples, or fragments thereof in the preadministration sample; (iii) obtaining one or more post-administration samples from the subject; (iv) detecting the level of expression or activity of the biomarker in the post-administration samples; (v) comparing the level of expression or activity of the biomarker or fragments thereof in the pre-administration sample with the that of the biomarker in the post administration sample or samples; and (vi) altering the administration of the agent to the subject accordingly. For example, increased administration of the agent may be desirable to increase the expression or activity of one or more biomarkers to higher levels than detected (e.g., to increase the effectiveness of the agent.) Alternatively, decreased administration of the agent may be desirable to decrease expression or activity of the biomarker to lower levels than detected (e.g., to decrease the effectiveness of the agent). According to such an embodiment, biomarker expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder characterized by insufficient or excessive production of biomarkers of the present invention, including biomarkers listed in Table 1, the Figures, and the Examples, or fragments thereof, which have aberrant expression or activity compared to a control. Moreover, agents of the present invention described herein can be used to detect and isolate the biomarkers or fragments thereof, regulate the bioavailability of the biomarkers or fragments thereof, and modulate biomarker expression levels or activity.

1. Prophylactic Methods

In one aspect, the present invention provides a method for preventing in a subject, a disease or condition associated with an aberrant expression or activity of one or more biomarkers of the present invention, including one or more biomarkers listed in Table 1, the Figures, and the Examples, or a fragment thereof, by administering to the subject an agent which modulates biomarker expression or at least one activity of the biomarker. Subjects at risk for a disease or disorder which is caused or contributed to by aberrant biomarker expression or activity can be identified by, for example, any or a combination of diagnostic or prognostic assays as described herein. Administration of a prophylactic agent can occur prior to the manifestation of symptoms characteristic of the biomarker expression or activity aberrancy, such that a disease or disorder is prevented or, alternatively, delayed in its progression.

2. Therapeutic Methods

Another aspect of the present invention pertains to methods of modulating the expression or activity or interaction with natural binding partner(s) of one or more biomarkers of the present invention, including one or more biomarkers listed in Table 1, the Figures, and the Examples, or fragments thereof, for therapeutic purposes. The biomarkers of the present invention have been demonstrated to correlate with adipose tissue thermogenesis and modulation of metabolism. Accordingly, the activity and/or expression of the biomarker, as well as the interaction between one or more biomarkers or a fragment thereof and its natural binding partner(s) or a fragment(s) thereof can be modulated in order to modulate the immune response.

Modulatory methods of the present invention involve contacting a cell with one or more biomarkers of the present invention, including one or more biomarkers of the present invention, including one or more biomarkers listed in Table 1, the Figures, and the Examples, or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the present invention, including one or more biomarkers listed in Table 1, the Figures, and the Examples, or a fragment thereof is a nucleic acid molecule described herein, e.g., an antisense nucleic acid molecule, RNAi molecule, shRNA, mature miRNA, pre-miRNA, pri-miRNA, miRNA*, piwiRNA, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the present invention, including one or more biomarkers listed in Table 1, the Figures, and the Examples, or a fragment thereof. Examples of such stimulatory agents include active biomarker polypeptides or a fragment thereof, such as Slit2 binding partners, and/or a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, piwiRNA, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1, the Figures, and the Examples, or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., metabolism enhancing agents, such as transplanted brown and/or beige fat cells, hormones, and the like. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of a metabolism modulatory agent.

The methods of the present invention relate to the expression and/or activity of Slit2 sufficient to modulate (e.g., induce or repress) brown and/or beige fat cell differentiation and/or activity, wherein increases in differentiated brown and/or beige fat cells or activity increase energy expenditure and favorably affect other metabolic processes and can therefore be used to treat metabolic disorders such as obesity, diabetes, decreased thermogenesis and subjects in need of more exercise; and, wherein decreases in differentiated brown and/or beige fat cells or activity decrease energy expenditure and can therefore be used to treat the effects of such conditions as cachexia, anorexia, and obesity-associated cancer.

The invention also relates to methods for increasing energy expenditure in a mammal comprising inducing expression and/or activity of Slit2 sufficient to activate brown and/or beige fat cell differentiation or activity in the mammal, wherein the differentiated and/or more active brown fat and/or beige fat cells promote energy expenditure thereby increasing energy expenditure in the mammal.

The term "sufficient to activate" is intended to encompass any increase in expression and/or activity of Slit2 that promotes, activates, stimulates, enhances, or results in brown fat and/or beige fat differentiation or activity.

In another aspect, the invention relates to methods for treating metabolic disorders in a subject comprising administering to the subject an agent that induces expression and/or activity of Slit2, wherein expression and/or activity of Slit2 increases respiration and energy expenditure to thereby treat the metabolic disorder. In one embodiment, total respiration is increased following the expression and/or activity of Slit2. In another embodiment, uncoupled respiration is increased following the expression and/or activity of Slit2. Uncoupled respiration dissipates heat and thereby increases energy expenditure in the subject.

As used herein, the term "agent" and "therapeutic agent" is defined broadly as anything that cells from a subject having a metabolic disorder may be exposed to in a therapeutic protocol. In one embodiment, the agent is a recombinant Slit2 protein, or fragment thereof, or nucleic acid molecule encoding such a polypeptide. In another embodiment, the agent is an anti-sense nucleic acid molecule having a sequence complementary to Slit2 (e.g., an RNAi, siRNA, or other RNA inhibiting nucleic acid molecule).

The term "administering" is intended to include routes of administration which allow the agent to perform its intended function of modulating (e.g., increasing or decreasing) expression and/or activity of Slit2. Examples of routes of administration which can be used include injection (subcutaneous, intravenous, parenterally, intraperitoneally, intrathecal, etc., such as in a subcutaneous injection into white fate depots), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

The term "effective amount" of an agent that induces expression and/or activity of Slit2 is that amount necessary or sufficient to modulate (e.g., increase or decrease) expression and/or activity of Slit2 in the subject or population of subjects. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular agent and its mode and route of administration; the desired time course of treatment; the species of mammal; its size, age, and general health; the specific disease involved;

the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular agent to treat a metabolic disorder can be monitored by comparing two or more samples obtained from a subject undergoing anti-obesity or obesity-related disorder treatment. In general, it is preferable to obtain a first sample from the subject prior to beginning therapy and one or more samples during treatment. In such a use, a baseline of expression of cells from subjects with obesity or obesity-related disorders prior to therapy is determined and then changes in the baseline state of expression of cells from subjects with obesity or obesity-related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with obesity or obesity-related disorders is increasing or decreasing.

Another aspect of the invention relates to a method for inducing brown fat and/or beige fat cell differentiation and/or activity in a mammal comprising expressing Slit2 nucleic acid and/or polypeptide molecules in a mammal and, optionally, monitoring the differentiation of brown fat cells in the mammal. Increased brown and/or beige adipose tissue in the mammal will warm up the body and blood of the mammal resulting in an increased energy expenditure from the cells. The increased energy expenditure will increase the metabolic rate of the subject and may be used for the treatment and/or prevention of obesity and obesity related disorders. The induction of brown fat cells may be monitored by analyzing a) brown fat and/or beige fat gene expression, such as expression of a marker selected from the group consisting of: cidea, adiponectin, adipsin, otopetrin, type II deiodinase, cig30, ppar gamma 2, pgc1+, ucp1, elov13, cAMP, Prdm16, cytochrome C, cox4i1, coxIII, cox5b, cox7a1, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) thermogenesis in adipose cells; c) differentiation of adipose cells; d) insulin sensitivity of adipose cells; e) basal respiration or uncoupled respiration; f) whole body oxygen consumption; g) obesity or appetite; h) insulin secretion of pancreatic beta cells; i) glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, HSL; k) modified expression of UCP1 protein; and l) growth and effects of metabolic disorders, such as obesity-associated cancer, cachexia, anorexia, diabetes, and obesity.

In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al.(1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant Slit2 polypeptides, and fragments thereof, can be administered to subjects. In some embodiments, fusion proteins can be constructed and administered which have enhanced biological properties (e.g., Fc fusion proteins discussed above). In addition, the Slit2 polypeptides, and fragment thereof, can be modified according to well known pharmacological methods in the art (e.g., pegylation, glycosylation, oligomerization, etc.) in order to further enhance desirable biological activities, such as increased bioavailability and decreased proteolytic degradation.

VI. Pharmaceutical Compositions

In another aspect, the present invention provides pharmaceutically acceptable compositions which comprise a therapeutically-effective amount of an agent that modulates (e.g., increases or decreases) Slit2 expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., enhances) Slit2 expression and/or activity, or expression and/or activity of the complex, or composition comprising an agent that modulates (e.g., enhances) Slit2 expression and/or activity, or expression and/or activity of the complex, which is effective for producing some desired therapeutic effect, e.g., weight loss, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) Slit2 expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) Slit2 expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) Slit2 expression and/or activity, with the carrier and, optionally, one or more accessory ingredients. In general, the formulations are prepared by uniformly and intimately bringing into association a agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) Slit2 expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) Slit2 expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) Slit2 expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) Slit2 expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1

Materials and Methods for Examples 1-7

A. Animals

All animal experiments were approved by the Institutional Animal Care and Use Committee of the Beth Israel Deaconess Medical Center. Mice (*Mus musculus*) were obtained from Jackson Laboratories, maintained in 12 hour light-lark cycles (6 a.m.-6 p.m.) at 22° C., and fed a standard irradiated rodent chow diet or a high-fat diet (60% fat) for 12-20 weeks. AAV-8 viruses (Penn Vector Core) and adenoviruses (Vector Biolabs or constructed in-house) were injected at a titer of $10^{11}$ or $10^{10}$ per mouse, respectively. All experiments were done with male mice. The aP2-PRDM16 transgenic mice have been previously described in Seale et al. (2011) *J. Clin. Invest.* 121:96-105. PRDM16-floxed mice were crossed with adiponectin-Cre and were maintained on a pure C57BL/6 background (Cohen et al. (2014) *Cell* 156:304-316). The Slit2-floxed mice have been described previously in Rama et al. (2015) *Nat. Med.* 21:483-491. Lean C57BL/6 mice were obtained from Jackson Laboratories and were fed a high-fat diet (60% fat) for 12-20 weeks.

B. Metabolic Phenotyping

Glucose tolerance tests were performed on mice 7 days post-injection with adenovirus. No significant difference was seen in weight loss in any of the groups upon injection. Animals were fasted overnight and then received intraperitoneal glucose at 1 mg/kg. Energy expenditure was analyzed using a Comprehensive Lab Animal Monitoring System (Columbus Instruments). Cold exposure and thermoneutrality experiments were performed in Balb/c mice at 4° C. or 30° C., respectively. Total levels of cholesterol, free fatty acids, triglycerides and insulin were measured at the Core Facility at Joslin Diabetes Center.

C. Respiration

Tissue respiration was performed using a Clark electrode (Stathkelvin Instruments). Freshly isolated tissues were dissected from mice treated with LacZ or Slit2-C adenovirus for 7 days. Equally sized pieces of tissue were minced and placed in respiration buffer containing PBS supplemented with 2% (w/v) bovine serum albumin, 1% (w/v) glucose, and 1 mM Na pyruvate. Oxygen ($O_2$) consumption was normalized to tissue weight. Cellular oxygen consumption rates were determined using an XF24 Extracellular Flux Analyzer (Seahorse Biosciences). Primary brown fat adipocytes were seeded at 15,000 cells/well, differentiation was induced the following day as previously described, and the cells were analyzed on day 5. On the day of analysis, the cells were washed once with Seahorse respiration buffer (8.3 g/l DMEM, 1.8 g/l NaCl, 1 mM pyruvate, 20 mM glucose, pen/strep), placed in 0.5 ml Seahorse respiration buffer, and incubated in a CO2-free incubator for 1 hr. Port injection solutions were prepared as follows: oligomycin (1 µM final concentration), norepinephrine (1 µM final concentration), FCCP (0.2 µM final concentration), and rotenone (3 µM final concentration). Each cycle consisted of the following: mix 4 min, wait 0 min, and measure 2 min. Data are presented as S.E.M.

D. Primary White and Brown Adipocyte Cultures

Inguinal and brown stromal-vascular fractions were obtained from 6 weeks old male or newborn mice (postnatal days 5-10) for white and brown fat cultures, respectively. Inguinal fat tissue was dissected and washed with PBS, minced and digested for 45 min at 37° C. in PBS containing 10 mM CaCl$_2$, 2.4 U/ml dispase II (Roche) and 10 mg/ml collagenase D (Roche). Brown fat tissue was dissected, washed with PBS, minced and digested for 45 min at 37° C. in PBS containing 1.3 mM CaCl$_2$, 123 mM NaCl, 5 mM KCl, 5.0 mM glucose, 100 mM HEPES, 4% BSA and 1.5 mg/ml collagenase B (Roche). Digested tissue was filtered through a 100-µm cell strainer and centrifuged at 600 g for 10 min. Pelleted inguinal stromal-vascular cells were grown to confluence and induced to differentiate by an adipogenic cocktail containing 0.02 µM insulin, 1 µM rosiglitazone, 5 dexamethasone, 0.5 µM isobuthylmethylxanthine. For differentiation of brown fat cells, 1 nM T3 and 125 µM indomethacin were also added to the adipogenic cocktail. Two days after induction, cells were maintained in adipocyte culture medium containing 0.02 µM insulin and 1 µM rosiglitazone. Where indicated, cells were treated with forskolin (10 µM), norepinephrine (100 nM) for 4 h or with recombinant proteins (1 µg/ml, R&D systems) for 24 h or for the indicated times. For adenoviral overexpression of Slit2-FL, Slit2-N, Slit2-C, LacZ or Cre, virus was added at day 2 of differentiation at a titer of $10^8$ particles/well and cells were analyzed at day 6-7. Where indicated, cells were treated with the drugs Erlotinib (SelleckChem), Lapatinib (Santa Cruz), PD0325901 (Santa Cruz), Propranolol (SelleckChem), H89 dihydrochloride (Santa Cruz), SQ-22536 (Santa Cruz) for indicated time points and concentrations.

E. Molecular Studies

RNA was extracted from cultured cells or frozen tissue samples using TRIzol®, purified with QIAGEN RNeasy® minicolumns. Normalized RNA was reversed transcribed using a high-capacity cDNA reverse transcription lot (Applied Biosystems) and cDNA was analyzed by qRT-CPR. Relative mRNA levels were calculated using the comparative CT method and normalized to cyclophilin mRNA. All primers used are listed with their sequences in Table 3 as follows:

TABLE 3

(SEQ ID NOs: 24-123, respectively)

| | Forward primer (5' to 3') | Reverse primer (5' to 3') |
|---|---|---|
| Adiponectin | TGTTCCTCTTAATCCTGCCCA | CCAACCTGCACAAGTTCCCTT |
| Acsl1 | GATCTGGTGGAACGAGGCAA | CTTCGGGTTCTGGAGGCTTG |
| Acox | GCCCAACTGTGACTTCCATTAA | GTAGCACTCCCCTCGAGTGAT |
| Ap2 | AAGGTGAAGAGCATCATAACCCT | TCACGCCTTTCATAACACATTCC |
| Atgl | CAG CAC ATT TAT CCC GGT GTA C | AAA TGC CGC CAT CCA CAT AG |
| Atp5b | CACAATGCAGGAAAGGATCA | GGTCATCAGCAGGCACATAG |
| Atp6v0d2 | ACTTTTGGTGTTGTTCTGGGAA | GCATGAACAGGATCTCAGGC |
| Atp9b | TCTGGTAGTGTCCTGCTCACAG | TCGTAACGGCCAAAACAAAT |
| Cd31 | ACGCTGGTGCTCTATGCAAG | TCAGTTGCTGCCCATTCATCA |
| Cd34 | AAGGCTGGGTGAAGACCCTTA | TGAATGGCCGTTTCTGGAAGT |
| Cidea | TGC TCT TCT GTA TCG CCC AGT | GCC GTG TTA GGG AAT CTG CTG |
| Cox2 | GCCGACTAAATCAAGCAACA | CAATGGGCATAAAGCTATGG |
| Cox4 | GCACATGGGAGTGTTGTGA | CCTTCTCCTTCTCCTTCAGC |
| Cox5α | GGGTCACACGAGACAGATGA | GGAACCAGATCATAGCCAACA |
| Cox8 | GAACCATGAAGTCAACGACT | GCGAAGTTCACAGTGGTTCC |
| Cytb | CATTTATTATCGCGGCCCTA | TGTTGGGTTGTTTGATCCTG |
| Cyclophilin | GGAGATGGCACAGGAGGAA | GCCCGTAGTGCTTCAGCTT |
| Dio2 | CAGTGTGGTGCACGTCTCCAATC | TGAACCAAAGTTGACCACCAG |
| Ear2 | CCTGTAACCCCAGAACTCCA | CAGATGAGCAAAGGTGCAAA |
| Elovl3 | TCC GCG TTC TCA TGT AGG TCT | GGA CCT GAT GCA ACC CTA TGA |
| Err-a | GCAGGGCAGTGGGAAGCTA | CCTCTTGAAGAAGGCTTTGCA |
| Eva1 | CCACTTCTCCTGAGTTTACAGC | GCATTTTAACCGAACATCTGTCC |
| FasN | AGGTGGTGATAGCCGGTATGT | TGGGTAATCCATAGAGCCCAG |
| Gatm | GACCTGGTCTTGTGCTCTCC | GGGATGACTGGTGTTGGAGG |
| Glut1 | GGGCTGCCAGGTTCTAGTC | CCTCCGAGGTCCTTCTCA |

TABLE 3-continued (SEQ ID NOs: 24-123, respectively)

| | Forward primer (5' to 3') | Reverse primer (5' to 3') |
|---|---|---|
| Glut4 | AGAGTCTAAAGCGCCT | CCGAGACCAACGTGAA |
| Hsl | GCTGGAGGAGTGTTTTTTGC | AGTTGAACCAAGCAGGTCACA3 |
| Leptin | GAGACCCCTGTGTCGGTTC | CTGCGTGTGTGAAATGTCATTG |
| Lxrα | AGGAGTGTCGACTTCGCAAA | CTCTTCTTGCCGCTTCAGTTT |
| Lxrβ | CTCCCACCCACGCTTACAC | GCCCTAACCTCTCTCCACTCA |
| Ng2 | GGGCTGTGCTGTCTGTTGA | TGATTCCCTTCAGGTAAGGCA |
| Nnmt | TTACAGCTTTGGGTCCAGACA | GGAGTTCTCCCTTTACAGCAC |
| Nrf1 | GAACTGCCAACCACAGTCAC | TTTGTTCCACCTCTCCATCA |
| Pepckm | GTGTGTACTGGGAAGGCATTGA | GCCACGAGGTTATGGTGACA |
| Pepckc | CAGGATCGAAAGCAAGACAGT | AAGTCCTCTTCCGACATCCAG |
| Pgc1α-total | TGATGTGAATGACTTGGATACAGACA | GCTCATTGTTGTACTGGTTGGATATG |
| Prdm16 | CAG CAC GGT GAA GCC ATT C | GCG TGC ATC CGC TTG TG |
| Ramp3 | GTGAGTGTGCCCAGGTATGC | CGACAGGTTGCACCACTTC |
| Resistin | CCAGAAGGCACAGCAGTCTT | CCGACATCAGGAAGCGACC |
| Slit1 | CTGCTCCCCGGATATGAACC | TAGCATGCACTCACACCTGG |
| Slit2 | GATTCTGGTGCACTTGTGCTG | TGTGTATTCCGGTGGGCAAA |
| Slit2-C | GCTGTGAACCATGCCACAAG | CACACATTTGTTTCCGAGGCA |
| Slit2-N | GCAACACCGAGAGACTGGATT | AGATCCTGGAATGCTCCCCT |
| Slit3 | CCACGCTGATCCTGAGCTAC | GCACTCGGAGGGATCTTAGC |
| Tgf-β | CCACCTGCAAGACCATCGAC | CTGGCGAGCCTTAGTTTGGAC |
| Tnf-α | CAGGCGGTGCCTATGTCTC | CGATCACCCCGAAGTTCAGTAG |
| Tyrosine | GTCTCAGAGCAGGATACCAAGC | CTCTCCTCGAATACCACAGCC |
| VE cadherin | CACTGCTTTGGGAGCCTTC | GGGGCAGCGATTCATTTTTCT |
| Ucp1 | AAGCTGTGCGATGTCCATGT | AAGCCACAAACCCTTTGAAAA |
| Uqcrb | AGGCTTCCTGAGGACCTTTA | TCCTTAGGCAAGATCTGATGC |

The compositions and methods of the present invention are characterized by many embodiments and each such embodiment can be applied to any combination of embodiments described herein. For example, in one embodiment, the expression and/or activity of Slit2 or the biologically active fragment thereof is upregulated. In another embodiment, expression and/or activity of Slit2 or the biologically active fragment thereof is upregulated using an agent selected from the group consisting of a nucleic acid molecule encoding a Slit2 polypeptide or fragment thereof, and a Slit2 polypeptide or fragment thereof. In still another embodiment, the medicament further comprises an additional agent that increases the metabolic response. In yet another embodiment, expression and/or activity of Slit2 or the biologically active fragment thereof is downregulated. In still another embodiment, expression and/or activity of Slit2 or the biologically active fragment thereof is downregulated using an agent selected from the group consisting of an anti-Slit2 antisense nucleic acid molecule, an anti-Slit2 RNA interference molecule, a blocking anti-Slit2 antibody, a non-activating form of Slit2 polypeptide or fragment thereof, and a small molecule that binds to Slit2. In yet another embodiment, the medicament further comprises an additional agent that decreases the metabolic response. In another embodiment, the metabolic response is selected from the group consisting of: a) modified expression of a marker selected from the group consisting of: cidea, adiponectin, adipsin, otopetrin, type II deiodinase, cig30, ppar gamma 2, pgc1α, ucp1, elov13, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1); b) modified thermogenesis in adipose cells; c) modified differentiation of adipose cells; d) modified insulin sensitivity of adipose cells; e) modified basal respiration or uncoupled respiration; f) modified whole body oxygen consumption; g) modified obesity or appetite; h) modified insulin secretion of pancreatic beta cells; i) modified glucose tolerance; j) modified phosphorylation of EGFR, ERK, AMPK, protein kinase A (PKA) substrates having an RRX(S/T) (SEQ ID NO: 127) motif, wherein the X is any amino acid and the (S/T) residue in a serine or theonine, HSL; and k) modified expression of UCP1 protein. another embodiment, the metabolic response is upregulated. In yet another embodiment, the metabolic response is downregulated.

For Western blotting, homogenized tissues, whole cell lysates, or concentrated serum free conditioned medium were lysed in RIPA buffer containing protease inhibitor cocktail (Thermo Scientific) and phosphatase inhibitor cocktail (Thermo Scientific), separated by SDS-PAGE and transferred to Immobilon-P® membranes (Millipore). For Western blotting of plasma samples, 1 µl of plasma was prepared containing 2× sample buffer (Invitrogen) with reducing agent, boiled and analyzed using Western blot against V5, FLAG, or the indicated antibody. V5-antibody was from Life Technologies and anti-Flag M2-HRP (A8592) from Sigma Aldrich. Anti-Slit2 antibody used was from Abcam (Abcam ab134166). Phospho-PKA Substrate, phospho-PKC Substrate, phospho-ERK1/2, total ERK, phospho-AKT, total AKT, phospho-AMPK, total AMPK, phospho-ATGL, ATGL, phospho-EGFR and EGFR were from Cell Signaling. Protein array was from R&D Systems (Proteome Profiler Mouse Phospho-RTK Array Kit, ARY014). Silverstain (SilverQuest™ Silver Staining Kit, LC6070) was purchased from Thermo Fisher.

F. Immunohistochemistry

Tissues were fixed in 4% paraformaldehyde. Paraffin embedding and sectioning were done by the Dana-Farber/Harvard Cancer Center Research Pathology core facility. For UCP1 immunohistochemistry, slides were deparaffinized in xylene, hydrated in descending 95%, 80% and 70% ethanol, and rinsed in water before heat-mediated antigen retrieval in 10 mM, pH 6.0 sodium citrate buffer. Quenching of endogenous peroxidases was performed using peroxidase quenching solution (Invitrogen). Slides were blocked in 10% goat serum and incubated with rabbit polyclonal UCP1 antibody (Abcam, ab10983) at 2 mg/ml in PBS-T/1% BSA overnight at 4° C. Slides were washed in PBS-T and incubated with 1:500 donkey anti-rabbit IgG HRP-linked antibody (GE healthcare) before developing using a SuperPicture™ 3rd Gen IHC Detection Kit (Invitrogen). Hematoxylin was used as counterstain. Immunohistochemical stainings of different fat depots were observed with a Nikon 80i upright light microscope using a 10× objective lens. Digital images were captured with a Nikon Digital Sight DS-Fi1 color camera and NIS-Elements acquisition software.

G. Construction of the Slit2 Adenoviral Expression Plasmid, Viral Packaging, Transduction, and Slit2-N and Slit2-C Expression Slit2 full-length (untagged and Myc-DDK tagged) expression plasmids and corresponding LacZ control plasmids in adenovirus was purchased from Vector Biolabs. To construct the Slit2-N and Slit2-C ENTR clones, PCR primers were designed to amplify the signal peptide, N-terminal, and C-terminal Slit2 from mouse cDNA (OriGene MR227608). To construct the Slit2-N and Slit2-C ENTR clone, the Slit2N gene was amplified from mouse Slit2 cDNA to create PCR fragments corresponding to Slit2-signal peptide and Slit2-N that were ligated into the pENTR1a dual selection vector. The Slit2-C PCR fragment was sub-cloned into the pENTR1a vector containing the signal peptide. The Slit2-N and Slit2-C expression clones in which the fragments are fused to a C-terminal V5 tag were generated by performing the LR reaction between pENTR/D-TOPO-Slit2N or pENTR/D-TOPO-Slit2-C and pAD/CMV/V5-DEST (Life Technologies). The expression construct was cut with Pac1 and transfected into HEK-293A cells to produce crude adenoviral stock. Amplified virus was purified and concentrated using the Vivapure® adenopack 100 (Sartorius Stedim Biotech) and buffer exchanged to 10 mM Tris-Cl at pH 8.0, 2 mM MgCl2, 4% w/v sucrose. Adenovirus titer was calculated using an Adeno-X™ Rapid Titer kit (Clontech). For primary adipocytes a concentration of $10^8$ pfu/well was used and $10^{10}$ pfu/mouse were used for in vivo experiments. Expression levels of Slit2-N and Slit2-C were confirmed after 48 hours post infection by Western blot analysis using a V5 antibody (Life Technologies). Expression of Slit2-N and Slit2-C was performed by amplification from mouse Slit2 cDNA and ligated into the pENTR dual selection vector with a signal peptide sequence.

H. Cloning and Purification of Mammalian Recombinant Slit2-C

The pENTR/D-TOPO-Slit2-C were shuttled with LR Clonase (Thermo Fisher Scientific) into an in-house generated gateway compatible variant of pCLHCX-DEST, modified from pCLNCX (Novus), for mammalian expression with a C-terminal FLAG tag. Protein was purified from mammalian cell culture medium. HEK293A cells were infected with retrovirus expressing Slit2-C-FLAG in the presence of polybrene (8 µg/ml). After two days, cells were selected with hygromycin (150 µg/ml, Sigma Aldrich). The stable 293A cells were then grown in complete media. At confluence, the media was changed and harvested after 24 h. Media was centrifuged to remove debris (1000×g, 10 min, 4° C.) and the supernatant containing Slit2-C FLAG was transferred into a new tube. Slit2-C FLAG was immunoaffinity purified overnight at 4° C. using magnetic Flag-M2 beads (Sigma Aldrich). The beads were collected, washed three times in PBS, eluted with 3×FLAG peptide (0.1 µg/ml in PBS, Sigma Aldrich) and used for downstream applications. Purity and concentration was assessed using silverstain with an albumin standard as a reference.

I. Mass Spectrometry Analysis: Protein Extraction, Digestion, and Tandem Mass Tagging Labeling i. Sample Preparation, Protein Digestion, and TMT-Labeling Secreted proteins from primary inguinal cells from wild type or ap2-PRDM16tg mice (100 ml of serum free media, 24 hour (hr) incubation) were concentrated by methanol chloroform precipitation and analyzed by mass spectrometry analysis. Immunoprecipitation of Slit2-FLAG was performed using conditioned serum free medium from primary inguinal cells expressing Slit2-FL-FLAG using anti-FLAG M2 magnetic beads (Sigma Aldrich). Mass spectrometry for the detection of FLAG-reactive bands was performed by in-gel digestion of immunopurified Slit2-CTF separated on SDS-page and stained with SimplyBlue™ SafeStain (Invitrogen). Corresponding cell lysates were scraped down and snap frozen. Cultured adipocytes (biological duplicates for each condition) were lysed with a mechanical homogenizer, disulfide bonds were reduced with DTT and cysteine residues alkylated with iodoacetamide essentially as previously described in Huttlin et al. (2010) Cell 143:1174-1189. Protein from cultured medias was extracted by methanol-chloroform precipitation and protein pellets were solubilized in buffer composed of 50 mM HEPES pH 8.5, 50 mM (3-glycerophosphate 2 mM sodium orthovanadate, 2 mM PMSF, and EDTA-free protease inhibitor cocktail (Promega) in 8 M Urea. Protein lysates were purified by methanol-chloroform precipitation and pellets were resuspended in 50 mM HEPES pH 8.5 in 8 M urea. Protein lysates were diluted to 4 M urea and digested with LysC (Wako) in a 1/200 enzyme/protein ratio overnight. Protein extracts were diluted further to a 1.0 M urea concentration and trypsin (Promega) was added to a final 1/200 enzyme/protein ratio for 6 hours at 37° C. Digests were acidified with 200 µL of 20% formic acid (FA) to a pH ~2 and subjected to 50 mg C18 solid-phase extraction (SPE) (Waters). Tryptic peptides were labeled with six-plex tandem mass tag (TMT) reagents (Thermo Scientific). Reagents (0.8 mg) were dissolved in 42 µl acetonitrile (ACN) and 20 µl of the solution was added to 150 µg of peptides dissolved in 100 µl of 50 mM HEPES, pH 8.5. After 1 hour, the reaction was quenched by adding 8 µl of 5% hydroxylamine for 15 minutes. Peptides were labeled with 4 reagents (126-129), combined and subjected to C18 SPE (50 mg).

ii. Basic pH Reversed-Phase HPLC (bpHrp)

TMT-labeled peptides were subjected to orthogonal bpHrp fractionation. TMT-labeled peptides were solubilized in 500 µl of buffer A (5% ACN 10 mM ammonium bicarbonate, pH 8.0) and separated by an Agilent 300 Extend C18 column (5 µm particles, 4.6 mm ID and 220 mm in length). Using an Agilent 1100 binary pump equipped with a degasser and a photodiode array (PDA) detector (Thermo Scientific), a 45 minute linear gradient from 18% to 35% acetonitrile in 10 mM ammonium bicarbonate pH 8 (0.8 mL/min flowrate) separated the peptide mixtures into a total of 96 fractions. Fractions were consolidation into 24 samples in a checkerboard manner, acidified with 20% formic acid, and vacuum dried. Samples were dissolved in 5% acetonitrile/ 5% formic acid, desalted via StageTip, dried by vacuum centrifugation, and reconstituted for LC-MS/MS analysis.

iii. Liquid Chromatography Tandem Mass Spectrometry (LC-MS/MS)

All LC-MS/MS experiments were performed on a Velos-Orbitrap Elite™ hybrid mass spectrometer (Thermo Scientific) equipped with a FAMOS™ autosampler (LC Packings) and an Agilent 1200 binary HPLC pump (Agilent Technologies). Peptides were separated on a 100 µm I.D. microcapillary column packed first with approximately 1 cm of Magic C4 resin (5 µm, 100 Å, Michrom Bioresources) followed by 25 cm of Maccel C18AQ resin (3 µm, 200 Å, Nest Group). Peptides were separated by applying a gradient from 10 to 35% ACN in 0.125% FA over 170 min. at approximately 250 nl/min. Electrospray ionization was enabled through applying a voltage of 1.8 kV through a PEEK junction at the inlet of the microcapillary column.

The Velos-Orbitrap Elite™ hybrid mass spectrometer was operated in data-dependent mode for both $MS^2$ and $MS^3$ scans. For the $MS^2$ method, the survey scan was performed in the Orbitrap Elite™ in the range of 400-1400 m/z at a resolution of $3 \times 10^4$, followed by the selection of the ten most intense ions (TOP 10) for CID-$MS^2$ fragmentation using a precursor isolation width window of 2 m/z. The AGC settings were $3 \times 10^6$ and $2.5 \times 10^5$ ions for survey and $MS^2$ scans, respectively. Ions were selected for $MS^2$ when their intensity reached a threshold of 500 counts and an isotopic envelope was assigned. Maximum ion accumulation times were set to 1,000 ms for survey MS scans and to 150 ms for $MS^2$ scans. Singly charged ion species and ions for which a charge state could not be determined were not subjected to $MS^2$. Ions within a 10 ppm m/z window around ions selected for $MS^2$ were excluded from further selection for fragmentation for 60 s.

In general, the survey MS scan settings were identical for the $MS^3$ method, where the ten most intense ions were first isolated for ion trap CID-$MS^2$ at a precursor ion isolation width of 2 m/z, using an AGC setting of $2 \times 10^3$, a maximum ion accumulation time of 150 ms, and with wide band activation. Directly following each $MS^2$ experiment, ions were selected with an isolation width 2.5 m/z, the $MS^3$ AGC was $2 \times 10^5$ and with a maximum ion time of 250 ms. Normalized collision energy was set to 35% and 60% at an activation time of 20 ms and 50 ms for $MS^2$ and $MS^3$ scans, respectively (McAlister et al. (2014) *Anal. Chem.* 86:7150-7158).

iv. Data Processing: MS2 Spectra Assignment, Data Filtering and Quantitative Data Analysis A suite of in-house developed software tools was used to convert mass spectrometric data from the RAW file to the mzXML format, as well as to correct inaccurate assignments of peptide ion charge state and monoisotopic m/z. The ReAdW.exe program was modified to include ion accumulation time in the output during conversion to the mzXML file format (available on the World Wide Web at sashimi.svn.sourceforge.net/viewvc/sashimi/) that had been modified to export ion accumulation times and FT peak noise. Assignment of $MS^2$ spectra was performed using the SEQUEST algorithm by searching the data against a protein sequence database containing all known translated proteins from the mouse UniProt database (downloaded on 08//2013) and known contaminants (porcine trypsin and human keratin). The forward (target) database component was followed by a decoy component including all listed protein sequences in reversed order. Searches were performed using a 25 ppm precursor ion tolerance, where both peptide termini were required to be consistent with trypsin specificity and allowing up to two missed cleavages. TMT tags on lysine residues and peptide N termini (+229.1629 Da) and carbamidomethylation of cysteine residues (+57.0214 Da) were set as static modifications, oxidation of methionine residues (+15.994 Da) as a variable modification. A $MS^2$ spectral assignment false discovery rate of less than 1% was achieved by applying the target-decoy database search strategy. Filtering was performed using a linear discrimination analysis method to create one combined filter parameter from the following peptide ion and $MS^2$ spectra properties: SEQUEST parameters XCorr and ΔCn, peptide ion mass accuracy, charge state and peptide length. Linear discrimination scores were used to assign probabilities to each $MS^2$ spectrum for being assigned correctly and these probabilities were used to filter the dataset with an $MS^2$ spectra assignment false discovery rate to obtain a protein identification false discovery rate of less than 1.0% (Huttlin et al. (2010) *Cell* 143:1174-1189). For quantification, a 0.03 m/z window centered on the theoretical m/z value of each reporter ion was monitored for ions, and the intensity of the signal closest to the theoretical m/z value was used. Reporter ion intensities were denormalized by multiplication with the ion accumulation time for each $MS^3$ spectrum and adjusted based on the overlap of isotopic envelopes of all reporter ions. Intensity distributions of isotopic envelopes were as provided by the manufacturer (Thermo Scientific). The total signal to noise (S/N) intensities across all peptides quantified were summed for each TMT channel, and all intensity values were normalized to account for potentially uneven TMT labeling (total minimum of 100 S/N). The intensities for all peptides of a given protein were summed to derive an overall protein abundance S/N value for each TMT signal (Ting et al. (2011) *Nat. Methods* 8:937-940). Proteins were filtered based on the criteria >1.3 fold enrichment in Prdm16tg conditioned medium (samples in duplicates), >1.3 fold enrichment in Prdm16tg BAT tissues and the presence of a signal peptide (see FIG. 1C for select genes). The values are expressed as fold change over control (wild type).

v. Mass Spectrometry from Slit2-CTF by in-Gel Digestion

In-gel protein tryptic digests were resuspended in 10 μL 1% formic acid, and 4 were analyzed by microcapillary liquid chromatography electrospray ionization tandem mass spectrometry (LC-MS/MS). Analyses were done on a LTQ Orbitrap Elite mass spectrometer (Thermo Scientific), an Agilent 1100 Series binary HPLC pump, and a Famos autosampler. Peptides were separated on a 100 μm×28 cm fused silica microcapillary column with an in-house made needle tip. The column was packed with MagicC18AQ $C_{18}$ reversed-phase resin (particle size, 3 μm; pore size, 200 Å; Michrom Bioresources). Separation was achieved applying a 45 min gradient from 5 to 35% acetonitrile in 0.125% formic acid. The mass spectrometer was operated in a data dependent mode essentially as described previously (Villen and Gygi (2008) *Nat. Protoc.* 3:1630-1638) with a full MS scan acquired with the Orbitrap, followed by up to 20 LTQ MS/MS spectra on the most abundant ions detected in the MS scan. Mass spectrometer settings were: full MS (AGC, $1×10^6$; resolution, $6×10^4$; m/z range, 375-1800; maximum ion time, 1000 ms); MS/MS (AGC, $5×10^3$; maximum ion time, 120 ms; minimum signal threshold, $4×10^3$; isolation width, 2 Da; dynamic exclusion time setting, 30 sec). For peptide identification, RAW files were converted into mzXML format and processed using a suite of software tools developed in-house for analysis. All precursors selected for MS/MS fragmentation were confirmed using algorithms to detect and correct errors in monoisotopic peak assignment and refine precursor ion mass measurements. All MS/MS spectra were then exported as individual DTA files and searched using the Sequest algorithm (Eng et al. (1994) *J. Am. Soc. Mass. Spectrom.* 5:976-989). These spectra were then searched non-tryptically against a database containing sequence of mouse Slit2 in both forward and reversed orientations. The following parameters were selected to identify the sequence coverage of slit2: 20 ppm precursor mass tolerance, 0.8 Da product ion mass tolerance, fully tryptic digestion, and up to two missed cleavages. Variable modifications for oxidation of methionine (+15.994915) and a fixed modification for the carbamidomethylation for cysteine (+57.021464) was used as well.

J. Statistical Analysis

All values in graphs are presented as mean +/−s.e.m. The Student's t-test was used for single comparisons. Two-way ANOVA with repeated-measures was used for the GTT studies. The error bars (s.e.m.) shown for all results were derived from biological replicates, not technical replicates. Significant differences between two groups (*p>0.05, p>0.01, *p>0.001) were evaluated using a two-tailed, unpaired t-test as the sample groups displayed a normal distribution and comparable variance.

K. Representative Brown and Beige Fat Markers

Table 2 below provides representative gene expression markers for brown and/or beige fat. In addition, assays for analyzing quantitative RT-PCR, mitochondrial biogenesis, oxygen consumption, glucose uptake, energy intake, energy expenditure, weight loss, multilocular lipid droplet morphology, mitochondrial content, and the like modulated by Slit2 and exhibited by brown and/or beige fat cells are well known in the art (see, at least Harms and Seale (2013) *Nat. Med.* 19:1252-1263 and U.S. Pat. Publ. 2013/0074199).

TABLE 2

| Gene Symbol | Gene Name | GenBank Gene Accession Number | GenBank Protein Accession Number | Gene ID |
| --- | --- | --- | --- | --- |
| adipsin | complement factor D | e.g., NM_013459.2 and NM_001928.2 | e.g., NP_038487.1 and NP_001919.2 | e.g., 11537 and 1675 |
| fatty acid transporter cd36 | fatty acid transporter/cd36 | e.g., NM_007643.3 and NM_000072.3 and NM_0010015472 and NM_001001548.2 and NM_001127443.1 and NM_001127444.1 | e.g., NP_031669.2 and NP_000063.2 and NP_001001547.1 and NP_001001548.1 and NP_001120915.1 and NP_001120916.1 | e.g., 12491 and 948 |
| adiponectin | adiponectin | e.g., NM_009605.4 and NM_004797.2 | e.g., NP_0033735.3 and NP_004788.1 | e.g., 11450 and 9370 |
| UCP-1 | uncoupling protein 1 | e.g., NM_009463.3 and NM_021833.4 | e.g., NP_033489.1 and NP_068605.1 | e.g., 22227 and 7350 |
| cidea | cell death-inducing DFFA-like effector a | e.g., NM_007702.2 and NM_001279.3 and NM_198289.2 | e.g., NP_031728.1 and NP_001270.1 and NP_938031.1 | e.g., 12683 and 1149 |
| PGC1a | Peroxisome proliferative activated receptor, gamma, coactivator 1 alpha | e.g., NM_008904.2 and NM_013261.3 | e.g., NP_032930.1 and NP_037393.1 | e.g., 19017 and 10891 |
| Elovl3 | elongation of very long chain fatty acids (FEN1/Elo2, SUR4/Elo3, yeast)-like 3 | e.g., NM_007703.2 and NM_152310.1 | e.g., NP_031729.1 and NP_689523.1 | e.g., 12686 and 83401 |
| C/EBPbeta | CCAAT/enhancer binding protein beta | e.g., NM_009883.3 and NM_005194.2 | e.g., NP_034013.1 and NP_005185.2 | e.g., 12608 and 1051 |
| Cox7a1 | cytochrome c oxidase subunit VIIa polypeptide 1 | e.g., NM_009944.3 and NM_001864.2 | e.g., NP_034074.1 and NP_001855.1 | e.g., 12865 and 1346 |
| Otopetrin | Otopetrin 1 | e.g., NM_172709.3 and NM_177998.1 | e.g., NP_766297.2 and NP_819056.1 | e.g., 21906 and 133060 |
| Type II deiodinase | Deiodinase, iodothyronine, type II | e.g., NM_010050.2 and NM_000793.4 and NM_001007023.2 and NM_013989.3 | e.g., NP_034180.1 and NP_000784.2 and NP_001007024.1 and NP_054644.1 | e.g., 13371 and 1734 |
| cytochrome C | cytochrome c | e.g., NM_009989.2 and NM_018947.4 | e.g., NP_034119.1 and NP_061820.1 | e.g., 13067 and 54205 |

TABLE 2-continued

| Gene Symbol | Gene Name | GenBank Gene Accession Number | GenBank Protein Accession Number | Gene ID |
|---|---|---|---|---|
| cox4i1 | cytochrome c oxidase subunit IV isoform 1 | e.g., NM_009941.2 and NM_001861.2 | e.g., NP_034071.1 and NP_001852.1 | e.g., 12857 and 1327 |
| coxIII | mitochondrially encoded cytochrome c oxidase III | e.g., NC_005089.1 and ENST00000362079 | e.g., NP_904334.1 and ENSP00000354982 | e.g., 17705 and 4514 |
| cox5b | cytochrome c oxidase subunit Vb | e.g., NM_009942.2 and NM_001862.2 | e.g., NP_034072.2 and NP_001853.2 | e.g., 12859 and 1329 |
| cox8b | cytochrome c oxidase subunit 8B, mitochondrial precursor | e.g., NM_007751.3 | e.g., NP_031777.1 | e.g., 12869 and 404544 |
| glut4 | solute carrier family 2 (facilitated glucose transporter), member 4 | e.g., NM_009204.2 and NM_001042.2 | e.g., NP_033230.2 and NP_001033.1 | e.g., 20528 and 6517 |
| atpase b2 | ATPase, H+ transportying, lysosomal 56/58 kDa, V1 subunit B2 | e.g., NM_057213.2 and NM_001693.3 | e.g., NP_476561.1 and NP_001684.2 | e.g., 117596 and 526 |
| coxII | mitochondrially encoded cytochrome c oxidase II | e.g., NC_005089.1 and ENST00000361739 | e.g., NP_904331 and ENSP00000354876 | e.g., 17709 and 4513 |
| atp5o | ATP synthase, H+ transporting, mitochondrial F1 complex, O subunit | e.g., NM_138597.2 and NM_001697.2 | e.g., NP_613063.1 and NP_001688.1 | e.g., 28080 and 539 |
| ndufb5 | NADH dehydrogenase (ubiquinone) 1 beta subcomplex, 5, 16 kDa | e.g., NM_025316.2 and NM_002492.2 | e.g., NP_079592.2 and NP_002483.1 | e.g., 66046 and 4711 |
| Rarres2 | retinoic acid receptor responder (tazarotene induced) 2 | e.g., NM_027852.2 and NM_002889.3 | e.g., NP_082128.1 and NP_002880.1 | e.g., 71660 and 5919 |
| Car3 | carbonic anhydrase 3 | e.g., NM_007606.3 and NM_005181.3 | e.g., NP_031632.2 and NP_005172.1 | e.g., 12350 and 761 |
| Peg10 | paternally expressed 10 | e.g., NM_001040611.1 and NM_001040152.1 and NM_001172437.1 and NM_001172438.1 and NM_015068.3 | e.g., NP_001035701.1 and NP_001035242.1 and NP_001165908.1 and NP_001165909.1 and NP_055883.2 | e.g., 170676 and 23089 |
| Cidec | Cidec cell death-inducing DFFA-like effector c | e.g., NM_178373.3 and NM_022094.2 | e.g., NP_848460.1 and NP_071377.2 | e.g., 14311 and 63924 |
| Cd24a | CD24a antigen | e.g., NM_009846.2 and NM_013230.2 | e.g., NP_033976.1 and NP_037362.1 | e.g., 12484 and 100133941 |
| Nr1d2 | nuclear receptor subfamily 1, group D, member 2 | e.g., NM_011584.4 and NM_001145425.1 and NM_005126.4 | e.g., NP_035714.3 and NP_001138897.1 and NP_005117.3 | e.g., 353187 and 9975 |
| Ddx17 | DEAD (Asp-Glu-Ala-Asp) box polypeptide 17 | e.g., NM_001040187.1 and NM_001098504.1 and NM_001098505.1 and NM_006386.4 and NM_030881.3 | e.g., NP_001035277.1 and NP_001091974.1 and NP_001091975.1 and NP_006377.2 and NP_112020.1 | e.g., 67040 and 10521 |
| Aplp2 | amyloid beta (A4) precursor-like protein 2 | e.g., NM_001102455.1 and NM_001142276.1 and NM_001142277.1 and NM_001142278.1 and NM_001642.2 | e.g., NP_001095925.1 and NP_001135748.1 and NP_001135749.1 and NP_001135750.1 and NP_001633.1 | e.g., 11804 and 334 |
| Nr3c1 | nuclear receptor subfamily 3, group C, member 1 | e.g., NM_008173.3 and NM_000176.2 and NM_001018074.1 and NM_001018075.1 and NM_001018076.1 and NM_001018077.1 and NM_001020825.1 and NM_001024094.1 | e.g., NP_032199.3 and NP_000167.1 and NP_001018084.1 and NP_001018085.1 and NP_001018086.1 and NP_001018087.1 and NP_001018661.1 and NP_001019265.1 | e.g., 14815 and 2908 |
| Rybp | RING1 and YY1 binding protein | e.g., NM_019743.3 and NM_012234.4 | e.g., NP_062717.2 and NP_036366.3 | e.g., 56353 and 23429 |
| Txnip | thioredoxin interacting protein | e.g., NM_001009935.2 and NM_006472.3 | e.g., NP_001009935.1 and NP_006463.3 | e.g., 56338 and 10628 |
| Cig30 | Elongation of very long chain fatty acids-like 3 | e.g., NM_152310.1 and NM_007703.1[1] | e.g., NP_689523.1 and NP_031729.1[1] | e.g., 83401 and 12686 |

TABLE 2-continued

| Gene Symbol | Gene Name | GenBank Gene Accession Number | GenBank Protein Accession Number | Gene ID |
|---|---|---|---|---|
| Ppar gamma 2 | Peroxisome proliferator-activated receptor gamma 2 | e.g., NM_015869.4 and NM_011146.2[1] | e.g., NP_056953 and NP_035276.1[1] | e.g., 5468 and 19016 |
| Prdm16 | PR domain containing 16 protein | e.g., NM_022114.3 and NM_199454.2 and NM_027504.3 | e.g., NP_071397.3 and NP_955533.2 and NP_081780.3 | e.g., 63976 and 70673 |
| Ap2 | Fatty acid binding protein 4 | e.g., NM_001442.2 and NM_024406.1 | e.g., NP_001433.1 and NP_077717.1 | e.g., 2167 and 11770 |
| Ndufs2 | NADH dehydrogenase (ubiquinone) Fe—S protein 2, 49 kDa (NADH-coenzyme Q reductase | e.g., NM_001166159.1 and NM_004550.4 and NM_153064.4 | e.g., NP_001159631.1 and NP_004541.1 and NP_694704.1 | e.g., 4720 and 226646 |
| Grp109A | Hydroxycarboxylic acid receptor 2 | e.g., NM_177551 and NM_030701.3 | e.g., NP_808219 and NP_109626.1 | e.g., 338442 and 80885 |
| AcylCoA-thioesterase 4 | Acyl-coenzyme A thioesterase 4 | e.g., NM_152331 and NM_134247.3 | e.g., NP_689544 and NP_599008.3 | e.g., 122970 and 171282 |
| Claudin1 | Claudin1 | e.g., NM_021101.4 and NM_016674.4 | e.g., NP_066924.1 and NP_057883.1 | e.g., 9076 and 12737 |
| PEPCK | Phosphoenolpyruvate carboxykinase (mitochondrial) | e.g., NM_001018073.1 and NM_004563.2 and NM_028994.2 | e.g., NP_001018083.1 and NP_004554.2 and NP_083270.1 | e.g., 5106 and 74551 |
| Fgf21 | Fibroblast growth factor 21 | e.g., NM_019113 and NM_020013.4 | e.g., NP_061986 and NP_064397.1 | e.g., 26291 and 56636 |
| AcyCoA-thioesterase 3 | Acyl-coenzyme A thioesterase 4 | e.g., NM_001037161.1 and NM_134246.3 | e.g., NP_001032238.1 and NP_599007.1 | e.g., 641371 and 171281 |
| Dio2 | Type II iodothyronine deiodinase | e.g., NM_00793.5 and NM_010050.2 | e.g., NP_000784.2 and NP_034180.1 | e.g., 1734 and 13371 |

L. Cell Surface Staining of Slit2-C Using Confocal Laser Scanning Microscopy

Live, primary differentiated adipocytes were incubated with recombinant Slit2-C FLAG-tagged protein for 1 h at 4° C. before fixation and staining with a fluorescent antibody for visualization of cell-surface bound proteins using a confocal laser scanning microscope. Experiments were performed using a Nikon Ti w/A1R confocal inverted microscope equipped with a Nikon Plan Apo 60x/NA 1.4 oil immersion objective lens using excitation wavelengths of 405 and 561 nm. All experiments were performed under confocal imaging conditions (pinhole<1 airy unit) and images taken with the same laser settings. Image analysis was performed using the Nikon Elements acquisition software. Primary inguinal cells differentiated until day 5 was gently trypsinized and seeded onto poly-D-lysine-coated coverslips (Corning Biocoat 12 mm German Glass coverslips, #08-774-385) in a 6-well plate at a density of 10,000 cells per well in growth medium. On the next day, cell surface binding was performed by adding 1 µg/ml purified protein to cells or FLAG peptide in PBS in serum-containing medium for 1 h at 4° C. on ice. Cells were washed three times in PBS, fixed in 4% paraformaldehyde for 10 min at 4° C., and washed with PBS three times before blocking with 5% BSA in PBS for 1 h at room temperature. Cells treated with protein or FLAG peptide alone were stained using 1:200 anti-Flag M2-HRP overnight at 4° C. Cells were washed with 5% BSA in PBS three times 10 min and stained with Alexa Fluor 568 goat-anti-mouse (10 µg/ml, A-11031, Invitrogen) and 1 µg/ml of nuclear stain (Hoechst33342, Invitrogen) for 30 min at room temperature. Cells were washed three times in 5% BSA in PBS before being mounted on glass slides using a water-based fluorescent mounting medium.

Example 2

Slit2 is a Factor Secreted from Beige Adipose Cells

Figures 2B, 2C:
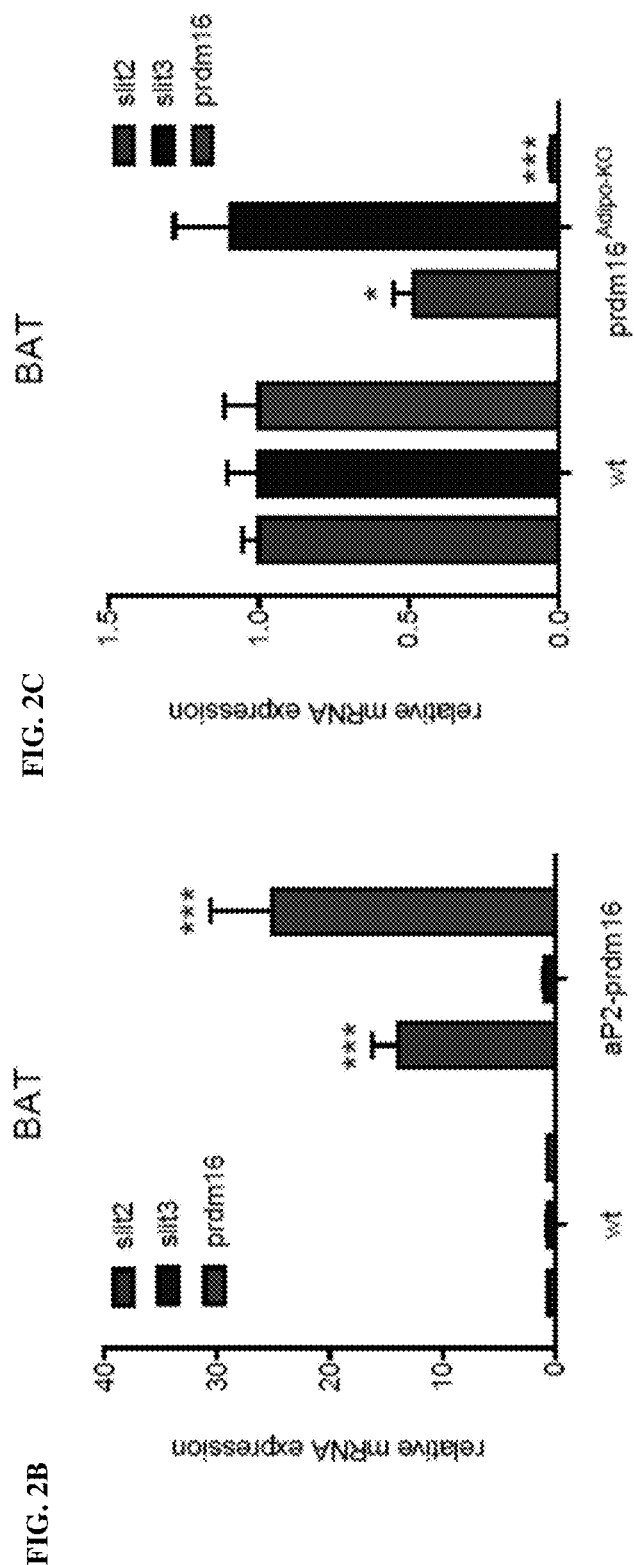
FIG. 2 includes 7 panels, identified as panels A, B, C, D, E, F, and G, which further show that Slit2 is a PRDM16-regulated secreted protein in adipose cells. Panel A shows peptides (bold text) corresponding to mouse Slit2 and Slit3 detected in conditioned medium from aP2-PRDM16 inguinal cells. Panels B and C show the normalized mRNA expression of Slit2, Slit3, and Prdm16 in brown fat tissue (BAT) from aP2-PRDM16 mice (Panel B) and adipocyte-specific deletion of PRDM16 (prdm16$^{adipo-KO}$) (Panel C). Panels D and E show tissue mRNA expression of Slit2 (Panel D) and Slit3 (Panel E) in 6 week old C57/b6 mice. Panel F shows normalized mRNA expression of Slit2 and Ucp1 in iWAT, eWAT and BAT after 3 days treatment with daily injections of CL 316,243 (1 mg/kg). Panel G shows normalized mRNA expression of Slit2 and Slit3 in BAT in lean mice or 16 weeks C57/b6 high fat diet mice.

In order to identify factors secreted from beige adipocytes, the aP2-PRDM16 transgenic mouse model was used as a discovery tool. As reported previously in Seale et al. (2011) *J. Clin. Invest.* 121:96-105, aP2-PRDM16 mice have much more beige fat in vivo, as indicated by the increased number of multilocular, UCP1-positive cells in their inguinal fat pad (iWAT) (FIG. 1A). Primary cultures of inguinal adipocytes from aP2-PRDM16 mice also show much higher expression of thermogenic genes such as Prdm16, Ucp1 and Cox8. In addition, the previously identified beige and brown markers Eva1, Ear2 (Wu et al. (2012) *Cell* 150:366-376) and the beige-enriched mitochondrial marker Gatm (Kazak et al. (2015) *Cell* 163:643-655) are elevated at the mRNA level compared to inguinal cultures from wild-type littermates (FIG. 1B). These data indicate that primary aP2-PRDM16 cultures are enriched in beige adipocytes. On day 6 of differentiation, when cultures were visibly differentiated more than 90%, serum-free conditioned media was collected for 24 h from aP2-PRDM16 and wild-type iWAT adipocytes. These supernatants were then analyzed by unbiased quantitative proteomics, using the TMT tagging method (see Example 1I). A total of 5,360 proteins were identified in this experiment, of which ~1260 were enriched in aP2-PRDM16 by more than >1.3 fold versus the wild-type adipocytes. Several criteria were established for prioritizing these candidates, including the presence of a signal peptide in the annotated gene and regulation by PRDM16 in tissues (see Example 1). This yielded a shortlist of 13 proteins of potential interest (FIG. 1C). Of these prioritized candidates, two belonged to the same family of *Drosophila* Slit homologs of extracellular proteins (Slit2 and Slit3). Multiple peptides from Slit2 and Slit3 were detected in conditioned medium from the beige cells (FIG. 2A) and tissues from aP2-PRDM16 and adipocyte-specific deletion of PRDM16 also indicated that Slit2 was a factor secreted from thermogenic adipocytes both in vitro and in vivo (FIGS. 2B-2C).

Figure 1G:
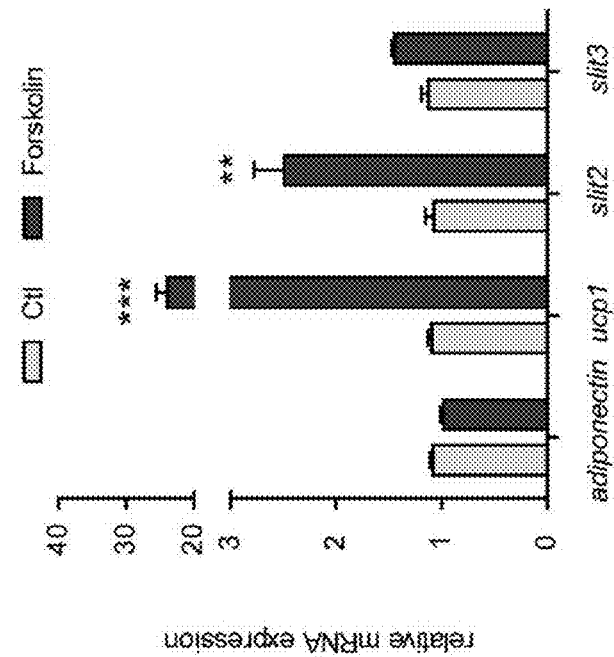
Figure 1F:
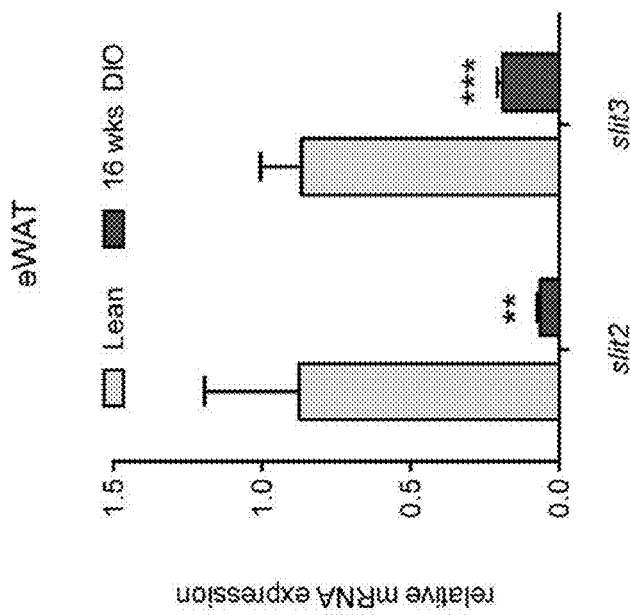
Figure 2D:
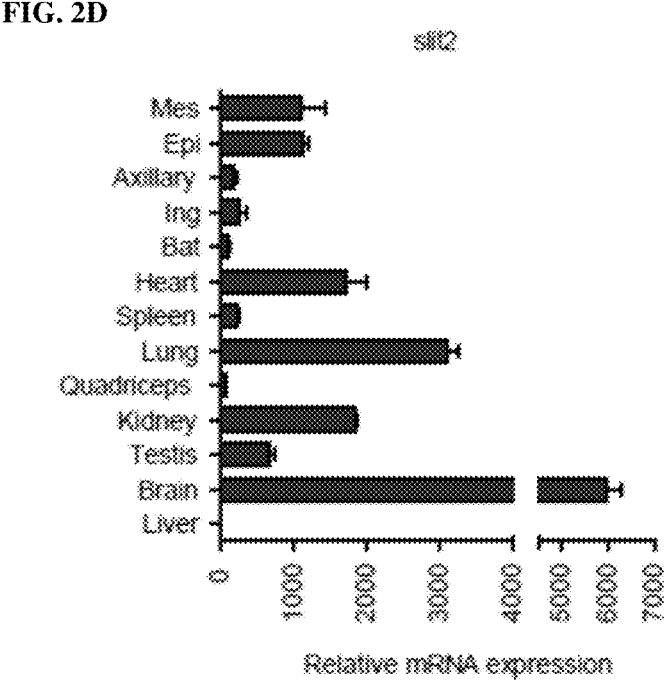
Figure 2E:
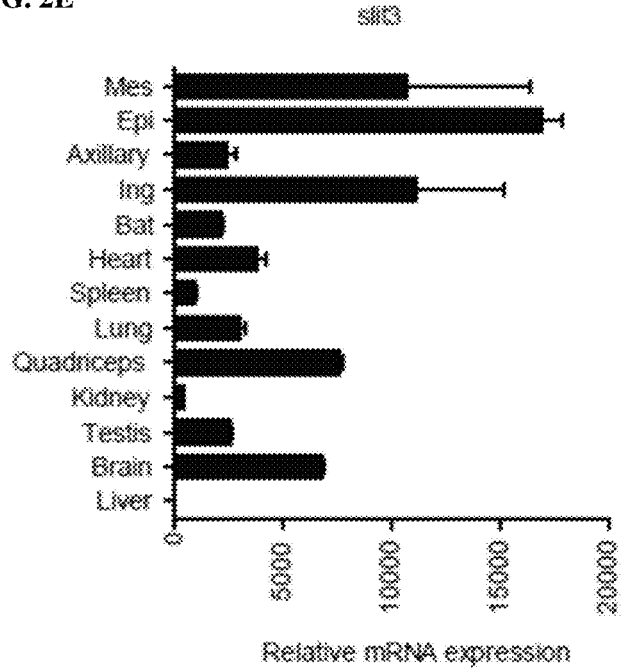
Figures 2F, 2G:
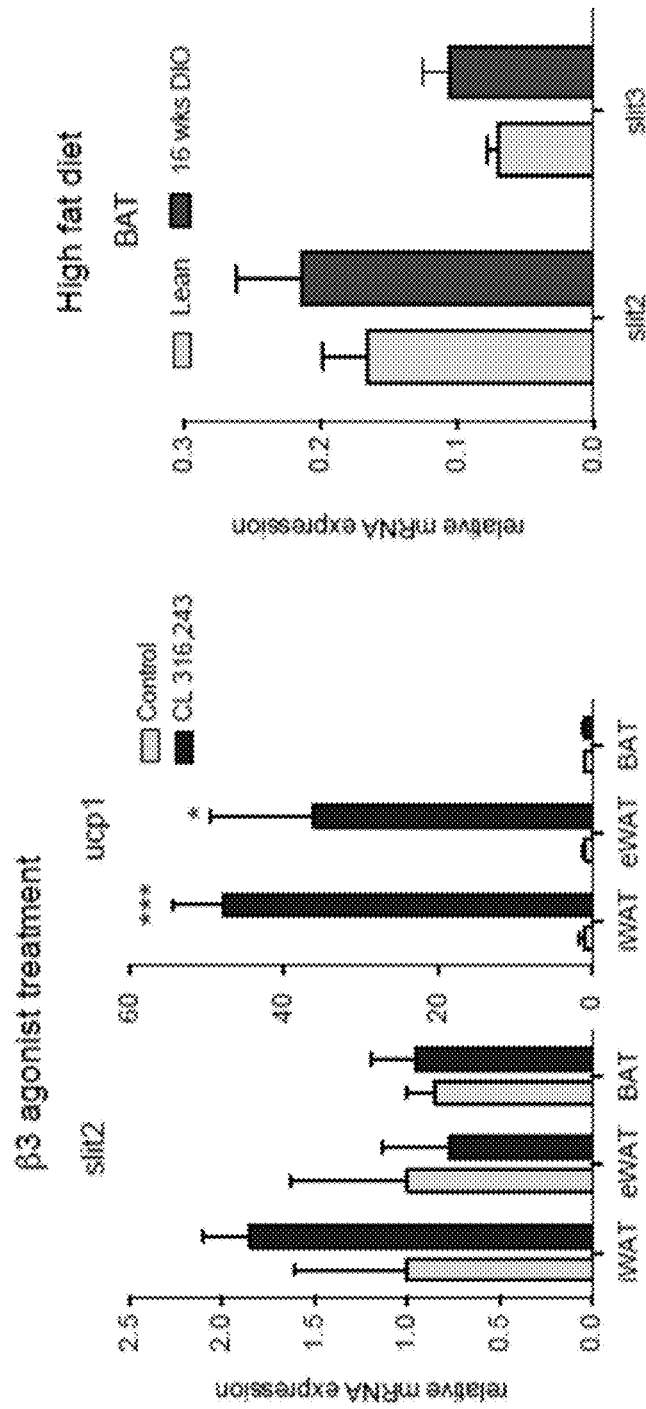

The Slit family in mouse and humans comprises three members—Slit1, Slit2 and Slit3. Slits are all extracellular matrix proteins of approximately 180 kDa with a 29 amino acid signal peptide for classical secretion. They have mainly been studied in the context of their important role in brain development (Brose et al. (1999) Cell 96:795-806; Nguyen et al. (1999) Neuron 22:463-473; Wang et al. (1999) Cell 96:771-784). Despite the broad tissue expression pattern of Slit2 and Slit3, none of the Slit proteins have been described to be present or functionally active in adult peripheral tissues. In order to investigate the function of the Slit members in the periphery, their expression and regulation in adipose tissues was analyzed. Slit2 and Slit3 mRNAs were present in all adipose tissues (FIGS. 1D and 2D-2E). Moreover, the mRNA expression of Slit2, but not Slit3, is also inducible in fat by actue but not long-term cold exposure in BAT and iWAT and suppressed by high fat diet (FIGS. 1D-1F). There was a trend to an increase in Slit2 gene expression in iWAT after 3 days treatment with the β-adrenergic agonist CL316, 243, but this did not reach statistical significance (FIG. 2F). This might be explained by a rapid desensitization mechanism upon long-term activation of cAMP, similar to the transient upregulation of Slit2 mRNA seen upon cold exposure (FIG. 1D). Interestingly, the expression of Slit2 is suppressed in iWAT in diet-induced obese mice that also presents very low Ucp1 and Adipsin mRNA levels (FIG. 1E). Slit2 mRNA is also downregulated in epididymal WAT (eWAT) (FIG. 1F) but not in classical BAT (FIG. 2G), suggesting distinct mechanisms of transcriptional regulation. In addition, Slit2 is induced in inguinal cells upon stimulation with the cyclic AMP-activator forskolin (FIG. 1G). These data point to a physiologic regulation of Slit2 in adipose cells and tissues and are suggestive of a link between Slit2 and thermogenic function.

Example 3

Slit2 Promotes a Thermogenic Program in Cells and in Mice

Figure 3A:
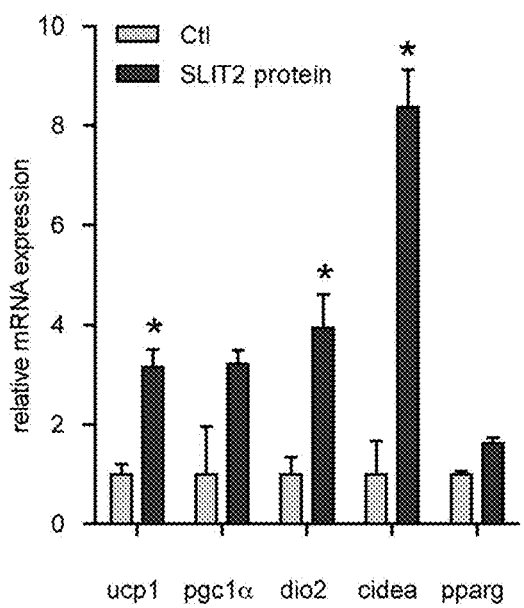
FIG. 3 includes 10 panels, identified as panels A, B, C, D, E, F, G, H, I, and J which show that Slit2 promotes a thermogenic program in cells and in mice. Panels A and B show thermogenic gene expression in primary inguinal cells treated for 24 h with 1 μg/ml of Slit2 (Panel A) or lysyl oxidase (LOX1), glypican1 (GPC1), chordin-like 1 (CHL1) or C—X—C motif chemokine 12 (CXCL12) recombinant proteins (Panel B) at day 6 of differentiation. Panel C shows the results of Western blotting against Slit2 in primary inguinal cells overexpressing full length Slit2 in adenoviral vectors. Panel D shows normalized thermogenic mRNA expression in primary inguinal cells overexpressing adenoviral full length Slit2 (Slit2-FL) or lacZ control. Panel E shows the results of C57/BL6 mice injected (i.v.) with adenoviral vectors Slit2-FL or LacZ (n=3) and Western blotting against Slit2 from plasma of these mice obtained at day 7 post-injection. Panel F shows normalized iWAT mRNA expression of thermogenesis genes and white fat selective genes at day 7 post-injection. Panel G shows representative images from UCP1 immunohistochemistry on sections of inguinal subcutaneous adipose tissue from mice injected with Slit2-FL or LacZ at day 7. Images are shown at 10× magnification. Scale bar, 100 μm. Panel H shows Western blotting against Slit2 in primary inguinal cells from Slit2$^{flox/flox}$ mice transduced with LacZ virus (Slit2$^{flox/flox}$) or Cre virus (Slit2$^{KO}$). Panel I shows gene expression in primary inguinal cells from Slit2$^{flox/flox}$ mice transduced with LacZ virus (Slit2$^{flox/flox}$) or CRE virus (Slit2$^{KO}$). Panel J shows gene expression in BAT tissue from Slit2flox/flox mice infected with with GFP-AAV8 (Slit2$^{flox/flox}$-AAV8-GFP) or Cre virus (Slit2$^{flox/flox}$-AAV8-CRE).
Figure 3B:
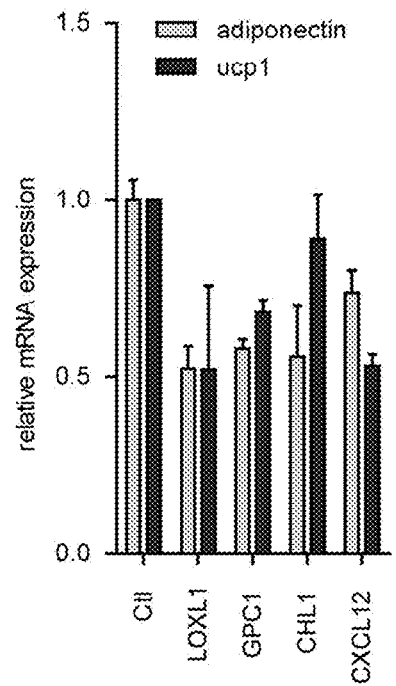
Figure 3C:
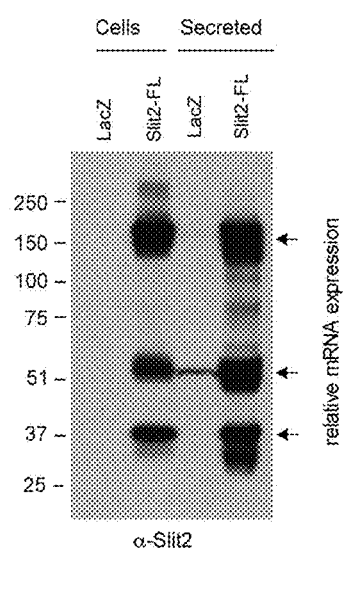
Figure 3D:
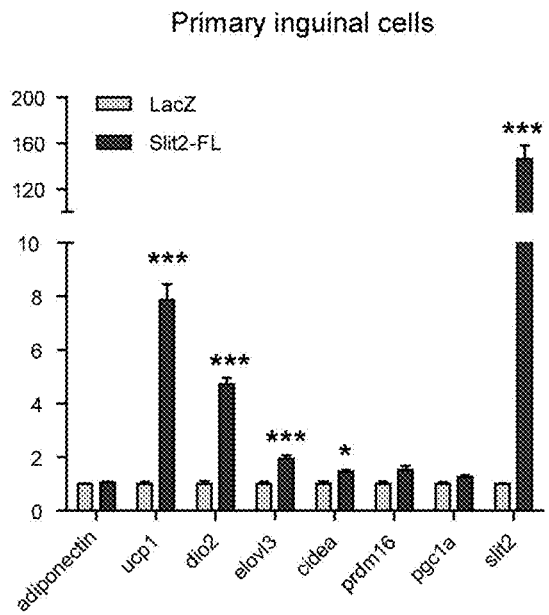

In order to assess whether Slit2 promotes thermogenesis in cultured cells, fully differentiated primary inguinal adipocytes were treated with recombinant Slit2 protein (1 µg/ml, 24 hours). Commercial recombinant Slit2 treatment induced an increase of ~3-fold in Ucp1 mRNA, as well as large increases in expression of other genes associated with thermogenesis, including Dio2 and Cidea (FIG. 3A). Importantly, recombinant protein treatment using several of the other 13 high-priority candidates (as commercially available recombinant proteins) did not produce a thermogenic response (FIG. 3B). As a complementary approach for Slit2, primary inguinal adipocytes were treated on day 2 of differentiation with adenoviruses expressing full-length Slit2 or lacZ control, and the cells were analyzed on day 7. Consistent with the recombinant protein treatment, ectopic expression of Slit2 robustly induced a thermogenic gene program leading to an 8-fold increase in Ucp1 mRNA and 2- to 5-fold elevations in Dio2, Elov13, and cidea (FIG. 3D). Western blotting using an antibody against Slit2 revealed the expression of full-length Slit2 (180 kDa), but also several additional cleavage products, including prominent bands migrating at ~50 kDa and ~37 kDa (FIG. 3C).

Figure 3E:
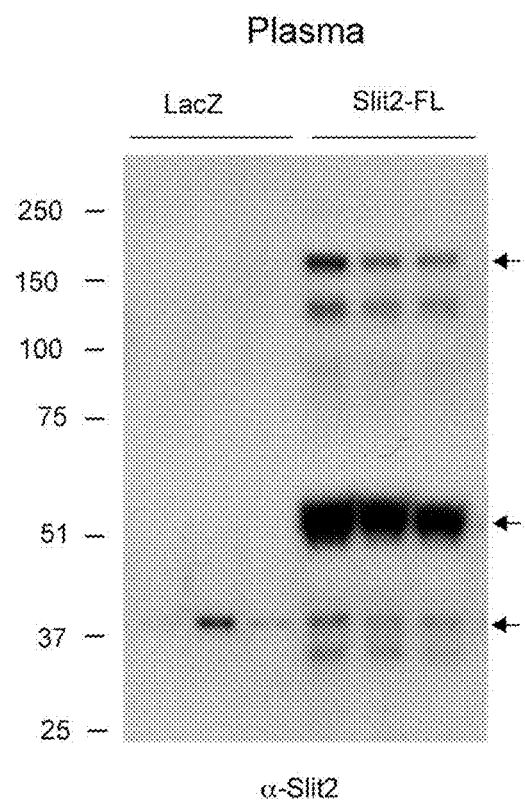
Figure 3F:
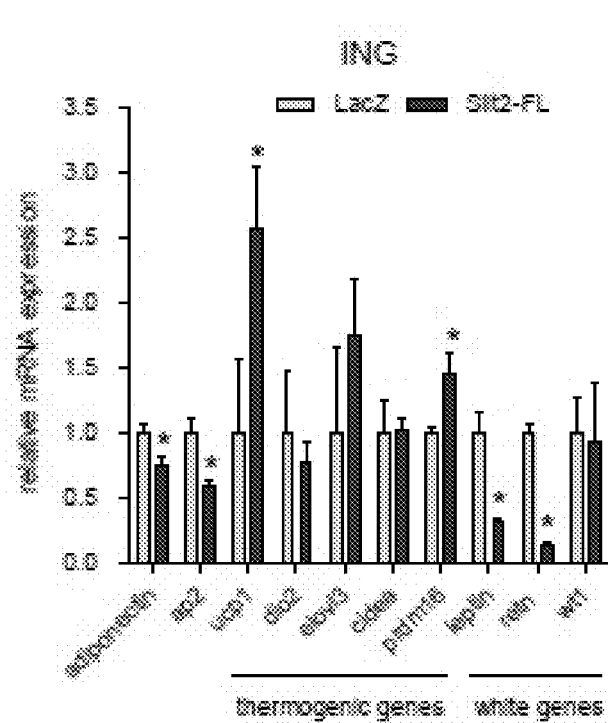
Figure 3G:
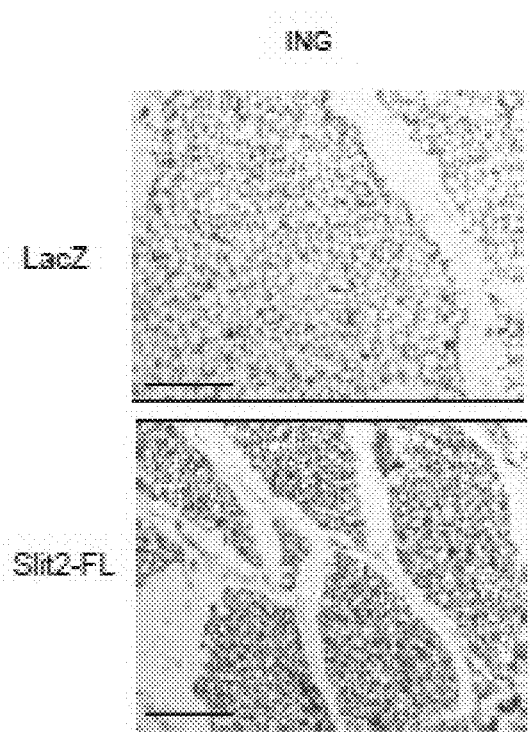
Figure 3H:
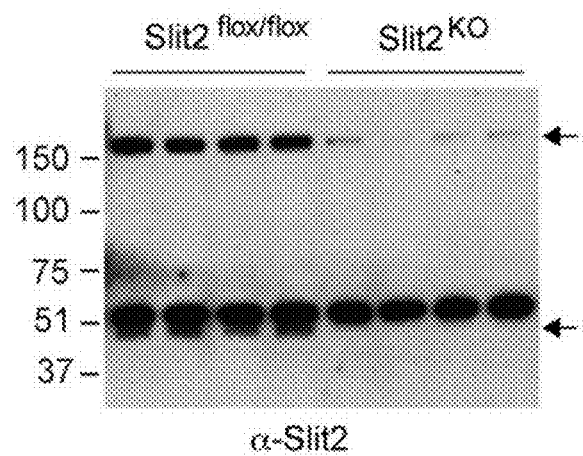
Figure 3I:
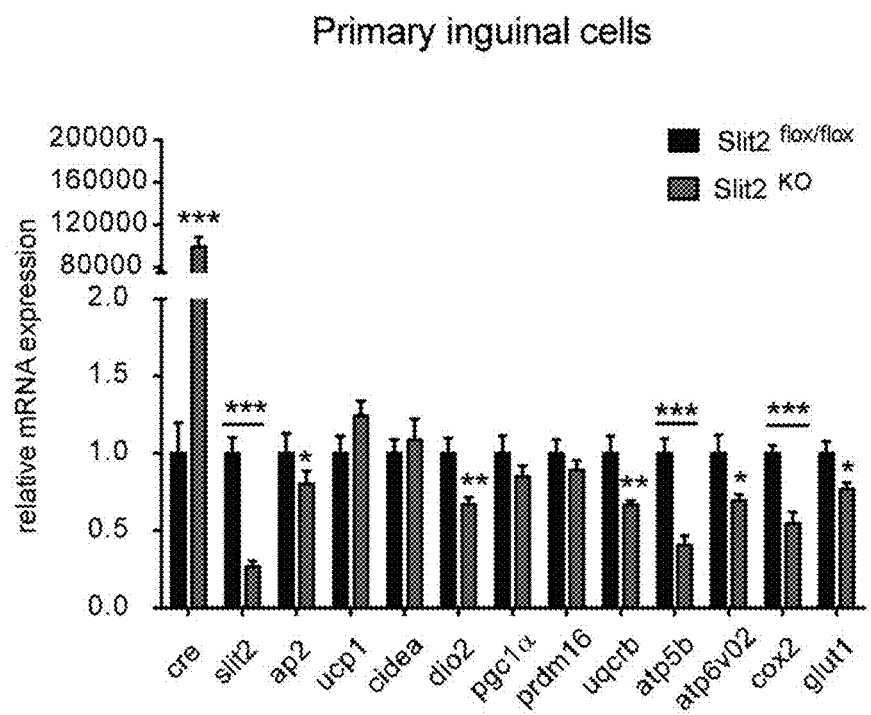
Figure 3J:
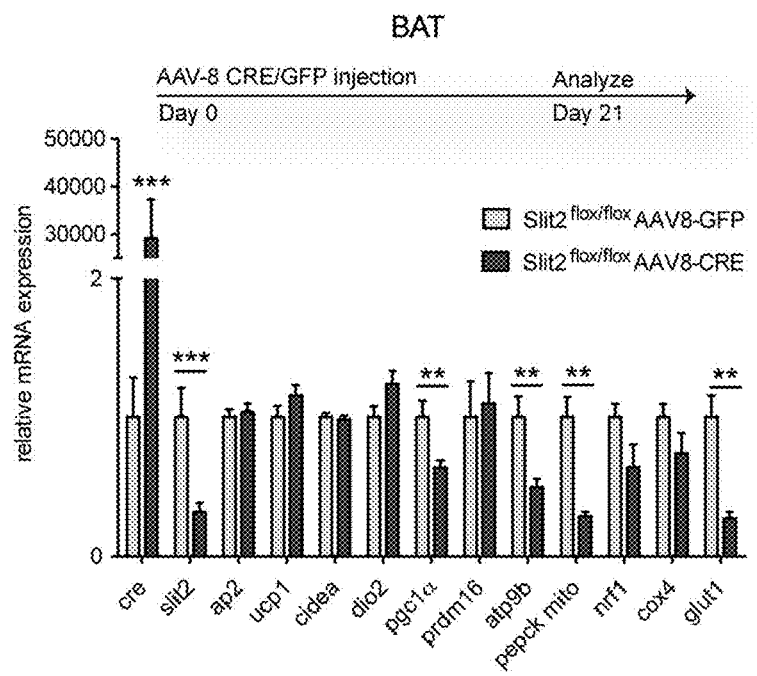

In order to determine whether Slit2 contributes to physiological browning, floxed SLIT2 mice were imported. These animals are on a mixed genetic background and hence are not suitable for metabolic analyses (Rama et al. (2015) Nat. Med. 21:483-491). Nevertheless, primary adipocytes from Slit2$^{flox/flox}$ mice were generated and both the full length and the cleaved 50 kDa form of Slit2 were deleted using adenovirus-mediated Cre expression (FIG. 3H). This resulted in a reduction in thermogenic gene expression and expression of mitochondrial genes in both primary inguinal fat cells and primary brown fat cells (FIGS. 3I and FIG. 12A). In primary brown fat cells, loss of Slit2 results in reduced oxygen consumption (FIG. 12B). To understand the molecular relevance of Slit2 in vivo, injection of Cre recombinase driven by an AAV vector (AAV-8-CRE) was used for 3 weeks, which reduced endogenous Slit2 levels in the brown fat by 70%. This resulted in a significant reduction in Ucp1 expression and also reductions in expression of several other mitochondrial genes in this tissue (FIG. 3J) without any difference in weight loss between the groups (FIG. 12C). Together these experiments suggest that Slit2 is involved in regulation of thermogenic gene expression in vivo.

Figure 4A:
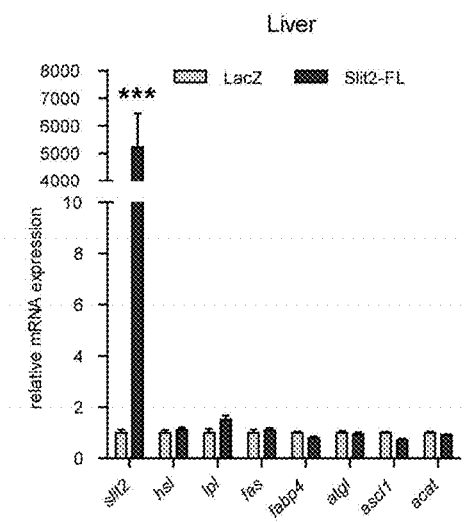
FIG. 4 includes 6 panels, identified as panels A, B, C, D, E and F, which further show that Slit2 promotes a thermogenic program in cells and in mice. Panels A-C show mRNA expression in liver (Panel A), quadriceps (Panel B) and brown fat (Panel C) in mice overexpressing LacZ or Slit2-FL. Panel D shows representative images from UCP1 immunohistochemistry on sections of BAT from mice injected with Slit2-FL or LacZ control at day 7. Images are shown at 10× magnification. Scale bar, 100 μm. Panel E shows normalized mRNA expression levels in iWAT (K) at day 7 postinjection. Panel F shows representative images from UCP1 immunohistochemistry of iWAT from C57/b6 mice injected with Slit2-FL or LacZ at day 7. Scale bar, 100 μm. Data are presented as mean±SEM. *$p<0.05$, $p<0.01$, *$p<0.001$.
Figure 4B:
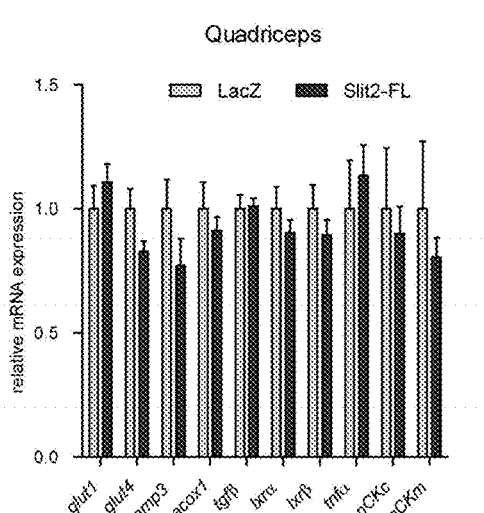
Figure 4C:
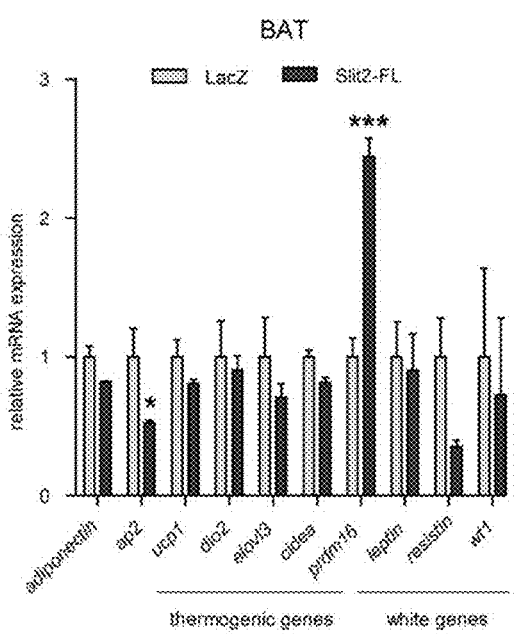
Figure 4D:
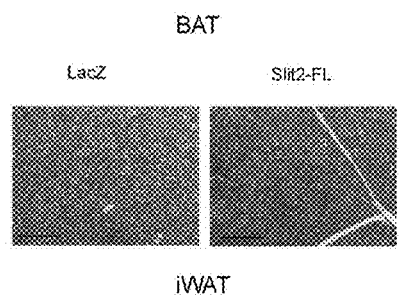
Figure 4E:
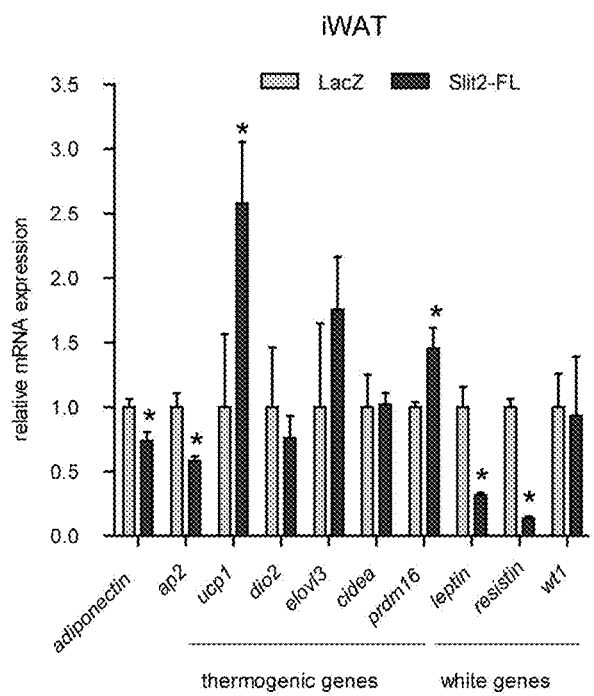
Figure 4F:
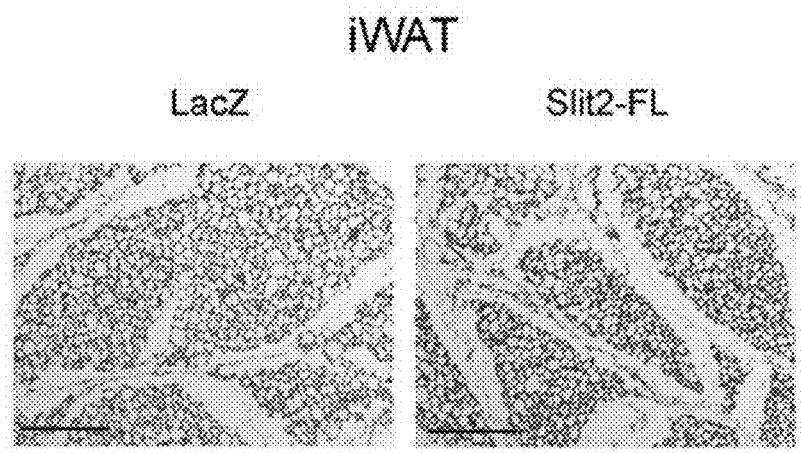

In order to investigate the capacity of pharmacological levels Slit2 to induce browning in vivo, either LacZ or Slit2 was overexpressed by intravenous delivery of adenovirus to lean mice. This protocol resulted in robust expression and secretion of Slit2 from the liver (FIGS. 3E and 4A). Western blotting of the plasma from LacZ- or Slit2-treated mice at 7-days post-injection demonstrated multiple Slit2 fragments secreted into the circulation, including a prominent ~50 kDa fragment similar or identical to the 50 kDa band also observed in cultured cells (FIG. 3E). No changes in lipolysis or lipogenesis gene expression were seen in the liver (FIG. 4A). In skeletal muscle, no gene expression changes in glucose transporters Glut1 and Glut4 or the inflammatory gene Tnfα were observed (FIG. 4B). In contrast, and consistent with the in vitro data, circulating Slit2 induced a thermogenic gene expression program in the iWAT, with a 2.5-fold induction of Ucp1 in iWAT and 1.5-fold induction of Prdm16 (FIG. 4E). Circulating Slit2 induced a thermogenic gene expression program with a 2-fold induction of Ucp1 and Elov13 in inguinal adipose tissue (FIG. 3F). By contrast, white fat selective genes, including Leptin and Resistin, were strongly suppressed by circulating Slit2 (FIG. 4E). No obvious changes in hepatic lipolysis or lipogenesis gene expression was observed (FIG. 4A). In skeletal muscle, no gene expression changes in glucose transporters Glut1 and Glut4 or the inflammatory gene TNFα was seen (FIG. 4B). Consistent with the increase of Ucp1 mRNA, iWAT UCP1 protein was also increased as shown in histological sections stained with an antibody against UCP1 (FIGS. 3G, 4D, and 4F). Circulating Slit2 induced PRDM16 greater than 2-fold in brown fat without any changes in the other thermogenic genes or UCP1 protein (FIGS. 4D-4E); however the tissue had a more dense looking appearance (FIG. 4C, 4D, 4F). Circulating Slit2 did not change any of the vascular and neuronal markers in fat or in skeletal muscle (FIGS. 12D-12F). Taken together, these results demonstrate that ectopic expressed Slit2 in circulation promotes a thermogenic program in cultured adipocytes and adipose tissues.

Example 4

Identification and Characterization of a Slit2 Cleavage Fragment

Figures 5A, 5B, 5C, 5D, 5E, 5F:
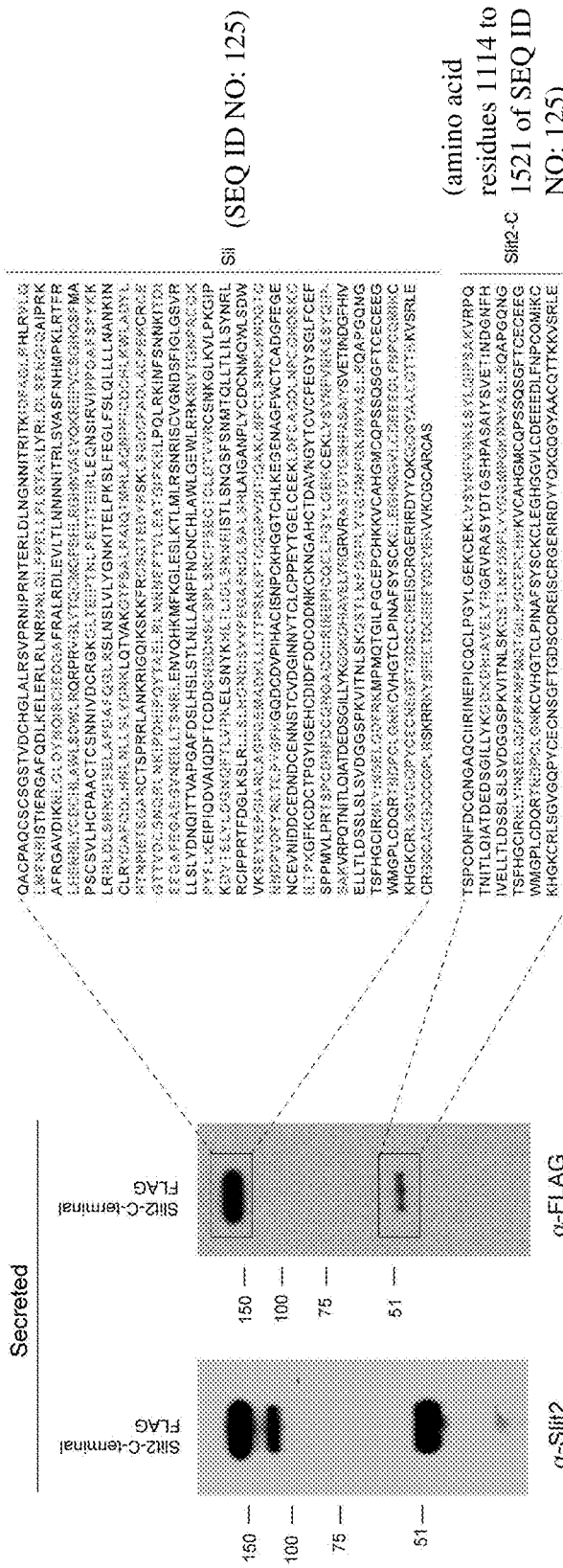
FIG. 5 includes 6 panels, identified as panels A, B, C, D, E, and F, which identify and characterize a Slit2 cleavage fragment. Panel A shows a Western blot of overexpressed full-length C-terminal FLAG-tagged Slit2 detected with a Slit2 antibody (left) and an anti-FLAG antibody (right). Boxed immunoreactive bands were analyzed using mass spectrometry. Panel B shows matched peptides to Slit2-FL or Slit2-C (bold text) using C-terminal FLAG-tagged Slit2 overexpression in primary inguinal cells. Panel C shows a cloning scheme for Slit2 full-length protein, Slit2-N, and Slit2-C protein domains. Panel D shows the results of Western blotting of overexpressed LacZ, Slit2-N, and Slit2-C in primary inguinal cells detected with a V5 antibody. Panel E shows Western blotting results for V5-expression in liver tissue after 6 days post-injection with LacZ, Slit2-N, or Slit2-C adenovirus. Panel F shows Western blotting results of mouse plasma after 6 days post-injection with LacZ, Slit2-N or Slit2-C adenovirus.

It was believed that the ~50 kDa cleavage product observed from full-length Slit2 expression represented a bioactive, thermogenic fragment of full-length Slit2. It was sought to characterize its molecular identity in more detail. However, commercially available anti-Slit2 antibodies were not effective for immunoaffinity purification of Slit2 from the conditioned media. As an alternative strategy, adenoviruses that express full-length Slit2 with a FLAG-tagged at the C-terminus (Slit2-CTF) were generated. Primary inguinal cultures were transduced with Slit2-CTF on day 2 and serum-free conditioned media was collected between days 6 and 7. Western blotting of conditioned media from Slit2-CTF-transduced adipocytes showed secretion of full-length Slit2 (~180 kDa), as well as fragments corresponding to ~140 kDa and ~50 kDa when using an anti-Slit2 antibody (FIG. 5A, left panel). Notably, the ~50 kDa fragment was also detected by an anti-FLAG antibody indicating that this band represents a C-terminal Slit2 fragment (FIG. 5A, right panel).

In order to definitively establish the fragments' identity, immunoaffinity purified, FLAG-tagged Slit2-CTF bands were subjected to mass spectrometry analysis. Peptides identified from the 50 kDa fragment mapped exclusively to the C-terminus of Slit2 (FIG. 5B). In contrast, peptides identified from the ~180 kDa band mapped to all portions of the Slit2 protein. Taken together, these results demonstrate that the smaller 50 kDa fragment of Slit2 from fat cells contains the entire C-terminal region of Slit2. The same or a similar cleavage product has been observed previously (Brose et al. (1999) Cell 96:795-806; Nguyen et al. (2001) J. Neurosci. 21:4281-4289), but has no established function.

In order to examine the activity of the C-terminal fragment (hereinafter referred to as "Slit2-C"), adenoviral constructs containing Slit2-C, a signal peptide for secretion, and a C-terminal V5-tag, were generated (FIG. 5C). As the N-terminus of this C-terminal fragment, the sequence encoding amino acids immediately downstream of the putative cleavage site beginning at TSP (Brose et al. (1999) Cell 96:795-806; Nguyen et al. (2001) J. Neurosci. 21:4281-4289) was chosen. A similar construct containing the N-terminal portion of Slit2 immediately upstream of the Slit2-C sequence (hereinafter referred to as "Slit2-N"), was also generated (FIG. 5C). Primary inguinal adipocytes were transduced with lacZ, Slit2-N, and Slit2-C viruses on day 2, and the cells were harvested on day 6. Both Slit2-N and Slit2-C proteins were efficiently expressed in adipocytes at the predicted molecular sizes; ~140 kDa and ~50 kDa, respectively (FIG. 5D). Both were detected in both the cells and conditioned media, indicating that these fragments are efficiently secreted from adipocytes (FIG. 5D). Interestingly, only Slit2-C, but not Slit2-N, was efficiently secreted into the blood following intravenous delivery of adenoviruses into mice (FIG. 5F), despite efficient hepatic transduction for both constructs (FIG. 5E). Although the experiments described below focus on the biological effects of Slit2-C in subsequent experiments in vitro and in vivo, Slit2-N also exhibits similar qualitative, although quantitatively lower, biological activity as Slit-C. Based on this data, the biological effects of Slit2-C was focused upon in subsequent experiments in vitro and in vivo.

Example 5

Slit2-C is Sufficient to Recapitulate the Thermogenic Activity of Full-Length Slit2

Figure 6B:
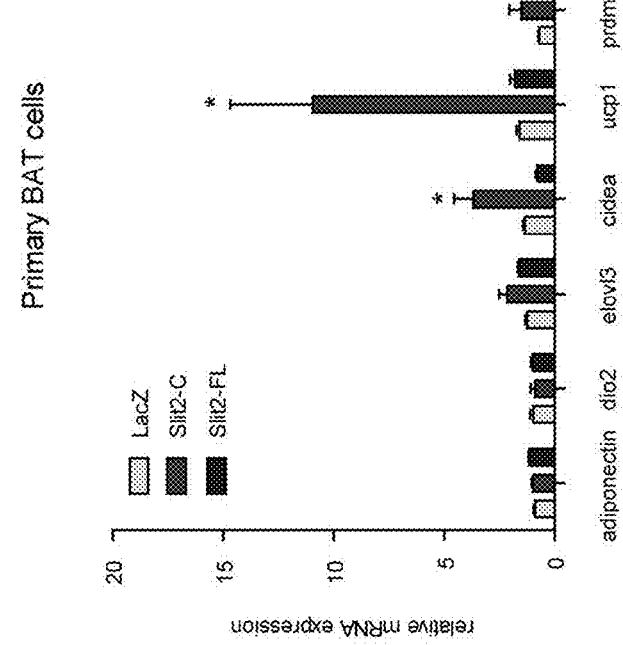
FIG. 6 includes 8 panels, identified as panels A, B, C, D, E, F, G, and H, which show that Slit2-C is sufficient to recapitulate the thermogenic activity of full-length Slit2. Panels A and B show normalized thermogenic mRNA expression in primary inguinal cells (Panel A) or primary brown fat cells (Panel B) overexpressing Ad-Slit2-N, Ad-Slit2-C, or Ad-lacZ control. Panels C and D show thermogenic mRNA expression in iWAT (Panel C) and BAT (Panel D) in mice overexpressing LacZ or Slit2-C. Panel E shows representative images from UCP1 immunohistochemistry on sections of inguinal subcutaneous adipose tissue (upper panel) and BAT (lower panel) from mice injected with Slit2-C or LacZ control at day 7. Images are shown at 10× magnification. Scale bar, 100 μm. Panel F shows $O_2$ consumption in inguinal white fat tissue (left panel) and brown fat tissue (right panel) from 6 week-old mice fed a chow diet. Animal number, n=10 per group. Data are presented as mean±SEM. *$p<0.05$, $p<0.01$, *$p<0.001$. Panel G shows UCP1 immunohistochemistry of iWAT (upper panel) and BAT (lower panel) from mice injected with Slit2-C or LacZ at day 7. Scale bar, 100 μm. Panel H shows $O_2$ consumption in iWAT (left panel) and BAT (right panel) from mice injected with Slit2-C or LacZ at day 7. n=10 per group. Data are presented as mean±SEM. *$p<0.05$, $p<0.01$, *$p<0.001$.
Figure 6A:
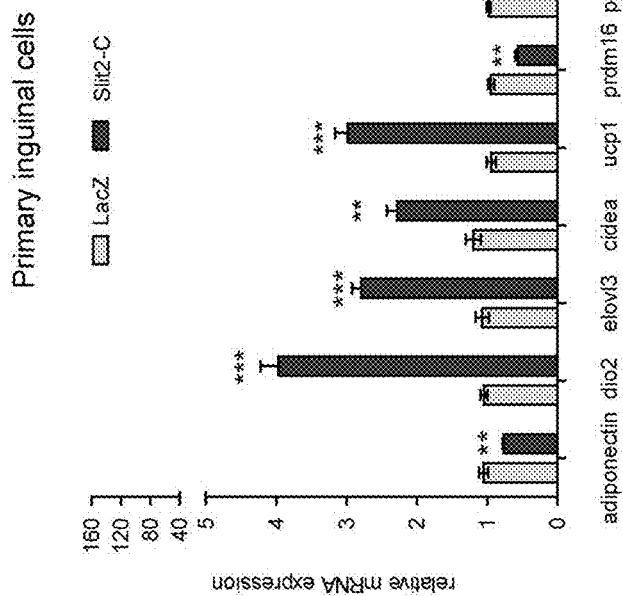
Figure 6D:
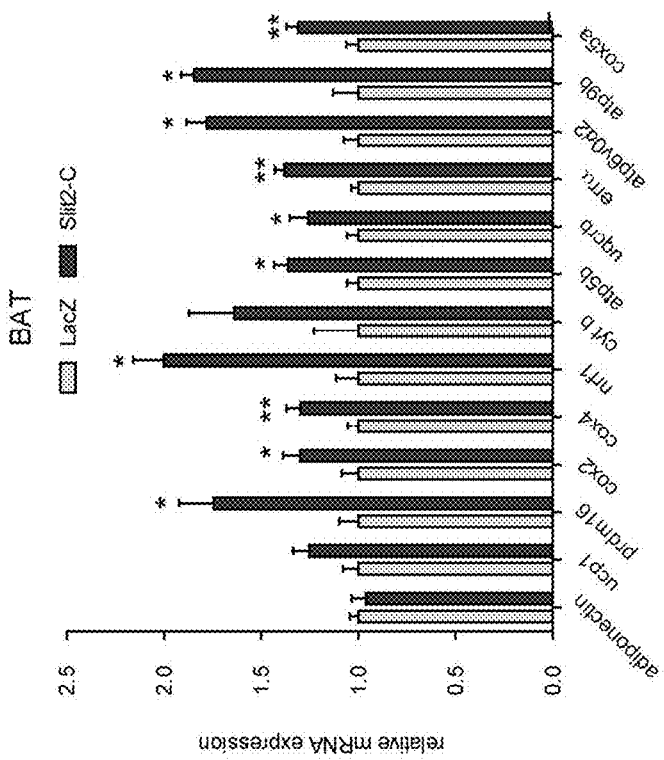
Figure 6C:
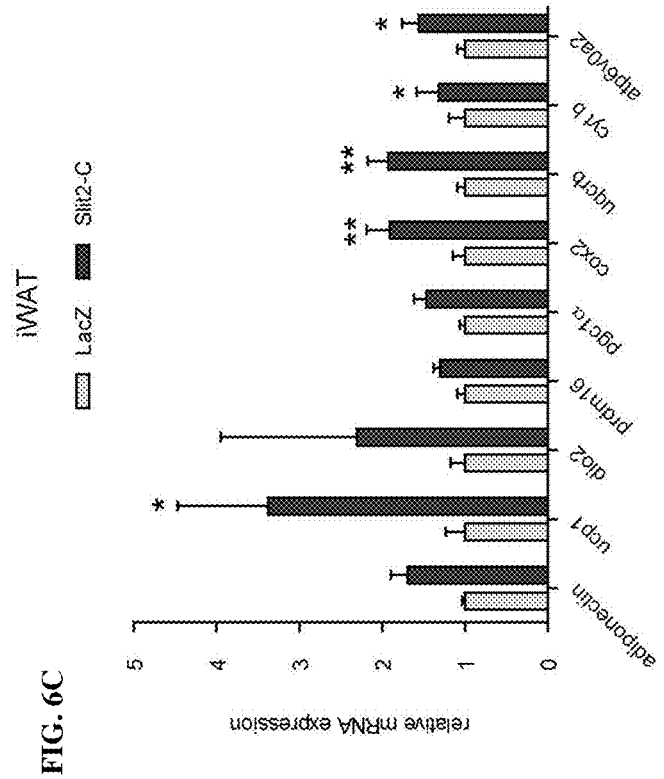
Figures 6E, 6F:
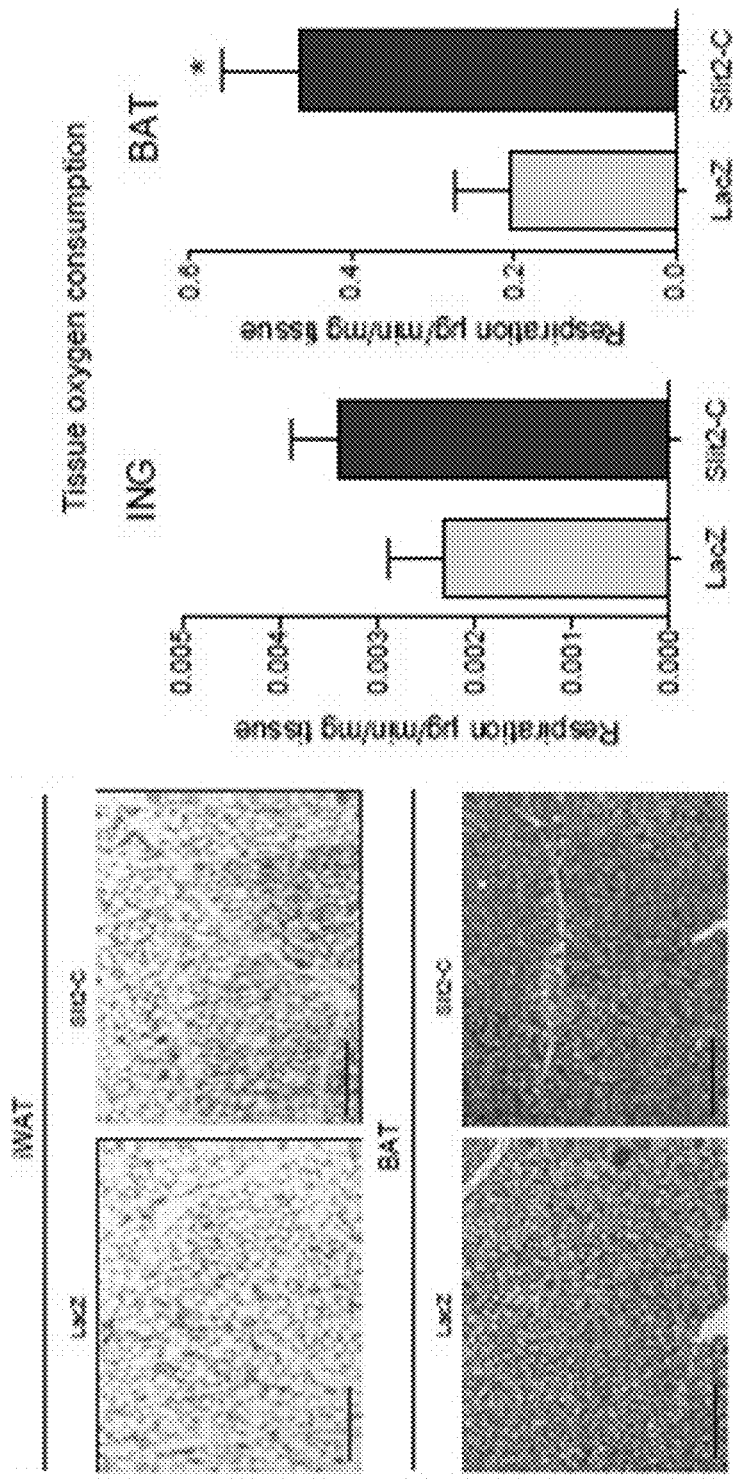
Figures 7A, 7B, 7C:
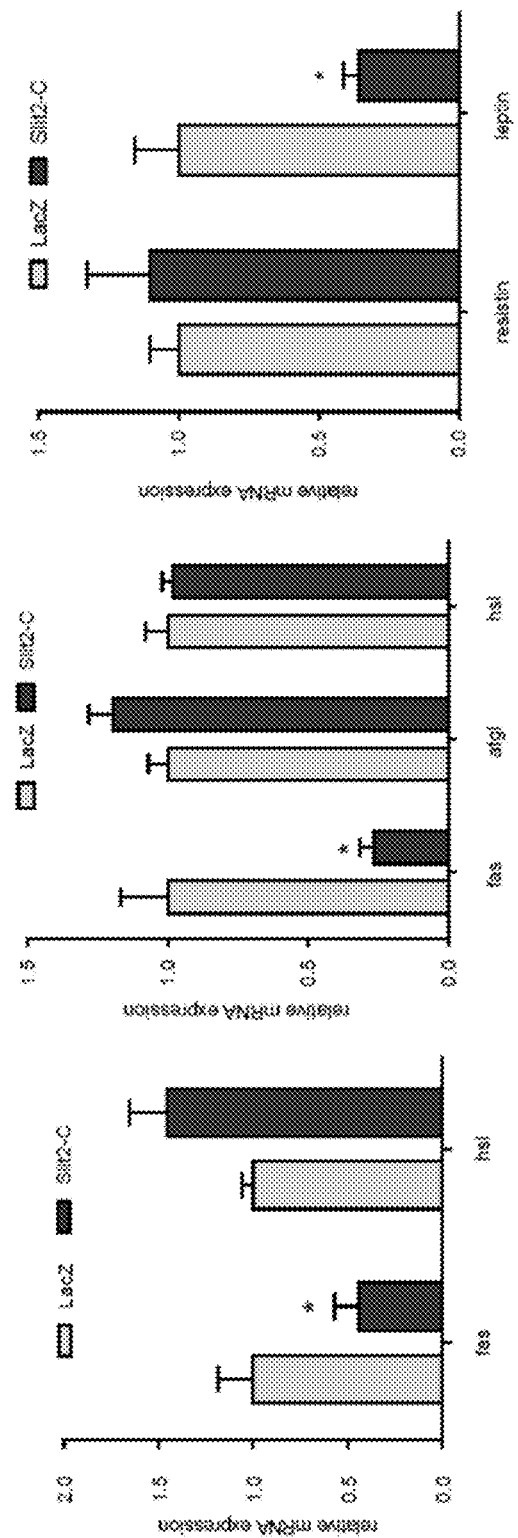
FIG. 7 includes 4 panels, identified as panels A, B, C, and D, which further show that Slit2-C is sufficient to recapitulate the thermogenic activity of full-length Slit2. Panel A shows normalized mRNA expression of fatty acid synthase (fas) and hormone-sensitive lipase (hsl) in inguinal fat 7 days post-injection with LacZ or Slit2-C adenovirus in DIO mice. Panel B shows normalized mRNA expression of fatty acid synthase (fas), adipose triglyceride lipase (atgl), and hormone-sensitive lipase (hsl) in BAT 7 days post-injection with LacZ or Slit2-C adenovirus in DIO mice. Panel C shows normalized mRNA expression of white fat selective genes, resistin and leptin, in BAT 7 days post-injection with LacZ or Slit2-C adenovirus. Panel D shows Western blot of UCP1 protein (left) and quantification of UCP1 protein intensities relative tubulin (right) in BAT 7 days post-injection with LacZ or Slit2-C adenovirus in DIO mice.
Figure 7D:
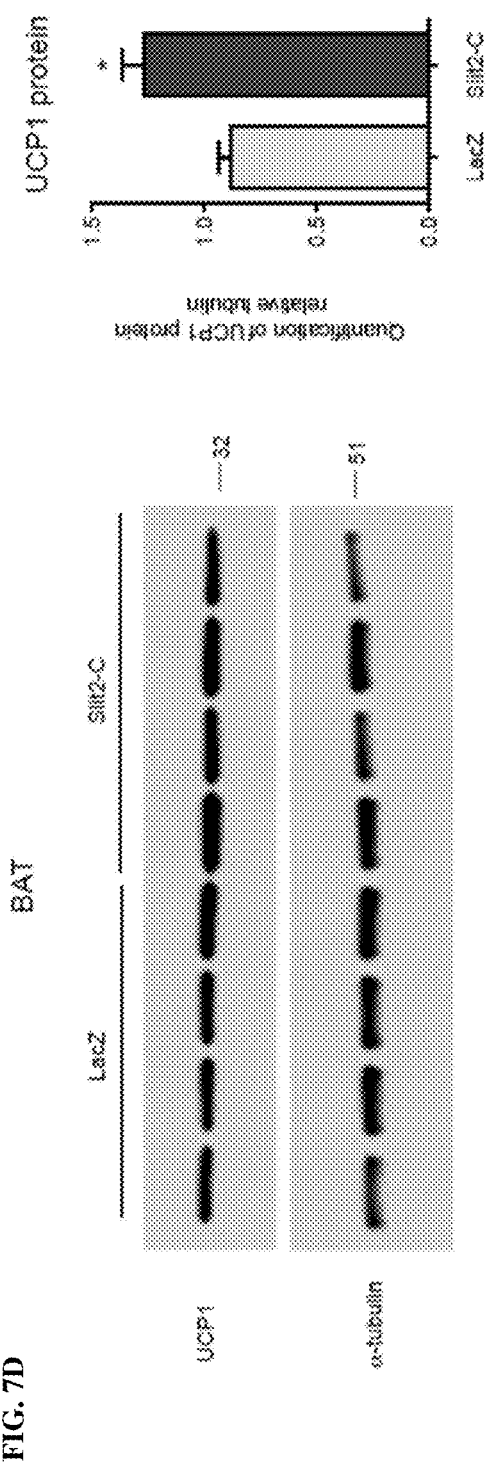

It was next determined whether Slit2-C possesses much or any of the thermogenic activity of full-length Slit2. Primary inguinal and brown fat cultures were transduced with the Slit2-C or LacZ control viruses, and thermogenic gene expression was analyzed at day 7. Under these conditions, Slit2-C induced a thermogenic gene expression comparable to full-length Slit2 in primary inguinal cells, while primary brown fat cells responded stronger to Slit2-C (FIGS. 6A-6B). Next, lean mice were injected with Slit2-C or control adenovirus and their adipose tissues were analyzed by gene expression methods. In the iWAT, Ucp1 mRNA was significantly induced 3-fold, and other mitochondrial genes also showed a modest, but significant, 1.5- to 2-fold increase (FIG. 6C). The classical brown fat showed significant changes in the transcriptional regulators, Prdm16, Nrf1, and Errα. In addition, there was also an upregulation of expression of several mitochondrial genes, such as Atp5b, Uqcrb, Atp6v0a2, Atp9b, and Cox5α, indicative of an activation of BAT (FIG. 6D). Similar experiments using 16-week diet-induced obese (DIO) mice showed a reduction in Fas in inguinal and brown fat, while Hsl and Atgl were unchanged (FIGS. 7A-7B). There was also a marked reduction in brown fat levels of Leptin upon Slit2-C treatment while another white-selective marker, Resistin, was unchanged (FIG. 7C). Consistent with this gene expression data, immunohistochemical analysis by UCP1 staining in the inguinal white fat depots showed multiple pockets of UCP1-positive cells in Slit2-C treated mice compared with control animals (FIG. 6E, upper panel, and 6G). In the BAT, UCP1 staining in BAT was similar between the two groups. However, the tissue in Slit2-C treated animals had a more dense looking appearance with smaller lipid droplets (FIG. 6E, lower panel, and 6G). Quantification of Ucp1 protein expression in BAT showed a 1.3-fold induction in BAT in Slit2-C treated animals (FIG. 7D).

Figure 6H:
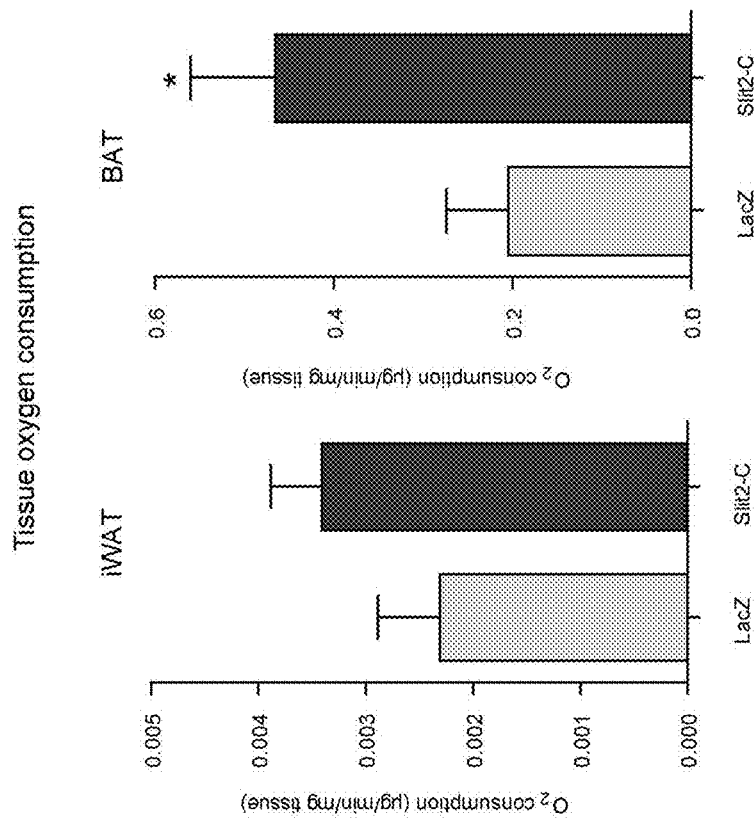
Figure 6G:
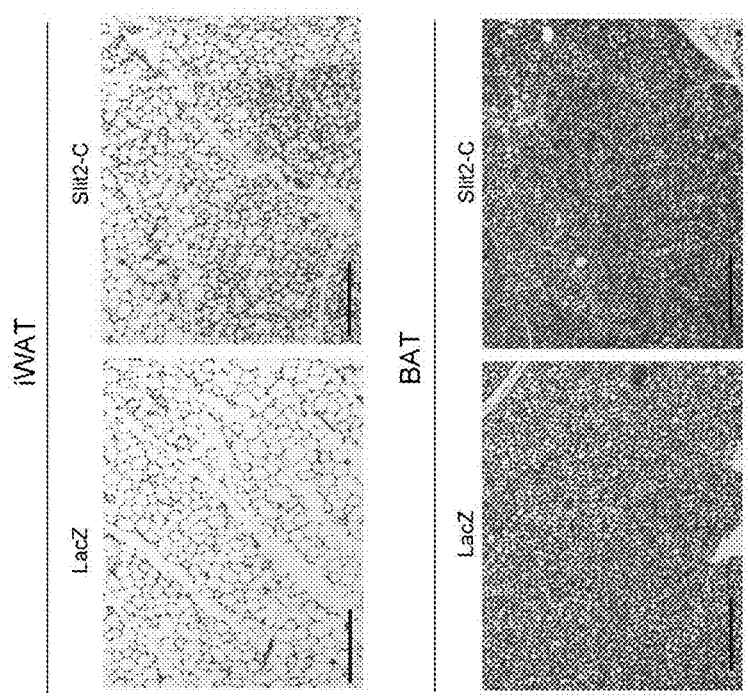

In order to assess the physiological effect of Slit2-C expression on tissue respiration, oxygen ($O_2$) consumption was analyzed as a readout. Brown and white adipose pads were dissected at day 7 after adenovirus injection and respiration of minced tissues was measured using a Clark electrode. $O_2$ consumption was elevated in both inguinal and BAT receiving Slit2-C mice compared to tissues from mice receiving LacZ, although this only reached significance in the BAT (FIGS. 6F and 6H). The data are further described in FIG. 7. Qualitatively similar increases were observed in the inguinal pad (FIG. 6F, left), though this only reached significance in the BAT (FIGS. 6F and 6H, right).

Example 6

Figure 8A:
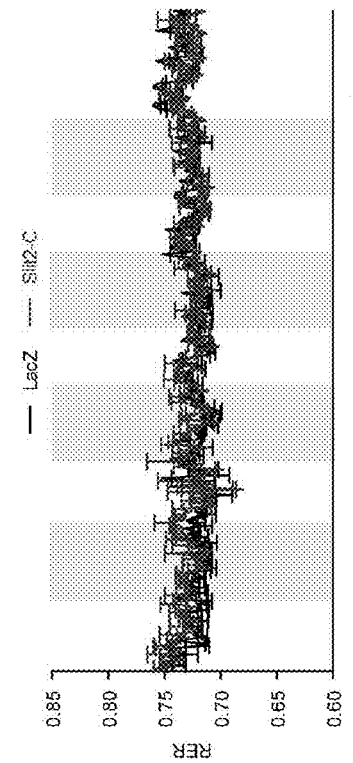
FIG. 8 includes 9 panels, identified as panels A, B, C, D, E, F, G, H, and I, which show that increased circulating Slit2-C augments whole body energy expenditure and improves glucose homeostasis in obese mice. Panels A-E shows the results of whole body energy expenditure measured in DIO mice 6 days after injection with LacZ or Slit2-C adenovirus. Oxygen ($O_2$) consumption (Panel A), respiratory exchange ratio (Panel B), locomotor activity (Panel C), food intake (Panel D), and body weight (Panel E) were measured at day 7. Panel F shows tissue weights of brown fat (BAT), inguinal fat (Ing), and epididymal fat (Epi) at day 7 post-njection with LacZ or Slit2-C adenovirus. Panel G shows the results of intraperitoneal glucose tolerance tests in 16 weeks diet-induced obese mice injected with Slit2-C or LacZ performed at day 7 (n=9-10). Data are presented as mean±SEM. *$p<0.05$, $p<0.01$, *$p<0.001$. Panel H shows averaged oxygen consumption at days 5-7 in mice with no significant different in body weight between the groups. Panel I shows tissue weights of BAT, iWAT and eWAT at day 7 post-injection with LacZ or Slit2-C adenovirus.
Figure 8B:
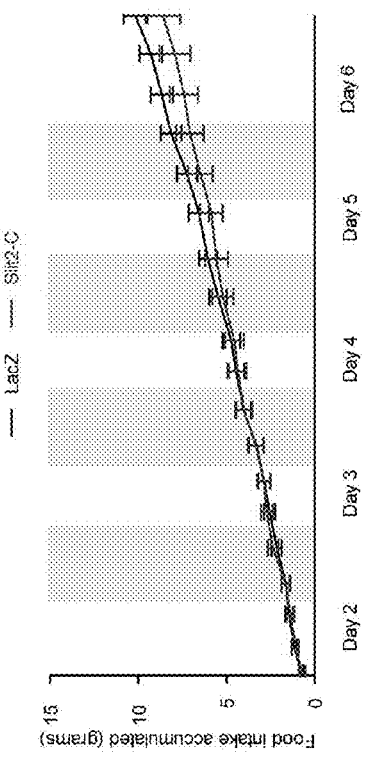
Figure 8C:
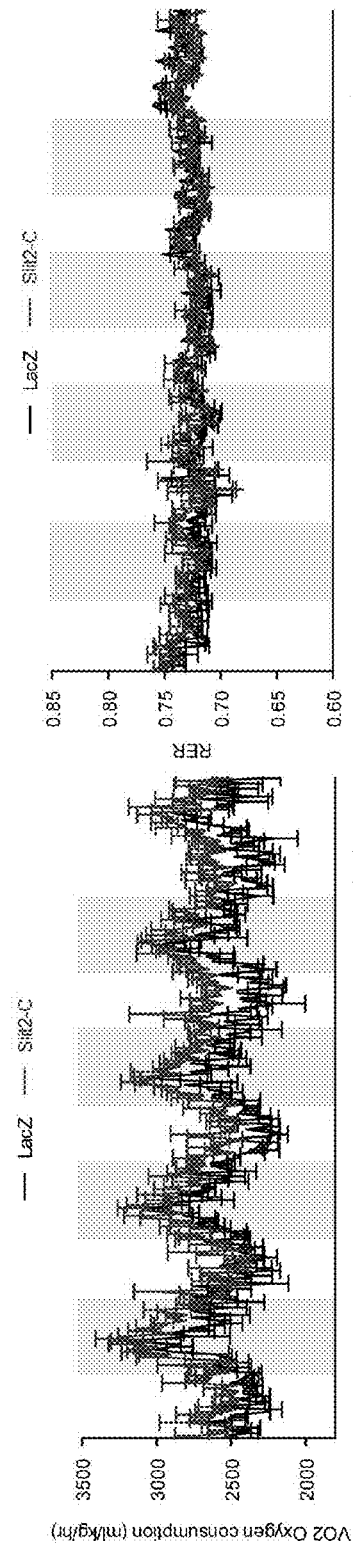
Figure 8D:
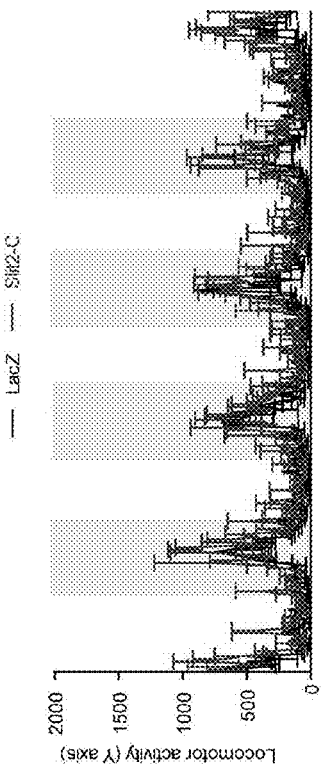
Figure 8E:
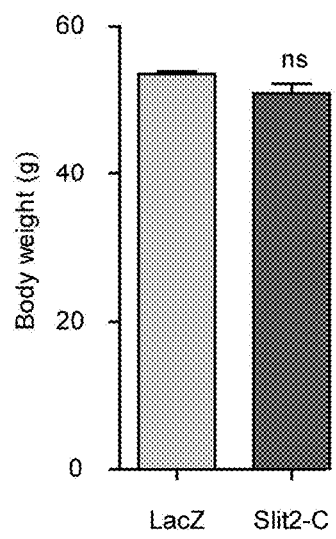
Figure 8F:
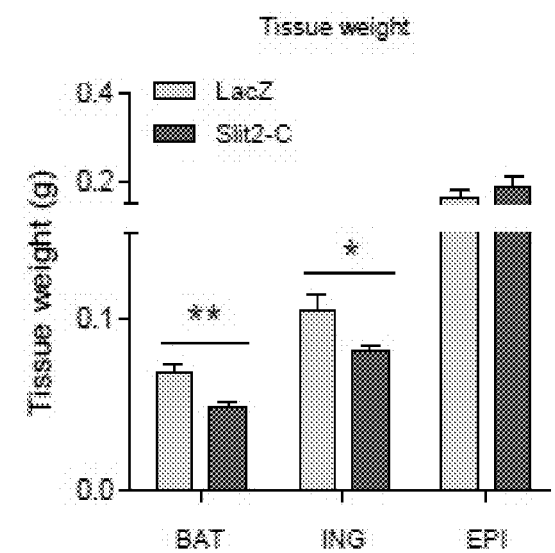
Figure 8G:
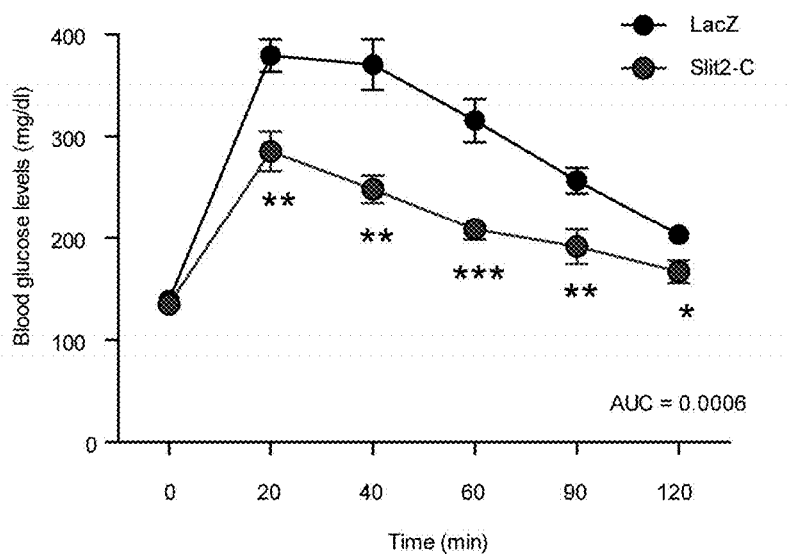
Figures 8H, 8I:
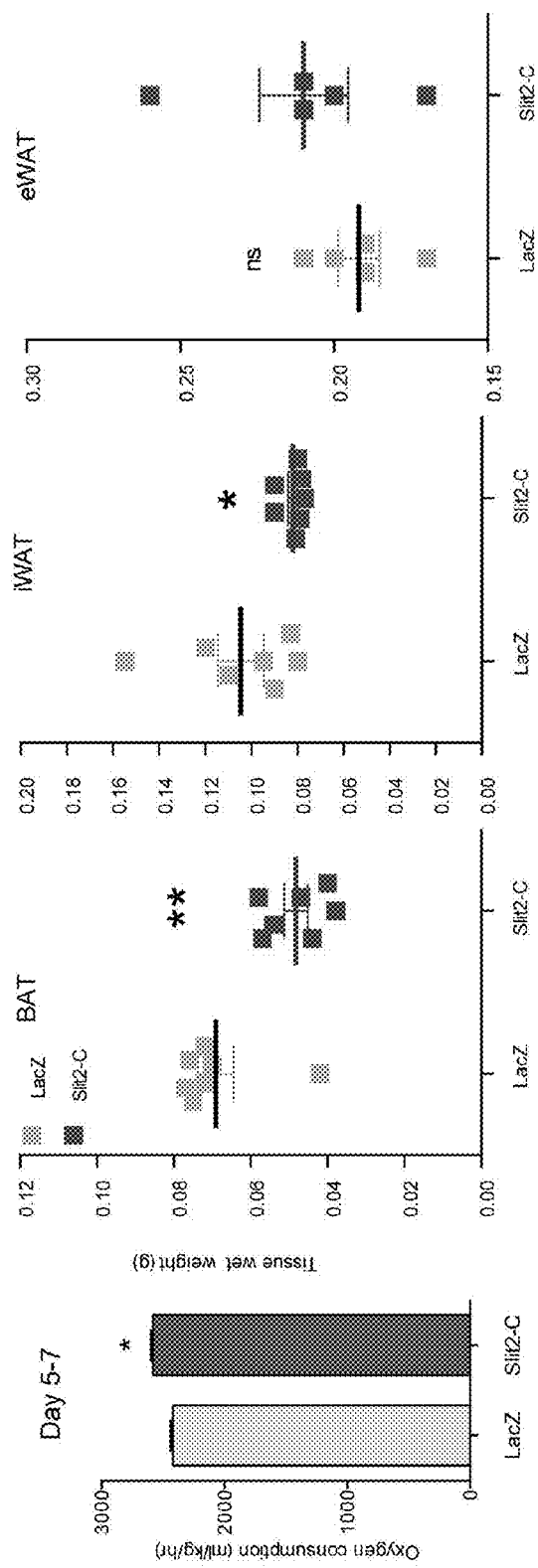
Figure 9C:
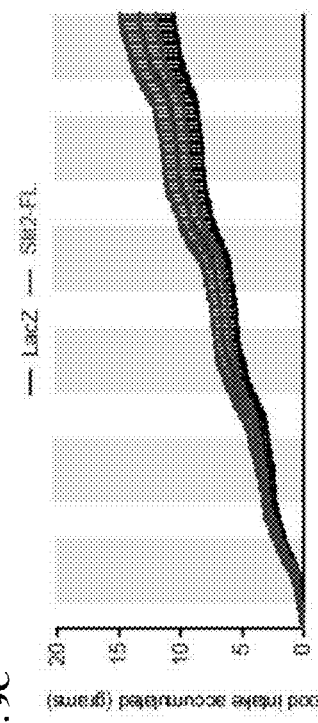
FIG. 9 includes 9 panels, identified as panels A, B, C, D, E, F, G, H, and I, which show that increased circulating full-length Slit2 (Slit2-FL) augments whole body energy expenditure and improves glucose homeostasis in obese mice. Panels A-E show the results of whole body energy expenditure measured in lean mice under 6 days after injection with with LacZ or Slit2-FL adenovirus. Oxygen ($O_2$) consumption (Panel A), respiratory exchange ratio (Panel B), food intake (Panel C), locomotor activity (Panel D), and body weight (Panel D) were measured at day 7. Panel F shows the results of intraperitoneal glucose tolerance tests in 16 weeks diet-induced obese mice injected with Slit2-FL or LacZ performed at day 7 (n=9-10). Panels G-I show plasma levels of total cholesterol (Panel G), triglycerides (Panel H), and non-fasting insulin (Panel I) in mice 7 days post-injection with LacZ or Slit2-C adenovirus.
Figure 9D:
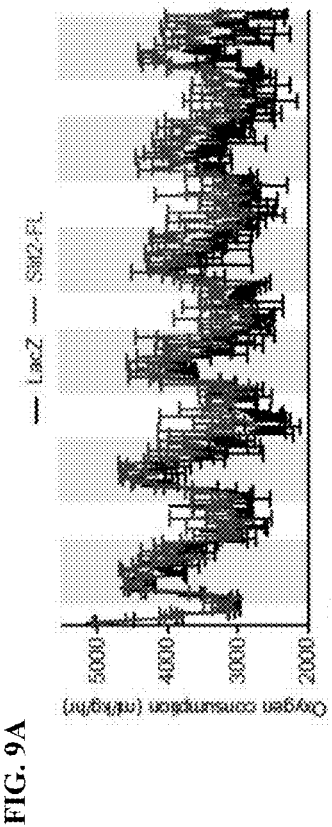
Figure 9A:
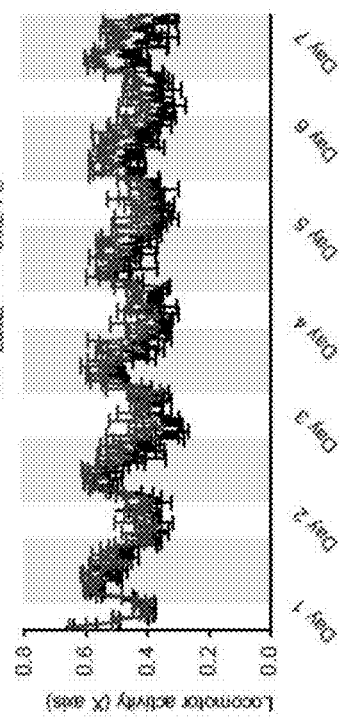
Figure 9B:
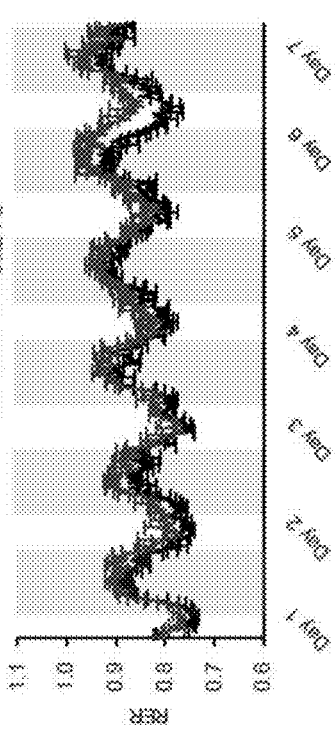

Increased Circulating Slit2-C Augments Whole Body Energy Expenditure and Improves Glucose Homeostasis in Obese Mice In order to study the metabolic effects of increased circulating Slit2-C, 16-week high fat diet-fed mice were injected with adenoviral vectors expressing Slit2-C or a LacZ control. Whole body energy expenditure was analyzed over the following 7 days using a comprehensive laboratory animal monitoring system (CLAMS). Slit2-C induced whole-body oxygen consumption with no observable difference in respiratory exchange ratio (RER), locomotor activity, food intake, or body weight (FIGS. 8A-8E and 8H). These oxygen consumption data were normalized to total body weight. The elevated whole body oxygen consumption in the Slit2-C animals was accompanied by a reduction in the mass of the brown and inguinal, but not epididymal, depots (FIGS. 8F and 8I). Importantly, circulating Slit2-C was found to dramatically improve glucose tolerance in diet-induced obese mice (FIG. 8G). Similar experiments performed with full-length Slit2 had comparable results on energy expenditure and glucose tolerance (FIGS. 9A-9F). Total plasma cholesterol, plasma triglycerides and non-fasting insulin levels were not affected by Slit2-C treatment (FIGS. 9G-9I). These data demonstrate a new function for the C-terminal fragment of the Slit2 protein in augmenting whole body energy expenditure and improving metabolic health.

Example 7

Figure 10A:
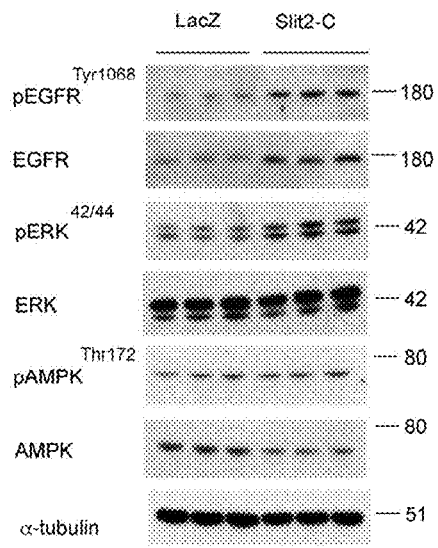
FIG. 10 includes 14 panels, identified as panels A, B, C, D, E, F, G, H, I, J, K, L, M, and N, which show that Slit2-C induces a thermogenesis program through the protein kinase A (PKA) signaling pathway in adipocytes. Panels A and B show the results of primary inguinal cells treated with Slit2-C or LacZ control at day 2 of differentiation ($10^8$ pfu/well), starved overnight at day 6, and analyzed at day 7 by Western blotting for phosphorylated (phospho-) and total protein amounts of epidermal growth factor receptor (EGFR), ERK1/2, and AMPK (Panel A), as well as PKA substrates, HSL, UCP1, α-tubulin protein (Panel B). As a positive control, similar samples were treated with 100 nM NE for 30 minutes. Panels C and D show the results of primary inguinal cells treated with Slit2-C or LacZ control at day 2 of differentiation ($10^8$ pfu/well) and then treated with PKA inhibitor, H89 (30 μM), for 2 h before either Western blot analysis for PKA signaling (Panel C) or gene expression analysis for aP2, Ucp1, and Dio2 (Panel D). Panel E shows primary cells treated as in Panel A and blotted for phospho- and total ATGL and phosphorylated PKC substrates. Panel F shows quantification of UCP1 protein levels relative α-tubulin in Panel B, n=3. Panel G shows Western blot analysis for PKA substrate phosphorylation upon acute treatment (30 min) with conditioned medium from cells expressing LacZ, Slit2-FL or Slit2-C. Panels H and I show thermogenic gene expression in primary inguinal cells overexpressing Slit2-C or LacZ at day and treated with β-receptor antagonist propranolol (100 nM) for 24 h (Panel H) or adenylyl cyclase inhibitor SQ-22536 (10 μM) for 24 h (Panel I). Panel J shows silverstain of immunopurified Slit2-C FLAG protein compared with an albumin standard. Panel K shows Western blot of immunopurified Slit2-C FLAG protein using antibodies for FLAG or Slit2. Panel L shows cell surface binding of FLAG peptide or Slit2-C protein to primary inguinal adipocytes. Panel M shows treatment of primary inguinal cells with 20 nM NE or 20 nM Slit2-C protein for 0, 5, 15, 30, 60 and 90 min. Panel N shows normalized gene expression in primary inguinal cells after treatment with Slit2-C protein for 2 h. Comparisons are presented as Slit2-C vs. LacZ (*), LacZ vs. Slit2-C with drug treatment (#) or LacZ vs. drug treatment ($). Data are presented as mean±SEM. *$p<0.05$, $p<0.01$, *$p<0.001$.
Figure 11A:
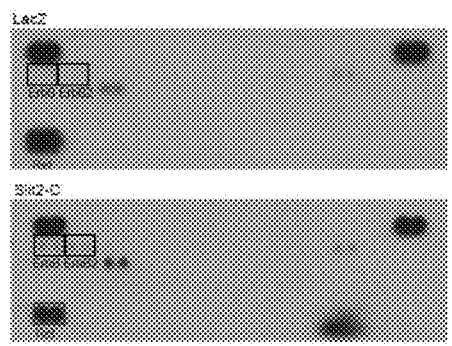
FIG. 11 includes 7 panels, identified as panels A, B, C, D, E, F, and G, which show that the EGFR and ERK pathways are activated by, but not required for, Slit2-C activity. Panel A shows the results of a phosphokinase array used to detect phosphorylated forms of proteins in LacZ or Slit2-C treated primary inguinal cells at day7 of differentiation. Panel B show Western blot results of phosphorylated EGFR in reposnse to increasing concentrations of EGFR tyrosine kinase inhibitors, erlotinib and lapatinib. Panel C shows normalized mRNA expression in primary inguinal cells treated with LacZ or Slit2-C adenovirus in the presence or absence of the EGFR inhibitors, erlotinib and lapatinib. Panel D shows normalized mRNA expression in primary inguinal cells treated with LacZ or Slit2-C adenovirus in the presence or absence of the ERK inhibitor, PD0325901. Panel E shows cell surface binding of either FLAG peptide, PM20D1 protein (100 nM) or Slit2-C protein (100 nM) to primary inguinal adipocytes. Panel F shows Western blot of phosphorylated PKA substrates after 60 min incubation with increasing concentrations of Slit2-C FLAG purified protein. Panel G shows quantification of phosphorylated PKA substrates in FIG. 6, Panel L after incubation with Slit2-C FLAG purified protein relative time point 0.
Figure 11B:
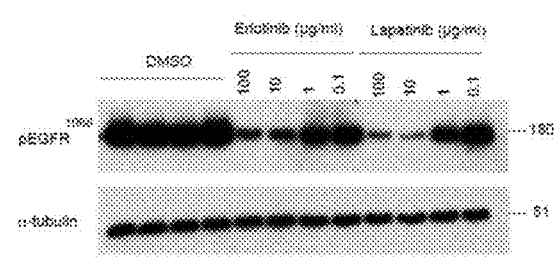
Figure 11C:
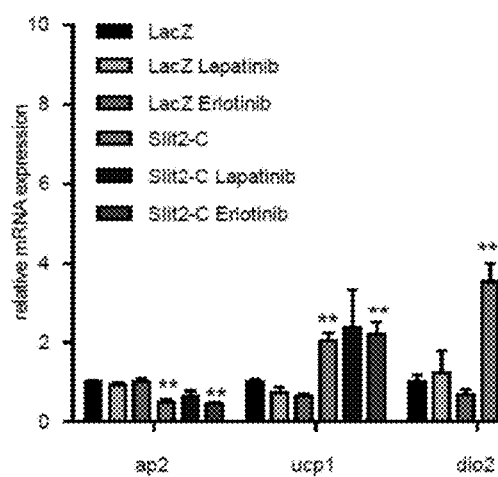
Figure 11D:
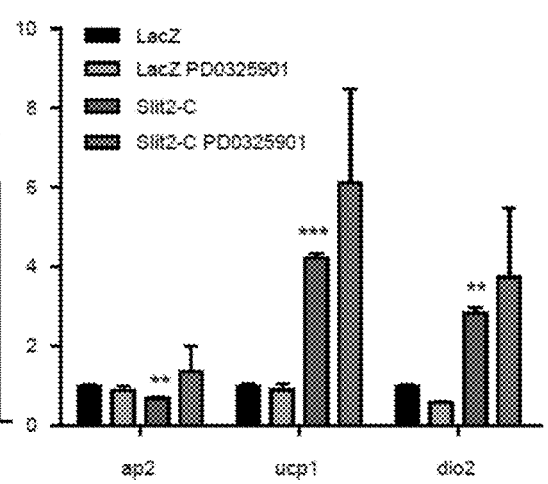

Slit2-C Induces a Thermogenesis Program Through the PKA Signaling Pathway in Adipocytes Canonical Slit signaling in the central nervous system occurs by interaction of the N-terminus of Slit proteins with the Robo family of receptors, resulting in signaling through the small GTPase Cdc42 involved in neuronal migration (Wong et al. (2001) *Cell* 107:209-221). No in vivo function for the C-terminal region of Slit proteins has been described. The Slit2-C fragment as defined here completely lacks this ROBO interaction domain, suggesting that other receptors might be involved in signaling from this protein in adipocytes. In order to understand the possible receptors and signaling pathways by which Slit2-C exerts its thermogenic effects, phospho-arrays were used to identify the intracellular signaling pathways activated in primary inguinal adipocytes transduced with Slit2-C versus lacZ adenovirus (see Example 1). Of the 39 receptor tyrosine kinases and intracellular kinases tested in these initial assays, robust phosphorylation changes were observed in only two proteins, phospho-EGFR and phospho-ERK1/2, together with changes in total EGFR upon Slit2-C overexpression (FIGS. 10A and 11A). The EGFR and ERK pathways were antagonized with specific inhibitors, but the treatments failed to reverse Slit2-C-induced thermogenic gene expression effects (FIGS. 11A-11D). These data indicate that the EGFR and ERK pathways are activated by, but not required for, the thermogenic activity of Slit2-C activity.

Figure 10B:
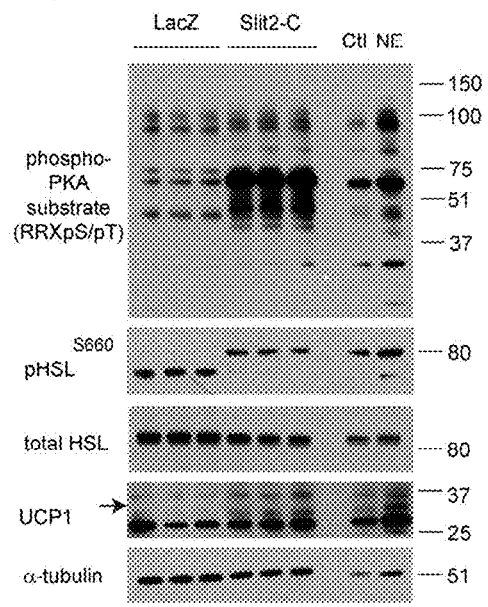
Figure 10C:
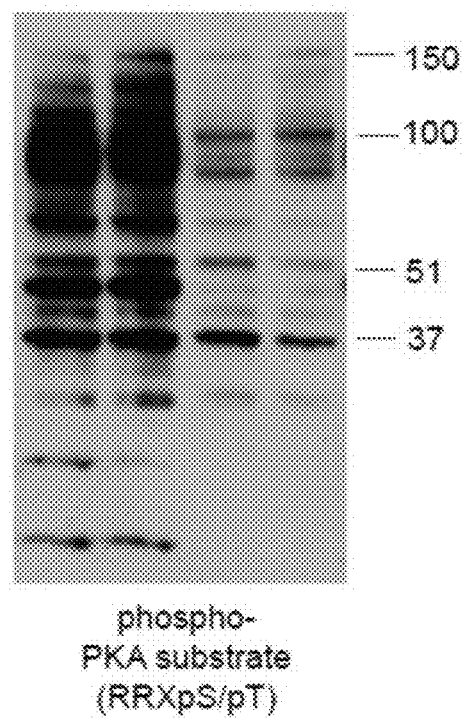
Figure 10D:
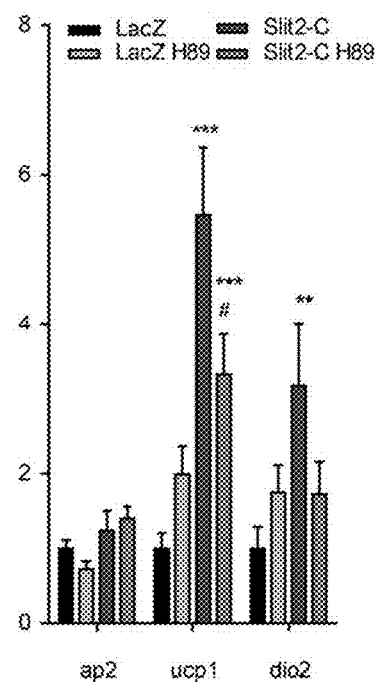
Figure 10E:
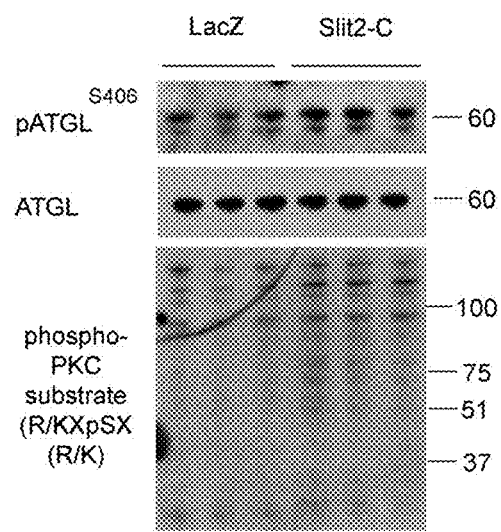
Figure 10F:
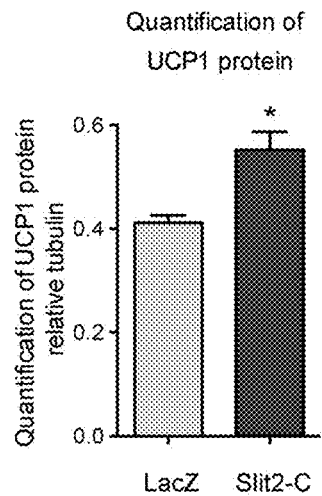

Analysis of PKA signaling was also performed since the PKA signaling pathway is known to be involved in the canonical thermogenic activation of fat cells. Slit2-C-transduced cells, but not lacZ-transduced cells, showed robust phosphorylation of PKA substrates (FIG. 10B). This Slit2-C-induced pattern is similar to the direct treatment of adipocytes with norepinephrine (NE). These observations indicate that Slit2-C activates an overlapping, but distinct, pathway from the canonical beta-adrenergic receptor-mediated signaling in adipocytes. Consistent with PKA activation, phosphorylation of hormone sensitive lipase ($HSL^{S660}$) was induced, while total HSL was unaffected (FIG. 10B). As a comparison, activation of protein kinase C (PKC) substrates and $ATGL^{S406}$ by Slit2-C was minimal (FIG. 10E). Under the same conditions, Slit2-C also increased the protein levels of UCP1, which result confirmed the gene expression levels upon Slit2-C overexpression (FIGS. 10B and 10F).

Figure 10G:
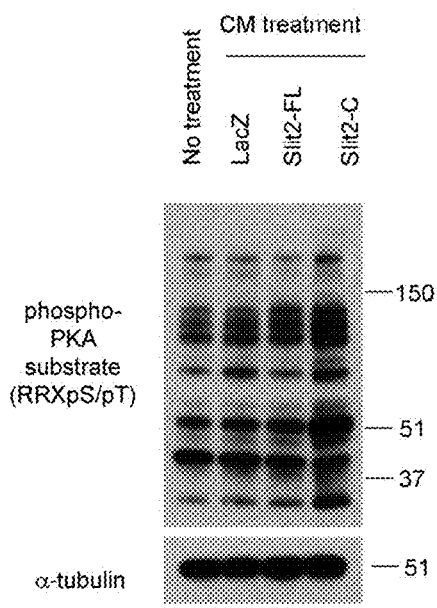

To exclude potential intracellular effects of adenoviral overexpression, serum-free conditioned media were generated from cells expressing LacZ, Slit2-FL, or Slit2-C. Treatment of primary inguinal cells with conditioned media also increased PKA signaling in a pattern similar to norepinephrine (FIG. 10G). These data demonstrate that extracellular Slit2-C activates the canonical β-adrenergic receptor-mediated signaling pathway in adipocytes through an unknown receptor. To more precisely map the mechanism of Slit2-C induced PKA signaling, Slit2-C transduced adipocytes were co-treated with various inhibitors. Propranolol, a pan-β-receptor antagonist did not inhibit Slit2-C induced thermogenesis (FIG. 10H), indicating that β-adrenergic signaling is not required for Slit2-C activity.

Figure 10H:
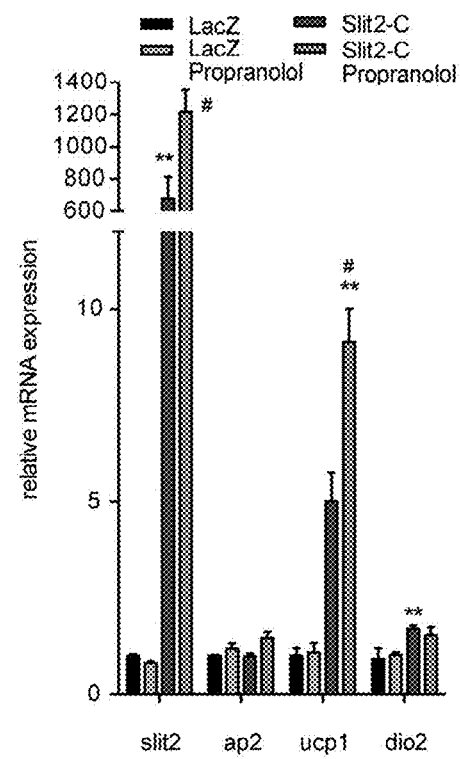
Figure 10I:
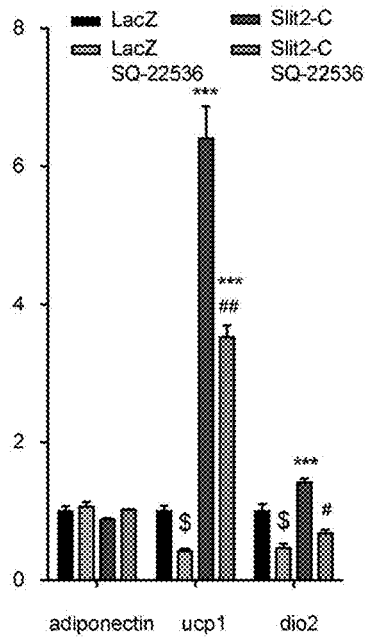

In addition, the PKA inhibitor, H89, was also used to inhibit this pathway in fat cells. At 30 μM concentration, H89 significantly reduced the phosphorylation of PKA substrates in primary inguinal cells (FIG. 10C). Under the same conditions, H89 significantly reduced Ucp1 mRNA by 50% and Dio2 down to baseline levels in cells receiving Slit2-C, indicating that the PKA pathway is responsible for the thermogenic response induced by Slit2-C overexpression (FIG. 10D). Similar effects were seen using the adenylyl cyclase inhibitor SQ-22536 that inhibits the formation of intracellular cAMP (FIG. 10I). Therefore, Slit2-C induces an activation of PKA signaling, which is required for its pro-thermogenesis activity. Together these data indicate that the generation of cAMP and activation of PKA signaling are important for the thermogenic activity of Slit2-C. Based on the foregoing, the data presented herein demonstrate a previously uncharacterized role for Slit2 and a C-terminal protein fragment of Slit2 in fat biology and glucose metabolism.

Figure 11E:
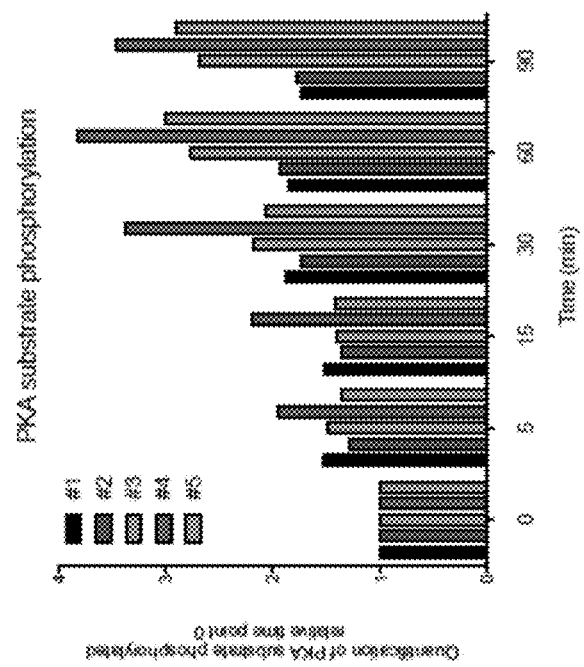
Figure 11F:
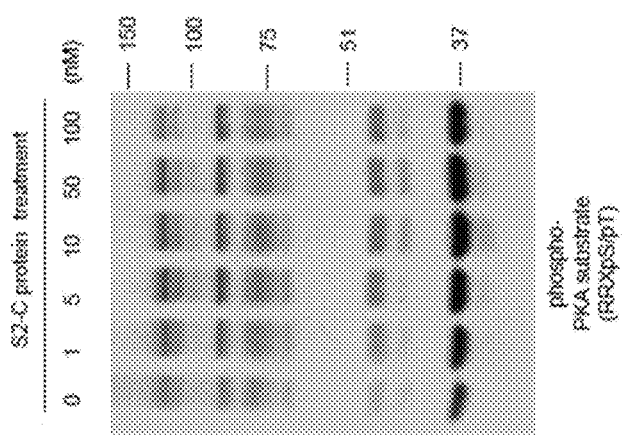
Figure 11G:
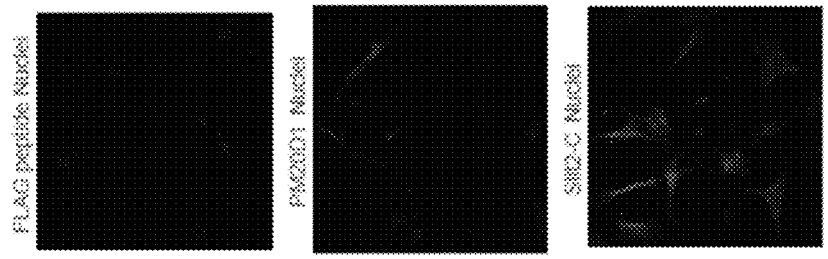

To provide direct evidence of a cell surface receptor for Slit2-C, small scale purified recombinant mammalian Slit2-C from HEK293 cells was generated. The purity and quantification of the protein content (compared with an albumin standard of known concentration) was verified by silver stained SDS gel electrophoresis (FIG. 10J). This shows a 50 kDa band as well as a single FLAG-reactive and Slit2-reactive band on a Western blot (FIG. 10K). Importantly, binding of nanomolar concentrations of purified Slit2-C to the cell surface on live adipocytes incubated at 4° C. was observed, suggesting the presence of a Slit2-C cell surface receptor on adipocytes (FIG. 10L). As a control for specific staining, side-by-side comparisons were performed using another FLAG-tagged protein secreted from thermogenic adipocytes, Pm20D1 (Long et al. (2014) *Cell metabolism* 19:810-820), demonstrating very limited binding to the cell surface of adipocytes compared with Slit2-C (FIG. 11E). Importantly, similarly to the virus overexpression experiments, a subset of PKA substrate phosphorylations was increased after Slit2-C protein treatment in a time-dependent (FIG. 10M) and dose-dependent (FIG. 11F) manner. In contrast with NE, which induces a full response by 5 minutes (min) of treatment, Slit2-C induces PKA phosphorylation at a slightly delayed time that peaks around 60 to 90 min (FIGS. 10M and 11G). The purified protein also induced subsequent changes in thermogenic gene expression in both white and brown adipocytes in culture 2 h after protein treatment (FIG. 10N). Taken together, these data suggests that Slit2-C is directly inducing the PKA pathway in adipocytes to induce thermogenesis by direct (and likely receptor-mediated) interaction with the target cell.

Human and rodent brown and beige fat have multiple shared characteristics, including a potent β-adrenergic receptor/PKA pathway that activates a thermogenic program. Recent studies in humans subjected to the β3-adrenergic receptor agonist mirabegron demonstrate an increased resting metabolic rate as well as an apparent activation of brown fat (Cypess et al. (2015) *Cell Metabolism* 21:33-38). These observations demonstrate that signaling through the β3 adrenergic receptors, which drive cAMP synthesis, are functional in human BAT in vivo. However, β-adrenergic receptor agonists suffer from untoward effects, limiting their clinical use for the treatment of obesity and diabetes.

Based on the foreoing, it has been determined that the C-terminal fragment of Slit2, which is produced endogenously by adipose cells, has several properties that make it of translational interest. First, Slit2 expression is under the control of PRDM16, an important regulator of both brown and beige fat in rodents. PRDM16 is also selectively expressed in human brown fat cells and tissues (Jespersen et al. (2013) *Cell Metabolism* 17:798-805; Shinoda et al. (2015) *Nat. Med.* 21:389-394). Secondly, and importantly, the Slit2 C-terminal fragment appears to function largely through the cAMP/PKA signaling system. Although the magnitude of induction is may be lower and delayed in time compared with direct β-adrenergic receptor activation, it has the advantage of not working through the widely distributed β-adrenergic receptors. It is thus expected that this molecule may circumvent some or all of the existing side effects of direct β-adrenergic receptor agonism.

The transcriptional regulation of Slit2 suggests that cold exposure may control its expression in a manner not completely dependent on the β-adrenergic systems in iWAT and BAT. The mechanism of transcriptional regulation of Ucp1 is somewhat independent of the adrenergic receptors; hence, a parallel pathway of regulation may exist (FIG. 10H). Furthermore, Slit2 mRNA is reduced in iWAT after high fat diet. Similar reductions of Slit2 mRNA in eWAT, but not in BAT, were observed in mice fed a high fat diet, pointing towards interesting and distinct regulation mechanisms in the different adipose depots.

Moreover, the results reveal a functional specificity of Slit2 C-terminal fragment that is distinct from previous studies of Slit2. In brain, the actions of Slit2 are principally thought to occur via its N-terminal ROBO binding domain (Kidd et al. (1999) *Cell* 96:785-794; Wang et al. (1999) *Cell* 96:771-784). It has been determined herein that Slit2-C, which does not contain this ROBO binding motif, nevertheless possesses potent anti-diabetic effect in vivo. These data demonstrate that the biological effects of Slit2 extend well beyond its ROBO binding activity and N-terminal domain. It is worth considering that, Slit2-C may also be important in other areas of physiology. Even this 50 kDa Slit2-C fragment has multiple domains and may activate other pathways. BAT and iWAT responds slightly differently to Slit2-C overexpression in terms of downstream transcriptional targets. This may be explained by, for example, differences in baseline levels of thermogenic genes, the presence and abundance of the receptor(s) or co-receptor(s) and also by the fact that there are preferential signaling pathways in BAT and iWAT induced upon stimulation. It has been determined that PKA signaling is one mechanism that at least in part is responsible for the thermogenic effects. Studies evaluating the physiological relevance of circulating Slit2 in plasma are important for its significance as an endogenous endocrine protein. To date, because of lack of specific reagents for the detection of Slit2 protein in plasma, absolute quantifications of the circulating levels are to be determined. However, multiple unique peptides of Slit2 from both the N- and C-terminal Slit2 have been found in an independent plasma proteomic study (Liu et al. (2007) *J. Am. Soc. Mass. Spectrom.* 18:1249-1264). Thus, the 50 kDa fragment of Slit2 is believed to function, at least in part, in an endocrine fashion. Moreover, the Slit2-C pathway is believed to be promising for the treatment of obesity and related metabolic disorders.

Example 8

Figure 13A:
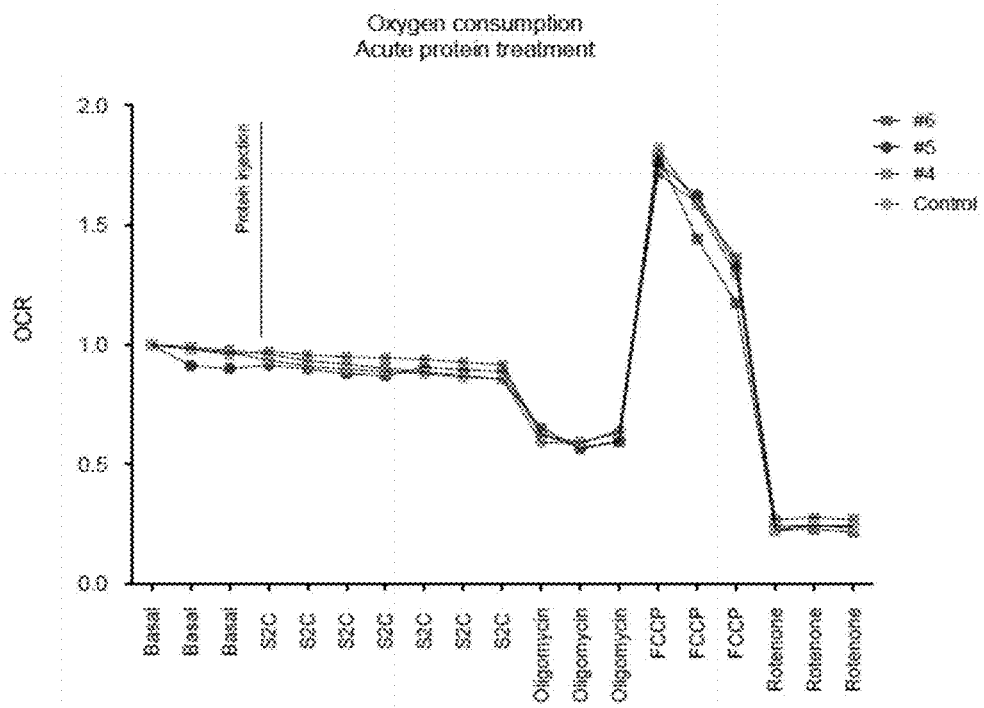
FIG. 13 includes 3 panels, identified as panels A, B, and C showing cellular oxygen consumption measured by Seahorse in primary inguinal fat cells after (Panel A) acute treatment (4 minutes) (Panel A) or long term treatment (2 h) (Panels B and C). Panel C shows statistical analysis of basal and oligomycin induced respiration shown in Panel B.
Figure 13B:
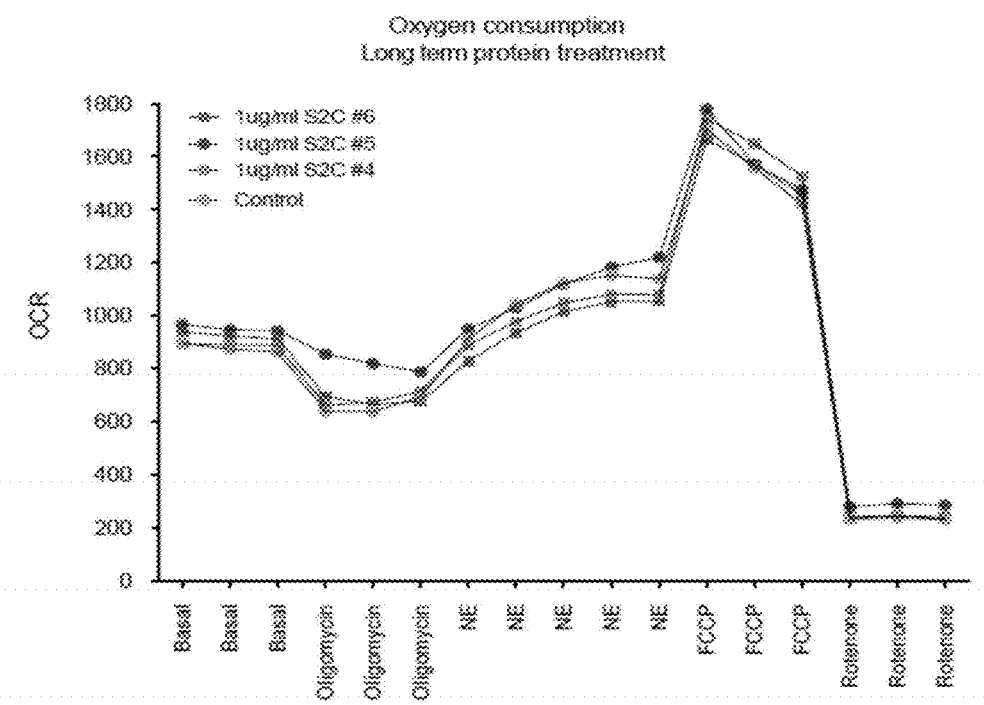
Figure 13C:
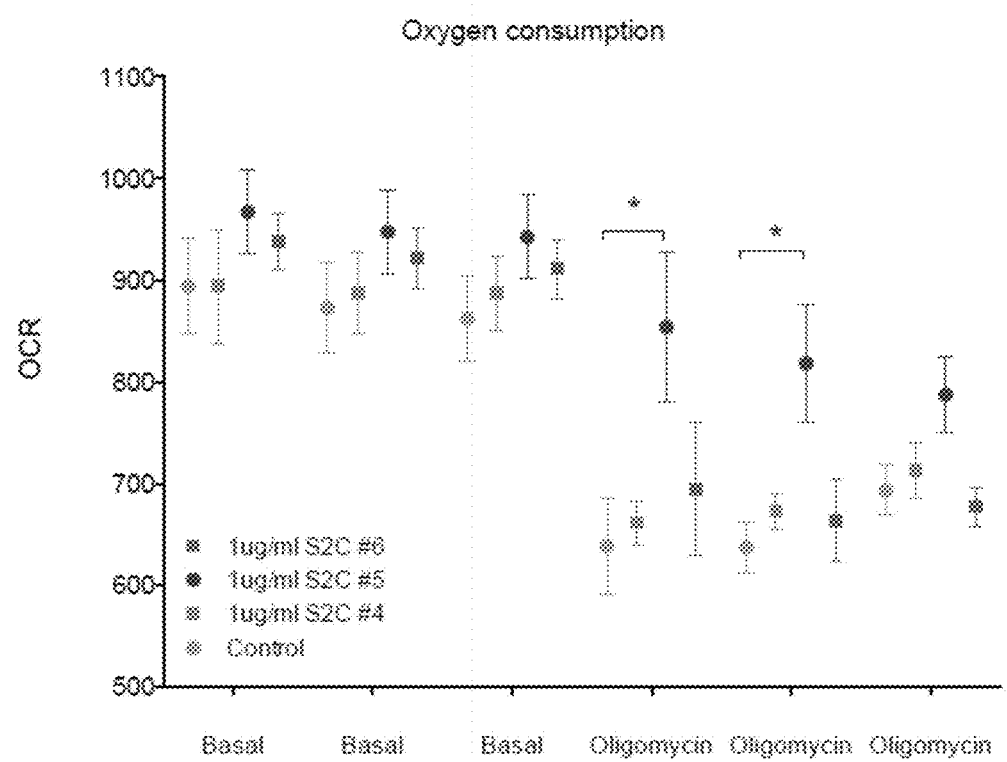

Cellular Oxygen Consumption Measured by Seahorse in Primary Inguinal Fat Cells After Treatment with Slit2-C As described above in Examples 5-7, in vitro and in vivo data on respiration using Slit2-C adenovirus overexpression models and loss-of-function analyses in Seahorse assays are described. In vitro confirmation of the results was determined using an alternative source of recombinant Slit2-C (FIG. 13). Briefly, primary white and brown adipocyte cultures were prepared as described in Example 1D, except that, where indicated in FIG. 13, cells were treated with norepinephrine (100 nM) or with recombinant proteins (1 ug/mL Slit2-C, Calico/AbbVie) for the indicated times. Cellular oxygen consumption rates were determined as described in Example 1 Statstical analysis was performed as described in Example 1C above. The data shown in FIG. 13 confirm the results described above in Examples 5-7.

INCORPORATION BY REFERENCE

The contents of all references, patent applications, patents, and published patent applications, as well as the Figures and the Sequence Listing, cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for modulating a metabolic response comprising contacting a cell in a subject with a biologically active C-terminal polypeptide fragment of Slit2 (Slit2-C), wherein the Slit2-C polypeptide consists of a sequence across its full length that is at least 90% identical to the sequence of SEQ ID NO: 22, optionally wherein the biologically active C-terminal polypeptide fragment of Slit2 further comprises a heterologous sequence and further optionally wherein the subject is an obese subject.

2. The method of claim 1, further comprising contacting the cell with an additional agent that modulates the metabolic response.

3. The method of claim 1, wherein the cell is selected from the group consisting of fibroblasts, adipoblasts, preadipocytes, adipocytes, white adipocytes, brown adipocytes, and beige adipocytes.

4. The method of claim 1, wherein the metabolic response is selected from the group consisting of:
   a) modified expression of a marker selected from the group consisting of: cidea, adiponectin, adipsin, otopetrin, type II deiodinase, cig30, ppar gamma 2, pgc1α, ucp1, elovl3, cAMP, Prdm16, cytochrome C, cox4i1, coxIII, cox5b, cox7al, cox8b, glut4, atpase b2, cox II, atp5o, ndufb5, ap2, ndufs1, GRP109A, acylCoA-thioesterase 4, EARA1, claudin1, PEPCK, fgf21, acylCoA-thioesterase 3, dio2, fatty acid synthase (fas), leptin, resistin, and nuclear respiratory factor-1 (nrf1);
   b) modified thermogenesis in adipose cells;
   c) modified differentiation of adipose cells;
   d) modified insulin sensitivity of adipose cells;
   e) modified basal respiration or uncoupled respiration;
   f) modified whole body oxygen consumption;
   g) modified obesity or appetite;
   h) modified insulin secretion of pancreatic beta cells;
   i) modified glucose tolerance;
   j) modified phosphorylation of EGFR, ERK, AMPK, protein kinase A (PKA) substrates having an RRX(S/T) (SEQ ID NO: 127) motif, wherein the X is any amino acid and the (S/T) residue is a serine or threonine, and/or HSL; and
   k) modified expression of UCP1 protein.

* * * * *